United States Patent
Kotterman et al.

(10) Patent No.: US 11,807,868 B2
(45) Date of Patent: *Nov. 7, 2023

(54) ADENO-ASSOCIATED VARIANTS, FORMULATIONS AND METHODS FOR PULMONARY DELIVERY

(71) Applicant: 4D MOLECULAR THERAPEUTICS INC., Emeryville, CA (US)

(72) Inventors: Melissa Kotterman, Emeryville, CA (US); Peter Francis, Emeryville, CA (US); Melissa Calton, Emeryville, CA (US); Johnny Gonzales, Emeryville, CA (US); Roxanne Croze, Emeryville, CA (US); Christopher Schmitt, Emeryville, CA (US)

(73) Assignee: 4D Molecular Therapeutics Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/938,641

(22) Filed: Oct. 6, 2022

(65) Prior Publication Data
US 2023/0257772 A1    Aug. 17, 2023

Related U.S. Application Data

(63) Continuation of application No. PCT/US2021/029253, filed on Apr. 26, 2021.

(60) Provisional application No. 63/088,432, filed on Oct. 6, 2020, provisional application No. 63/016,246, filed on Apr. 27, 2020.

(51) Int. Cl.
| | | |
|---|---|---|
| *C12N 15/86* | (2006.01) | |
| *C07K 14/005* | (2006.01) | |
| *A61K 9/12* | (2006.01) | |
| *A61K 9/00* | (2006.01) | |
| *C07K 14/47* | (2006.01) | |
| *A61P 11/00* | (2006.01) | |

(52) U.S. Cl.
CPC ............ *C12N 15/86* (2013.01); *A61K 9/0078* (2013.01); *A61K 9/12* (2013.01); *A61P 11/00* (2018.01); *C07K 14/005* (2013.01); *C07K 14/4712* (2013.01); *C12N 2750/14121* (2013.01); *C12N 2750/14122* (2013.01); *C12N 2750/14141* (2013.01); *C12N 2750/14142* (2013.01); *C12N 2750/14143* (2013.01); *C12N 2750/14151* (2013.01)

(58) Field of Classification Search
None
See application file for complete search history.

(56) References Cited

U.S. PATENT DOCUMENTS

| | | | |
|---|---|---|---|
| 8,137,962 B2* | 3/2012 | Flotte | A61K 48/005 435/320.1 |
| 11,499,166 B2* | 11/2022 | Kotterman | C07K 14/4712 |
| 2007/0098690 A1 | 5/2007 | Ostedgaard et al. | |
| 2008/0003204 A1 | 1/2008 | Flotte et al. | |
| 2016/0017295 A1 | 1/2016 | Schaffer et al. | |
| 2022/0143115 A1* | 5/2022 | Marshall | A61K 47/34 |

FOREIGN PATENT DOCUMENTS

| | | |
|---|---|---|
| WO | 2014/194132 A1 | 12/2014 |
| WO | 2017/201121 A1 | 11/2017 |
| WO | 2020/014479 A1 | 1/2020 |
| WO | 2020/117898 A1 | 6/2020 |

OTHER PUBLICATIONS

Potter, et al. (2014) "A simplified purification protocol for recombinant adeno-associated virus vectors", Molecular Therapy, 1. Article 14034. (Year: 2014).*
Santry, et al. (2017) "AAV vector distribution in the mouse respiratory tract following four different methods of administration", BMC Biotechnology, 17: article 43, 11 pages, as printed. (Year: 2017).*
Norrman, et al. (2010) "Quantitative Comparison of Constitutive Promoters in Human ES cells", PLoS One, 5(8): e12431, 10 pages. (Year: 2010).*
Ali (2010) "Pulmonary Drug Delivery", Chapter 9, Handbook of Non-Invasive Drug Delivery Systems, Published by Elsevier, pp. 209-246. (Year: 2010).*
Kurosaki et al., Optimization of adeno-associated virus vector-mediated gene transfer to the respiratory tract. Gene Ther 24, 290-297 (2017).
MacLoughlin et al., Hum Gene Ther., 2015, 26(1), pp. 36-46, "Aerosol-Mediated Delivery of AAV2/6IkBa Attenuates Lipopolysaccharide-Induced Acute Lung Injury in Rats".
Notice of Acceptance—corresponding Australian application No. 2021265768, 2023, IP Australia, 3 pages long.
Accepted Claims—corresponding Australian application No. 2021265768, (claims, 4 pages long, 2023.
International Search Report of PCT/US2021/029253 dated Oct. 21, 2021, no author given, 6 pages long.
Written Opinion of PCT/US2021/029253 dated Oct. 21, 2021, No Author, 12 pages long.
Ostedgaard et al., Proc Natl Acad Sci USA, 108(7):2921-2926 (2011), "Cystic fibrosis transmembrane conductance regulator with a shortened R domain rescues the intestinal phenotype of CFTR-/- mice".
Ostedgaard et al., Proc Natl Acad Sci USA, 102(8):2952-2957 (2005, "A shortened adeno-associated virus expression cassette for CFTR gene transfer to cystic fibrosis airway epithelia".

(Continued)

*Primary Examiner* — Robert M Kelly
(74) *Attorney, Agent, or Firm* — Much Shelist, P.C.; Christopher M. Cabral

(57) ABSTRACT

The present disclosure provides a variant AAV capsid protein that confers tropism to lung cells and recombinant adeno-associated viruses comprising the variant AAV and pharmaceutical compositions comprising same and their use in the delivery of heterologous nucleic acids to lung cells for the treatment of pulmonary disorders.

28 Claims, 63 Drawing Sheets

Specification includes a Sequence Listing.

(56) References Cited

OTHER PUBLICATIONS

Corbiere et al., Respiratory Research, DOI: 10.1186/1465-9921-12-15 (2011), "Phenotypic characteristics of human type II alveolar epithelial cells suitable for antigen presentation to T lymphocytes".
Plebani et al., Laboratory Investigation, vol. 97, 1375-1384 (2017), Establishment and long-term culture of human cystic fibrosis endothelial cells.
Vidovic et al., Am J Respir Care Med, 193(3):288-298 (2016), "rAAV-CFTRdeltaR Rescues the Cystic Fibrosis Phenotype Human Intestinal Organoids and Cystic Fibrosis Mice".
Guggino et al., Expert Opin. Biol. Ther., 17(10):1265-1273 (2017).
Bohinski et al., Molecular and Cellular Biol., 14(9):5671-5681 (1994) The Lung-Specific Surfactant Protein B Gene Promoter Is a Target for Thyroid Transcription Factor 1 and Hepatocyte Nucleax Factor 3, indicating Common Factors for Organ Specific Gene Expression along the Foregut Axis.
McCarron, et al. "Effective viral-mediated lung gene therapy: is airway surface preparation necessary?", Gene Therapy (2022): 1-9, vol. 30.

\* cited by examiner

FIG. 2B

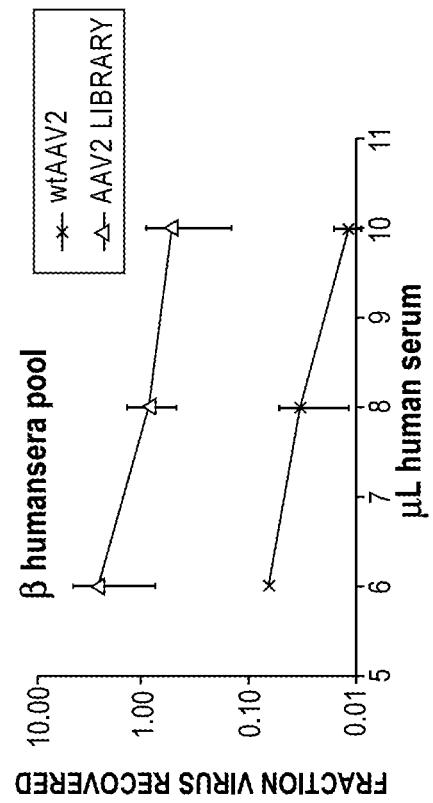
FIG. 7A
FIG. 7B
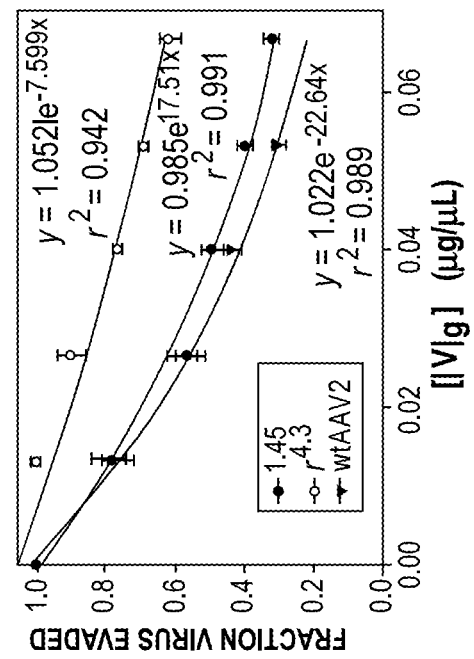
FIG. 7C
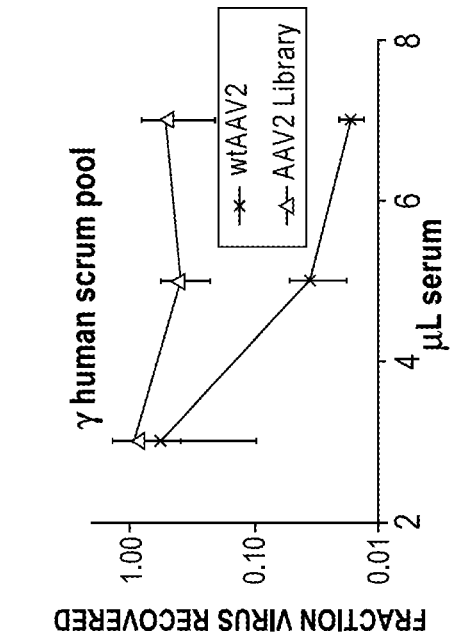
FIG. 7D

```
                              1         10        20        30
                              |         |         |         |
Consensus                     MAADGYLPDWLEDNLSEGIREWWALKPGAP
Identity 1. AAV1 translation           MAADGYLPDWLEDNLSEGIREWWDLKPGAP
2. AAV2 translation           MAADGYLPDWLEDTLSEGIRQWWKLKPGPP
3. AAV3 translation           MAADGYLPDWLEDNLSEGIREWWALKPGVP
4. AAV4 translation            MTDGYLPDWLEDNLSEGVREWWALQPGAP
5. AAV5 translation           MSFVDHPPDWLEE-VGEGLREFLGLEAGPP
6. AAV6 translation           MAADGYLPDWLEDNLSEGIREWWDLKPGAP
7. AAV7 translation           MAADGYLPDWLEDNLSEGIREWWDLKPGAP
8. AAV8 translation           MAADGYLPDWLEDNLSEGIREWWALKPGAP
9. AAV9 translation           MAADGYLPDWLEDNLSEGIREWWALKPGAP
10. Shuffle 100.1 Translation MAADGYLPDWLEDTLSEGIRQWWKLKPGPP 40        50        60
                                        |         |         |
Consensus                     KPKANQQHQDDGRGLVLPGYKYLGPFNGLD
Identity 1. AAV1 translation           KPKANQQKQDDGRGLVLPGYKYLGPFNGLD
2. AAV2 translation           PPKPAERHKDDSRGLVLPGYKYLGPFNGLD
3. AAV3 translation           QPKANQQHQDNRRGLVLPGYKYLGPGNGLD
4. AAV4 translation           KPKANQQHQDNARGLVLPGYKYLGPGNGLD
5. AAV5 translation           KPKPNQQHQDQARGLVLPGYNYLGPGNGLD
6. AAV6 translation           KPKANQQKQDDGRGLVLPGYKYLGPFNGLD
7. AAV7 translation           KPKANQQKQDNGRGLVLPGYKYLGPFNGLD
8. AAV8 translation           KPKANQQKQDDGRGLVLPGYKYLGPFNGLD
9. AAV9 translation           QPKANQQHQDNARGLVLPGYKYLGPGNGLD
10. Shuffle 100.1 Translation PPKPAERHKDDSRGLVLPGYKYLGPFNGLD 70        80        90
                                        |         |         |
Consensus                     KGEPVNAADAAALEHDKAYDQQLKAGDNPY
Identity 1. AAV1 translation           KGEPVNAADAAALEHDKAYDQQLKAGDNPY
2. AAV2 translation           KGEPVNEADAAALEHDKAYDRQLDSGDNPY
3. AAV3 translation           KGEPVNEADAAALEHDKAYDQQLKAGDNPY
4. AAV4 translation           KGEPVNAADAAALEHDKAYDQQLKAGDNPY
5. AAV5 translation           RGEPVNRADEVAREHDISYNEQLEAGDNPY
6. AAV6 translation           KGEPVNAADAAALEHDKAYDQQLKAGDNPY
7. AAV7 translation           KGEPVNAADAAALEHDKAYDQQLKAGDNPY
8. AAV8 translation           KGEPVNAADAAALEHDKAYDQQLQAGDNPY
9. AAV9 translation           KGEPVNAADAAALEHDKAYDQQLKAGDNPY
10. Shuffle 100.1 Translation KGEPVNEADAAALEHDKAYDQQLKAGDNPY
```

FIG. 8A

```
                                        100              110              120
Consensus               LKYN HA DA E F QER LQEDTS FGGN LGRAV F Q
Identity                ▬▬▬▬▬▬▬▬▬▬▬▬▬▬▬▬▬▬▬▬▬▬▬▬▬▬▬▬▬▬▬▬

1. AAV1 translation     LRYN HA DA E F QER LQEDTS FGGN LGRAV F Q
2. AAV2 translation     LKYN HA DA E F QER LKEDTS FGGN LGRAV F Q
3. AAV3 translation     LKYN HA DA E F QER LQEDTS FGGN LGRAV F Q
4. AAV4 translation     LKYN HA DA E F QQR LQGDTS FGGN LGRAV F Q
5. AAV5 translation     LKYN HA DA E F QEK LADDTS FGGN LGKAV F Q
6. AAV6 translation     LRYN HA DA E F QER LQEDTS FGGN LGRAV F Q
7. AAV7 translation     LRYN HA DA E F QER LQEDTS FGGN LGRAV F Q
8. AAV8 translation     LRYN HA DA E F QER LQEDTS FGGN LGRAV F Q
9. AAV9 translation     LKYN HA DA E F QER LKEDTS FGGN LGRAV F Q
10. Shuffle 100.1 Translation  LKYN HA DA E F QQR LQGDTS FGGN LGRAV F Q
                        AAV4

130              140              150
Consensus               AKKRV LEPLG LV EEGAK TA PGKKR PVEQS P
Identity                ▬▬▬▬▬▬▬▬▬▬▬▬▬▬▬▬▬▬▬▬▬▬▬▬▬▬▬▬▬▬▬▬

1. AAV1 translation     AKKRV LEPLG LV EEGAK TA PGKKR PVEQS P
2. AAV2 translation     AKKRV LEPLG LV EEPVK TA PGKKR PVEHS P
3. AAV3 translation     AKKRI LEPLG LV EEAAK TA PGKKG AVDQS P
4. AAV4 translation     AKKRV LEPLG LV EQAGE TA PGKKR PLIES P
5. AAV5 translation     AKKRV LEPFG LV EEGAK TA PTGKR IDDHF P
6. AAV6 translation     AKKRV LEPFG LV EEGAK TA PGKKR PVEQS P
7. AAV7 translation     AKKRV LEPLG LV EEGAK TA PAKKR PVEPS P
8. AAV8 translation     AKKRV LEPLG LV EEGAK TA PGKKR PVEPS P
9. AAV9 translation     AKKRL LEPLG LV EEAAK TA PGKKR PVEQS P
10. Shuffle 100.1 Translation  AKKRV LEPLG LV EQAGE TA PGKKR PLIES P
                        AAV4

160              170              180
Consensus               QE- PDSS XGIGKKG QQPAKKR LN FGQTG DS
Identity                ▬▬ ▬▬▬▬▬ ▬▬ ▬▬▬ ▬ ▬▬▬▬▬ ▬▬ ▬▬▬▬▬ ▬▬

1. AAV1 translation     QE- PDSSSGIGKTGQQPAKKR LN FGQTG DS
2. AAV2 translation     VE- PDSSSGTGKAGQQPARKR LN FGQTG DA
3. AAV3 translation     QE- PDSSSGVGKSGKQPARKR LN FGQTG DS
4. AAV4 translation     QQ- PDSSTGIGKKGKQPAKKK LVFE---DE
5. AAV5 translation     KR----KKAR TEEDSK PST-------SSDA
6. AAV6 translation     QE- PDSSSGIGKTGQQPAKKR LN FGQTG DS
7. AAV7 translation     QRS PDSSTGIGKKGQQPARKR LN FGQTG DS
8. AAV8 translation     QRS PDSSTGIGKKGQQPARKR LN FGQTG DS
9. AAV9 translation     QE- PDSSAGIGKSGAQPAKKR LN FGQTG DT
10. Shuffle 100.1 Translation  QQ- PDSSTGIGKKGKQPAKKR LN FGQTG DS
                        AAV4
```

FIG. 8B

```
                              190          200          210
Consensus               ESVPDPQPLGEPPAAP-SSVGXXTMASGGG
Identity                ▬▬▬▬▬▬▬▬▬▬▬▬▬▬▬ ▬▬▬▬ ▬▬▬▬▬▬▬▬▬

1. AAV1 translation     ESVPDPQPLGEPPATP-AAVGPTTMASGGG
2. AAV2 translation     DSVPDPQPLGQPPAAP-SGLGTNTMATGSG
3. AAV3 translation     ESVPDPQPLGEPPAAP-TSLGSNTMASGGG
4. AAV4 translation     TGAGDGPPEGSTSGA--MSDDSEMRAAAGG
5. AAV5 translation     EAGPSGSQQLQIPAQPASSLGADTMSAGGG
6. AAV6 translation     ESVPDPQPLGEPPATP-AAVGPTTMASGGG
7. AAV7 translation     ESVPDPQPLGEPPAAP-SSVGSGTVAAGGG
8. AAV8 translation     ESVPDPQPLGEPPAAP-SGVGPNTMAAGGG
9. AAV9 translation     ESVPDPQPIGEPPAAP-SGVGSLTMASGGG
10. Shuffle 100.1 Translation ESVPDPQPLGEPPATP-AAVGPTTMASGGG
                        ⟨AAV1/6                  ⟩⟨A...

220          230          240
Consensus               APMADNNEGADGVGNASGNWHCDSTWLGDR
Identity                ▬▬▬▬▬▬▬▬▬▬▬▬▬▬▬▬▬▬▬▬▬▬▬▬▬▬▬▬▬

1. AAV1 translation     APMADNNEGADGVGNASGNWHCDSTWLGDR
2. AAV2 translation     APMADNNEGADGVGNSSGNWHCDSTWMGDR
3. AAV3 translation     APMADNNEGADGVGNSSGNWHCDSQWLGDR
4. AAV4 translation     AAV-EGGQGADGVGNASGDWHCDSTWSEGH
5. AAV5 translation     GPLGDNNQGADGVGNASGDWHCDSTWMGDR
6. AAV6 translation     APMADNNEGADGVGNASGNWHCDSTWLGDR
7. AAV7 translation     APMADNNEGADGVGNASGNWHCDSTWLGDR
8. AAV8 translation     APMADNNEGADGVGSSSGNWHCDSTWLGDR
9. AAV9 translation     APVADNNEGADGVGSSSGNWHCDSQWLGDR
10. Shuffle 100.1 Translation APMADNNEGADGVGNASGNWHCDSTWLGDR
                        ⟨A⟩⟨AAV1

250          260          270
Consensus               VITTSTRTWALPTYNNHLYKQISSASX-GA
Identity                ▬▬▬▬▬▬▬▬▬▬▬▬▬▬▬▬▬▬▬▬▬▬▬▬▬ ▬▬

1. AAV1 translation     VITTSTRTWALPTYNNHLYKQISSAST-GA
2. AAV2 translation     VITTSTRTWALPTYNNHLYKQISSQS--GA
3. AAV3 translation     VITTSTRTWALPTYNNHLYKQISSQS--GA
4. AAV4 translation     VTTSTRTWVLPTYNNHLYKRLGESL----
5. AAV5 translation     VVTKSTRTWVLPSYNNHQREIKSGSVDG-
6. AAV6 translation     VITTSTRTWALPTYNNHLYKQISSAST-GA
7. AAV7 translation     VITTSTRTWALPTYNNHLYKQISSETA-GS
8. AAV8 translation     VITTSTRTWALPTYNNHLYKQISNGTSGGA
9. AAV9 translation     VITTSTRTWALPTYNNHLYKQISNSTSGGS
10. Shuffle 100.1 Translation VITTSTRTWALPTYNNHLYKQISSAST-GA
                        ⟨AAV1                          ⟩
```

FIG. 8C

|  | 280 | 290 | 300 |
|---|---|---|---|

Consensus: SNDNHYFGYSTPWGYFDFNRFHCHFSPRDW
Identity

1. AAV1 translation: SNDNHYFGYSTPWGYFDFNRFHCHFSPRDW
2. AAV2 translation: SNDNHYFGYSTPWGYFDFNRFHCHFSPRDW
3. AAV3 translation: SNDNHYFGYSTPWGYFDFNRFHCHFSPRDW
4. AAV4 translation: -QSNTYNGFSTPWGYFDFNRFHCHFSPRDW
5. AAV5 translation: SNANAYFGYSTPWGYFDFNRFHSHWSPRDW
6. AAV6 translation: SNDNHYFGYSTPWGYFDFNRFHCHFSPRDW
7. AAV7 translation: TNDNTYFGYSTPWGYFDFNRFHCHFSPRDW
8. AAV8 translation: TNDNTYFGYSTPWGYFDFNRFHCHFSPRDW
9. AAV9 translation: SNDNAYFGYSTPWGYFDFNRFHCHFSPRDW
10. Shuffle 100.1 Translation: SNDNHYFGYSTPWGYFDFNRFHCHFSPRDW

AAV1

|  | 310 | 320 | 330 |
|---|---|---|---|

Consensus: QRLINNNWGFRPKRLNFKLFNIQVKEVTTN
Identity

1. AAV1 translation: QRLINNNWGFRPKRLNFKLFNIQVKEVTTN
2. AAV2 translation: QRLINNNWGFRPKRLNFKLFNIQVKEVTQN
3. AAV3 translation: QRLINNNWGFRPKKLSFKLFNIQVRGVTQN
4. AAV4 translation: QRLINNNWGMRPKAMRVKIFNIQVKEVTTS
5. AAV5 translation: QRLINNYWGFRPRSLRVKIFNIQVKEVTVQ
6. AAV6 translation: QRLINNNWGFRPKRLNFKLFNIQVKEVTTN
7. AAV7 translation: QRLINNNWGFRPKKLRFKLFNIQVKEVTTN
8. AAV8 translation: QRLINNNWGFRPKRLSFKLFNIQVKEVTQN
9. AAV9 translation: QRLINNNWGFRPKRLNFKLFNIQVKEVTDN
10. Shuffle 100.1 Translation: QRLINNNWGFRPKRLNFKLFNIQVKEVTTN

AAV1

|  | 340 | 350 | 360 |
|---|---|---|---|

Consensus: DGVTTIANNLTSTVQVFTDSEYQLPYVLGS
Identity

1. AAV1 translation: DGVTTIANNLTSTVQVFSDSEYQLPYVLGS
2. AAV2 translation: DGTTTIANNLTSTVQVFTDSEYQLPYVLGS
3. AAV3 translation: DGTTTIANNLTSTVQVFTDSEYQLPYVLGS
4. AAV4 translation: NGETTVANNLTSTVQIFADSSYELPYVMDA
5. AAV5 translation: DSTTTIANNLTSTVQVFTDDDYQLPYVVGN
6. AAV6 translation: DGVTTIANNLTSTVQVFSDSEYQLPYVLGS
7. AAV7 translation: DGVTTIANNLTSTIQVFSDSEYQLPYVLGS
8. AAV8 translation: EGTKTIANNLTSTIQVFTDSEYQLPYVLGS
9. AAV9 translation: NGVKTIANNLTSTVQVFTDSDYQLPYVLGS
10. Shuffle 100.1 Translation: DGVTTIANNLTSTVQVFSDSDYQLPYVLGS

AAV1  AAV9

FIG. 8D

```
                                    370         380         390
Consensus                   AHQGCLPPFPADVFMIPQYGYLTLN--NGS
Identity                    ██████████████████████████  ███

1. AAV1 translation         AHQGCLPPFPADVFMIPQYGYLTLN--NGS
2. AAV2 translation         AHQGCLPPFPADVFMVPQYGYLTLN--NGS
3. AAV3 translation         AHQGCLPPFPADVFMVPQYGYLTLN--NGS
4. AAV4 translation         GQEGSLPPFPNDVFMVPQYGYCGLVTGNTS
5. AAV5 translation         GTEGCLPAFPPQVFTLPQYGYATLNRDNTE
6. AAV6 translation         AHQGCLPPFPADVFMIPQYGYLTLN--NGS
7. AAV7 translation         AHQGCLPPFPADVFMIPQYGYLTLN--NGS
8. AAV8 translation         AHQGCLPPFPADVFMIPQYGYLTLN--NGS
9. AAV9 translation         AHEGCLPPFPADVFMIPQYGYLTLN--DGS
10. Shuffle 100.1 Translation AHEGCLPPFPADVFMVPQYGYLTLN--NGS
                            ◄AAV9    ◄AAV2

400         410         420
Consensus                   QA-VGRSSFYCLEYFPSQMLRTGNNFTFSY
Identity                    ██ █████ █████████████████ ████

1. AAV1 translation         QA-VGRSSFYCLEYFPSQMLRTGNNFTFSY
2. AAV2 translation         QA-VGRSSFYCLEYFPSQMLRTGNNFTFSY
3. AAV3 translation         QA-VGRSSFYCLEYFPSQMLRTGNNFQFSY
4. AAV4 translation         QQQTDRNAFYCLEYFPSQMLRTGNNFEITY
5. AAV5 translation         NP-TERSSFFCLEYFPSKMLRTGNNFEFTY
6. AAV6 translation         QA-VGRSSFYCLEYFPSQMLRTGNNFTFSY
7. AAV7 translation         QS-VGRSSFYCLEYFPSQMLRTGNNFEFSY
8. AAV8 translation         QA-VGRSSFYCLEYFPSQMLRTGNNFQFTY
9. AAV9 translation         QA-VGRSSFYCLEYFPSQMLRTGNNFQFSY
10. Shuffle 100.1 Translation QA-VGRSSFYCLEYFPSQMLRTGNNFTFSY
                            ◄AAV2

430         440         450
Consensus                   TFEDVPFHSSYAHSQSLDRLMNPLIDQYLY
Identity                    ████████████████████████████████

1. AAV1 translation         TFEEVPFHSSYAHSQSLDRLMNPLIDQYLY
2. AAV2 translation         TFEDVPFHSSYAHSQSLDRLMNPLIDQYLY
3. AAV3 translation         TFEDVPFHSSYAHSQSLDRLMNPLIDQYLY
4. AAV4 translation         SFEKVPFHSMYAHSQSLDRLMNPLIDQYLW
5. AAV5 translation         NFEEVPFHSSFAPSQNLFKLANPLVDQYLY
6. AAV6 translation         TFEDVPFHSSYAHSQSLDRLMNPLIDQYLY
7. AAV7 translation         SFEDVPFHSSYAHSQSLDRLMNPLIDQYLY
8. AAV8 translation         TFEDVPFHSSYAHSQSLDRLMNPLIDQYLY
9. AAV9 translation         EFENVPFHSSYAHSQSLDRLMNPLIDQYLY
10. Shuffle 100.1 Translation TFEDVPFHSSYAHSQSLDRLMNPLIDQYLY
                            ◄AAV2
```

FIG. 8E

```
                                        460              470              480
Consensus                    YLNRTQN-XSGTAXNKXLLFSQGGPXGMSV
Identity 1. AAV1 translation          YLNRTQN-QSGSAQNKDLLFSRGSPAGMSV
2. AAV2 translation          YLSRTNT-PSGTTTQSRLQFSQAGASDIRD
3. AAV3 translation          YLNRTQGTTSGTTNQSRLLFSQAGPQSMSL
4. AAV4 translation          GLQSTTTGTTLNAGTATTNFTKLRPTNFSN
5. AAV5 translation          RFVSTNN-------TGGVQFNKNLAGRYAN
6. AAV6 translation          YLNRTQN-QSGSAQNKDLLFSRGSPAGMSV
7. AAV7 translation          YLARTQSNPGGTAGNRELQFYQGGPSTMAE
8. AAV8 translation          YLSRTQT-TGGTANTQTLGFSQGGPNTMAN
9. AAV9 translation          YLSKTIN--GSGQNQQTLKFSVAGPSNMAV
10. Shuffle 100.1 Translation YLNRTQN-QSGSAQNKDLLFSRGSPAGMSV
                             AAV1/6  AAV6                    AAV1

490              500              510
Consensus                    QXKNWLPGPCYRQQRVSKTKTDN-NNSNFA
Identity 1. AAV1 translation          QPKNWLPGPCYRQQRVSKTKTDN-NNSNFT
2. AAV2 translation          QSRNWLPGPCYRQQRVSKTSADN-NNSEYS
3. AAV3 translation          QARNWLPGPCYRQQRLSKTANDN-NNSNFP
4. AAV4 translation          FKKNWLPGPSIKQQGFSKTANQNYKIPATG
5. AAV5 translation          TYKNWFPGPMGRTQGWNLGSGVN-RASVSA
6. AAV6 translation          QPKNWLPGPCYRQQRVSKTKTDN-NNSNFT
7. AAV7 translation          QAKNWLPGPCFRQQRVSKTLDQN-NNSNFA
8. AAV8 translation          QAKNWLPGPCYRQQRVSTTTGQN-NNSNFA
9. AAV9 translation          QGRNYIPGPSYRQQRVSTTVTQN-NNSEFA
10. Shuffle 100.1 Translation QPKNWLPGPCYRQQRVSKTKTDN-NNSNFT
                             AAV1

520              530              540
Consensus                    WTGASKYH----LNGRXSLVNPGPAMASHK
Identity 1. AAV1 translation          WTGASKYN----LNGRESIINPGTAMASHK
2. AAV2 translation          WTGATKYH----LNGRDSLVNPGPAMASHK
3. AAV3 translation          WTAASKYH----LNGRDSLVNPGPAMASHK
4. AAV4 translation          SDSLIKYETHSTLDGRWSALTPGPPMATAG
5. AAV5 translation          FATTNRME----LEGASYQVPPQPNGMTNN
6. AAV6 translation          WTGASKYN----LNGRESIINPGTAMASHK
7. AAV7 translation          WTGATKYH----LNGRNSLVNPGVAMATHK
8. AAV8 translation          WTAGTKYH----LNGRNSLANPGIAMATHK
9. AAV9 translation          WPGASSWA----LNGRNSLMNPGPAMASHK
10. Shuffle 100.1 Translation WTGASKYN----LNGRESIINPGTAMASHK
                             AAV6
```

FIG. 8F

|   | 550 | 560 | 570 |
|---|---|---|---|
| Consensus | DDEDKFFPMSGVLIFGKQGAGASNTAL--- | | |

| | |
|---|---|
| 1. AAV1 translation | DDEDKFFPMSGVMIFGKESAGASNTAL--- |
| 2. AAV2 translation | DDEEKFFPQSGVLIFGKQGSEKTNVDI--- |
| 3. AAV3 translation | DDEEKFFPMHGNLIFGKEGTTASNAEL--- |
| 4. AAV4 translation | PADSKFSNSQLIFAGPKQNGNTATVP---- |
| 5. AAV5 translation | LQGSNTYALENTMIFNSQPANPGTTATYLE |
| 6. AAV6 translation | DDKDKFFPMSGVMIFGKESAGASNTAL--- |
| 7. AAV7 translation | DDEDRFFPSSGVLIFGKTGATNKTTL---- |
| 8. AAV8 translation | DDEERFFPSNGILIFGKQNAARDNADY--- |
| 9. AAV9 translation | EGEDRFFPLSGSLIFGKQGTGRDNVDA--- |
| 10. Shuffle 100.1 Translation | DDKDKFFPMSGVMIFGKESAGASNTAL--- |

AAV6

|   | 580 | 590 | 600 |
|---|---|---|---|
| Consensus | DNVMITDEEEIKXTNPVATERYGTVAXNLQ | | |

| | |
|---|---|
| 1. AAV1 translation | DNVMITDEEEIKATNPVATERFGTVAVNFQ |
| 2. AAV2 translation | EKVMITDEEEIRTTNPVATEQYGSVSTNLQ |
| 3. AAV3 translation | DNVMITDEEEIRTTNPVATEQYGTVANNLQ |
| 4. AAV4 translation | GTLIFTSEEELAATNATDTDMWGNLPGGDQ |
| 5. AAV5 translation | GNMLITSESETQPVNRVAYNVGGQMATNNQ |
| 6. AAV6 translation | DNVMITDEEEIKATNPVATERFGTVAVNLQ |
| 7. AAV7 translation | ENVLMTNEEEIRPTNPVATEEYGIVSSNLQ |
| 8. AAV8 translation | SDVMLTSEEEIKTTNPVATEEYGIVADNLQ |
| 9. AAV9 translation | DKVMITNEEEIKTTNPVATESYGQVATNHQ |
| 10. Shuffle 100.1 Translation | DNVMITDEEEIKATNPVATERFGTVAVNLQ |

AAV6  AAV1/6  AAV6

|   | 610 | 620 | 630 |
|---|---|---|---|
| Consensus | SSXTAPATGDVNXQGALPGMVWQDRDVYLQ | | |

| | |
|---|---|
| 1. AAV1 translation | SSSTDPATGDVHAMGALPGMVWQDRDVYLQ |
| 2. AAV2 translation | RGNRQAATADVNTQGVLPGMVWQDRDVYLQ |
| 3. AAV3 translation | SSNTAPTTGTVNHQGALPGMVWQDRDVYLQ |
| 4. AAV4 translation | SNSNLPTVDRLTALGAVPGMVWQNRDIYYQ |
| 5. AAV5 translation | SSTTAPATGTYNLQEIVPGSWMERDVYLQ |
| 6. AAV6 translation | SSSTDPATGDVHVMGALPGMVWQDRDVYLQ |
| 7. AAV7 translation | AANTAAQTQVVNNQGALPGMVWQNRDVYLQ |
| 8. AAV8 translation | QQNTAPQIGTVNSQGALPGMVWQNRDVYLQ |
| 9. AAV9 translation | SAQAQAQTGWVQNQGILPGMVWQDRDVYLQ |
| 10. Shuffle 100.1 Translation | SSSTDPATGDVHVMGALPGMVWQDRDVYLQ |

AAV6  AAV6

FIG. 8G

|                              | 640                          | 650                | 660         |
|------------------------------|------------------------------|--------------------|-------------|
| Consensus                    | G P I W A K I P H T D G H F H P S P L M G G F G L K H P P P |
| Identity                     |                              |                    |             |
| 1. AAV1 translation          | G P I W A K I P H T D G H F H P S P L M G G F G L K N P P P |
| 2. AAV2 translation          | G P I W A K I P H T D G H F H P S P L M G G F G L K H P P P |
| 3. AAV3 translation          | G P I W A K I P H T D G H F H P S P L M G G F G L K H P P P |
| 4. AAV4 translation          | G P I W A K I P H T D G H F H P S P L I G G F G L K H P P P |
| 5. AAV5 translation          | G P I W A K I P E T G A H F H P S P A M G G F G L K H P P P |
| 6. AAV6 translation          | G P I W A K I P H T D G H F H P S P L M G G F G L K H P P P |
| 7. AAV7 translation          | G P I W A K I P H T D G N F H P S P L M G G F G L K H P P P |
| 8. AAV8 translation          | G P I W A K I P H T D G N F H P S P L M G G F G L K H P P P |
| 9. AAV9 translation          | G P I W A K I P H T D G N F H P S P L M G G F G M K H P P P |
| 10. Shuffle 100.1 Translation| G P I W A K I P H T D G H F H P S P L M G G F G L K N P P P |
|                              | ⟨AAV6    ⟨AAV1               |                    |             |

|                              | 670                          | 680                | 690         |
|------------------------------|------------------------------|--------------------|-------------|
| Consensus                    | Q I L I K N T P V P A N P P T T F S A T K F A S F I T Q Y S |
| Identity                     |                              |                    |             |
| 1. AAV1 translation          | Q I L I K N T P V P A N P P A E F S A T K F A S F I T Q Y S |
| 2. AAV2 translation          | Q I L I K N T P V P A N P S T T F S A A K F A S F I T Q Y S |
| 3. AAV3 translation          | Q I M I K N T P V P A N P P T T F S P A K F A S F I T Q Y S |
| 4. AAV4 translation          | Q I F I K N T P V P A N P A T T F S S T P V N S F I T Q Y S |
| 5. AAV5 translation          | M M L I K N T P V P G N - I T S F S D V P V S S F I T Q Y S |
| 6. AAV6 translation          | Q I L I K N T P V P A N P P A E F S A T K F A S F I T Q Y S |
| 7. AAV7 translation          | Q I L I K N T P V P A N P P E V F T P A K F A S F I T Q Y S |
| 8. AAV8 translation          | Q I L I K N T P V P A D P P T T F N Q S K L N S F I T Q Y S |
| 9. AAV9 translation          | Q I L I K N T P V P A D P P T A F N K D K L N S F I T Q Y S |
| 10. Shuffle 100.1 Translation| Q I L I K N T P V P A N P P A E F S A T K F A S F I T Q Y S |

|                              | 700                          | 710                | 720         |
|------------------------------|------------------------------|--------------------|-------------|
| Consensus                    | T G Q V S V E I E W E L Q K E N S K R W N P E I Q Y T S N Y |
| Identity                     |                              |                    |             |
| 1. AAV1 translation          | T G Q V S V E I E W E L Q K E N S K R W N P E V Q Y T S N Y |
| 2. AAV2 translation          | T G Q V S V E I E W E L Q K E N S K R W N P E I Q Y T S N Y |
| 3. AAV3 translation          | T G Q V S V E I E W E L Q K E N S K R W N P E I Q Y T S N Y |
| 4. AAV4 translation          | T G Q V S V Q I D W E I Q K E R S K R W N P E V Q F T S N Y |
| 5. AAV5 translation          | T G Q V T V E M E W E L K K E N S K R W N P E I Q Y T N N Y |
| 6. AAV6 translation          | T G Q V S V E I E W E L Q K E N S K R W N P E V Q Y T S N Y |
| 7. AAV7 translation          | T G Q V S V E I E W E L Q K E N S K R W N P E I Q Y T S N F |
| 8. AAV8 translation          | T G Q V S V E I E W E L Q K E N S K R W N P E I Q Y T S N Y |
| 9. AAV9 translation          | T G Q V S V E I E W E L Q K E N S K R W N P E I Q Y T S N Y |
| 10. Shuffle 100.1 Translation| T G Q V S V E I E W E L Q K E N S K R W N P E V Q Y T S N Y |
|                              | ⟨AAV6                        |                    |             |

FIG. 8H

|  | 1 | 10 | 20 | 30 |
|---|---|---|---|---|

```
                              1         10        20        30
                              |         |         |         |
Consensus                     MAADGYLPDWLEDNLSEGIREWWALKPGAP
Identity                      ████████████▄▄▄▄▄▄▄████▄▄████▄

1. AAV1 translation           MAADGYLPDWLEDNLSEGIREWWDLKPGAP
2. AAV2 translation           MAADGYLPDWLEDTLSEGIRQWWKLKPGPP
3. AAV3 translation           MAADGYLPDWLEDNLSEGIREWWALKPGVP
4. AAV4 translation            MTDGYLPDWLEDNLSEGVREWWALQPGAP
5. AAV5 translation           MSFVDHPPDWLEE-VGEGLREFLGLEAGPP
6. AAV6 translation           MAADGYLPDWLEDNLSEGIREWWDLKPGAP
7. AAV7 translation           MAADGYLPDWLEDNLSEGIREWWDLKPGAP
8. AAV8 translation           MAADGYLPDWLEDNLSEGIREWWALKPGAP
9. AAV9 translation           MAADGYLPDWLEDNLSEGIREWWALKPGAP
10. Shuffle 100-3 Translation MAADGYLPDWLEDTLSEGIRQWWKLKPGPP
                              ▐A...▌AAV2                    ▌

40        50        60
                                        |         |         |
Consensus                     KPKANQQHQDDGRGLVLPGYKYLGPFNGLD
Identity                      ▄▄▄▄▄▄▄▄▄▄▄▄████████████▄▄████

1. AAV1 translation           KPKANQQKQDDGRGLVLPGYKYLGPFNGLD
2. AAV2 translation           PPKPAERHKDDSRGLVLPGYKYLGPFNGLD
3. AAV3 translation           QPKANQQHQDNRRGLVLPGYKYLGPGNGLD
4. AAV4 translation           KPKANQQHQDNARGLVLPGYKYLGPGNGLD
5. AAV5 translation           KPKPNQQHQDQARGLVLPGYNYLGPGNGLD
6. AAV6 translation           KPKANQQKQDDGRGLVLPGYKYLGPFNGLD
7. AAV7 translation           KPKANQQKQDNGRGLVLPGYKYLGPFNGLD
8. AAV8 translation           KPKANQQKQDDGRGLVLPGYKYLGPFNGLD
9. AAV9 translation           QPKANQQHQDNARGLVLPGYKYLGPGNGLD
10. Shuffle 100-3 Translation PPKPAERHKDDSRGLVLPGYKYLGPFNGLD
                              ▐AAV2                         ▌

70        80        90
                                        |         |         |
Consensus                     KGEPVNAADAAALEHDKAYDQQLKAGDNPY
Identity                      ████████▄████████████▄▄▄▄▄████

1. AAV1 translation           KGEPVNAADAAALEHDKAYDQQLKAGDNPY
2. AAV2 translation           KGEPVNEADAAALEHDKAYDRQLDSGDNPY
3. AAV3 translation           KGEPVNEADAAALEHDKAYDQQLKAGDNPY
4. AAV4 translation           KGEPVNAADAAALEHDKAYDQQLKAGDNPY
5. AAV5 translation           RGEPVNRADEVAREHDISYNEQLEAGDNPY
6. AAV6 translation           KGEPVNAADAAALEHDKAYDQQLKAGDNPY
7. AAV7 translation           KGEPVNAADAAALEHDKAYDQQLKAGDNPY
8. AAV8 translation           KGEPVNAADAAALEHDKAYDQQLQAGDNPY
9. AAV9 translation           KGEPVNAADAAALEHDKAYDQQLKAGDNPY
10. Shuffle 100-3 Translation KGEPVNEADAAALEHDKAYDQQLKAGDNPY
                              ▐AAV2    ▌AAV1,6,7            ▌
```

FIG. 9A

```
                                         100              110              120
Consensus                   LKYN HADAEF QERLQEDTS FGGN LGRAVFQ
Identity                    ████████████████████████████████

1. AAV1 translation        LRYN HADAEF QERLQEDTS FGGN LGRAVFQ
 2. AAV2 translation        LKYN HADAEF QERLKEDTS FGGN LGRAVFQ
 3. AAV3 translation        LKYN HADAEF QERLQEDTS FGGN LGRAVFQ
 4. AAV4 translation        LKYN HADAEF QQRLQGDTS FGGN LGRAVFQ
 5. AAV5 translation        LKYN HADAEF QEKLADDTS FGGN LGKAVFQ
 6. AAV6 translation        LRYN HADAEF QERLQEDTS FGGN LGRAVFQ
 7. AAV7 translation        LRYN HADAEF QERLQEDTS FGGN LGRAVFQ
 8. AAV8 translation        LRYN HADAEF QERLQEDTS FGGN LGRAVFQ
 9. AAV9 translation        LKYN HADAEF QERLKEDTS FGGN LGRAVFQ
10. Shuffle 100-3 Translation  LKYN HADAEF QQRLQGDTS FGGN LGRAVFQ
                            ◀AAV4
```

```
                                         130              140              150
Consensus                   AKKRVLEPLG LVEEGAK TAPGKKRPVEQSP
Identity                    ████████████████████████████████

1. AAV1 translation        AKKRVLEPLG LVEEGAK TAPGKKRPVEQSP
 2. AAV2 translation        AKKRVLEPLG LVEEPVK TAPGKKRPVEHSP
 3. AAV3 translation        AKKRILEPLG LVEEAAK TAPGKKGAVDQSP
 4. AAV4 translation        AKKRVLEPLG LVEQAGE TAPGKKRPLIESP
 5. AAV5 translation        AKKRVLEPFG LVEEGAK TAPTGKRIDDHFP
 6. AAV6 translation        AKKRVLEPFG LVEEGAK TAPGKKRPVEQSP
 7. AAV7 translation        AKKRVLEPLG LVEEGAK TAPAKKRPVEPSP
 8. AAV8 translation        AKKRVLEPLG LVEEGAK TAPGKKRPVEPSP
 9. AAV9 translation        AKKRLLEPLG LVEEAAK TAPGKKRPVEQSP
10. Shuffle 100-3 Translation  AKKRVLEPLG LVEQAGE TAPGKKRPLIESP
                            ◀AAV4
```

```
                                         160              170              180
Consensus                   QE-PDSS XGIGKKG QQPAKKRLNFGQTGDS
Identity                    ▅▅█▅█████▅████▅████████████████

1. AAV1 translation        QE-PDSSSGIGKTGQQPAKKRLNFGQTGDS
 2. AAV2 translation        VE-PDSSSGTGKAGQQPARKRLNFGQTGDA
 3. AAV3 translation        QE-PDSSSGVGKSGKQPARKRLNFGQTGDS
 4. AAV4 translation        QQ-PDSSTGIGKKGKQPAKKKLVFE---DE
 5. AAV5 translation        KR----KKARTEEDSKPST-------SSDA
 6. AAV6 translation        QE-PDSSSGIGKTGQQPAKKRLNFGQTGDS
 7. AAV7 translation        QRSPDSSTGIGKKGQQPARKRLNFGQTGDS
 8. AAV8 translation        QRSPDSSTGIGKKGQQPARKRLNFGQTGDS
 9. AAV9 translation        QE-PDSSAGIGKSGAQPAKKRLNFGQTGDT
10. Shuffle 100-3 Translation  QQ-PDSSTGIGKKGKQPAKKRLNFGQTGDS
                                                    ▶AAV1/6◀
```

FIG. 9B

```
                                    190           200           210
Consensus                   ESVPDPQPLGEPPAAP-SSVGXXTMASGGG
Identity 1. AAV1 translation         ESVPDPQPLGEPPATP-AAVGPTTMASGGG
2. AAV2 translation         DSVPDPQPLGQPPAAP-SGLGTNTMATGSG
3. AAV3 translation         ESVPDPQPLGEPPAAP-TSLGSNTMASGGG
4. AAV4 translation         TGAGDGPPEGSTSGA--MSDDSEMRAAAGG
5. AAV5 translation         EAGPSGSQQLQIPAQPASSLGADTMSAGGG
6. AAV6 translation         ESVPDPQPLGEPPATP-AAVGPTTMASGGG
7. AAV7 translation         ESVPDPQPLGEPPAAP-SSVGSGTVAAGGG
8. AAV8 translation         ESVPDPQPLGEPPAAP-SGVGPNTMAAGGG
9. AAV9 translation         ESVPDPQPIGEPPAAP-SGVGSLTMASGGG
10. Shuffle 100-3 Translation  ESVPDPQPLGEPPATP-AAVGPTTMASGGG
                            〈AAV1/6                        〉A...

220           230           240
Consensus                   APMADNNEGADGVGNASGNWHCDSTWLGDR
Identity 1. AAV1 translation         APMADNNEGADGVGNASGNWHCDSTWLGDR
2. AAV2 translation         APMADNNEGADGVGNSSGNWHCDSTWMGDR
3. AAV3 translation         APMADNNEGADGVGNSSGNWHCDSQWLGDR
4. AAV4 translation         AAV-EGGQGADGVGNASGDWHCDSTWSEGH
5. AAV5 translation         GPLGDNNQGADGVGNASGDWHCDSTWMGDR
6. AAV6 translation         APMADNNEGADGVGNASGNWHCDSTWLGDR
7. AAV7 translation         APMADNNEGADGVGNASGNWHCDSTWLGDR
8. AAV8 translation         APMADNNEGADGVGSSSGNWHCDSTWLGDR
9. AAV9 translation         APVADNNEGADGVGSSSGNWHCDSQWLGDR
10. Shuffle 100-3 Translation  APMADNNEGADGVGNASGNWHCDSTWLGDR
                            〉A 〉AAV1

250           260           270
Consensus                   VITTSTRTWALPTYNNHLYKQISSASX-GA
Identity 1. AAV1 translation         VITTSTRTWALPTYNNHLYKQISSAST-GA
2. AAV2 translation         VITTSTRTWALPTYNNHLYKQISSQS--GA
3. AAV3 translation         VITTSTRTWALPTYNNHLYKQISSQS--GA
4. AAV4 translation         VTTTSTRTWVLPTYNNHLYKRLGESL----
5. AAV5 translation         VVTKSTRTWVLPSYNNHQYREIKSGSVDG-
6. AAV6 translation         VITTSTRTWALPTYNNHLYKQISSAST-GA
7. AAV7 translation         VITTSTRTWALPTYNNHLYKQISSETA-GS
8. AAV8 translation         VITTSTRTWALPTYNNHLYKQISNGTSGGA
9. AAV9 translation         VITTSTRTWALPTYNNHLYKQISNSTSGGS
10. Shuffle 100-3 Translation  VITTSTRTWALPTYNNHLYKQISSAST-GA
                            〈AAV1
```

FIG. 9C

```
                                        280            290            300
Consensus                   S N D N H Y F G Y S T P W G Y F D F N R F H C H F S P R D W
Identity 1. AAV1 translation         S N D N H Y F G Y S T P W G Y F D F N R F H C H F S P R D W
2. AAV2 translation         S N D N H Y F G Y S T P W G Y F D F N R F H C H F S P R D W
3. AAV3 translation         S N D N H Y F G Y S T P W G Y F D F N R F H C H F S P R D W
4. AAV4 translation         - Q S N T Y N G F S T P W G Y F D F N R F H C H F S P R D W
5. AAV5 translation         S N A N A Y F G Y S T P W G Y F D F N R F H S H W S P R D W
6. AAV6 translation         S N D N H Y F G Y S T P W G Y F D F N R F H C H F S P R D W
7. AAV7 translation         T N D N T Y F G Y S T P W G Y F D F N R F H C H F S P R D W
8. AAV8 translation         T N D N T Y F G Y S T P W G Y F D F N R F H C H F S P R D W
9. AAV9 translation         S N D N A Y F G Y S T P W G Y F D F N R F H C H F S P R D W
10. Shuffle 100-3 Translation S N D N H Y F G Y S T P W G Y F D F N R F H C H F S P R D W
                            ‹AAV1

310            320            330
Consensus                   Q R L I N N N W G F R P K R L N F K L F N I Q V K E V T T N
Identity 1. AAV1 translation         Q R L I N N N W G F R P K R L N F K L F N I Q V K E V T T N
2. AAV2 translation         Q R L I N N N W G F R P K R L N F K L F N I Q V K E V T Q N
3. AAV3 translation         Q R L I N N N W G F R P K K L S F K L F N I Q V R G V T Q N
4. AAV4 translation         Q R L I N N N W G M R P K A M R V K I F N I Q V K E V T T S
5. AAV5 translation         Q R L I N N Y W G F R P R S L R V K I F N I Q V K E V T V Q
6. AAV6 translation         Q R L I N N N W G F R P K R L N F K L F N I Q V K E V T T N
7. AAV7 translation         Q R L I N N N W G F R P K K L R F K L F N I Q V K E V T T N
8. AAV8 translation         Q R L I N N N W G F R P K R L S F K L F N I Q V K E V T Q N
9. AAV9 translation         Q R L I N N N W G F R P K R L N F K L F N I Q V K E V T D N
10. Shuffle 100-3 Translation Q R L I N N N W G F R P K R L N F K L F N I Q V K E V T T N
                            ‹AAV1

340            350            360
Consensus                   D G V T T I A N N L T S T V Q V F T D S E Y Q L P Y V L G S
Identity 1. AAV1 translation         D G V T T I A N N L T S T V Q V F S D S E Y Q L P Y V L G S
2. AAV2 translation         D G T T T I A N N L T S T V Q V F T D S E Y Q L P Y V L G S
3. AAV3 translation         D G T T T I A N N L T S T V Q V F T D S E Y Q L P Y V L G S
4. AAV4 translation         N G E T T V A N N L T S T V Q I F A D S S Y E L P Y V M D A
5. AAV5 translation         D S T T T I A N N L T S T V Q V F T D D D Y Q L P Y V V G N
6. AAV6 translation         D G V T T I A N N L T S T V Q V F S D S E Y Q L P Y V L G S
7. AAV7 translation         D G V T T I A N N L T S T I Q V F S D S E Y Q L P Y V L G S
8. AAV8 translation         E G T K T I A N N L T S T I Q V F T D S E Y Q L P Y V L G S
9. AAV9 translation         N G V K T I A N N L T S T V Q V F T D S D Y Q L P Y V L G S
10. Shuffle 100-3 Translation D G V T T I A N N L T S T V Q V F S D S D Y Q L P Y V L G S
                            ‹AAV1                              ‹AAV9
```

FIG. 9D

```
                                    370        380        390
Consensus                   A H Q G C L P P F P A D V F M I P Q Y G Y L T L N - - N G S
Identity                    ████████████████████████████▀▀▀▀▀▀▀███████████▀▀▀████

1. AAV1 translation         A H Q G C L P P F P A D V F M I P Q Y G Y L T L N - - N G S
2. AAV2 translation         A H Q G C L P P F P A D V F M V P Q Y G Y L T L N - - N G S
3. AAV3 translation         A H Q G C L P P F P A D V F M V P Q Y G Y L T L N - - N G S
4. AAV4 translation         G Q E G S L P P F P N D V F M V P Q Y G Y C G L V T G N T S
5. AAV5 translation         G T E G C L P A F P P Q V F T L P Q Y G Y A T L N R D N T E
6. AAV6 translation         A H Q G C L P P F P A D V F M I P Q Y G Y L T L N - - N G S
7. AAV7 translation         A H Q G C L P P F P A D V F M I P Q Y G Y L T L N - - N G S
8. AAV8 translation         A H Q G C L P P F P A D V F M I P Q Y G Y L T L N - - N G S
9. AAV9 translation         A H E G C L P P F P A D V F M I P Q Y G Y L T L N - - D G S
10. Shuffle 100-3 Translation A H E G C L P P F P A D V F M V P Q Y G Y L T L N - - N G S
                            ◀AAV9    ◀AAV2

400        410        420
Consensus                   Q A - V G R S S F Y C L E Y F P S Q M L R T G N N F T F S Y
Identity                    ████▀▀▀███████████████████████████████████████▀▀███████

1. AAV1 translation         Q A - V G R S S F Y C L E Y F P S Q M L R T G N N F T F S Y
2. AAV2 translation         Q A - V G R S S F Y C L E Y F P S Q M L R T G N N F T F S Y
3. AAV3 translation         Q A - V G R S S F Y C L E Y F P S Q M L R T G N N F Q F S Y
4. AAV4 translation         Q Q Q T D R N A F Y C L E Y F P S Q M L R T G N N F E I T Y
5. AAV5 translation         N P - T E R S S F F C L E Y F P S K M L R T G N N F E F T Y
6. AAV6 translation         Q A - V G R S S F Y C L E Y F P S Q M L R T G N N F T F S Y
7. AAV7 translation         Q S - V G R S S F Y C L E Y F P S Q M L R T G N N F E F S Y
8. AAV8 translation         Q A - V G R S S F Y C L E Y F P S Q M L R T G N N F Q F T Y
9. AAV9 translation         Q A - V G R S S F Y C L E Y F P S Q M L R T G N N F Q F S Y
10. Shuffle 100-3 Translation Q A - V G R S S F Y C L E Y F P S Q M L R T G N N F T F S Y
                            ◀AAV2

430        440        450
Consensus                   T F E D V P F H S S Y A H S Q S L D R L M N P L I D Q Y L Y
Identity                    ███▀▀███████████████████████████████████████████████████

1. AAV1 translation         T F E E V P F H S S Y A H S Q S L D R L M N P L I D Q Y L Y
2. AAV2 translation         T F E D V P F H S S Y A H S Q S L D R L M N P L I D Q Y L Y
3. AAV3 translation         T F E D V P F H S S Y A H S Q S L D R L M N P L I D Q Y L Y
4. AAV4 translation         S F E K V P F H S M Y A H S Q S L D R L M N P L I D Q Y L W
5. AAV5 translation         N F E E V P F H S S F A P S Q N L F K L A N P L V D Q Y L Y
6. AAV6 translation         T F E D V P F H S S Y A H S Q S L D R L M N P L I D Q Y L Y
7. AAV7 translation         S F E D V P F H S S Y A H S Q S L D R L M N P L I D Q Y L Y
8. AAV8 translation         T F E D V P F H S S Y A H S Q S L D R L M N P L I D Q Y L Y
9. AAV9 translation         E F E N V P F H S S Y A H S Q S L D R L M N P L I D Q Y L Y
10. Shuffle 100-3 Translation T F E D V P F H S S Y A H S Q S L D R L M N P L I D Q Y L Y
                            ◀AAV2
```

FIG. 9E

```
                                    550           560           570
Consensus               D D E D K F F P M S G V L I F G K Q G A G A S N T A L - - -
Identity 1. AAV1 translation     D D E D K F F P M S G V M I F G K E S A G A S N T A L - - -
2. AAV2 translation     D D E E K F F P Q S G V L I F G K Q G S E K T N V D I - - - -
3. AAV3 translation     D D E E K F F P M H G N L I F G K E G T T A S N A E L - - -
4. AAV4 translation     P A D S K F S N S Q L I F A G P K Q N G N T A T V P - - - -
5. AAV5 translation     L Q G S N T Y A L E N T M I F N S Q P A N P G T T A T Y L E
6. AAV6 translation     D D K D K F F P M S G V M I F G K E S A G A S N T A L - - -
7. AAV7 translation     D D E D R F F P S S G V L I F G K T G A T N K T T L - - - -
8. AAV8 translation     D D E E R F F P S N G I L I F G K Q N A A R D N A D Y - - -
9. AAV9 translation     E G E D R F F P L S G S L I F G K Q G T G R D N V D A - - -
10. Shuffle 100-3 Translation   D D K D K F F P M S G V M I F G K E S A G A S N T A L - - -
                        AAV6

580           590           600
Consensus               D N V M I T D E E E I K X T N P V A T E R Y G T V A X N L Q
Identity 1. AAV1 translation     D N V M I T D E E E I K A T N P V A T E R F G T V A V N F Q
2. AAV2 translation     E K V M I T D E E E I R T T N P V A T E Q Y G S V S T N L Q
3. AAV3 translation     D N V M I T D E E E I R T T N P V A T E Q Y G T V A N N L Q
4. AAV4 translation     G T L I F T S E E E L A A T N A T D T D M W G N L P G G D Q
5. AAV5 translation     G N M L I T S E S E T Q P V N R V A Y N V G G Q M A T N N Q
6. AAV6 translation     D N V M I T D E E E I K A T N P V A T E R F G T V A V N L Q
7. AAV7 translation     E N V L M T N E E E I R P T N P V A T E E Y G I V S S N L Q
8. AAV8 translation     S D V M L T S E E E I K T T N P V A T E E Y G I V A D N L Q
9. AAV9 translation     D K V M I T N E E E I K T T N P V A T E S Y G Q V A T N H Q
10. Shuffle 100-3 Translation   D N V M I T D E E E I K A T N P V A T E R F G T V A V N L Q
                        AAV6                        AAV1/6   AAV6

610           620           630
Consensus               S S X T A P A T G D V N A Q G A L P G M V W Q D R D V Y L Q
Identity 1. AAV1 translation     S S S T D P A T G D V H A M G A L P G M V W Q D R D V Y L Q
2. AAV2 translation     R G N R Q A A T A D V N T Q G V L P G M V W Q D R D V Y L Q
3. AAV3 translation     S S N T A P T T G T V N H Q G A L P G M V W Q D R D V Y L Q
4. AAV4 translation     S N S N L P T V D R L T A L G A V P G M V W Q N R D I Y Y Q
5. AAV5 translation     S S T T A P A T G T Y N L Q E I V P G S V W M E R D V Y L Q
6. AAV6 translation     S S S T D P A T G D V H V M G A L P G M V W Q D R D V Y L Q
7. AAV7 translation     A A N T A A Q T Q V V N N Q G A L P G M V W Q N R D V Y L Q
8. AAV8 translation     Q Q N T A P Q I G T V N S Q G A L P G M V W Q N R D V Y L Q
9. AAV9 translation     S A Q A Q A Q T G W V Q N Q G I L P G M V W Q D R D V Y L Q
10. Shuffle 100-3 Translation   S S S T D P A T G D V H A M G A L P G M V W Q D R D V Y L Q
                        AAV6            AAV1   AAV6
```

FIG. 9G

```
                                        640              650              660
Consensus                        G P I W A K I P H T D G H F H P S P L M G G F G L K H P P P
Identity 1. AAV1 translation              G P I W A K I P H T D G H F H P S P L M G G F G L K N P P P
2. AAV2 translation              G P I W A K I P H T D G H F H P S P L M G G F G L K H P P P
3. AAV3 translation              G P I W A K I P H T D G H F H P S P L M G G F G L K H P P P
4. AAV4 translation              G P I W A K I P H T D G H F H P S P L I G G F G L K H P P P
5. AAV5 translation              G P I W A K I P E T G A H F H P S P A M G G F G L K H P P P
6. AAV6 translation              G P I W A K I P H T D G H F H P S P L M G G F G L K H P P P
7. AAV7 translation              G P I W A K I P H T D G N F H P S P L M G G F G L K H P P P
8. AAV8 translation              G P I W A K I P H T D G N F H P S P L M G G F G L K H P P P
9. AAV9 translation              G P I W A K I P H T D G N F H P S P L M G G F G M K H P P P
10. Shuffle 100-3 Translation    G P I W A K I P H T D G H F H P S P L M G G F G L K N P P P
                                 <AAV6                                  <AAV1

670              680              690
Consensus                        Q I L I K N T P V P A N P P T T F S A T K F A S F I T Q Y S
Identity 1. AAV1 translation              Q I L I K N T P V P A N P P A E F S A T K F A S F I T Q Y S
2. AAV2 translation              Q I L I K N T P V P A N P S T T F S A A K F A S F I T Q Y S
3. AAV3 translation              Q I M I K N T P V P A N P P T T F S P A K F A S F I T Q Y S
4. AAV4 translation              Q I F I K N T P V P A N P A T T F S S T P V N S F I T Q Y S
5. AAV5 translation              M M L I K N T P V P G N - I T S F S D V P V S S F I T Q Y S
6. AAV6 translation              Q I L I K N T P V P A N P P A E F S A T K F A S F I T Q Y S
7. AAV7 translation              Q I L I K N T P V P A N P P E V F T P A K F A S F I T Q Y S
8. AAV8 translation              Q I L I K N T P V P A D P P T T F N Q S K L N S F I T Q Y S
9. AAV9 translation              Q I L I K N T P V P A D P P T A F N K D K L N S F I T Q Y S
10. Shuffle 100-3 Translation    Q I L I K N T P V P A N P P A E F S A T K F A S F I T Q Y S
                                 <AAV1                                          <A...

700              710              720
Consensus                        T G Q V S V E I E W E L Q K E N S K R W N P E I Q Y T S N Y
Identity 1. AAV1 translation              T G Q V S V E I E W E L Q K E N S K R W N P E V Q Y T S N Y
2. AAV2 translation              T G Q V S V E I E W E L Q K E N S K R W N P E I Q Y T S N Y
3. AAV3 translation              T G Q V S V E I E W E L Q K E N S K R W N P E I Q Y T S N Y
4. AAV4 translation              T G Q V S V Q I D W E I Q K E R S K R W N P E V Q F T S N Y
5. AAV5 translation              T G Q V T V E M E W E L K K E N S K R W N P E I Q Y T N N Y
6. AAV6 translation              T G Q V S V E I E W E L Q K E N S K R W N P E V Q Y T S N Y
7. AAV7 translation              T G Q V S V E I E W E L Q K E N S K R W N P E I Q Y T S N F
8. AAV8 translation              T G Q V S V E I E W E L Q K E N S K R W N P E I Q Y T S N Y
9. AAV9 translation              T G Q V S V E I E W E L Q K E N S K R W N P E I Q Y T S N Y
10. Shuffle 100-3 Translation    T G Q V S V E I E W E L Q K E N S K R W N P E V Q Y T S N Y
                                 <AAV6
```

FIG. 9H

```
                                          730          740          750
Consensus                    X K S A N V D F X V D T N G V Y S E P R P I G T R Y L T R N
Identity 1. AAV1 translation          A K S A N V D F T V D N N G L Y T E P R P I G T R Y L T R P
2. AAV2 translation          N K S V N V D F T V D T N G V Y S E P R P I G T R Y L T R N
3. AAV3 translation          N K S V N V D F T V D T N G V Y S E P R P I G T R Y L T R N
4. AAV4 translation          G Q Q N S L L W A P D A A G K Y T E P R A I G T R Y L T H H
5. AAV5 translation          N D P Q F V D F A P D S T G E Y R T T R P I G T R Y L T R P
6. AAV6 translation          A K S A N V D F T V D N N G L Y T E P R P I G T R Y L T R P
7. AAV7 translation          E K Q T G V D F A V D S Q G V Y S E P R P I G T R Y L T R N
8. AAV8 translation          Y K S T S V D F A V N T E G V Y S E P R P I G T R Y L T R N
9. AAV9 translation          Y K S N N V E F A V N T E G V Y S E P R P I G T R Y L T R N
10. Shuffle 100-3 Translation A K S A N V D F T V D N N G L Y T E P R P I G T R Y L T R P
                             AAV6

752
Consensus                    L *
Identity

1. AAV1 translation          L *
2. AAV2 translation          L *
3. AAV3 translation          L *
4. AAV4 translation          L *
5. AAV5 translation          L *
6. AAV6 translation          L *
7. AAV7 translation          L *
8. AAV8 translation          L *
9. AAV9 translation          L *
10. Shuffle 100-3 Translation L *
```

FIG. 9I

|  | 1 10 20 30 |
|---|---|
| Consensus | M A A D G Y L P D W L E D N L S E G I R E W W A L K P G A P |
| Identity |  |
| 1. AAV1 translation | M A A D G Y L P D W L E D N L S E G I R E W W D L K P G A P |
| 2. AAV2 translation | M A A D G Y L P D W L E D T L S E G I R Q W W K L K P G P P |
| 3. AAV3 translation | M A A D G Y L P D W L E D N L S E G I R E W W A L K P G V P |
| 4. AAV4 translation |    M T D G Y L P D W L E D N L S E G V R E W W A L Q P G A P |
| 5. AAV5 translation | M S F V D H P P D W L E E - V G E G L R E F L G L E A G P P |
| 6. AAV6 translation | M A A D G Y L P D W L E D N L S E G I R E W W D L K P G A P |
| 7. AAV7 translation | M A A D G Y L P D W L E D N L S E G I R E W W D L K P G A P |
| 8. AAV8 translation | M A A D G Y L P D W L E D N L S E G I R E W W A L K P G A P |
| 9. AAV9 translation | M A A D G Y L P D W L E D N L S E G I R E W W A L K P G A P |
| 10. Shuffle 100.7 Translation | M A A D G Y L P D W L E D N L S E G I R E W W A L K P G A P |
|  | AAV8 |

|  | 40 50 60 |
|---|---|
| Consensus | K P K A N Q Q X Q D D G R G L V L P G Y K Y L G P F N G L D |
| Identity |  |
| 1. AAV1 translation | K P K A N Q Q K Q D D G R G L V L P G Y K Y L G P F N G L D |
| 2. AAV2 translation | P P K P A E R H K D D S R G L V L P G Y K Y L G P F N G L D |
| 3. AAV3 translation | Q P K A N Q Q H Q D N R R G L V L P G Y K Y L G P G N G L D |
| 4. AAV4 translation | K P K A N Q Q H Q D N A R G L V L P G Y K Y L G P G N G L D |
| 5. AAV5 translation | K P K P N Q Q H Q D Q A R G L V L P G Y N Y L G P G N G L D |
| 6. AAV6 translation | K P K A N Q Q K Q D D G R G L V L P G Y K Y L G P F N G L D |
| 7. AAV7 translation | K P K A N Q Q K Q D N G R G L V L P G Y K Y L G P F N G L D |
| 8. AAV8 translation | K P K A N Q Q K Q D D G R G L V L P G Y K Y L G P F N G L D |
| 9. AAV9 translation | Q P K A N Q Q H Q D N A R G L V L P G Y K Y L G P G N G L D |
| 10. Shuffle 100.7 Translation | K P K A N Q Q K Q D D G R G L V L P G Y K Y L G P F N G L D |
|  | AAV8 |

|  | 70 80 90 |
|---|---|
| Consensus | K G E P V N A A D A A A L E H D K A Y D Q Q L K A G D N P Y |
| Identity |  |
| 1. AAV1 translation | K G E P V N A A D A A A L E H D K A Y D Q Q L K A G D N P Y |
| 2. AAV2 translation | K G E P V N E A D A A A L E H D K A Y D R Q L D S G D N P Y |
| 3. AAV3 translation | K G E P V N E A D A A A L E H D K A Y D Q Q L K A G D N P Y |
| 4. AAV4 translation | K G E P V N A A D A A A L E H D K A Y D Q Q L K A G D N P Y |
| 5. AAV5 translation | R G E P V N R A D E V A R E H D I S Y N E Q L E A G D N P Y |
| 6. AAV6 translation | K G E P V N A A D A A A L E H D K A Y D Q Q L K A G D N P Y |
| 7. AAV7 translation | K G E P V N A A D A A A L E H D K A Y D Q Q L K A G D N P Y |
| 8. AAV8 translation | K G E P V N A A D A A A L E H D K A Y D Q Q L Q A G D N P Y |
| 9. AAV9 translation | K G E P V N A A D A A A L E H D K A Y D Q Q L K A G D N P Y |
| 10. Shuffle 100.7 Translation | K G E P V N A A D A A A L E H D K A Y D Q Q L K A G D N P Y |
|  | AAV8　　AAV6 |

FIG. 10A

|                              | 100                          110                       120 |
|---|---|
| Consensus                    | L X Y N H A D A E F Q E R L Q E D T S F G G N L G R A V F Q |
| Identity                     |                                                             |
| 1. AAV1 translation          | L R Y N H A D A E F Q E R L Q E D T S F G G N L G R A V F Q |
| 2. AAV2 translation          | L K Y N H A D A E F Q E R L K E D T S F G G N L G R A V F Q |
| 3. AAV3 translation          | L K Y N H A D A E F Q E R L Q E D T S F G G N L G R A V F Q |
| 4. AAV4 translation          | L K Y N H A D A E F Q Q R L Q G D T S F G G N L G R A V F Q |
| 5. AAV5 translation          | L K Y N H A D A E F Q E K L A D D T S F G G N L G K A V F Q |
| 6. AAV6 translation          | L R Y N H A D A E F Q E R L Q E D T S F G G N L G R A V F Q |
| 7. AAV7 translation          | L R Y N H A D A E F Q E R L Q E D T S F G G N L G R A V F Q |
| 8. AAV8 translation          | L R Y N H A D A E F Q E R L Q E D T S F G G N L G R A V F Q |
| 9. AAV9 translation          | L K Y N H A D A E F Q E R L K E D T S F G G N L G R A V F Q |
| 10. Shuffle 100.7 Translation | L R Y N H A D A E F Q E R L Q E D T S F G G N L G R A V F Q |

AAV6

|                              | 130                          140                       150 |
|---|---|
| Consensus                    | A K K R V L E P L G L V E E G A K T A P G K K R P V E Q S P |
| Identity                     |                                                             |
| 1. AAV1 translation          | A K K R V L E P L G L V E E G A K T A P G K K R P V E Q S P |
| 2. AAV2 translation          | A K K R V L E P L G L V E E P V K T A P G K K R P V E H S P |
| 3. AAV3 translation          | A K K R I L E P L G L V E E A A K T A P G K K G A V D Q S P |
| 4. AAV4 translation          | A K K R V L E P L G L V E Q A G E T A P G K K R P L I E S P |
| 5. AAV5 translation          | A K K R V L E P F G L V E E G A K T A P T G K R I D D H F P |
| 6. AAV6 translation          | A K K R V L E P F G L V E E G A K T A P G K K R P V E Q S P |
| 7. AAV7 translation          | A K K R V L E P L G L V E E G A K T A P A K K R P V E P S P |
| 8. AAV8 translation          | A K K R V L E P L G L V E E G A K T A P G K K R P V E P S P |
| 9. AAV9 translation          | A K K R L L E P L G L V E E A A K T A P G K K R P V E Q S P |
| 10. Shuffle 100.7 Translation | A K K R V L E P L G L V E E G A K T A P G K K R P V E Q S P |

|                              | 160                          170                       180 |
|---|---|
| Consensus                    | Q E - P D S S S G I G K X G Q Q P A K K R L N F G Q T G D S |
| Identity                     |                                                             |
| 1. AAV1 translation          | Q E - P D S S S G I G K T G Q Q P A K K R L N F G Q T G D S |
| 2. AAV2 translation          | V E - P D S S S G T G K A G Q Q P A R K R L N F G Q T G D A |
| 3. AAV3 translation          | Q E - P D S S G V G K S G K Q P A R K R L N F G Q T G D S |
| 4. AAV4 translation          | Q Q - P D S S T G I G K K G K Q P A K K K L V F - - - E D E |
| 5. AAV5 translation          | K R - - - - K K A R T E E D S K P S T - - - - - - - S S D A |
| 6. AAV6 translation          | Q E - P D S S S G I G K T G Q Q P A K K R L N F G Q T G D S |
| 7. AAV7 translation          | Q R S P D S S T G I G K K G Q Q P A R K R L N F G Q T G D S |
| 8. AAV8 translation          | Q R S P D S S T G I G K K G Q Q P A R K R L N F G Q T G D S |
| 9. AAV9 translation          | Q E - P D S S A G I G K S G A Q P A K K R L N F G Q T G D T |
| 10. Shuffle 100.7 Translation | Q E - P D S S S G I G K T G Q Q P A K K R L N F G Q T G D S |

AAV1

FIG. 10B

|   | 190 | 200 | 210 |
|---|---|---|---|
| Consensus | ESVPDPQPLG | EPPAAP-SSVG | XXTMASGGG |

| | |
|---|---|
| 1. AAV1 translation | ESVPDPQPLGEPPATP-AAVGPTTMASGGG |
| 2. AAV2 translation | DSVPDPQPLGQPPAAP-SGLGTNTMATGSG |
| 3. AAV3 translation | ESVPDPQPLGEPPAAP-TSLGSNTMASGGG |
| 4. AAV4 translation | TGAGDGPPEGSTSGA--MSDDSEMRAAAGG |
| 5. AAV5 translation | EAGPSGSQQLQIPAQPASSLGADTMSAGGG |
| 6. AAV6 translation | ESVPDPQPLGEPPATP-AAVGPTTMASGGG |
| 7. AAV7 translation | ESVPDPQPLGEPPAAP-SSVGSGTVAAGGG |
| 8. AAV8 translation | ESVPDPQPLGEPPAAP-SGVGPNTMAAGGG |
| 9. AAV9 translation | ESVPDPQPIGEPPAAP-SGVGSLTMASGGG |
| 10. Shuffle 100.7 Translation | ESVPDPQPLGEPPATP-AAVGPTTMASGGG |

|   | 220 | 230 | 240 |
|---|---|---|---|
| Consensus | APMADNNEGA | DGVGNASGNW | HCDSTWLGDR |

| | |
|---|---|
| 1. AAV1 translation | APMADNNEGADGVGNASGNWHCDSTWLGDR |
| 2. AAV2 translation | APMADNNEGADGVGNSSGNWHCDSTWMGDR |
| 3. AAV3 translation | APMADNNEGADGVGNSSGNWHCDSQWLGDR |
| 4. AAV4 translation | AAV-EGGQGADGVGNASGDWHCDSTWSEGH |
| 5. AAV5 translation | GPLGDNNQGADGVGNASGDWHCDSTWMGDR |
| 6. AAV6 translation | APMADNNEGADGVGNASGNWHCDSTWLGDR |
| 7. AAV7 translation | APMADNNEGADGVGNASGNWHCDSTWLGDR |
| 8. AAV8 translation | APMADNNEGADGVGSSSGNWHCDSTWLGDR |
| 9. AAV9 translation | APVADNNEGADGVGSSSGNWHCDSQWLGDR |
| 10. Shuffle 100.7 Translation | APMADNNEGADGVGNASGNWHCDSTWLGDR |

|   | 250 | 260 | 270 |
|---|---|---|---|
| Consensus | VITTSTRTWA | LPTYNNHLYK | QISSASX-GA |

| | |
|---|---|
| 1. AAV1 translation | VITTSTRTWALPTYNNHLYKQISSAST-GA |
| 2. AAV2 translation | VITTSTRTWALPTYNNHLYKQISSQS--GA |
| 3. AAV3 translation | VITTSTRTWALPTYNNHLYKQISSQS--GA |
| 4. AAV4 translation | VTTTSTRTWVLPTYNNHLYKRLGES----- |
| 5. AAV5 translation | VVTKSTRTWVLPSYNNHQYREIKSGSVDG- |
| 6. AAV6 translation | VITTSTRTWALPTYNNHLYKQISSAST-GA |
| 7. AAV7 translation | VITTSTRTWALPTYNNHLYKQISSETA-GS |
| 8. AAV8 translation | VITTSTRTWALPTYNNHLYKQISNGTSGGA |
| 9. AAV9 translation | VITTSTRTWALPTYNNHLYKQISNSTSGGS |
| 10. Shuffle 100.7 Translation | VITTSTRTWALPTYNNHLYKQISSAST-GA |

FIG. 10C

|                          | 280                            | 290                     | 300         |
|---|---|---|---|
| Consensus                | S N D N H Y F G Y S T P W G Y F D F N R F H C H F S P R D W |
| Identity                 |                                |                         |             |
| 1. AAV1 translation      | S N D N H Y F G Y S T P W G Y F D F N R F H C H F S P R D W |
| 2. AAV2 translation      | S N D N H Y F G Y S T P W G Y F D F N R F H C H F S P R D W |
| 3. AAV3 translation      | S N D N H Y F G Y S T P W G Y F D F N R F H C H F S P R D W |
| 4. AAV4 translation      | L Q S N T Y N G F S T P W G Y F D F N R F H C H F S P R D W |
| 5. AAV5 translation      | S N A N A Y F G Y S T P W G Y F D F N R F H S H W S P R D W |
| 6. AAV6 translation      | S N D N H Y F G Y S T P W G Y F D F N R F H C H F S P R D W |
| 7. AAV7 translation      | T N D N T Y F G Y S T P W G Y F D F N R F H C H F S P R D W |
| 8. AAV8 translation      | T N D N T Y F G Y S T P W G Y F D F N R F H C H F S P R D W |
| 9. AAV9 translation      | S N D N A Y F G Y S T P W G Y F D F N R F H C H F S P R D W |
| 10. Shuffle 100.7 Translation | S N D N H Y F G Y S T P W G Y F D F N R F H C H F S P R D W |

⟨AAV1            ⟨AAV8

|                          | 310                       | 320                 | 330       |
|---|---|---|---|
| Consensus                | Q R L I N N N W G F R P K R L N F K L F N I Q V K E V T T N |
| Identity                 |                           |                     |           |
| 1. AAV1 translation      | Q R L I N N N W G F R P K R L N F K L F N I Q V K E V T T N |
| 2. AAV2 translation      | Q R L I N N N W G F R P K R L N F K L F N I Q V K E V T Q N |
| 3. AAV3 translation      | Q R L I N N N W G F R P K K L S F K L F N I Q V R G V T Q N |
| 4. AAV4 translation      | Q R L I N N N W G M R P K A M R V K I F N I Q V K E V T T S |
| 5. AAV5 translation      | Q R L I N N Y W G F R P R S L R V K I F N I Q V K E V T V Q |
| 6. AAV6 translation      | Q R L I N N N W G F R P K R L N F K L F N I Q V K E V T T N |
| 7. AAV7 translation      | Q R L I N N N W G F R P K K L R F K L F N I Q V K E V T T N |
| 8. AAV8 translation      | Q R L I N N N W G F R P K R L S F K L F N I Q V K E V T Q N |
| 9. AAV9 translation      | Q R L I N N N W G F R P K R L N F K L F N I Q V K E V T D N |
| 10. Shuffle 100.7 Translation | Q R L I N N N W G F R P K R L S F K L F N I Q V K E V T T N |

|                          | 340                     | 350                   | 360       |
|---|---|---|---|
| Consensus                | D G V T T I A N N L T S T V Q V F T D S E Y Q L P Y V L G S |
| Identity                 |                         |                       |           |
| 1. AAV1 translation      | D G V T T I A N N L T S T V Q V F S D S E Y Q L P Y V L G S |
| 2. AAV2 translation      | D G T T T I A N N L T S T V Q V F T D S E Y Q L P Y V L G S |
| 3. AAV3 translation      | D G T T T I A N N L T S T V Q V F T D S E Y Q L P Y V L G S |
| 4. AAV4 translation      | N G E T T V A N N L T S T V Q I F A D S S Y E L P Y V M D A |
| 5. AAV5 translation      | D S T T T I A N N L T S T V Q V F T D D D Y Q L P Y V V G N |
| 6. AAV6 translation      | D G V T T I A N N L T S T V Q V F S D S E Y Q L P Y V L G S |
| 7. AAV7 translation      | D G V T T I A N N L T S T I Q V F S D S E Y Q L P Y V L G S |
| 8. AAV8 translation      | E G T K T I A N N L T S T I Q V F T D S E Y Q L P Y V L G S |
| 9. AAV9 translation      | N G V K T I A N N L T S T V Q V F T D S D Y Q L P Y V L G S |
| 10. Shuffle 100.7 Translation | D G V T T I A N N L T S T V Q V F S D S E Y Q L P Y V L G S |

⟨AAV1

FIG. 10D

|                              | 370                               380                               390         |
|------------------------------|---------------------------------------------------------------------------------|
| Consensus                    | A H Q G C L P P F P A D V F M I P Q Y G Y L T L N - - N G S                     |
| Identity                     |                                                                                 |
| 1. AAV1 translation          | A H Q G C L P P F P A D V F M I P Q Y G Y L T L N - - N G S                     |
| 2. AAV2 translation          | A H Q G C L P P F P A D V F M V P Q Y G Y L T L N - - N G S                     |
| 3. AAV3 translation          | A H Q G C L P P F P A D V F M V P Q Y G Y L T L N - - N G S                     |
| 4. AAV4 translation          | G Q E G S L P P F P N D V F M V P Q Y G Y C G L V T G N T S                     |
| 5. AAV5 translation          | G T E G C L P A F P P Q V F T L P Q Y G Y A T L N R D N T E                     |
| 6. AAV6 translation          | A H Q G C L P P F P A D V F M I P Q Y G Y L T L N - - N G S                     |
| 7. AAV7 translation          | A H Q G C L P P F P A D V F M I P Q Y G Y L T L N - - N G S                     |
| 8. AAV8 translation          | A H Q G C L P P F P A D V F M I P Q Y G Y L T L N - - N G S                     |
| 9. AAV9 translation          | A H E G C L P P F P A D V F M I P Q Y G Y L T L N - - D G S                     |
| 10. Shuffle 100.7 Translation| A H Q G C L P P F P A D V F M I P Q Y G Y L T L N - - N G S                     |

|                              | 400                               410                               420         |
|------------------------------|---------------------------------------------------------------------------------|
| Consensus                    | - Q A V G R S S F Y C L E Y F P S Q M L R T G N N F T F S Y                     |
| Identity                     |                                                                                 |
| 1. AAV1 translation          | - Q A V G R S S F Y C L E Y F P S Q M L R T G N N F T F S Y                     |
| 2. AAV2 translation          | - Q A V G R S S F Y C L E Y F P S Q M L R T G N N F T F S Y                     |
| 3. AAV3 translation          | - Q A V G R S S F Y C L E Y F P S Q M L R T G N N F Q F S Y                     |
| 4. AAV4 translation          | Q Q Q T D R N A F Y C L E Y F P S Q M L R T G N N F E I T Y                     |
| 5. AAV5 translation          | - N P T E R S S F F C L E Y F P S K M L R T G N N F E F T Y                     |
| 6. AAV6 translation          | - Q A V G R S S F Y C L E Y F P S Q M L R T G N N F T F S Y                     |
| 7. AAV7 translation          | - Q S V G R S S F Y C L E Y F P S Q M L R T G N N F E F S Y                     |
| 8. AAV8 translation          | - Q A V G R S S F Y C L E Y F P S Q M L R T G N N F Q F T Y                     |
| 9. AAV9 translation          | - Q A V G R S S F Y C L E Y F P S Q M L R T G N N F Q F S Y                     |
| 10. Shuffle 100.7 Translation| - Q A V G R S S F Y C L E Y F P S Q M L R T G N N F T F S Y                     |

|                              | 430                               440                               450         |
|------------------------------|---------------------------------------------------------------------------------|
| Consensus                    | T F E D V P F H S S Y A H S Q S L D R L M N P L I D Q Y L Y                     |
| Identity                     |                                                                                 |
| 1. AAV1 translation          | T F E E V P F H S S Y A H S Q S L D R L M N P L I D Q Y L Y                     |
| 2. AAV2 translation          | T F E D V P F H S S Y A H S Q S L D R L M N P L I D Q Y L Y                     |
| 3. AAV3 translation          | T F E D V P F H S S Y A H S Q S L D R L M N P L I D Q Y L Y                     |
| 4. AAV4 translation          | S F E K V P F H S M Y A H S Q S L D R L M N P L I D Q Y L W                     |
| 5. AAV5 translation          | N F E E V P F H S S F A P S Q N L F K L A N P L V D Q Y L Y                     |
| 6. AAV6 translation          | T F E D V P F H S S Y A H S Q S L D R L M N P L I D Q Y L Y                     |
| 7. AAV7 translation          | S F E D V P F H S S Y A H S Q S L D R L M N P L I D Q Y L Y                     |
| 8. AAV8 translation          | T F E D V P F H S S Y A H S Q S L D R L M N P L I D Q Y L Y                     |
| 9. AAV9 translation          | E F E N V P F H S S Y A H S Q S L D R L M N P L I D Q Y L Y                     |
| 10. Shuffle 100.7 Translation| T F E E V P F H S S Y A H S Q S L D R L M N P L I D Q Y L Y                     |

FIG. 10E

|  | 460 | 470 | 480 |
|---|---|---|---|
| Consensus | YLNRTQN-XSGTAXNKXLLFSQGGPXGMSV | | |

| | |
|---|---|
| 1. AAV1 translation | YLNRTQN-QSGSAQNKDLLFSRGSPAGMSV |
| 2. AAV2 translation | YLSRTNT-PSGTTTQSRLQFSQAGASDIRD |
| 3. AAV3 translation | YLNRTQGTTSGTTNQSRLLFSQAGPQSMSL |
| 4. AAV4 translation | GLQSTTTGTTLNAGTATTNFTKLRPTNFSN |
| 5. AAV5 translation | RFVSTNN-------TGGVQFNKNLAGRYAN |
| 6. AAV6 translation | YLNRTQN-QSGSAQNKDLLFSRGSPAGMSV |
| 7. AAV7 translation | YLARTQSNPGGTAGNRELQFYQGGPSTMAE |
| 8. AAV8 translation | YLSRTQT-TGGTANTQTLGFSQGGPNTMAN |
| 9. AAV9 translation | YLSKTIN--GSGQNQQTLKFSVAGPSNMAV |
| 10. Shuffle 100.7 Translation | YLNRTQN-QSGSAQNKDLLFSRGSPAGMSV |

AAV1

|  | 490 | 500 | 510 |
|---|---|---|---|
| Consensus | QXKNWLPGPCYRQQRVSKTKTDN-----NN | | |

| | |
|---|---|
| 1. AAV1 translation | QPKNWLPGPCYRQQRVSKTKTDN-----NN |
| 2. AAV2 translation | QSRNWLPGPCYRQQRVSKTSADN-----NN |
| 3. AAV3 translation | QARNWLPGPCYRQQRLSKTANDN-----NN |
| 4. AAV4 translation | FKKNWLPGPSIKQQGFSKTANQNYKIPATG |
| 5. AAV5 translation | TYKNWFPGPMGRTQGWNLGSGVN-----RA |
| 6. AAV6 translation | QPKNWLPGPCYRQQRVSKTKTDN-----NN |
| 7. AAV7 translation | QAKNWLPGPCFRQQRVSKTLDQN-----NN |
| 8. AAV8 translation | QAKNWLPGPCYRQQRVSTTTGQN-----NN |
| 9. AAV9 translation | QGRNYIPGPSYRQQRVSTTVTQN-----NN |
| 10. Shuffle 100.7 Translation | QPKNWLPGPCYRQQRVSKTKTDN-----NN |

AAV1

|  | 520 | 530 | 540 |
|---|---|---|---|
| Consensus | SNFAWTGASKYHLNGRXSLVNPGPAMASHK | | |

| | |
|---|---|
| 1. AAV1 translation | SNFTWTGASKYNLNGRESIINPGTAMASHK |
| 2. AAV2 translation | SEYSWTGATKYHLNGRDSLVNPGPAMASHK |
| 3. AAV3 translation | SNFPWTAASKYHLNGRDSLVNPGPAMASHK |
| 4. AAV4 translation | SDSLIKYETHSTLDGRWSALTPGPPMATAG |
| 5. AAV5 translation | SVSAFATTNRMELEGASYQVPPQPNGMTNN |
| 6. AAV6 translation | SNFTWTGASKYNLNGRESIINPGTAMASHK |
| 7. AAV7 translation | SNFAWTGATKYHLNGRNSLVNPGVAMATHK |
| 8. AAV8 translation | SNFAWTAGTKYHLNGRNSLANPGIAMATHK |
| 9. AAV9 translation | SEFAWPGASSWALNGRNSLMNPGPAMASHK |
| 10. Shuffle 100.7 Translation | SNFTWTGASKYNLNGRESIINPGTAMASHK |

AAV1

FIG. 10F

|  | 550 | 560 | 570 |
|---|---|---|---|

Consensus: DDEDKFFPMSGVLIFGKQGAGASNTAL---
Identity

1. AAV1 translation: DDEDKFFPMSGVMIFGKESAGASNTAL---
2. AAV2 translation: DDEEKFFPQSGVLIFGKQGSEKTNVDI---
3. AAV3 translation: DDEEKFFPMHGNLIFGKEGTTASNAEL---
4. AAV4 translation: PADSKFSNSQLIFAGPKQNGNTATVP----
5. AAV5 translation: LQGSNTYALENTMIFNSQPANPGTTATYLE
6. AAV6 translation: DDKDKFFPMSGVMIFGKESAGASNTAL---
7. AAV7 translation: DDEDRFFPSSGVLIFGKTGATNKTTL----
8. AAV8 translation: DDEERFFPSNGILIFGKQNAARDNADY---
9. AAV9 translation: EGEDRFFPLGSLIFGKQGTGRDNVDA---
10. Shuffle 100.7 Translation: DDEDKFFPMSGVMIFGKESAGASNTAL---

|  | 580 | 590 | 600 |
|---|---|---|---|

Consensus: DNVMITDEEEIKXTNPVATERYGTVAXNLQ
Identity

1. AAV1 translation: DNVMITDEEEIKATNPVATERFGTVAVNFQ
2. AAV2 translation: EKVMITDEEEIRTTNPVATEQYGSVSTNLQ
3. AAV3 translation: DNVMITDEEEIRTTNPVATEQYGTVANNLQ
4. AAV4 translation: GTLIFTSEEELAATNATDTDMWGNLPGGDQ
5. AAV5 translation: GNMLITSESETQPVNRVAYNVGGQMATNNQ
6. AAV6 translation: DNVMITDEEEIKATNPVATERFGTVAVNLQ
7. AAV7 translation: ENVLMTNEEEIRPTNPVATEEYGIVSSNLQ
8. AAV8 translation: SDVMLTSEEEIKTTNPVATEEYGIVADNLQ
9. AAV9 translation: DKVMITNEEEIKTTNPVATESYGQVATNHQ
10. Shuffle 100.7 Translation: DNVMITDEEEIKATNPVATERFGTVAVNFQ

|  | 610 | 620 | 630 |
|---|---|---|---|

Consensus: SSXTAPATGDVNAQGALPGMVWQDRDVYLQ
Identity

1. AAV1 translation: SSSTDPATGDVHAMGALPGMVWQDRDVYLQ
2. AAV2 translation: RGNRQAATADVNTQGVLPGMVWQDRDVYLQ
3. AAV3 translation: SSNTAPTTGTVNHQGALPGMVWQDRDVYLQ
4. AAV4 translation: SNSNLPTVDRLTALGAVPGMVWQNRDIYYQ
5. AAV5 translation: SSTTAPATGTYNLQEIVPGSVWMERDVYLQ
6. AAV6 translation: SSSTDPATGDVHVMGALPGMVWEDRDVYLQ
7. AAV7 translation: AANTAAQTQVVNNQGALPGMVWQNRDVYLQ
8. AAV8 translation: QQNTAPQIGTVNSQGALPGMVWQNRDVYLQ
9. AAV9 translation: SAQAQAQTGWVQNQGILPGMVWQDRDVYLQ
10. Shuffle 100.7 Translation: SSSTDPATGDVHAMGALPGMVWQDRDVYLQ

FIG. 10G

|  | 640 | 650 | 660 |
|---|---|---|---|

```
                              640              650             660
Consensus               GPIWAKIPHTDGHFHPSPLMGGFGLKHPPP
Identity                ■■■■■■■■■■■■■■■■■■■■■■■■■■■■■

1. AAV1 translation     GPIWAKIPHTDGHFHPSPLMGGFGLKNPPP
2. AAV2 translation     GPIWAKIPHTDGHFHPSPLMGGFGLKHPPP
3. AAV3 translation     GPIWAKIPHTDGHFHPSPLMGGFGLKHPPP
4. AAV4 translation     GPIWAKIPHTDGHFHPSPLIGGFGLKHPPP
5. AAV5 translation     GPIWAKIPETGAHFHPSPAMGGFGLKHPPP
6. AAV6 translation     GPIWAKIPHTDGHFHPSPLMGGFGLKHPPP
7. AAV7 translation     GPIWAKIPHTDGNFHPSPLMGGFGLKHPPP
8. AAV8 translation     GPIWAKIPHTDGNFHPSPLMGGFGLKHPPP
9. AAV9 translation     GPIWAKIPHTDGNFHPSPLMGGFGMKHPPP
10. Shuffle 100.7 Translation  GPIWAKIPHTDGHFHPSPLMGGFGLKNPPP
                        ▬AAV1▬▬▬▬▬▬▬▬▬▬▬▬▬▬▬▬▬▬▬▬▬▬▬▬▬▬

670              680             690
Consensus               QILIKNTPVPANPPTTFSATKFASFITQYS
Identity                ■■■■■■■■■■■■■■■■■■■■■■■■■■■■■

1. AAV1 translation     QILIKNTPVPANPPAEFSATKFASFITQYS
2. AAV2 translation     QILIKNTPVPANPSTTFSAAKFASFITQYS
3. AAV3 translation     QIMIKNTPVPANPPTTFSPAKFASFITQYS
4. AAV4 translation     QIFIKNTPVPANPATTFSSTPVNSFITQYS
5. AAV5 translation     MMLIKNTPVPGN-ITSFSDVPVSSFITQYS
6. AAV6 translation     QILIKNTPVPANPPAEFSATKFASFITQYS
7. AAV7 translation     QILIKNTPVPANPPEVFTPAKFASFITQYS
8. AAV8 translation     QILIKNTPVPADPPTTFNQSKLNSFITQYS
9. AAV9 translation     QILIKNTPVPADPPTAFNKDKLNSFITQYS
10. Shuffle 100.7 Translation  QILIKNTPVPANPPAEFSATKFASFITQYS
                        ▬AAV1▬▬▬▬▬▬▬▬▬▬▬▬▬▬▬▬▬▬▬▬▬▬▬▬▬▬

700              710             720
Consensus               TGQVSVEIEWELQKENSKRWNPEIQYTSNY
Identity                ■■■■■■■■■■■■■■■■■■■■■■■■■■■■■

1. AAV1 translation     TGQVSVEIEWELQKENSKRWNPEVQYTSNY
2. AAV2 translation     TGQVSVEIEWELQKENSKRWNPEIQYTSNY
3. AAV3 translation     TGQVSVEIEWELQKENSKRWNPEIQYTSNY
4. AAV4 translation     TGQVSVQIDWEIQKERSKRWNPEVQFTSNY
5. AAV5 translation     TGQVTVEMEWELKKENSKRWNPEIQYTNNY
6. AAV6 translation     TGQVSVEIEWELQKENSKRWNPEVQYTSNY
7. AAV7 translation     TGQVSVEIEWELQKENSKRWNPEIQYTSNF
8. AAV8 translation     TGQVSVEIEWELQKENSKRWNPEIQYTSNY
9. AAV9 translation     TGQVSVEIEWELQKENSKRWNPEIQYTSNY
10. Shuffle 100.7 Translation  TGQVSVEIEWELQKENSKRWNPEVQYTSNY
                        ▬AAV1▬▬▬▬▬▬▬▬▬▬▬▬▬▬AAV6▬▬▬▬▬▬▬▬▬
```

FIG. 10H

```
                                    730              740              750
Consensus                   X K S A N V D F X V D T N G V Y S E P R P I G T R Y L T R N
Identity 1. AAV1 translation         A K S A N V D F T V D N N G L Y T E P R P I G T R Y L T R P
2. AAV2 translation         N K S V N V D F T V D T N G V Y S E P R P I G T R Y L T R N
3. AAV3 translation         N K S V N V D F T V D T N G V Y S E P R P I G T R Y L T R N
4. AAV4 translation         G Q Q N S L L W A P D A A G K Y T E P R A I G T R Y L T H H
5. AAV5 translation         N D P Q F V D F A P D S T G E Y R T T R P I G T R Y L T R P
6. AAV6 translation         A K S A N V D F T V D N N G L Y T E P R P I G T R Y L T R P
7. AAV7 translation         E K Q T G V D F A V D S Q G V Y S E P R P I G T R Y L T R N
8. AAV8 translation         Y K S T S V D F A V N T E G V Y S E P R P I G T R Y L T R N
9. AAV9 translation         Y K S N N V E F A V N T E G V Y S E P R P I G T R Y L T R N
10. Shuffle 100.7 Translation  A K S A N I D F T V D N N G L Y T E P R P I G T R Y L T R P
                            [AAV6 > AAV6]

752
Consensus                   L *
Identity

1. AAV1 translation         L *
2. AAV2 translation         L *
3. AAV3 translation         L *
4. AAV4 translation         L *
5. AAV5 translation         L *
6. AAV6 translation         L *
7. AAV7 translation         L *
8. AAV8 translation         L *
9. AAV9 translation         L *
10. Shuffle 100.7 Translation  Q *
```

FIG. 10I

| Serotype | Animal | Neutralizing Serum Dilution | | | | | |
|---|---|---|---|---|---|---|---|
| | | AAV1 | AAV2 | AAV8 | Shuffle 100-3 | Shuffle 100-7 | SM 10-2 |
| AAV1 | 1 | 1:1000 | none | 1:250 | 1:250 | 1:1000 | none |
| | 2 | 1:1000 | 1:25 | 1:250 | 1:250 | 1:1000 | none |
| | 3 | 1:1000 | none | 1:250 | 1:250 | 1:1000 | none |
| AAV2 | 1 | 1:50 | 1:500 | 1:100 | none | none | 1:250 |
| | 2 | 1:50 | 1:500 | 1:100 | none | 1:25 | 1:500 |
| | 3 | 1:1000 | 1:1000 | 1:100 | none | 1:100 | 1:500 |
| AAV8 | 1 | 1:100 | none | 1:250 | none | 1:100 | none |
| | 2 | 1:250 | none | 1:100 | none | 1:100 | none |
| | 3 | 1:250 | none | 1:250 | none | 1:250 | none |
| Shuffle 100-3 | 1 | 1:1000 | none | 1:500 | 1:100 | 1:1000 | none |
| | 2 | 1:1000 | none | 1:500 | 1:100 | 1:1000 | none |
| | 3 | 1:1000 | none | 1:100 | 1:250 | 1:1000 | none |
| Shuffle 100-7 | 1 | 1:1000 | none | 1:100 | 1:100 | 1:500 | none |
| | 2 | 1:1000 | none | 1:50 | 1:250 | 1:1000 | none |
| | 3 | 1:1000 | none | 1:50 | 1:100 | 1:1000 | none |

FIG. 11 n = 91 sequences   ▓ Chimera  ▒ Other   n = 92 sequences n = 44 sequences                n = 92 sequences
▓ AIOI  ▒ Other Chimera FIG. 20
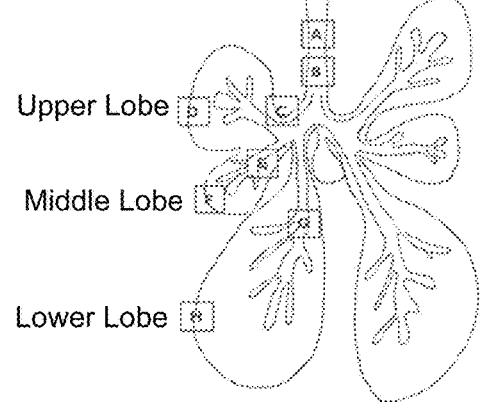
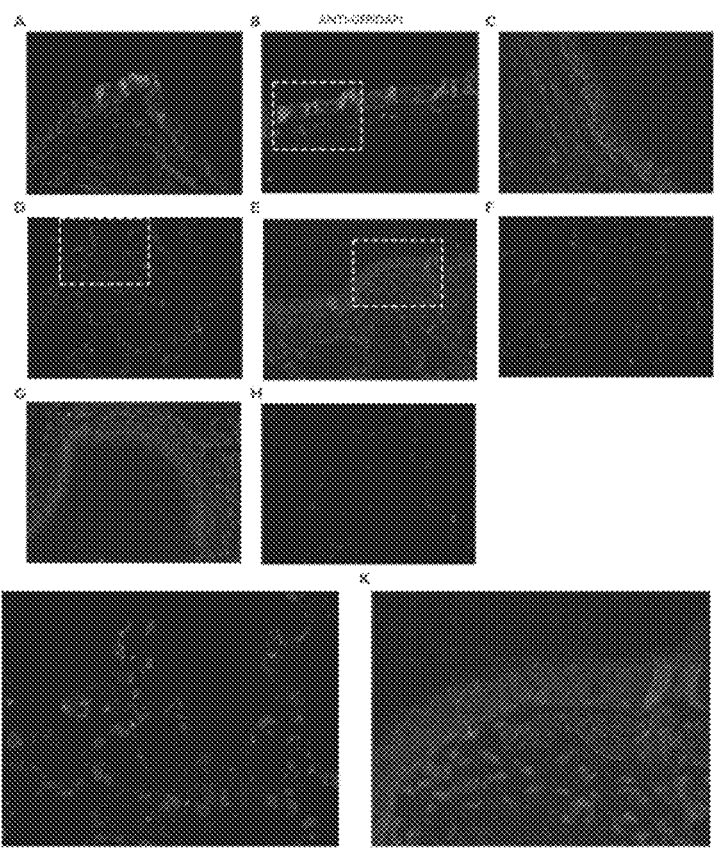

SEQUENCE LISTING

```
Sequence total quantity: 45
SEQ ID NO: 1              moltype = AA   length = 736
FEATURE                   Location/Qualifiers
source                    1..736
                          mol_type = protein
                          organism = adeno-associated virus 1
SEQUENCE: 1
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEEVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD EDKFFPMSGV  540
MIFGKESAGA SNTALDNVMI TDEEEIKATN PVATERFGTV AVNFQSSSTD PATGDVHAMG  600
ALPGMVWQDR DVYLQGPIWA KIPHTDGHFH PSPLMGGFGL KNPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                  736

SEQ ID NO: 2              moltype = AA   length = 735
FEATURE                   Location/Qualifiers
source                    1..735
                          mol_type = protein
                          organism = adeno-associated virus 2
SEQUENCE: 2
MAADGYLPDW LEDTLSEGIR QWWKLKPGPP PPKPAERHKD DSRGLVLPGY KYLGPFNGLD   60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                   735

SEQ ID NO: 3              moltype = AA   length = 736
FEATURE                   Location/Qualifiers
source                    1..736
                          mol_type = protein
                          organism = adeno-associated virus 3
SEQUENCE: 3
MAADGYLPDW LEDNLSEGIR EWWALKPGVP QPKANQQHQD NRRGLVLPGY KYLGPGNGLD   60
KGEPVNEADA AALEHDKAYD QQLKAGDNPY LKYNHADAEF QERLQEDTSF GGNLGRAVFQ  120
AKKRILEPLG LVEEAAKTAP GKKGAVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGASNDN HYFGYSTPWG YFDFNRFHCH FSPRDWQRLI  300
NNNWGFRPKK LSFKLFNIQV RGVTQNDGTT TIANNLTSTV QVFTDSEYQL PYVLGSAHQG  360
CLPPFPADVF MVPQYGYLTL NNGSQAVGRS SFYCLEYFPS QMLRTGNNFQ FSYTFEDVPF  420
HSSYAHSQSL DRLMNPLIDQ YLYYLNRTQG TTSGTTNQSR LLFSQAGPQS MSLQARNWLP  480
GPCYRQQRLS KTANDNNNSN FPWTAASKYH LNGRDSLVNP GPAMASHKDD EEKFFPMHGN  540
LIFGKEGTTA SNAELDNVMI TDEEEIRTTN PVATEQYGTV ANNLQSSNTA PTTGTVNHQG  600
ALPGMVWQDR DVYLQGPIWA KIPHTDGHFH PSPLMGGFGL KHPPPQIMIK NTPVPANPPT  660
TFSPAKFASF ITQYSTGQVS VEIEWELQKE NSKRWNPEIQ YTSNYNKSVN VDFTVDTNGV  720
YSEPRPIGTR YLTRNL                                                  736
```

```
SEQ ID NO: 4              moltype = AA  length = 734
FEATURE                   Location/Qualifiers
source                    1..734
                          mol_type = protein
                          organism = adeno-associated virus 4
SEQUENCE: 4
MTDGYLPDWL EDNLSEGVRE WWALQPGAPK PKANQQHQDN ARGLVLPGYK YLGPGNGLDK  60
GEPVNAADAA ALEHDKAYDQ QLKAGDNPYL KYNHADAEFQ QRLQGDTSFG GNLGRAVFQA 120
KKRVLEPLGL VEQAGETAPG KKRPLIESPQ QPDSSTGIGK KGKQPAKKKL VFEDETGAGD 180
GPPEGSTSGA MSDDSEMRAA AGGAAVEGGQ GADGVGNASG DWHCDSTWSE GHVTTTSTRT 240
WVLPTYNNHL YKRLGESLQS NTYNGFSTPW GYFDFNRFHC HFSPRDWQRL INNNWGMRPK 300
AMRVKIFNIQ VKEVTTSNGE TTVANNLTST VQIFADSSYE LPYVMDAGQE GSLPPFPNDV 360
FMVPQYGYCG LVTGNTSQQQ TDRNAFYCLE YFPSQMLRTG NNFEITYSFE KVPFHSMYAH 420
SQSLDRLMNP LIDQYLWGLQ STTTGTTLNA GTATTNFTKL RPTNFSNFKK NWLPGPSIKQ 480
QGFSKTANQN YKIPATGSDS LIKYETHSTL DGRWSALTPG PPMATAGPAD SKFSNSQLIF 540
AGPKQNGNTA TVPGTLIFTS EEELAATNAT DTDMWGNLPG GDQSNSNLPT VDRLTALGAV 600
PGMVWQNRDI YYQGPIWAKI PHTDGHFHPS PLIGGFGLKH PPPQIFIKNT PVPANPATTF 660
SSTPVNSFIT QYSTGQVSVQ IDWEIQKERS KRWNPEVQFT SNYGQQNSLL WAPDAAGKYT 720
EPRAIGTRYL THHL                                                  734

SEQ ID NO: 5              moltype = AA  length = 724
FEATURE                   Location/Qualifiers
source                    1..724
                          mol_type = protein
                          organism = adeno-associated virus 5
SEQUENCE: 5
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA 120
KKRVLEPFGL VEEGAKTAPT GKRIDDHFPK RKKARTEEDS KPSTSSDAEA GPSGSQQLQI 180
PAQPASSLGA DTMSAGGGGP LGDNNQGADG VGNASGDWHC DSTWMGDRVV TKSTRTWVLP 240
SYNNHQYREI KSGSVDGSNA NAYFGYSTPW GYFDFNRFHS HWSPRDWQRL INNYWGFRPR 300
SLRVKIFNIQ VKEVTVQDST TTIANNLTST VQVFTDDDYQ LPYVVGNGTE GCLPAFPPQV 360
FTLPQYGYAT LNRDNTENPT ERSSFFCLEY FPSKMLRTGN NFEFTYNFEE VPFHSSFAPS 420
QNLFKLANPL VDQYLYRFVS TNNTGGVQFN KNLAGRYANT YKNWFPGPMG RTQGWNLGSG 480
VNRASVSAFA TTNRMELEGA SYQVPPQPNG MTNNLQGSNT YALENTMIFN SQPANPGTTA 540
TYLEGNMLIT SESETQPVNR VAYNVGGQMA TNNQSSTTAP ATGTYNLQEI VPGSVWMERD 600
VYLQGPIWAK IPETGAHFHP SPAMGGFGLK HPPPMMLIKN TPVPGNITSF SDVPVSSFIT 660
QYSTGQVTVE MEWELKKENS KRWNPEIQYT NNYNDPQFVD FAPDSTGEYR TTRPIGTRYL 720
TRPL                                                             724

SEQ ID NO: 6              moltype = AA  length = 736
FEATURE                   Location/Qualifiers
source                    1..736
                          mol_type = protein
                          organism = adeno-associated virus 6
SEQUENCE: 6
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ 120
AKKRVLEPFG LVEEGAKTAP GKKRPVEQSP QEPDSSSGIG KTGQQPAKKR LNFGQTGDSE 180
SVPDPQPLGE PPATPAAVGP TTMASGGGAP MADNNEGADG VGNASGNWHC DSTWLGDRVI 240
TTSTRTWALP TYNNHLYKQI SSASTGASND NHYFGYSTPW GYFDFNRFHC HFSPRDWQRL 300
INNNWGFRPK RLNFKLFNIQ VKEVTTNDGV TTIANNLTST VQVFSDSEYQ LPYVLGSAHQ 360
GCLPPFPADV FMIPQYGYLT LNNGSQAVGR SSFYCLEYFP SQMLRTGNNF TFSYTFEDVP 420
FHSSYAHSQS LDRLMNPLID QYLYYLNRTQ NQSGSAQNKD LLFSRGSPAG MSVQPKNWLP 480
GPCYRQQRVS KTKTDNNNSN FTWTGASKYN LNGRESIINP GTAMASHKDD KDKFFPMSGV 540
MIFGKESAGA SNTALDNVMI TDEEEIKATN PVATERFGTV AVNLQSSSTD PATGDVHVMG 600
ALPGMVWQDR DVYLQGPIWA KIPHTDGHFH PSPLMGGFGL KHPPPQILIK NTPVPANPPA 660
EFSATKFASF ITQYSTGQVS VEIEWELQKE NSKRWNPEVQ YTSNYAKSAN VDFTVDNNGL 720
YTEPRPIGTR YLTRPL                                                736

SEQ ID NO: 7              moltype = AA  length = 735
FEATURE                   Location/Qualifiers
source                    1..735
                          mol_type = protein
                          organism = adeno-associated virus 7
SEQUENCE: 7
AADGYLPDWL EDNLSEGIRE WWDLKPGAPK PKANQQKQDN GRGLVLPGYK YLGPFNGLDK  60
GEPVNAADAA ALEHDKAYDQ QLKAGDNPYL RYNHADAEFQ ERLQEDTSFG GNLGRAVFQA 120
KKRVLEPLGL VEEGAKTAPA KKRPVEPSPQ RSPDSSTGIG KKGQQPARKR LNFGQTGDSE 180
SVPDPQPLGE PPAAPSSVGS GTVAAGGGAP MADNNEGADG VGNASGNWHC DSTWLGDRVI 240
TTSTRTWALP TYNNHLYKQI SSETAGSTND NTYFGYSTPW GYFDFNRFHC HFSPRDWQRL 300
INNNWGFRPK RLRFKLFNIQ VKEVTTNDGV TTIANNLTST IQVFSDSEYQ LPYVLGSAHQ 360
GCLPPFPADV FMIPQYGYLT LNNGSQSVGR SSFYCLEYFP SQMLRTGNNF EFSYSFEDVP 420
FHSSYAHSQS LDRLMNPLID QYLYYLARTQ SNPGGTAGNR ELQFYQGGPS TMAEQAKNWL 480
PGPCFRQQRV SKTLDQNNNS NFAWTGATKY HLNGRNSLVN PGVAMATHKD DEDRFFPSSG 540
VLIFGKTGAT NKTTLENVLM TNEEEIRPTN PVATEEYGIV SSNLQAANTA AQTQVVNNQG 600
ALPGMVWQNR DVYLQGPIWA KIPHTDGNFH PSPLMGGFGL KHPPPQILIK NTPVPANPPE 660
VFTPAKFASF ITQYSTGQVS VEIEWELQKE NSKRWNPEIQ YTSNFEKQTG VDFAVDSQGV 720
YSEPRPIGTR YLTRN                                                 735
```

```
SEQ ID NO: 8            moltype = AA  length = 738
FEATURE                 Location/Qualifiers
source                  1..738
                        mol_type = protein
                        organism = adeno-associated virus 8
SEQUENCE: 8
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFQFTYTFED   420
VPFHSSYAHS QSLDRLMNPL IDQYLYYLSR TQTTGGTANT QTLGFSQGGP NTMANQAKNW   480
LPGPCYRQQR VSTTTGQNNN SNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

SEQ ID NO: 9            moltype = AA  length = 736
FEATURE                 Location/Qualifiers
source                  1..736
                        mol_type = protein
                        organism = adeno-associated virus 9
SEQUENCE: 9
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRK RLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN PQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNPH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 10           moltype = AA  length = 735
FEATURE                 Location/Qualifiers
REGION                  1..735
                        note = Synthetic amino acid sequence
source                  1..735
                        mol_type = protein
                        organism = synthetic construct
SEQUENCE: 10
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LKFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTDT PSGTTTQSRL QFSQAGASDI RNQSRNWLPG   480
PCYRQQRVSK TSADNNNSEY SWTGATKYHL NGRDSLVNPG PAMASHKDDE EKFFPQSGVL   540
IFGKQGSEKT SVDIEKVMIT DEEEIRTTNP VATEQYGSVS TNLQRGNRQA ATADVNTQGV   600
LPGMVWQDRD VYLQGPIWAK IPHTDGHFHP SPLMGGFGLK HPPPQILIKN TPVPANPSTT   660
FSAAKFASFI TQYSTGQVSV EIEWELQKEN SKRWNPEVQY TSNYNKSVNV DFTVDTNGVY   720
SEPRPIGTRY LTRNQ                                                    735

SEQ ID NO: 11           moltype = AA  length = 736
FEATURE                 Location/Qualifiers
REGION                  1..736
                        note = Synthetic amino acid sequence
source                  1..736
                        mol_type = protein
                        organism = synthetic construct
SEQUENCE: 11
MAADGYLPDW LEDTLSEGIR QWWKLKPGPP PPKPAERHKD DSRGLVLPGY KYLGPFNGLD    60
KGEPVNEADA AALEHDKAYD QQLKAGDNPY LKYNHADAEF QQRLQGDTSF GGNLGRAVFQ   120
AKKRVLEPLG LVEQAGETAP GKKRPLIESP QQDSSTGIG KKGKQPAKKR LNFGQTGDSE    180
SVPDPQPLGE PPATPAAVGP TTMASGGGAP MADNNEGADG VGNASGNWHC DSTWLGDRVI   240
TTSTRTWALP TYNNHLYKQI SSASTGASND NHYFGYSTPW GYFDFNRFHC HFSPRDWQRL   300
INNNWGFRPK RLNFKLFNIQ VKEVTTNDGV TTIANNLTST VQVFSDSDYQ LPYVLGSAHE   360
GCLPPFPADV FMVPQYGYLT LNNGSQAVGR SSFYCLEYFP SQMLRTGNNF TFSYTFEDVP   420
FHSSYAHSQS LDRLMNPLID QYLYYLNRTQ NQSGSAQNKD LLFSRGSPAG MSVQPKNWLP   480
```

```
GPCYRQQRVS KTKTDNNNSN FTWTGASKYN LNGRESIINP GTAMASHKDD KDKFFPMSGV    540
MIFGKESAGA SNTALDNVMI TDEEEIKATN PVATERFGTV AVNLQSSSTD PATGDVHVMG    600
ALPGMVWQDR DVYLQGPIWA KIPHTDGHFH PSPLMGGFGL KNPPPQILIK NTPVPANPPA    660
EFSATKFASF ITQYSTGQVS VEIEWELQKE NSKRWNPEVQ YTSNYAKSAN VDFTVDNNGL    720
YTEPRPIGTR YLTRPL                                                   736

SEQ ID NO: 12           moltype = AA   length = 736
FEATURE                 Location/Qualifiers
REGION                  1..736
                        note = Synthetic amino acid sequence
source                  1..736
                        mol_type = protein
                        organism = synthetic construct
SEQUENCE: 12
MAADGYLPDW LEDTLSEGIR QWWKLKPGPP PPKPAERHKD DSRGLVLPGY KYLGPFNGLD     60
KGEPVNEADA AALEHDKAYD QQLKAGDNPY LKYNHADAEF QQRLQGDTSF GGNLGRAVFQ    120
AKKRVLEPLG LVEQAGETAP GKKRPLIESP QQPDSSTGIG KKGKQPAKKR LNFGQTGDSE    180
SVPDPQPLGE PPATPAAVGP TTMASGGGAP MADNNEGADG VGNASGNWHC DSTWLGDRVI    240
TTSTRTWALP TYNNHLYKQI SSASTGASND NHYFGYSTPW GYFDFNRFHC HFSPRDWQRL    300
INNNWGFRPK RLNFKLFNIQ VKEVTTNDGV TTIANNLTST VQVFSDSDYQ LPYVLGSAHE    360
GCLPPFPADV FMVPQYGYLT LNNGSQAVGR SSFYCLEYFP SQMLRTGNNF TFSYTFEDVP    420
FHSSYAHSQS LDRLMNPLID QYLYYLNRTQ NQSGSAQNKD LLFSRGSPTG MSVQPKNWLP    480
GPCYRQQRVS KTKTDNNNSN FTWTGASKYN LNGRESIINP GTAMASHKDD KDKFFPMSGV    540
MIFGKESAGA SNTALDNVMI TDEEEIKATN PVATERFGTV AVNLQSSSTD PATGDVHAMG    600
ALPGMVWQDR DVYLQGPIWA KIPHTDGHFH PSPLMGGFGL KNPPPQILIK NTPVPANPPA    660
EFSATKFASF ITQYSTGQVS VEIEWELQKE NSKRWNPEVQ YTSNYAKSAN VDFTVDNNGL    720
YTEPRPIGTR YLTRPL                                                   736

SEQ ID NO: 13           moltype = AA   length = 736
FEATURE                 Location/Qualifiers
REGION                  1..736
                        note = Synthetic amino acid sequence
source                  1..736
                        mol_type = protein
                        organism = synthetic construct
SEQUENCE: 13
MAADGYLPDW LEDNLSEGIR EWWALKPGAP KPKANQQKQD DGRGLVLPGY KYLGPFNGLD     60
KGEPVNAADA AALEHDKAYD QQLKAGDNPY LRYNHADAEF QERLQEDTSF GGNLGRAVFQ    120
AKKRVLEPLG LVEEGAKTAP GKKRPVEQSP QEPDSSSGIG KTGQQPAKKR LNFGQTGDSE    180
SVPDPQPLGE PPATPAAVGP TTMASGGGAP MADNNEGADG VGNASGNWHC DSTWLGDRVI    240
TTSTRTWALP TYNNHLYKQI SSASTGASND NHYFGYSTPW GYFDFNRFHC HFSPRDWQRL    300
INNNWGFRPK RLSFKLFNIQ VKEVTTNDGV TTIANNLTST VQVFSDSEYQ LPYVLGSAHQ    360
GCLPPFPADV FMIPQYGYLT LNNGSQAVGR SSFYCLEYFP SQMLRTGNNF TFSYTFEEVP    420
FHSSYAHSQS LDRLMNPLID QYLYYLNRTQ NQSGSAQNKD LLFSRGSPAG MSVQPKNWLP    480
GPCYRQQRVS KTKTDNNNSN FTWTGASKYN LNGRESIINP GTAMASHKDD EDKFFPMSGV    540
MIFGKESAGA SNTALDNVMI TDEEEIKATN PVATERFGTV AVNFQSSSTD PATGDVHAMG    600
ALPGMVWQDR DVYLQGPIWA KIPHTDGHFH PSPLMGGFGL KNPPPQILIK NTPVPANPPA    660
EFSATKFASF ITQYSTGQVS VEIEWELQKE NSKRWNPEVQ YTSNYAKSAN IDFTVDNNGL    720
YTEPRPIGTR YLTRPQ                                                   736

SEQ ID NO: 14           moltype = DNA   length = 23
FEATURE                 Location/Qualifiers
misc_feature            1..23
                        note = Artificial nucleic acid sequence
source                  1..23
                        mol_type = other DNA
                        organism = synthetic construct
SEQUENCE: 14
gcggaagctt cgatcaacta cgc                                            23

SEQ ID NO: 15           moltype = DNA   length = 41
FEATURE                 Location/Qualifiers
misc_feature            1..41
                        note = Synthetic nucleic acid sequence
source                  1..41
                        mol_type = other DNA
                        organism = synthetic construct
SEQUENCE: 15
ggggcggccg caattacaga ttacgagtca ggtatctggt g                        41

SEQ ID NO: 16           moltype = DNA   length = 25
FEATURE                 Location/Qualifiers
misc_feature            1..25
                        note = Synthetic nucleic acid sequence
misc_feature            5..6
                        note = n is a, c, g, or t
source                  1..25
                        mol_type = other DNA
                        organism = synthetic construct
```

```
SEQUENCE: 16
cattnnkgac cagtctagga actgg                                         25

SEQ ID NO: 17           moltype = DNA  length = 90
FEATURE                 Location/Qualifiers
misc_feature            1..90
                        note = Synthetic nucleic acid sequence
misc_feature            21..22
                        note = n is a, c, g, or t
misc_feature            69..70
                        note = n is a, c, g, or t
source                  1..90
                        mol_type = other DNA
                        organism = synthetic construct
SEQUENCE: 17
gccacaagga cgatgaagaa nnkttttttc ctcagagcgg ggttctcatc tttgggaagc   60
aaggctcann kaaaacaagt gtggacattg                                    90

SEQ ID NO: 18           moltype = DNA  length = 35
FEATURE                 Location/Qualifiers
misc_feature            1..35
                        note = Synthetic nucleic acid sequence
misc_feature            18..19
                        note = n is a, c, g, or t
source                  1..35
                        mol_type = other DNA
                        organism = synthetic construct
SEQUENCE: 18
ccaacctcca gagaggcnnk agacaagcag ctacc                              35

SEQ ID NO: 19           moltype = DNA  length = 57
FEATURE                 Location/Qualifiers
misc_feature            1..57
                        note = Synthetic nucleic acid sequence
misc_feature            18..19
                        note = n is a, c, g, or t
misc_feature            42..43
                        note = n is a, c, g, or t
source                  1..57
                        mol_type = other DNA
                        organism = synthetic construct
SEQUENCE: 19
ccaactacaa caagtctnnk aatgtggact ttactgtgga cnnkaatggc gtgtatt      57

SEQ ID NO: 20           moltype = DNA  length = 20
FEATURE                 Location/Qualifiers
misc_feature            1..20
                        note = Synthetic nucleic acid sequence
source                  1..20
                        mol_type = other DNA
                        organism = synthetic construct
SEQUENCE: 20
catgggaaag gtgccagacg                                               20

SEQ ID NO: 21           moltype = DNA  length = 20
FEATURE                 Location/Qualifiers
misc_feature            1..20
                        note = Synthetic nucleic acid sequence
source                  1..20
                        mol_type = other DNA
                        organism = synthetic construct
SEQUENCE: 21
accatcggca gccatacctg                                               20

SEQ ID NO: 22           moltype = DNA  length = 2208
FEATURE                 Location/Qualifiers
misc_feature            1..2208
                        note = Synthetic nucleic acid sequence
source                  1..2208
                        mol_type = other DNA
                        organism = synthetic construct
SEQUENCE: 22
atggctgccg atggttatct tccagattgg ctcgaggaca ctctctctga aggaataaga   60
cagtggtgga agctcaaacc tggcccacca ccaccaaagc ccgcagagcg cataaggac   120
gacagcaggg gtcttgtgct tcctgggtac aagtacctcg gacccttcaa cggactcgac  180
aagggagagc cggtcaacga ggcagacgcc gcggccctcg agcacgacaa agcctatgac  240
cggcagctcg acagcggaga caacccgtac ctcaagtaca accacgccga cgcggagttt  300
caggaacgcc ttaaagaaga tacgtctttt gggggcaacc tcggacgagc agtcttccag  360
gcgaaaaaga gggttcttga acctctgggc ctggttgagg aacctgttaa gacggctccg  420
```

```
ggaaaaaaga ggccggtaga gcactctcct gtggagccag actcctcctc gggaaccgga  480
aaggcgggcc agcagcctgc aagaaaaaga ttgaattttg gtcagactgg agacgcagac  540
tcagtacctg accccccagcc tctcggacag ccaccagcag cccctctgg tctgggaact  600
aatacgatgg ctacaggcag tggcgcacca atggcagaca ataacgaggg cgccgacgga  660
gtgggtaatt cctcgggaaa ttggcattgc gattccacat ggatgggcga cagagtcatc  720
accaccagca cccgaacctg ggccctgccc acctacaaca accacctcta caaacaaatt  780
tccagccaat caggagcctc gaacgacaat cactactttg gctacagcac cccttggggg  840
tattttgact tcaacagatt ccactgccac ttttcaccac gtgactggca aagactcatc  900
aacaacaact ggggattccg acccaagaga ctcaagttca agctcttaa cattcaagtc  960
aaagaggtca cgcagaatga cggtacgacg acgattgcca ataaccttac cagcacggtt 1020
caggtgttta ctgactcgga gtaccagctc ccgtacgtcc tcggctcggc gcatcaagga 1080
tgcctcccgc cgttcccagc agacgtcttc atggtgccac agtatggata cctcacctg  1140
aacaacggga gtcaggcagt aggacgctct tcatttact gcctggagta ctttccttct  1200
cagatgctgc gtaccggtaa caactttacc ttcagctaca cttttgagga cgttcctttc  1260
cacagcagct acgctcacag ccagagtctg gaccgtctca tgaatcctct catcgaccag  1320
tacctgtatt acttgagcag aacagacact ccaagtggaa ccaccacgca gtcaaggctt  1380
cagttttctc aggccggagc gagtgacatt cggaaccagt ctaggaactg gcttcctgga  1440
ccctgttacc gccagcagcg agtatcaaag acatctggag ataacaacaa cagtgaatac  1500
tcgtggactg gagctaccaa gtaccacctc aatggcagag actctctggt gaatccggcc  1560
ccggccatgg caagccacaa ggacgatgaa gaaagttt ttcctcagag cggggttctc  1620
atctttggga agcaaggctc agagaaaaca agtgtggaca ttgaaaaggt catgattaca  1680
gacgaagagg aaatcaggac aaccaatccc gtggctcaga agcagtatgg ttctgtatct  1740
accaacctcc agagaggcaa cagacaagca gctaccgcag atgtcaacac acaaggcgtt  1800
cttccaggca tggtctggca ggacagagat gtgtaccttc aggggcccat ctgggcaaag  1860
attccacaca cggacggaca tttcacccc tctcccctca tgggtggatt cggacttaaa  1920
caccctcctc cacagattct catcaagaac accccgtac ctgcaatcc ttcgaccacc  1980
ttcagtgcgg caaagtttgc ttccttcatc acacagtact ccacgggaca ggtcagcgtg  2040
gagatcgagt gggagctgca gaaggaaaac agcaaacgct ggaatccga agttcagtac  2100
acttccaact acaacaagtc tgttaatgtg gactttactg tggacactaa tggcgtgtat  2160
tcagagcctc gccccattgg caccagatac ctgactcgta atcagtaa             2208

SEQ ID NO: 23           moltype = DNA   length = 2211
FEATURE                 Location/Qualifiers
misc_feature            1..2211
                        note = Synthetic nucleic acid sequence
source                  1..2211
                        mol_type = other DNA
                        organism = synthetic construct
SEQUENCE: 23
atggctgctg atggttatct tccagattgg ctcgaggaca ctctctctga aggaataaga   60
cagtggtgga agctcaaacc tggcccacca ccaccaaagc ccgcagagcg cataaggac   120
gacagcaggg gtcttgtgct tcctgggtac aagtacctcg gacccttcaa cggactcgac  180
aagggagagc cggtcaacga ggcagacgca gcggcccctcg agcacgacaa ggcctacgac  240
cagcagctca aggccggtga caaccccctac ctcaagtaca ccacgccgga cgcggagttc  300
cagcagcggc ttcagggcga cacatcgttt gggggcaacc tcggcagagc agtcttccag  360
gccaaaaaga gggttcttga acctcttggt ctggttgagc aagcgggtga cggctcct   420
ggaaagaaga gaccgttgat tgaatccccc cagcagccg tcctccac ggtgtatcggc  480
aaaaaaggca agcagccggc taaaagaga ctcaattttg gtcagactgg cgactcagag  540
tcagtccccg acccacaacc tctcggagaa cctccagcaa cccccgctgc tgtgggacct  600
actacaatgg cttcaggtgg tggcgcacca atggcagaca ataacgaagg cgccgacgga  660
gtgggtaatg cctcaggaaa ttggcattgc gattccacat ggctgggcga cagagtcatc  720
accaccagca cccgcacctg ggccttgccc acctacaata accacctcta caagcaaatc  780
tccagtgctt caacggggc cagcaacgac aaccactact cggctacag caccccctgg  840
gggtattttg acttcaacag attccactgc cacttttcac cacgtgactg gcagcgactc  900
atcaacaaca attgggggatt ccggcccaag agactcaaact tcaacatccaa  960
gtcaaggagg tcacgacgaa tgatggcgtc acaaccatcg ctaataacct taccagcacg  1020
gttcaagtct tctcggactc agactatcag ctcccgtacg tgctcgggtc ggctcacgag  1080
ggctgcctcc cgccgttccc agcagacgtc ttcatggtgc acagtatgg atacctcacc  1140
ctgaacaacg ggagtcaggc agtaggacgc tcttcatttt actgcctgga gtactttcct  1200
tctcagatgc tgcgtaccgg aaacaacttt accttcagct acacttttga ggacgttcct  1260
ttccacagca gctacgctca cagccagagt ctggaccgtc tcatgaatcc tctcatcgac  1320
cagtacctgt attacctgaa cagaactcag aatcagtccg gaagtgccca aaacaaggac  1380
ttgctgttta gccggggtc tccagctggc atgtctgttc agcccaaaa ctggctacct  1440
ggaccctgtt atcggccaga gcgcgttct aaaacaaaa cagacaacaa caacagcaac  1500
tttacctgga ctggtgcttc aaaatataac cttaatgggc gtgaatctat aatcaaccct  1560
ggcactgcta tggcctcaca caagacgac aagacaagt tctttcccat gagcggtgtc  1620
atgattttg gaaggagag cgccggagct tcaaacactg cattgacaa tgtcatgatc  1680
acagacgaag aggaaatcaa agccactaac cccgtggcca ccgaaagatt tgggactgtg  1740
gcagtcaatc tccagagcag cagcacagac cctgcgaccg gagatgtgca tgttatggga  1800
gccttacctg gaatggtgtg gcaagacaga gacgtatacc tgcagggtcc catttgggcc  1860
aaaattcctc acacagatgg acactttcac ccgtctcctc ttatgggcgg ctttggactc  1920
aagaacccgc tcctcagat cctcatcaaa aacacgcctg ttcctgcgaa tcctccggcg  1980
gagttttcag ctacaaagtt tgcttcattc atcacccaat actccacagg acaagtgagt  2040
gtggaaattg aatgggggct gcagaaagaa aacagcaaac gctggaatcc cgaagttcag  2100
tacacatcca attatgcaaa atctgccaac gttgatttta ctgtggacaa caatggactt  2160
tatactgagc ctcgccccat tggcacccgt acctcaccc gtcccctgta a           2211

SEQ ID NO: 24           moltype = DNA   length = 2211
FEATURE                 Location/Qualifiers
```

| misc_feature | 1..2211 |
| | note = Synthetic nucleic acid sequence |
| source | 1..2211 |
| | mol_type = other DNA |
| | organism = synthetic construct |

SEQUENCE: 24

```
atggctgctg atggttatct tccagattgg ctcgaggaca ctctctctga aggaataaga    60
cagtggtgga agctcaaacc tggcccacca ccaccaaagc ccgcagagcg cataaggac    120
gacagcaggg gtcttgtgct tcctgggtac aagtacctcg gacccttcaa cggactcgac   180
aagggagagc cggtcaacga ggcgacgaca gcggccctcg agcacgacaa ggcctacgac   240
cagcagctca aggccggtga caaccccac ctcaagtaca accacgccga cgcggagttc    300
cagcagcggc ttcagggcga cacatcgttt ggggcaacc tcggcagagc agtcttccag    360
gccaaaaaga gggttcttga acctcttggt ctggttgagc aagcgggtga gacggctcct   420
ggaaagaaga gaccgttgat tgaatccccc cagcagcccg actcctccaa gggtatcgat   480
aaaaaaggca agcagccggc taaaaagaga ctcaattttg gtcagactgg cgactcagag   540
tcagtccccg acccacaacc tctcggagaa cctccagcaa ccccgctgc tgtgggacct    600
actacaatgg cttcaggtgg tggcgcacca atggcagaca taacgaagg cgccgacgga    660
gtgggtaatg cctcaggaaa ttggcattgc gattccacat ggctgggcga cagagtcatc   720
accaccagca cccgcacctg ggccttgccc acctacaata accacctcta caagcaaatc   780
tccagtgctt caacggggc cagcaacgac aaccactact cggctacag cacccctgg     840
gggtattttg acttcaacag attccactgc cacttttcac cacgtgactg gcagcgactc    900
atcaacaaca attgggatt ccggcccaag agactcaaat tcaaactctt caacatccaa   960
gtcaaggagg tcacgacgaa tgatggcgtc acaaccatcg ctaataacct taccagcacg   1020
gttcaagtct tctcggactc agactatcag ctcccgtacg tgctcgggtc ggctcacgag   1080
ggctgcctcc cgccgttccc agcagacgtc ttcatggtgc cacagtatgg atacctcacc   1140
ctgaacaacg ggagtcaggc agtaggacgc tcttcatttt actgcctgga gtactttcct   1200
tctcagatgc tgcgtaccgg aaacaacttt accttcagct cacttttga ggacgttcct   1260
ttccacagca gctacgctca cagccagagt ctggaccgtc tcatgaatcc tctcatcgac   1320
cagtacctgt attacctgaa cagaactcag aatcagtccg gaagtgccca aaacaaggac   1380
ttgctgttta gccgggggtc tccaactggc atgtctgttc agcccaaaaa ctggctacct   1440
ggaccctgtt atcggcagca gcgcgttttct aaaacaaaaa cagacaacaa caacagcaac   1500
tttacctgga ctggtgcttc aaaatataac cttaatgggc gtgaatctat aatcaaccct   1560
ggcactgcta tggcctcaca caaagacgac aaagacaagt ctttcccat gagcggtgtc   1620
atgattttg gaaaggagag cgccggagct tcaaacactg cattggacaa tgtcatgatc   1680
acagacgaag aggaaatcaa agccactaac cccgtggcca ctgaaagatt tgggactgtg   1740
gcagtcaatc tccagagcag cagcacagac cctgcgaccg gagatgtgca tgccatggga   1800
gccttacctg gaatggtgtg gcaagacaga gacgtataccc tgcagggtcc tatttgggcc   1860
aaaattcctc acacggatgg acactttcac ccgtctcctc tcatgggcgg ctttggactc   1920
aagaacccgc ctcctcagat cctcatcaaa aacacgcctg ttcctgcgaa tcctcccgcg   1980
gagttttcag ctacaaagtt tgcttcattc atcacccagt attccacagg acaagtgagc   2040
gtggagattg aatgggagct gcagaaagaa aacagcaaac gctggaatcc cgaagtgcag   2100
tatacatcta actatgcaaa atctgccaac gttgatttca ctgtggacaa caatggactt   2160
tatactgagc ctcgccccat tggcacccgt tacctcaccc gtcccctgta a             2211
```

| SEQ ID NO: 25 | moltype = DNA length = 2211 |
| FEATURE | Location/Qualifiers |
| misc_feature | 1..2211 |
| | note = Synthetic nucleic acid sequence |
| source | 1..2211 |
| | mol_type = other DNA |
| | organism = synthetic construct |

SEQUENCE: 25

```
atggctgccg atggttatct tccagattgg ctcgaggaca acctctctga gggcattcgc    60
gagtggtggg cgctgaaacc tggagccccg aagcccaaag ccaaccagca aaagcaggac   120
gacgccggg gtctggtgct tcctggctac aagtacctcg gacccttcaa cggactcgac   180
aagggggagc ccgtcaacgc ggcggatgca gcggccctcg agcacgacaa ggcctacgac   240
cagcagctca aagcggtga caatccgtac ctgcggtata ccacgccga cgccgagttt   300
caggagcgtc tgcaagaaga tacgtctttt ggggcaacc tcgggcgagc agtcttccag   360
gccaagaagc gggttctcga acctctcggt ctggttgagg aaggcgctaa gacggctcct   420
ggaaagaaac gtccggtaga gcaatcgcca caagccag actcctcctc gggcatccgg   480
aagcaggcc agcagcccgc taaaaagaga ctcaattttg gtcagactgg cgactcagag   540
tcagtccccg acccacaacc tctcggagaa cctccagcaa ccccgctgc tgtgggacct    600
actacaatgg cttcaggcgg tggcgcacca atggcagaca taacgaagg cgccgacgga    660
gtgggtaatg cctcaggaaa ttggcattgc gattccacat ggctgggcga cagagtcatc   720
accaccagca cccgaacatg gccttgccc acctataata accacctcta caagcaaatc    780
tccagtgctt cgacggggc cagcaacgac aaccactact cggctacag cacccctgg     840
gggtattttg actttaacag attccactgc cacttttcac cacgtgactg gcagcgactc    900
atcaacaaca ctgggattt ccggcccaag agactcagct tcaagctctt caacatccag   960
gtcaaggagg tcacgacgaa tgatggcgtc acaaccatcg ctaataacct taccagcacg   1020
gttcaagtct tctcggactc ggagtaccag cttccgtacg tcctcggctc tgcgcaccag   1080
ggctgcctcc ctccgttccc ggcggacgtg ttcatgattc gcaatacgg ctacctgacg   1140
ctcaacaatg cagccaagc cgtgggacgt tcatcctttt actgcctgga atatttccct   1200
tctcagatgc tgagaacggg caacaacttt accttcagct caccttttga ggaagtgcct   1260
ttccacagcg gctacgcgca cagccagagc ctggaccgtc tgatgaatcc tctcatcgat   1320
caatacctgt attacctgaa cagaactcaa aatcagtccg gaagtgccca aaacaaggac   1380
ttgctgttta gccgtgggtc tccagctggc atgtctgttc agcccaaaaa ctggctacct   1440
ggaccctgtt atcggcagca gcgcgtttct aaaacaaaaa cagacaacaa caacagcaat   1500
tttacctgga ctggtgcttc aaaatataac cttaatgggc gtgaatccat catcaaccct   1560
ggcactgcta tggcctcaca taaagacgac gaagacaagt ctttcccat gagcggtgtc   1620
```

```
atgattttg  gaaaagagag  cgccggagct  tcaaacactg  cattggacaa  tgtcatgatt  1680
acagacgaag  aggaaattaa  agccactaac  cctgtggcca  ccgaaagatt  tgggaccgtg  1740
gcagtcaatt  tccagagcag  cagcacagac  cctgcgaccg  gagatgtgca  tgctatggga  1800
gcattacctg  gcatggtgtg  gcaagataga  acgtgtacc   tgcagggtcc  catttgggcc  1860
aaaattcctc  acacagatgg  acactttcac  ccgtctcctc  ttatgggagg  ctttggactc  1920
aagaacccgc  ctcctcagat  cctcatcaaa  aacacgcctg  ttcctgcgaa  tcctccggcg  1980
gagttttcag  ctacaaagtt  tgcttcattc  atcacccaat  actccacagg  acaagtgagc  2040
gtggagattg  aatgggagct  gcagaaagaa  aacagcaaac  gctggaatcc  cgaagtgcag  2100
tatacatcta  actatgcaaa  atctgccaac  attgatttca  ctgtggacaa  caatggactt  2160
tatactgagc  ctcgccccat  tggcacccgt  tacctcaccc  gtccccagta  a           2211

SEQ ID NO: 26           moltype = AA  length = 736
FEATURE                 Location/Qualifiers
REGION                  1..736
                        note = Synthetic amino acid sequence
source                  1..736
                        mol_type = protein
                        organism = synthetic construct
SEQUENCE: 26
MAADGYLPDW  LEDNLSEGIR  EWWDLKPGAP  KPKANQQKQD  DGRGLVLPGY  KYLGPFNGLD   60
KGEPVNAADA  AALEHDKAYD  QQLKAGDNPY  LRYNHADAEF  QERLQEDTSF  GGNLGRAVFQ  120
AKKRVLEPLG  LVEEAKTAP   GKKRPVEQSP  QEPDSSSGIG  KTGQQPAKKR  LNFGQTGDSE  180
SVPDPQPLGE  PPAAPSGVGS  LTMASGGGAP  MADNNEGADG  VGNASGNWHC  DSTWLGDRVI  240
TTSTRTWALP  TYNNHLYKQI  SSASTGASND  NHYFGYSTPW  GYFDFNRFHC  HFSPRDWQRL  300
INNNWGFRPK  RLNFKLFNIQ  VKEVTTNDGV  TTIANNLTST  VQVFSDSEYQ  LPYVLGSAHQ  360
GCLPPFPADV  FMIPQYGYLT  LNNGSQAVGR  SSFYCLEYFP  SQMLRTGNNF  TFSYTFEEVP  420
FHSSYAHSQS  LDRLMNPLID  QYLYYLNRTQ  NQSGSAQNKD  LLFSRGSPAG  MSVQPKNWLP  480
GPCYRQQCVS  KTKTDNNNSN  FTWTGASKYN  LNGRESIINP  GTAMASHKDD  KDKFFPMSGV  540
MIFGKESAGA  SNTALDNVMI  TDEEEIKATN  PVATERFGTV  AVNLQSSSTD  PATGDVHVMG  600
ALPGMVWQDR  DVYLQGPIWA  KIPHTDGHFH  PSPLMGGFGL  KNPPPQILIK  NTPVPANPPA  660
EFSATKFASF  ITQYSTGQVS  VEIEWELQKE  NSKRWNPEVQ  YTSNYAKSAN  VDFTVDNNGL  720
YTEPRPIGTR  YLTRPL                                                     736

SEQ ID NO: 27           moltype = AA  length = 736
FEATURE                 Location/Qualifiers
REGION                  1..736
                        note = Synthetic amino acid sequence
source                  1..736
                        mol_type = protein
                        organism = synthetic construct
SEQUENCE: 27
MAADGYLPDW  LEDNLSEGIR  EWWDLKPGAP  KPKVNQQKQD  NARGLVLPGY  KYLGPFNGLD   60
KGEPVNAADA  AALEHDKAYD  QQLKAGDNPY  LRYNHADAEF  QERLQEDTSF  GGNLGRAVFQ  120
AKKRVLEPFG  LVEEGAKTAP  GKKRPVEQSP  QEPDSSSGIG  KTGQQPAKKR  LNFGQTGDSE  180
SVPDPQPLGE  PPATPAAVGP  TTMASGGGAP  MADNNEGADG  VGNASGNWHC  DSTWLGDRVI  240
TTSTRTWALP  TYNNHLYKQI  SSASTGASND  NHYFGYSTPW  GYFDFNRFHC  HFSPRDWQRL  300
INNNWGFRPK  RLNFKLFNIQ  VKEVTTNDGV  TTIANNLTST  VQVFSDSEYQ  LPYVLGSAHQ  360
GCLPPFPADV  FMIPQYGYLT  LNNGSQAVGR  SSFYCLEYFP  SQMLRTGNNF  TFSYTFEDVP  420
FHSSYAHSQS  LDRLMNPLID  QYLYYLNRTQ  NQSGSAQNKD  LLFSRGSPTG  MSVQPKNWLP  480
GPCYRQQRVS  KTKTDNNNSN  FTWTGASKYN  LNGRESIINP  GTAMASHKDD  EDKFFPMSGV  540
MIFGKESAGA  SNTALDNVMI  TDEEEIKATN  PVATERFGTV  AVNLQSSSTD  PATGDVHAMG  600
ALPGMVWQDR  DVYLQGPIWA  KIPHTDGHFH  PSPLMGGFGL  KHPPPQILIK  NTPVPANPPA  660
EFSATKFASF  ITQYSTGQVS  VEIEWELQKE  NSKRWNPEVQ  YTSNYAKSAN  VDFTVDNNGL  720
YTEPRPIGTR  YLTRPL                                                     736

SEQ ID NO: 28           moltype = AA  length = 723
FEATURE                 Location/Qualifiers
REGION                  1..723
                        note = Synthetic amino acid sequence
source                  1..723
                        mol_type = protein
                        organism = synthetic construct
SEQUENCE: 28
MAADGYLPDW  LEDNLSEGIR  EWWDLKPGAP  KPKVNQQKQD  NARGLVLPGY  KYLGPFNGLD   60
KGEPVNAADA  AALEHDKAYD  QQLKAGDNPY  LRYNHADAEF  QERLQEDTSF  GGNLGRAVFQ  120
AKKRVLEPFG  LVEEGAKTAP  GKKRPVEQSP  QEPDSSSGIG  KTGQQPAKKR  LNFGQTGDSE  180
SVPDPQPLGE  PPATPAAVGP  TTMASGGGAP  MADNNEGADG  VGNASGNWHC  DSTWLGDRVI  240
TTSTRTWALP  TYNNHLYKQI  SSASTGASND  NHYFGYSTPW  GYFDFNRFHC  HFSPRDWQRL  300
INNNWGFRPK  RLNFKLFNQV  KETTDVTTIA  NNLTSTVQVF  SDSEYQLPYV  LGSAHQGCLP  360
PFPADVFMIP  QYGYLTLNNG  SQAVGRSSFY  CLEYFPSQML  RTGNNFTSYT  FEDVPFHSSY  420
AHSQSLDRLM  NPLIDQYLYY  LNRTQNQSGS  AQNKDLLFSR  GSPTGMSVQP  KNWLPGPCYR  480
QQRVSKTKTD  NNNSNFTWTG  ASKYNLNGRE  SIINPGTAMA  SHKDDEDKFF  PMSGVMIFGK  540
ESAGASNTAL  DNVMITDEEA  TNPVATERFG  TVAVNLQSSS  ATDVHAMGAL  PGMVWQDRDV  600
YLQGPIWAKI  PHTDGHFHPS  PLMGGFGLKH  PPPQILIKNT  PVPANPPAEF  SATKFASFIT  660
QYSTGQVSVE  IEWELQKENS  KRWNPEVQYT  SNYAKSANVD  FTVDNNGLYT  EPRPIGTRYL  720
TRP                                                                    723

SEQ ID NO: 29           moltype = AA  length = 736
FEATURE                 Location/Qualifiers
```

```
REGION                     1..736
                           note = Synthetic amino acid sequence
source                     1..736
                           mol_type = protein
                           organism = synthetic construct
SEQUENCE: 29
MASDGYLPDW LEDNLSEGIR EWWDLKPGAP KPKANQQKQD DGRGLVLPGY KYLGPFNGLD    60
KGEPVNAADA AALEHDKAYD QQLRAGDNPY LRYNHADAEF QERLQEDTSF GGNLGRAVFQ   120
AKKRVLEPFG LVEEGAKTAP GKKRPVEQSP QEPDSSSGIG KTGQQPAKKR LNFGQTGDSE   180
SVPDPQPLGE PPATPAAVGP TTMASGGGAP MADNNEGADG VGNASGNWHC DSTWLGDRVI   240
TTSTRTWALP TYNNHLYKQI SSASTGASND NHYFGYSTPW GYFDFNRFHC HFSPRDWQRL   300
INNNWGFRPK RLNFKLFNIQ VKEVTTNDGV TTIANNLTST VQVFSDSEYQ LPYVLGSAHQ   360
GCLPPFPADV FMIPQYGYLT LNNGSQAVGR SSFYCLEYFP SQMLRTGNNF TFSYTFEDVP   420
FHSSYAHSQS LDRLMNPLID QYLYYLNRTQ NQSGSAQNKD LLFSRGSPAG MSVQPKNWLP   480
GPCYRQQRVS KTKTDNNNSN FTWTGASKYN LNGRESIINP GTAMASHKDD KDKFFPMSGV   540
MIFGKESAGA SNTALDNVMI TDEEEIKATN PVATERFGTV AVNLQSSSTD PATGDVHVMG   600
ALPGMVWQDR DVYLQGPIWA KIPHTDGHFH PSPLMGGFGL KHPPPQILIK NTPVPANPPA   660
EFSATKFASF ITQYSTGQVS VEIEWELQKE NSKRWNPEVQ YTSNYAKSAN VDFTVDNNGL   720
YTEPRPIGTR YLTRPL                                                  736

SEQ ID NO: 30              moltype = AA  length = 736
FEATURE                    Location/Qualifiers
REGION                     1..736
                           note = Synthetic amino acid sequence
source                     1..736
                           mol_type = protein
                           organism = synthetic construct
SEQUENCE: 30
MAADGYLPDW LEDTLSEGIR QWWKLKPGPP PPKPAERHKD DSRGLVLPGY KYLGPFNGLD    60
KGEPVNEADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KTGQQPAKKR LNFGQTGDSE   180
SVPDPQPLGE PPATPAAVGP TTMASGGGAP MADNNEGADG VGNASGNWHC DSTWLGDRVI   240
TTSTRTWALP TYNNHLYKQI SSASTGASND NHYFGYSTPW GYFDFNRFHC HFSPRDWQRL   300
INNNWGFRPK RLSFKLFNIQ VKEVTTNDGV TTIANNLTST VQVFSDSEYQ LPYVLGSAHQ   360
GCLPPFPADV FMIPQYGYLT LNNGSQAVGR SSFYCLEYFP SQMLRTGNNF TFSYTFEEVP   420
FHSSYAHSQS LDRLMNPLID QYLYYLNRTQ NQSGSAQNKD LLFSRGSPAG MSVQPKNWLP   480
GPCYRQQRVS KTKTDNNNSN FTWTGASKYN LNGRESIINP GTAMASHKDD EDKFFPMSGV   540
MIFGKESAGA SNTALDNVMI TDEEEIKATN PVATERFGTV AVNFQSSSTD PATGDVHAMG   600
ALPGMVWQDR DVYLQGPIWA KIPHTDGHFH PSPLMGGFGL KNPPPQILIK NTPVPANPPA   660
EFSATKFASF ITQYSTGQVS VEIEWELQKE NSKRWNPEVQ YTSNYAKSAN VDFTVDNNGL   720
YTEPRPIGTR YLTRPL                                                  736

SEQ ID NO: 31              moltype = AA  length = 735
FEATURE                    Location/Qualifiers
REGION                     1..735
                           note = Synthetic amino acid sequence
source                     1..735
                           mol_type = protein
                           organism = synthetic construct
SEQUENCE: 31
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAPSGLGT NTMATGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI   300
NNNWGFRPKR LKFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTDT PSGTTTQSRL QFSQAGASDI RDQSRNWLPG   480
PCYRQQRVSK TSADNNNSEY SWTGATKYHL NGRDSLVNPG PAMASHKDDE EKFFPQSGVL   540
IFGKQGSEKT SVDIEKVMIT DEEEIRTTNP VATEQYGSVS TNLQRGNRQA ATADVNTQGV   600
LPGMVWQDRD VYLQGPIWAK IPHTDGHFHP SPLMGGFGLK HPPPQILIKN TPVPANPSTT   660
FSAAKFASFI TQYSTGQVSV EIEWELQKEN SKRWNPEVQY TSNYNKSVNV DFTVDTNGVY   720
SEPRPIGTRY LTRNL                                                   735

SEQ ID NO: 32              moltype = AA  length = 735
FEATURE                    Location/Qualifiers
REGION                     1..735
                           note = Synthetic amino acid sequence
source                     1..735
                           mol_type = protein
                           organism = synthetic construct
SEQUENCE: 32
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAN   180
SVPDPQPLGQ PPAPSGLGT NTMATGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI   300
NNNWGFRPKR LKFKLFNIQV KEVTQNDGTT TIANNLTSTV QVFTDSEYQL PYVLGSAHQG   360
CLPPFPADVF MVPQYGYLTL NNGSRAVGRS SFYCLEYFPS QMLRTGNNFT FSYTFEDVPF   420
```

```
HSSYAHSQSL DRLMNPLIDQ YLYYLSRTDT PSGTTTQSRL QFSQAGASDI RDQSRNWLPG    480
PCYRQQRVSK TSADNNNSEY SWTGATKYHL NGRDSLVNPG PAMASHKDDE EKFFPQSGVL    540
IFGKQGSEKT SVDIEKVMIT DEEEIRTTNP VATEQYGSVS TNLQRGNRQA ATADVNTQGV    600
LPGMVWQDRD VYLQGPIWAK IPHTDGHFHP SPLMGGFGLK HPPPQILIKN TPVPANPSTT    660
FSAAKFASFI TQYSTGQVSV EIEWELQKEN SKRWNPEVQY TSNYNKSVNV DFTVDTNGVY    720
TEPRPIGTRY LTRNL                                                     735

SEQ ID NO: 33            moltype = AA   length = 735
FEATURE                  Location/Qualifiers
REGION                   1..735
                         note = Synthetic amino acid sequence
source                   1..735
                         mol_type = protein
                         organism = synthetic construct
SEQUENCE: 33
MAADGYLPDW LEDTLSEGIR QWWKLKPGPP PPKPAERHKD DSRGLVLPGY KYLGPFNGLD     60
KGEPVNEADA AALEHDKAYD RQLDSGDNPY LKYNHADAEF QERLKEDTSF GGNLGRAVFQ    120
AKKRVLEPLG LVEEPVKTAP GKKRPVEHSP VEPDSSSGTG KAGQQPARKR LNFGQTGDAD    180
SVPDPQPLGQ PPAAPSGLGT NTMATGSGAP MADNNEGADG VGNSSGNWHC DSTWMGDRVI    240
TTSTRTWALP TYNNHLYKQI SSQSGASNDN HYFGYSTPWG YFDFNRFHCH FSPRDWQRLI    300
NNNWGFRPKR LKFKLFNIQV KEVTQNDGTT TIANNLTSTV QVFTDSEYQL PYVLGSAHQG    360
CLPPFPADVF MVPQYGYLTL NNGSQAVGRS SFYCLEYFPS QMLRTGNNFT FSYTFEDVPF    420
HSSYAHSQSL DRLMNPLIDQ YLYYLSRTDA PSGTTTQSRL QFSQAGASDI RDQSRNWLPG    480
PCYRQQRVSK TSADNNNSEY SWTGATKYHL NGRDSLVNPG PAMASHKDDE EKFFPQSGVL    540
IFGKQGSEKT SVDIEKVMIT DEEEIRTTNP VATEQYGSVS TNLQRGNRQA ATADVNTQGV    600
LPGMVWQDRD VYLQGPIWAK IPHTDGHFHP SPLMGGFGLK HPPPQILIKN TPVPANPSTT    660
FSAAKFASFI TQYSTGQVSV EIEWELQKEN SKRWNPEVQY TSNYNKSVNV DFTVDTNGVY    720
SEPRPIGTRY LTRNL                                                     735

SEQ ID NO: 34            moltype = DNA   length = 2211
FEATURE                  Location/Qualifiers
misc_feature             1..2211
                         note = Synthetic nucleic acid sequence
source                   1..2211
                         mol_type = other DNA
                         organism = synthetic construct
SEQUENCE: 34
atggctgccg atggttatct tccagattgg ctcgaggaca acctctctga gggcattcgc     60
gagtggtggg acttgaaacc tggagccccg aaacccagca aaagcaggac                120
gacggccggg gtctggtgct tcctggctac aagtacctcg gacccttcaa cggactcgac    180
aagggggagc ccgtcaacgc ggcggatgca gcggccctcg agcacgacaa ggcctacgac    240
cagcagctca aagcgggtga caatccgtac cttcggtata accacgccga cgccgagttt    300
caggacgtc tgcaagaaga tacgtctttt ggggcaacc tcgggcgagc agtcttccag     360
gccaaaaaga gggttctcga acctctcggt ctggttgagg aagcggctaa gacggctcct    420
ggaaagaaac gtccggtaga gcagtcgcca caagagccag actcctcctc gggcattggc    480
aagacaggcc agcagcccgc taaaaagaga ctcaattttg gtcagactgg cgactcagag    540
tcagtcccg acccacaacc tctcggagaa cctcccgcag cccctcaggt gtgggatct     600
cttacaatgg cttcaggtgg tggcgcacca atggcagaca ataacgaagg cgccgacgga    660
gtgggtaatg cctcaggaaa ttggcattgc gattccacat ggctgggcga cagagtcatc    720
accaccagca cccgcacctg gccttgccc acctacaata accctcta caagcaaatc      780
tccagtgctt caacggggc cagcaacgac aaccactact tcggctacag caccccctcg    840
gggtatttg acttcaacag attccactgc cacttttcac cacgtgactg gcaaagactc    900
atcaacaaca attggggatt ccggcccaag agactcaact tcaagctctt caacatccaa    960
gtcaaggagg tcacgacgaa tgatggcgtc acgaccatcg ctaataacct taccagcacg   1020
gttcaagtct tctcggactc ggagtaccag ttgccgtacg tcctcggctc tgcgcaccag   1080
ggctgcctcc ctccgttccc ggcggacgtg ttcatgatcc gcagtacgg ctacctaacg    1140
ctcaacaatg gcagccaggc agtgggacgg tcatccttt actgcctgga atattcca     1200
tcgcagatgc tgaaacgggg caacaacttt accttcagct acaccttga ggaagtgcct    1260
ttccacagca gctacgcgca cagccagagc ctggaccggc tgatgaatcc tctcatcgac   1320
cagtacctgt attacctgaa cagaactcaa aatcagtccg gaagtgccca aaacaaggac   1380
ttgctgttta gccgtgggtc tccagctggc atgtctgttc agcccaaaaa ctggctacct   1440
ggacctgtt accggcagca gtgcgtttct aaaacaaaaa cagacaacaa caacagcaac    1500
tttaccgga ctggtgcttc aaaatataac cttaatgggc gtgaatctat aatcaaccct    1560
ggcactgcta tggcctcaca caagacgac aaagacaagt tctttccat gagcggtgtc     1620
atgattttg gaaggagag cgccggagct tcaaacactg cattggaaca tgtcatgatc    1680
acagacgaag aggaaatcaa agccactaac ccgtggcca ccgaaagatt tgggactgtg   1740
gcagtcaatc ccagagcag cagcacagac cctgcgaccg gagatgtgca tgttatggga   1800
gccttacctg gaatggtgtg gcaagacaga gacgtatacc tgcagggtcc tatttgggact 1860
aaattcctc acacagatgg gcactttcac cgtctcctc ttatgggcgg ctttggactc   1920
aagaacccgc ctcctcagat cctcatcaaa aacacgcctg ttcctgcgaa tcctccggcg   1980
gagttttcag ctacaaagtt tgcttcattc atcacccaat actccacagg acaagtgagc   2040
gtggagattg aatgggagct gcagaaagaa acagcaagc gctggaatcc gaagtgcag    2100
tacacatcca attatgcaaa atctgccaac gttgatttca ctgtgacaa caatggactt   2160
tatactgagc ctcgccccat tggcacccgt tacctcaccc gtcccctgta a           2211

SEQ ID NO: 35            moltype = DNA   length = 2211
FEATURE                  Location/Qualifiers
misc_feature             1..2211
                         note = Synthetic nucleic acid sequence
```

```
source              1..2211
                    mol_type = other DNA
                    organism = synthetic construct
SEQUENCE: 35
atggctgccg atggttatct tccagattgg ctcgaggaca acctctctga gggcattcgc    60
gaatggtggg acttgaaacc tggagccccg aaacccaaag tcaaccagca aaagcaggac   120
aacgctcggg gtcttgtgct tccgggttac aaataccctcg gacccttcaa cggactcgac   180
aagggggagc ccgtcaacgc ggcggacgca gcggccctcg agcacgacaa ggcctacgac   240
cagcagctca aagcgggtga caatccgtac cttcggtata accacgccga cgccgagttt   300
caggagcgtc tgcaagaaga tacgtctttt gggggcaacc ttggacgagc agtcttccag   360
gccaagaaga gggttctcga acctttggt ctggttgagg aaggtgctaa gacggctcct   420
ggaaagaaac gtccggtaga gcagtcgcca aagagccag actcctcctc gggcattggc    480
aagacaggcc agcagcccgc taaaaagaga ctcaattttg gtcagactgg cgactcagag   540
tcagtccccg acccacaacc tctcggagaa cctccagcaa ccccgctgc tgtgggacct   600
actacaatgg cttcaggcgg tggcgcacca atggcagaca taacgaagg cgccgacgga   660
gtgggtaatg cctcaggaaa ttggcattgc gattccacat ggctgggcga cagagtcatc   720
accaccagca cccgcacctg ggccttgccc acctacaata accacctcta aagcaaatc    780
tccagtgctt caacggggggc cagcaacgac aaccactact tcggctacag cacccccgg   840
gggtatttg acttcaacag attccactgc cacttttcac cacgtgactg gcaaagactc   900
atcaacaaca attggggatt ccggcccaag agactcaact tcaagctctt caacatccaa   960
gtcaaggagg tcacgacgaa tgatggcgtc acgaccatcg ctaataacct taccagcacg  1020
gttcaagtct tctcggactc ggagtaccag ttgccgtacg tcctcggctc tgcgcaccag  1080
ggctgcctcc ctccgttccc ggcggacgtg ttcatgattc cgcaatacgg ctacctgacg  1140
ctcaacaatg gcagccaggc agtgggacgg tcatccttt actgcctgga atattcccca  1200
tcgcagatgc tgagaacggg caataacttt accttcagct cacttttga ggacgttcct  1260
ttccacgcca gctacgctca cagccagagc ctggaccggc tgatgaatcc tctcatcgac  1320
cagtacctgt attacctgaa cagaactcag aatcagtccg gaagtgccca aaacaaggac  1380
ttgctgtttta gccgtgggtc tccaactggc atgtctgttc agcccaaaaa ctggctacct  1440
ggaccctgtt atcggcagca gcgcgtttct aaaacaaaaa cagacaacaa caacagcaac  1500
tttacctgga ctgtgctttc aaaatataac cttaatgggc gtgaatctat aatcaaccct  1560
ggcactgcta tggcctcaca caaagacgag gaagacaagt tctttcccat gagcggtgtc  1620
atgattttg aaaggagag cgccggagct tcaaacactg cattggacaa tgtcatgatc  1680
acagacgaag aggaaatcaa agccactaac cccgtggcca ctgaaagatt tgggactgtg  1740
gcagtcaatc tccagagcag cagcacagac cctgcgaccg gagatgtgca tgccatggga  1800
gccttacctg gaatggtgtg gcaagacaga gactgtacc tgcagggtcc tatttgggcc  1860
aaaattcctc acacgatgg acactttcac ccgtctcctc tcatgggcgg cttttggact  1920
aagcacccgc ctcctcagat cctcatcaaa aacacgcctg ttcctgcgaa tcctccggca  1980
gagttttcgg ctacaaagtt tgcttcattc atcacccagt attccacagg acaagtgagc  2040
gtggagattg aatgggagct gcagaaagaa aacagcaagc gctggaatcc cgaagtgcag  2100
tatacatcta actatgcaaa atctgccaac gttgatttca ctgtggacaa caatggactt  2160
tatactgagc ctcgccccat tggcacccgt tacctcaccc gtcccctgta a           2211

SEQ ID NO: 36      moltype = DNA   length = 2208
FEATURE            Location/Qualifiers
misc_feature       1..2208
                   note = Synthetic nucleic acid sequence
misc_feature       955
                   note = n is a, c, g, or t
misc_feature       971..972
                   note = n is a, c, g, or t
misc_feature       981
                   note = n is a, c, g, or t
misc_feature       986
                   note = n is a, c, g, or t
misc_feature       1235
                   note = n is a, c, g, or t
misc_feature       1694..1696
                   note = n is a, c, g, or t
misc_feature       1698
                   note = n is a, c, g, or t
misc_feature       1763..1765
                   note = n is a, c, g, or t
misc_feature       1778
                   note = n is a, c, g, or t
misc_feature       2204
                   note = n is a, c, g, or t
source             1..2208
                   mol_type = other DNA
                   organism = synthetic construct
SEQUENCE: 36
atggctgccg atggttatct tccagattgg ctcgaggaca acctctctga gggcattcgc    60
gaatggtggg acttgaaacc tggagccccg aaacccaaag tcaaccagca aaagcaggac   120
aacgctcggg gtcttgtgct tccgggttac aaataccctcg gacccttcaa cggactcgac   180
aagggggagc ccgtcaacgc ggcggacgca gcggccctcg agcacgacaa ggcctacgac   240
cagcagctca aagcgggtga caatccgtac cttcggtata accacgccga cgccgagttt   300
caggagcgtc tgcaagaaga tacgtctttt gggggcaacc ttggacgagc agtcttccag   360
gccaagaaga gggttctcga acctttggt ctggttgagg aaggtgctaa gacggctcct   420
ggaaagaaac gtccggtaga gcagtcgcca aagagccag actcctcctc gggcattggc    480
aagacaggcc agcagcccgc taaaaagaga ctcaattttg gtcagactgg cgactcagag   540
```

```
tcagtccccg acccacaacc tctcggagaa cctccagcaa ccccgctgc tgtgggacct    600
actacaatgg cttcaggcgg tggcgcacca atggcagaca ataacgaagg cgccgacgga   660
gtgggtaatg cctcaggaaa ttggcattgc gattccacat ggctgggcga cagagtcatc   720
accaccagca cccgaacatg ggccttgccc acctataaca accacctcta caagcaaatc   780
tccagtgctt caacggggc cagcaacgac aaccactact tcggctacag caccccctgg    840
gggtattttg atttcaacag attccactgc cactttcac cacgtgactg gcagcgactc     900
atcaataaca attggggatt ccggcccaag agactcaact tcaaactctt caacntccaa   960
gtcaaggagg nnacgacgaa ngatgncgtc acaaccatcg ctaataacct taccagcacg  1020
gttcaagtct tctcggactc ggagtaccag cttccgtacg tcctcggctc tgcgcaccag  1080
ggctgcctcc ctccgttccc ggcggacgtg ttcatgatcc cgcaatacgg ctacctgacg  1140
ctcaacaatg gcagccaggc agtgggacgg tcatccttt actgcctgga atatttccca    1200
tcgcagatgc tgagaacggg caataacttt acctncagct acactttga ggacgttcct   1260
ttccacagca gctacgctca cagccagagc ctggaccggt tgatgaatcc tctcatcgac  1320
cagtacctgt attacctgaa cagaactcag aatcagtccg gaagtgccca aaacaaggac  1380
ttgctgttta gccgtgggtc tccaactggc atgtctgttc agcccaaaaa ctggctacct  1440
ggaccctgtt atcggcagca gcgcgtttct aaaacaaaaa cagacaacaa caacagcaac  1500
tttacctgga ctggtgcttc aaaatataac cttaatgggc gtgaatctat aatcaaccct  1560
ggcactgcta tggcctcaca caaagacgac aagacaagt tctttcccat gagcggtgtc  1620
atgattttg gaaggagag cgccggagct tcaaacactg cattggacaa tgtcatgatc    1680
acagacgaag agannncnaa gccactaacc ccgtggccac tgaaagattt gggactgtgg  1740
cagtcaatct ccaagcagca cannnaccct gcgaccgnag atgtgcatgc catgggagcc  1800
ttacctggaa tggtgtggca agacagagac gtataccctg agggtcctat ttgggccaaa  1860
attcctcaca cggatggaca cttcaccccg tctcctctca tgggcggctt tggacttaag  1920
cacccgcctc ctcagatcct catcaaaaac acgcctgttc ctgcgaatcc tccggcagag  1980
ttttcggcta caaagtttgc ttcattcatc acccagtatt ccacaggaca agtgagcgtg  2040
gagattgaat gggagctgca gaaagaaaac agcaaacgct agcaaacgct agtgcagtat  2100
acatctaact atgcaaaatc tgccaacgtt gatttcactg tggacaacaa tggactttat  2160
actgagcctc gccccattgg cacccgttac ctcacccgtc cccngtaa               2208

SEQ ID NO: 37           moltype = DNA  length = 2211
FEATURE                 Location/Qualifiers
misc_feature            1..2211
                        note = Synthetic nucleic acid sequence
source                  1..2211
                        mol_type = other DNA
                        organism = synthetic construct
SEQUENCE: 37
atggcttccg atggttatct tccagattgg ctcgaggaca acctctctga gggcatccgc    60
gagtggtggg acttgaaacc tggagcccg aaacccaagca ccaaccagca aaagcaggac    120
gacggccggg gtctggtgct tcctggctac aagtacctcg gacccttcaa cggactcgac   180
aaggggggagc ccgtcaacgc ggcggatgca gcggccctcg agcacgacaa ggcctacgac   240
cagcagctca gagcgggtga caatccgtac ctgcggtata accacgccga cgccgagttt   300
caggagcgtc tgcaagaaga tacgtctttt gggggcaacc tcgggcgagc agtcttccag   360
gccaagaaga gggttctcga acctttggt ctggttgagg aaggtgctaa gacggctcct   420
ggaaagaaac gtccggtaga gcagtcgcca caagagccag actcctcctc gggcattggc  480
aagacaggcc agcagcccgc taaaagaga ctcaattttg gtcagactgg cgactcagag   540
tcagtccccg acccacaacc tctcggagaa cctccagcaa ccccgctgc tgtgggacct    600
actacaatgg cttcaggcgg tggcgcacca atggcagaca ataacgaagg cgccgacgga   660
gtgggtaatg cctcaggaaa ttggcattgc gattccacat ggctgggcga cagagtcatc   720
accaccagca cccgaacatg ggccttgccc acctataaca accacctcta caagcaaatc   780
tccagtgctt caacggggc cagcaacgac aaccactact tcggctacag caccccctgg    840
gggtattttg atttcaacag attccactgc catttctcac cacgtgactg gcagcgactc    900
atcaacaaca attggggatt ccggcccaag agactcaact tcaaactctt caacatccaa   960
gtcaaggagg tcacgacgaa tgatggcgtc acaaccatcg ctaataacct taccagcacg  1020
gttcaagtct tctcggactc ggagtaccag cttccgtacg tcctcggctc tgcgcaccag  1080
ggctgcctcc ctccgttccc ggcggacgtg ttcatgatcc cgcagtacgg ctacctaacg  1140
ctcaacaatg gcagccaggc agtgggacgg tcatccttt actgcctgga atatttccca    1200
tcgcagatgc tgagaacggg caataacttt accttcagct acaccttcga ggacgtgcct  1260
ttccacagca gctacgcgca cagccagagc ctggaccggt tgatgaatcc tctcatcgac  1320
cagtacctgt attacctgaa cagaactcag aatcagtccg gaagtgccca aaacaaggac  1380
ttgctgttta gccggggtc tccagctggc atgtctgttc agcccaaaaa ctggctacct   1440
ggaccctgtt accggcagca gcgcgtttct aaaacaaaaa cagacaacaa caacagcaac  1500
tttacctgga ctggtgcttc aaaatataac cttaatgggc gtgaatctat aatcaaccct  1560
ggcactgcta tggcctcaca caaagacgac aagacaagt tctttcccat gagcggtgtc   1620
atgattttg gaaggagag cgccggagct tcaaacactg cattggacaa tgtcatgatc    1680
acagacgaag aggaaatcaa agccactaac ccgtggcca ccgaaagatt tgggactgtg   1740
gcagtcaatc tccagagcag cagcacagac cctgcgaccg gagatgtgca tgttatggga  1800
gccttacctg gaatggtgtg gcaagacaga gacgtatacc tgcgggtcc catttgggcc   1860
aaaattcctc acacagatgg acactttcac ccgtctcctc ttatgggcgg ctttggactt  1920
aagcacccgc ctcctcagat cctcatcaaa aacacgcctg ttcctgcgaa tcctccggca  1980
gagtttcgg ctacaaagtt tgcttcattc atcacccagt attctactgg ccaagtcagc   2040
gtggagattg aatgggagct gcagaaagaa aacagcaaac gctggaatcc gaagtcag    2100
tatacatcta actatgcaaa atctgccaac gttgatttca ctgtggacaa caatggactt  2160
tatactgagc ctcgtcccat ggcacccgt tacctcaccc gtccctgta a             2211

SEQ ID NO: 38           moltype = DNA  length = 2211
FEATURE                 Location/Qualifiers
misc_feature            1..2211
                        note = Synthetic nucleic acid sequence
```

| source | 1..2211 |
| --- | --- |
| | mol_type = other DNA |
| | organism = synthetic construct |

SEQUENCE: 38

```
atggctgccg atggttatct tccagattgg ctcgaggaca ctctctctga aggaataaga    60
cagtggtgga agctcaaacc tggcccacca ccaccaaagc ccgcagagcg cataaggac    120
gacagcaggg gtcttgtgct tcctgggtac aagtacctcg gacccttcaa cggactcgac   180
aagggagagc cggtcaacga ggcagacgcc gcggccctcg agcacgacaa ggcctacgac   240
cagcagctca aagcgggtga caatccgtac ctgcggtata accacgcga cgccgagttt   300
caggagcgtc tgcaagaaga tacgtctttt gggggcaacc tcgggcgagc agtcttccag   360
gccaagaagc gggttctcga acctctcggt ctggttgagg aaggcgctaa gacggctcct   420
ggaaagaaac gtccggtaga gcagtcgcca aagagccag actcctcctc gggcatcggc    480
aagacaggcc agcagcccgc taaaaagaga ctcaattttg gtcagactgg cgactcagag   540
tcagtccccg acccacaacc tctcggagaa cctccagcaa ccccccgctgc tgtgggacct 600
actacaatgg cttcaggcgg tggcgcacca atggcagaca ataacgaagg cgccgacgga   660
gtgggtaatg cctcaggaaa ttggcattgc gattccacat ggctgggcga cagagtcatc   720
accaccagca cccgaacatg ggccttgccc acctataaca accacctcta caagcaaatc   780
tccagtgctt cgacggggc cagcaacgac aaccactact tcggctacag caccccctgg  840
gggtattttg actttaacag attccactgc cacttttcac cacgtgactg gcagcgactc  900
atcaacaata actggggatt ccggcccaag agactcagct tcaagctctt caacatccag  960
gtcaaggagg tcacgacgaa tgatggcgtc acaaccatcg ctaataacct taccagcacg  1020
gttcaagtct tctcggactc ggagtaccag cttccgtacg tcctcggctc tgcgcaccag  1080
ggctgcctcc ctccgttccc ggcggacgtg ttcatgattc cgcaatacgg ctacctgacg  1140
ctcaacaatg gcagccaagc cgtgggacgt tcatccttt actgcctgga atatttccct  1200
tctcagatgc tgagaacggg caacaacttt accttcagct cacctttga ggaagtgcct  1260
ttccacagca gctacgcgca cagccagagc ctggaccggc tgatgaatcc tctcatcgat  1320
caatacctgt attacctgaa cagaactcaa aatcagtccg gaagtgccca aaacaaggac  1380
ttgctgttta gccgtgggtc tccagctggc atgtctgttc agcccaaaa ctggctacct  1440
ggaccctgtt atcggcagca gcgcgtttct aaaacaaaaa cagacaacaa caacagcaat  1500
tttacctgga ctgtgtcttc aaaatataac ctcaatgggc gtgaatcat catcaaccct  1560
ggcactgcta tggcctcaca caaagacgac gaagacaagt tctttcccat gagcggtgtc  1620
atgattttg gaaagagag cgccggagct tcaaacactg cattggacaa tgtcatgatt  1680
acggacgaag aggaaattaa agccactaac cctgtggcca ccgaaagatt tgggaccgtg  1740
gcagtcaatt tccagagcag cagcacagac cctgcgacg gagatgtgca tgctatggga  1800
gcattacctg gcatggtgtg gcaagataga gacgtgtacc tgcagggtcc catttgggcc  1860
aaaattcctc acacagatgg acactttcac ccgtctcctc ttatgggcgg ctttggactc  1920
aagaacccgc ctcctcagat cctcatcaaa aacacgcctg ttcctgcgaa tcctccggcg  1980
gagttttcag ctacaaagtt tgcttcattc atcactcaat actccacagg acaagtgagc  2040
gtggaaattg aatgggagct gcagaaagaa aacagcaagt tcgaagtgca caacaggcag 2100
tatacatcta actatgcaaa atctgccaac gttgatttca ctgtggacaa caatggactt  2160
tatactgagc ctcgccccat tggcacccgt tacctcaccc gtcccctgta a            2211
```

| SEQ ID NO: 39 | moltype = DNA  length = 2208 |
| --- | --- |
| FEATURE | Location/Qualifiers |
| misc_feature | 1..2208 |
| | note = Synthetic nucleic acid sequence |
| source | 1..2208 |
| | mol_type = other DNA |
| | organism = synthetic construct |

SEQUENCE: 39

```
atggctgccg atggttatct tccagattgg ctcgaggaca ctctctctga aggaataaga    60
cagtggtgga agctcaaacc tggcccacca ccaccaaagc ccgcagagcg cataaggac    120
gacagcaggg gtcttgtgct tcctgggtac aagtacctcg gacccttcaa cggactcgac   180
aagggagagc cggtcaacga ggcagacgcc gcggccctcg agcacgacaa agcctatgac   240
cggcagctcg acagcggaga caacccgtac ctcaagtaca accacgcga cgcggagttt   300
caggagcgcc ttaaagaaga tacgtctttt gggggcaacc tcggacgagc agtcttccag   360
gcgaaaaaga gggttcttga acctctgggc ctggttgagg aacctgttaa gacggctccg   420
ggaaaaaaga ggccggtaga gcactctcct gtggagccag actcctcctc gggaaccgga   480
aaggcgggcc agcagcctgc aagaaaaaga ttgaattttg gtcagactgg agacgagag   540
tcagtacctg atcccagcc ccaccagcag cccctctg tctgggaact   600
aatacgatgg ctacaggcag tggcgcacca atggcagaca ataacgaggg cgccgacgga   660
gtgggtaatt cctcgggaaa ttggcattgc gattccacat ggatgggcga cagagtcatc   720
accaccagca cccgaacctg ggccctgccc acctacaaca accacctcta caaacaaatt   780
tccagccaat caggagcctc gaacgacaat cactactttg gctacagcac ccctgggga   840
tattttgact tcaacagatt ccactgccac ttttcaccac gtgactggca agactcatc    900
aacaacaact ggggattccg acccaagaga ctcaagttca gctctttaa cattcaagtc   960
aaagaggtca cgcagaatga cggtacgacg acgattgcca ataacttac cagcacggtt  1020
caggtgttta ctgactcgga gtaccagctc cgtatgtcc tcggctcggc gcatcaagga  1080
tgcctcccgc cgttcccagc agacgtcttc atggtgccac agtatggata cctcacccg  1140
aacaacggga gtcaggcagt aggacgctct tcatttact gcctggagta ctttccttct  1200
cagatgctgc gtaccggtaa aactttacc ttcagctaca cttttgagga cgttcctttc  1260
cacagcagct acgctcacag ccagagtctg gaccgtctca tgaatcctct catcgaccag  1320
tacctgtatt acttgagcag aacagacact ccaagtggaa ccaccacgca gtcaaggctt  1380
cagttttctc aggccggagc gagtgacatt cgggaccagt ctaggaacta gcttcctgga  1440
ccctgttacc gccagcagcg agtatcaaag acatctgcgg ataacaacaa cagtgaatac  1500
tcgtggactg gagctaccaa gtaccactc aatggcagag actctctggt gaatccgggc  1560
ccggccatgg caagccacaa ggacgatgaa gaaaagtttt ttcctcagag cggggttctc  1620
atctttggga gcaaggctc agagaaaaca agtgtggaca ttgaaaaggt catgattaca  1680
gacgaagagg aaatcaggac aaccaatccc gtggctacga gcagtatgg ttctgtatct  1740
```

```
accaacctcc agagaggcaa cagacaagca gctaccgcag atgtcaacac acaaggcgtt   1800
cttccaggca tggtctggca ggacagagat gtgtaccttc aggggcccat ctgggcaaag   1860
attccacaca cggacggaca ttttcacccc tctcccctca tgggtggatt cggacttaaa   1920
caccctcctc cacagattct catcaagaac accccggtac ctgcgaatcc ttcgaccacc   1980
ttcagtgcgg caaagtttgc ttccttcatc acacagtact ccacggacac ggtcagcgtg   2040
gagatcgagt gggagctgca gaaggaaaac agcaaacgct ggaatcccga agttcagtac   2100
acttccaact acaacaagtc tgttaatgtg gactttactg tggacactaa tggcgtgtat   2160
tcagagcctc gccccattgg caccagatac ctgactcgta atctgtaa              2208
```

```
SEQ ID NO: 40          moltype = DNA   length = 2208
FEATURE                Location/Qualifiers
misc_feature           1..2208
                       note = Synthetic nucleic acid sequence
source                 1..2208
                       mol_type = other DNA
                       organism = synthetic construct
SEQUENCE: 40
atggctgccg atggttatct tccagattgg ctcgaggaca ctctctctga aggaataaga    60
cagtggtgga agctcaaacc tggcccacca ccaccaaagc ccgcagagcg gcataaggac   120
gacagcaggg gtcttgtgct tcctgggtac aagtacctcg gacccttcaa cggactcgac   180
aagggagagc cggtcaacga ggcagacgcc gcggccctcg agcacgacaa agcctatgac   240
cggcagctcg acagcggaga caacccgtac ctcaagtaca accacgccga gcgcggagttt   300
caggagcgcc ttaaagaaga tacgtctttt gggggcaacc tcggacgagc agtcttccag   360
gcgaaaaaga gggttcttga acctctgggc ctggttgagg aacctgttaa gacggctccg   420
ggaaaaaaga ggccggtaga gcactctcct gtggagccag actcctcctc gggaaccgga   480
aaggcgggtc agcagcctgc aagaaaaaga ttgaattttg gtcagactgg agacgcaaac   540
tcagtacctg accccagcc tctcggacag ccaccagcag cccctctgg tctgggaact   600
aatacgatgg ctacaggcag tggcgcacca atggcagaca ataacgaggg cgccgacgga   660
gtgggtaatt cctcgggaaa ttggcattgc gattccacat ggatgggcga cagagtcatc   720
accaccagca cccgaacctg ggccctgccc acctacaaca accacctcta caaacaaatt   780
tccagccaat caggagcctc gaacgacaat cactactttg gctacagcac cccttggggg   840
tatttttgact tcaacagatt ccactgccac ttttcaccac gtgactggca aagactcatc   900
aacaacaact ggggattccg acccaagaga ctcaagttca gctctttaa cattcaagtc   960
aaagaggtca cgcagaatga cggtacgacg acgattgcca ataaccttac cagcacggtt  1020
caggtgttta ctgactcgga gtaccagctc ccgtacgtcc tcggctcggc gcatcaagga  1080
tgcctcccgc cgttcccagc agacgtcttc atggtgccac agtatggata cctcacctg  1140
aacaacggga gtcgggcagt aggacgctct tcatttttact gcctggagta ctttcctcct  1200
cagatgctgc gtaccggtaa caactttacc ttcagctaca cttttgagga cgttcctttc  1260
cacagcagct acgctcacag ccagagtctg gaccgtctca tgaatcctct catcgaccag  1320
tacctgtatt acttgagcag aacagacact ccaagtggaa ccaccacgca gtcaaggctt  1380
cagttttctc aggccggagc gagtgacatt cgggaccagt ctaggaactg gcttcctgga  1440
ccctgttacc gccagcagcg agtatcaaag acatctgcgg ataacaacaa cagtgaatac  1500
tcgtggactg gagctaccaa gtaccacctc aatggcagag actctctggt gaatccggac  1560
ccggccatgg caagccacaa ggacgatgaa gaaaagttt tcctcagag cggggttctc  1620
atctttggga agcaaggctc agagaaaaca agtgtgtgaca ttgaaaaaggt catgattaca  1680
gacgaagagg aaatcaggac gaccaatccc gtggctacgg agcagtatgg ttctgtatct  1740
accaacctcc agagaggcaa cagacaagca gctaccgcag atgtcaacac acaaggcgtt  1800
cttccaggca tggtctggca ggacagagat gtgtaccttc aggggcccat ctgggcaaag  1860
attccacaca cggacggaca ttttcacccc tctcccctca tgggtggatt cggacttaaa  1920
caccctcctc cacagattct catcaagaac accccggtac ctgcgaatcc ttcgaccacc  1980
ttcagtgcgg caaagtttgc ttccttcatc acacagtact ccacgggaca gtcagcgtg  2040
gagatcgagt gggagctgca gaaggaaaac agcaaacgct ggaatcccga agttcagtac  2100
acttccaact acaacaagtc tgttaatgtg gactttactg tggacactaa tggcgtgtat  2160
acagagcctc gccccattgg caccagatac ctgactcgta atctgtaa              2208
```

```
SEQ ID NO: 41          moltype = DNA   length = 2208
FEATURE                Location/Qualifiers
misc_feature           1..2208
                       note = Synthetic nucleic acid sequence
source                 1..2208
                       mol_type = other DNA
                       organism = synthetic construct
SEQUENCE: 41
atggctgccg atggttatct tccagattgg ctcgaggaca ctctctctga aggaataaga    60
cagtggtgga agctcaaacc tggcccacca ccaccaaagc ccgcagagcg gcataaggac   120
gacagcaggg gtcttgtgct tcctgggtac aagtacctcg gacccttcaa cggactcgac   180
aagggagagc cggtcaacga ggcagacgcc gcggccctcg agcacgacaa agcctatgac   240
cggcagctcg acagcggaga caacccgtac ctcaagtaca accacgccga cgcggagttt   300
caggagcgcc ttaaagaaga tacgtctttt gggggcaacc tcggacgagc agtcttccag   360
gcgaaaaaga gggttcttga acctctgggc ctggttgagg aacctgttaa gacggctccg   420
ggaaaaaaga ggccggtaga gcactctcct gtggagccag actcctcctc gggaaccgga   480
aaggcgggtc agcagcctgc aagaaaaaga ttgaattttg gtcagactgg agacgcagac   540
tcagtacctg accccagcc tctcggacag ccaccagcag cccctctgg tctgggaact   600
aatacgatgg ctacaggcag tggcgcacca atggcagaca ataacgaggg cgccgacgga   660
gtgggtaatt cctcgggaaa ttggcattgc gattccacat ggatgggcga cagagtcatc   720
accaccagca cccgaacctg ggccctgccc acctacaaca accacctcta caaacaaatt   780
tccagccaat caggagcctc gaacgacaat cactactttg gctacagcac cccttggggg   840
tatttttgact tcaacagatt ccactgccac ttttcaccac gtgactggca aagactcatc   900
aacaacaact ggggattccg acccaagaga ctcaagttca gctctttaa cattcaagtc   960
```

```
aaagaggtca cgcagaatga cggtacgacg acgattgcca ataaccttac cagcacggtt  1020
caggtgttta ctgactcgga gtaccagctc ccgtacgtcc tcggctcggc gcatcaagga  1080
tgcctcccgc cgttcccagc agacgtcttc atggtgccac agtatggata cctcaccctg  1140
aacaacggga gtcaggcagt aggacgctct tcatttact gcctggagta ctttccttct  1200
cagatgctgc gtaccggtaa caactttacc ttcagctaca cttttgagga cgttcctttc  1260
cacagcagct acgctcacag ccagagtctg gaccgtctca tgaatcctct catcgaccag  1320
tacctgtatt acttgagcag aacagacgct ccaagtggaa ccaccacgca gtcaaggctt  1380
cagttttctc aggccggagc gagtgacatt cgggaccagt ctaggaactg gcttcctgga  1440
ccctgttacc gccagcagcg agtatcaaag acatctgcgg ataacaacaa cagtgaatac  1500
tcgtggactg gagctaccaa gtaccacctc aatggcagag actctctggt gaatccggcc  1560
ccggccatgg caagccacaa ggacgatgaa gaaaagtttt ttcctcagag cggggttctc  1620
atctttggga agcaaggctc agagaaaaca agtgtggaca ttgaaaaggt catgattaca  1680
gacgaagagg aaatcaggac aaccaatccc gtggctacga agcagtatgg ttctgtatct  1740
accaacctcc agagaggcaa cagacaagca gctaccgcag atgtcaacac acaaggcgtt  1800
cttccaggca tggtctggca ggacagagat gtgtaccttc aggggcccat ctgggcaaag  1860
attccacaca cggacggaca ttttcacccc tctcccctca tgggtggatt cggacttaaa  1920
caccctcctc cacagattct catcaagaac accccgtac ctgcgaatcc ttcgaccacc  1980
ttcagtgcgg caaagtttgc ttccttcatc acacagtact ccacgggaca ggtcagcgtg  2040
gagatcgagt gggagctgca gaaggaaaac agcaaacgct ggaatcccga agttcagtac  2100
acttccaact acaacaagtc tgttaatgtg gactttactg tggacactaa tggcgtgtat  2160
tcagagcctc gccccattgg caccagatac ctgactcgta atctgtaa              2208

SEQ ID NO: 42         moltype = DNA  length = 4443
FEATURE               Location/Qualifiers
source                1..4443
                      mol_type = other DNA
                      organism = Homo sapiens
SEQUENCE: 42
atgcagaggt cgcctctgga aaaggccagc gttgtctcca acttttttt cagctggacc   60
agaccaattt tgaggaaagg atacagacag cgcctgaact tgtcagacat ataccaaatc  120
ccttctgttg attctgctca caatctatct gaaaaattgg aaagagaatg ggatagagag  180
ctggcttcaa agaaaaatcc taaactcatt aatgccttc ggcgatgttt tttctggaga  240
tttatgttct atggaatctt tttatattta ggggaagtca ccaaagcagt acagcctctc  300
ttactgggaa gaatcatagc ttcctatgac ccggataaga aggagaacg ctctatcgcg  360
atttatctag gcataggctt atgccttctc tttattgtga ggacactgct cctacaccca  420
gccattttg gccttcatca cattggaatg cagatgagaa tagctatgtt tagtttgatt  480
tataagaaga ctttaaagct gtcaagccgt gttctagata aataagtat tggacaactt  540
gttagtctcc tttccaacaa cctgaacaaa tttgatgaag gacttgcatt ggcacatttc  600
gtgtgatcg ctccttgca atggcactc ctcatgtggg taatctggga gttgttacag  660
gcgtctgcct tctgtggact tggttcctg atagtccttg ccctttttca ggctgggcta  720
gggagaatga tgatgaagta cagagatcag agagctggga agatcagtga aagacttgtg  780
attacctcag aaatgattga aaatatccaa tctgttaagg catactgctg gaagaagca  840
atggaaaaaa tgattgaaaa cttaagacaa acagaactga aactgactcg gaaggcagcc  900
tatgtgagat acttcaatag ctcagccttc ttcttctcag gttcttgt ggtgttttta  960
tctgtgcttc cctatgcact aatcaaagga atcatcctcc ggaaaatatt caccaccatc 1020
tcattctgca ttgttctgcg catggcggtc actcggcaat ttccctgggc tgtacaaaca 1080
tggtatgact ctcttggagc aataaacaaa atacaggatt tcttacaaaa gcaagaatat 1140
aagacattgg aatataactt aacgactaca gaagtagtga tggagaatgt aacagccttc 1200
tgggaggagg gatttgggga attatttgag aaagcaaaac aaaacaataa caatagaaaa 1260
acttctaatg tgtgatgacag cctcttcttc agtaatttct cacttcttgg tactcctgtc 1320
ctgaaagata ttaatttcaa gatagaaaga ggacagttgt tggcggttgc tggatcccat 1380
ggagcaggca agacttcact tctaatggtg attatgggag aactgagcc ttcagagggt 1440
aaaattaagc acagtggaag aatttcattc tgttctcagt tttcctggat tatgcctggc 1500
accattaaag aaaaatatcat ctttggtgtt tcctatgatg aatatagata cagaagcgtc 1560
atcaaagcat gccaactaga agaggacatc tccaagtttg cagagaaaga caatatagtt 1620
cttggagaag gtggaatcac actgagtgga ggtcaacgag caagaatttc tttagcaaga 1680
gcagtataca aagatgctga tttgtattta ttagactctc cttttggata cctagatgtt 1740
ttaacagaaa agaaaatatt tgaaagctgt gtctgtaaac tgatggctaa caaaactagg 1800
attttggtca cttctaaaat ggaacattta aagaaagctg acaaaatatt aatttttgcat 1860
gaaggtagca gctatttta tgggacatt tcagaactcc aaaatctaca gccagacttt 1920
agctcaaaac tcatgggatg tgattctttc gaccaattta gtgcagaaag aagaaattca 1980
atcctaactg agaccttaca ccgtttctca ttagaaggag atgctcctgt ctcctggaca 2040
gaaacaaaaa aacaatcttt taaacagact ggagagtttg gggaaaaaag gaagaattct 2100
attctcaatc caatcaactc tatacgaaaa tttttccattg tgcaaaagac tcccttacaa 2160
atgaatggca tcgaagagga ttctgatgag cctttagaga aaggctgtc cttagtacca 2220
gattctgagc agggagaggc gatactgcct cgcatcagcg tgatcagcac tggccccacg 2280
cttcaggcac gaaggaggca gtctgtcctg aacctgatga cacactcagt taaccaaggt 2340
cagaacattc accgaaagac aacagcatcc acacgaaaag tgtcactggc ccctcaggca 2400
aacttgactg aactggatat atattcaaga aggttatctc aagaaactgg cttggaaata 2460
agtgaagaaa ttaacgaaga agacttaaag gagtgctttt tgatgatat ggagagcata 2520
ccagcagtga ctacatggaa cacatacctt cgatatatta ctgtccacaa gagcttaatt 2580
tttgtgctaa tttggtgctt agtaattttt ctggcagagg tggctgcttc ttggttgtg 2640
ctgtggctcc ttgaaacac tcctcttcaa gacaaaggga atagtactca tagtagaaat 2700
aacagctatg cagtgattat caccagcacc agttcgtatt atgttttta catttacgtg 2760
ggagtagccg acactttgct tgctatggga ttcttcagag tctaccact ggtgcatact 2820
ctaatcacag tgtcgaaaat tttacaccac aaaatgttac attctgttct tcaagcacct 2880
atgtcaaccc tcaacacgtt gaaagcaggt gggattctta atagattctc caagatata 2940
gcaatttgtg atgaccttct gcctcttacc atatttgact tcatccagtt ttattaatt 3000
gtgattggag ctatagcagt tgtcgcagtt ttacaaccct acatctttgt tgcaacgtg 3060
```

```
ccagtgatag tggcttttat tatgttgaga gcatatttcc tccaaacctc acagcaactc  3120
aaacaactgg aatctgaagg caggagtcca attttcactc atcttgttac aagcttaaaa  3180
ggactatgga cacttcgtgc cttcggacgg cagccttact ttgaaactct gttccacaaa  3240
gctctgaatt tacatactgc caactggttc ttgtacctgt caacactgcg ctggttccaa  3300
atgagaatag aaatgatttt tgtcatcttc ttcattgctg ttaccttcat ttccatttta  3360
acaacaggag aaggagaagg aagagttggt attatcctga ctttagccat gaatatcatg  3420
agtacattgc agtgggctgt aaactccagc atagatgtgg atagcttgat gcgatctgtg  3480
agccgagtct ttaagttcat tgacatgcca acagaaggta aacctaccaa gtcaaccaaa  3540
ccatacaaga atggccaact ctcgaaagtt atgattattg agaattcaca cgtgaagaaa  3600
gatgacatct ggccctcagg gggccaaatg actgtcaaag atctcacagc aaaatacaca  3660
gaaggtggaa atgccatatt agagaacatt tccttctcaa taagtcctgg ccagagggtg  3720
ggcctcttgg gaagaactgg atcagggaag agtactttgt tatcagcttt tttgagacta  3780
ctgaacactg aaggagaaat ccagatcgat ggtgtgtctt gggattcaat aactttgcaa  3840
cagtggagga aagcctttgg agtgatacca cagaaagtat ttatttttc tggaacattt  3900
agaaaaaact tggatcccta tgaacagtgg agtgatcaag aaatatggaa agttgcagat  3960
gaggttgggc tcagatctgt gatagaacag tttcctggga agcttgactt tgtccttgtg  4020
gatggggggct gtgtcctaag cctatggccac aagcagttga tgtgcttggc tagatctgtt  4080
ctcagtaagg cgaagatctt gctgctgtgat gaacccagtg ctcatttgga tccagtaaca  4140
taccaaataa ttagaagaac tctaaaacaa gcatttgctg attgcacagt aattctctgt  4200
gaacacagga tagaagcaat gctggaatgc caacaatttt tggtcataga agagaacaaa  4260
gtgcggcagt acgattccat ccagaaactg ctgaacgaga ggagcctctt ccggcaagcc  4320
atcagcccct ccgacagggt gaagctcttt ccccaccgga actcaagcaa gtgcaagtct  4380
aagccccaga ttgctgctct gaaagaggag acagaagaag aggtgcaaga tacaaggctt  4440
tag                                                                4443

SEQ ID NO: 43      moltype = DNA  length = 3464
FEATURE            Location/Qualifiers
misc_feature       1..3464
                   note = Synthetic nucleic acid sequence
source             1..3464
                   mol_type = other DNA
                   organism = synthetic construct
SEQUENCE: 43
atgcagcgca gcccactgga gaaggcaagc gtggtgtcca agctgttctt ttcctggacc    60
aggcctatcc tgaggaaggg atacaggcag cggctggagc tgagcgacat ctatcagatc   120
ccttctgtgg acagcgccga taatctgtcc gagaagctgg agagagagtg ggataggag    180
ctggcctcta agaagaaccc aaagctgatc aatgccctgc ggagatgctt cttttggcgg   240
ttcatgttct acggcatctt cctgtatctg ggcgaggtga ccaaggccgt gcagccactg   300
ctgctgggca gaatcatcgc ctcttacgac cccgataaca aggaggagag gagcatccac   360
atctatctgg gcatcggcct gtgcctgctg tttatcgtga ggacactgct gctgcaccca   420
gccatcttcg gcctgcacca catcggcatg cagatgagaa tcgccatgtt cagcctgatc   480
tacaagaaga ccctgaagct gagctccagg gtgctgacag atctccat cggccagctg    540
gtgtccctgc tgtctaacaa tctgaacaag tttgatgagg gactggccct ggcacactgt   600
gtgtggatcg caccactgca ggtggccctg ctgatgggcc tgatctggga gctgctgcag   660
gcaagcgcct tttgcggact gggcttcctg atcgtgctgg ccctgttcca ggcaggactg   720
ggacgcatga tgatgaagta cagagaccag agggccggca gatctctga gcggctggtc   780
atcaccagcg agatgatcga gaacatccag tccgtgaagg cctattgttg ggaggaggcc   840
atggagaaga tgatcgagaa tctgcgccaa acagagctga agctgaccag aaaggccgcc   900
tacgtgaggt acttcaactc tagccgcctt tttttctctg gcttttttcgt ggtgttcctg   960
agcgtgctgc catacgccct gatcaagggc atcatcctgc ggaagatctt taccacaatc  1020
tccttctgca tcgtgctgag aatggccgtc acaaggcagt ttccctggcc cgtgcagacc  1080
tggtatgact ctctgggcgc catcaataag atccaggatt tcctgcagaa gcaggagtac  1140
aagcactgg agtataacct gaccacaacc gaggtggtca tggagaatgt gaccgccttc  1200
tgggaggagg gctttggcga gctgttcgag aaggccaagc agaacaataa caatcgcaag  1260
acatctaacg gcgacgatag cctgttttc agcaattttt ccctgctggg cacccccgtg  1320
ctgaaggaca tcaacttcaa gatcgagagg ggacagctgc tggcagtggc aggctccaca  1380
ggcgccggca gacctctct gctgatgatg atcatggggcg agctggagcc aagcgagggc  1440
aagatcaagc actccggccg gatctctttt tgcagccagt tctcctggat catgcccggc  1500
accatcaagg agaatatcat ctttggcgtg tcctacgatg agtacagata taggtctgtg  1560
atcaaggcct gtcagctgga ggaggacatc agcaagttcg ccgagaagga taacatcgtg  1620
ctgggcgagg gcggcatcac actgagcgga ggacagaggg caaggatctc cctggccaga  1680
gccgtgtaca ggacgccga tctgtatctg ctggacagcc cctttggcta tctggatgtg  1740
ctgaccgaga aggagatctt cgagtcctgc gtgtgcaagc tgatggccaa taagacaagg  1800
atcctggtga cctctaagat ggagcacctg aagaaggccg acaagatcct gatcctgcac  1860
gagggctcct cttacttta tggcacattc agcgagctgc agaatctgca gcctgacttc  1920
agctccaagc tgatgggctg tgactccttt gatcagttct ctgccgagag cgcaactcc  1980
atcctgacag agaccctgca cagattctct ctggagggcg acgcacccgt gagctggaca  2040
gagaccaaga agcagtcctt taagcagacc ggcgagttcg gcgagaagga gaagaattct  2100
atcctgaacc ctatcaatag cacactgcag gcccggagaa ggcagtctgt gctgaacctg  2160
atgacccaca cgtgaacca gggccagaat atccacagaa agacaaccgc cagcacaagg  2220
aaggtgtccc tggcacctca ggcaaacctg accgagctgg acatcactc ccgccggctg  2280
tctcaggaga ccggactgga gatctctgag agatcaatg aggaggatct gaaggagtgc  2340
tttttcgacg atatggagag catcccagcc gtgacaacct ggaacacata cctgcgctat  2400
atcaccgtgc acaagtccgt gatctttgtg ctgatctggt gtctggtcat cttcctggca  2460
gaggtgcag catctctggt ggtgctgtgg ctgctgggca acaccccct ccaggacaag  2520
ggcaattcta cccacagccg caacaattcc tacgccgtga tcatcacatc tacctctagc  2580
tactacgtgt tctacatcta tgtgggcgtg gccgatacac tgctggccat gggcttttc  2640
cggggcctgc cctggtgca cactgatc accgtgagca agatcctgca ccacaagatg  2700
ctgcacagcg tgctgcaggc ccctatgtcc acactgaaca ccctgaaggc cggcggcatc  2760
```

```
ctgaatcggt tttccaagga catcgccatc ctggacgatc tgctgcctct gaccatcttt  2820
gatttcatcc agctgctgct gatcgtgatc ggagcaatcg cagtggtggc cgtgctgcag  2880
ccttacatct tcgtggccac agtgccagtg atcgtggcct ttatcatgct gcgcgcctat  2940
ttcctgcaga ccagccagca gctgaagcag ctggagagcg agggccggtc ccctatcttt  3000
acacacctgg tgacctccct gaagggactg tggacactga ggccttcgg ccggcagcca   3060
tactttgaga ccctgttcca caaggccctg aacctgcaca cagccaattg gtttctgtat  3120
ctgagcaccc tgcgctggtt tcagatgcgg atcgagatga tcttcgtgat cttttttcatc 3180
gccgtgacct tcatctccat cctgacaacc ggagagggag agggaagagt gggaatcatc  3240
ctgacactgg ccatgaacat catgtctacc ctgcagtggg ccgtgaattc ctctatcgac  3300
gtggatagcc tgatgagatc tgtgagcagg gtgtttaagt tcatcgacat gcccacagag  3360
ggcaagccta caaagagcac caagccatac aagaacggcc agctgtccaa agtgatgatc  3420
atcgagaatt ctcacgtgaa gaaggacgat atctggccat ccgg                   3464

SEQ ID NO: 44         moltype = DNA  length = 173
FEATURE               Location/Qualifiers
misc_feature          1..173
                      note = Synthetic nucleic acid sequence
source                1..173
                      mol_type = other DNA
                      organism = synthetic construct
SEQUENCE: 44
actcacgggg atttccaagt ctccaccca ttgacgtcaa tgggagtttg ttttggcacc    60
aaaatcaacg ggactttcca aaatgtcgta ataaccccgc cccgttgacg caaatgggcg   120
gtaggcgtgt acggtgggag gtctatataa gcagagctcg tttagtgaac cgt          173

SEQ ID NO: 45         moltype = DNA  length = 4874
FEATURE               Location/Qualifiers
misc_feature          1..4874
                      note = Synthetic nucleic acid sequence
source                1..4874
                      mol_type = other DNA
                      organism = synthetic construct
SEQUENCE: 45
ttggccactc cctctctgcg cgctcgctcg ctcactgagg ccgggcgacc aaaggtcgcc   60
cgacgcccgg gctttgcccg ggcggcctca gtgagcgagc gagcgcgcag agagggagtg   120
gccaactcca tcactagggg ttcctgcggc cgcactcacg gggatttcca agtctccacc   180
ccattgacgt caatgggagt tgtttttggc accaaaatca cgggactttt ccaaaatgtc   240
gtaataaccc cgccccgttg acgcaaatgg gcggtaggcg tgtacggtgg gaggtctata   300
taagcagagc tcgtttagtg aaccgtcaga attctcagct gatcgaaaga gcctgctaaa   360
gcaaaaaaga agtcaccatg cagcgcagcc cactggagaa ggcaagcgtg gtgtccaagc   420
tgttctttc ctgaccagg cctatcctga ggaagggata caggcagcgg ctggagctga    480
gcgacatcta tcagatccct tctgtggaca gcgccgataa tctgtccgag aagctggaga   540
gagagtggga tagggagctg gcctctaaga agaacccaaa gctgatcaat gccctgcagg   600
gatgcttctt ttggcggttc atgttctacg gcatcttcct gtatctgggc gaggtgacca   660
aggccgtgca gccactgctg ctgggcagaa tcatcgcctc ttacgacccc gataacaagg   720
aggagaggag catcgccatc tatctgggca tcggcctgtg cctgctgttt atcgtgagga   780
cactgctgct gcacccagcc atcttcggcc tgcaccacat cggcatgcag atgagaatcg   840
ccatgttcag cctgatctac aagaagaccc tgaagctgag ctccagggtg ctggacaaga   900
tctccatcgg ccagctggtg tccctgctgt ctaacaatct gaacaagttt gatgagggac   960
tggccctggc acttcgtg tggatcgcac cactgcaggt ggccctgctg atgggcctga    1020
tctgggagct gctgcaggca agcgccttt gcggactggg cttcctgatc gtgctggcc    1080
tgttccaggc aggactggga cgcatgatga tgaagtacag agaccagagg gccggcaaga   1140
tctctgagcg gctggtcatc accagcgaga tgatcgagaa catccagtcc gtgaaggcct   1200
attgttggga ggaggccatg gagaagatga tcgagaatct cgccagaca gagctgaagc    1260
tgaccagaaa ggccgcctac gtgaggtact tcaactctag ggccttcttt ttctctggct   1320
ttttcgtggt gttcctgagc gtgctgccat acgccctgat caagggcatc atcctgcgca   1380
agatctttac cacaatctcc ttctgcatcg tgctgagaat ggccgtgaca aggcagtttc   1440
cctgggccgt gcagacctgg tatgactctc tgggcgccat caataagatc caggatttcc   1500
tgcagaagca ggagtacaag acactggagt ataacctgac cacaaccgga gtgtgcatgg   1560
agaatgtgac cgccttctgg gaggagggct ttggcgagct gttcgagaag gccaagcaga   1620
acaataacaa tcgcaagaca tctaacggcg acgatagcct gttttcagc aattttttccc    1680
tgctgggcac cccgtgctg aaggacatca acttcaagat cgagagggga cagctgctgg    1740
cagtggcagg ctccacaggc gccggcaaga cctctctgct gatgatgatc atgggcgagc   1800
tggagccaag cgagggcaag atcaagcact ccggccgagt ctctttttgc agccagttct   1860
cctggatcat gcccggcacc atcaaggaga atatcatctt tggcgtgtcc tacgatgagt   1920
acagatatag gtctgtgatc aaggcctgtc agctggagga ggacatcagc aagttcgccg   1980
agaaggataa catcgtgctg ggcgagggcg gcatcacact gagcggagga cagaggcaa    2040
ggatctccct ggccagagcc gtgtacaagg acgccgatct gtatctgctg gacagcccct   2100
ttggctatct ggatgtgctg accgagaagg agatcttcga gtcctgcgtg tgcaagctga   2160
tggccaataa gaccaaggat ctggtgacct ctaagatgga gcacctgaag aaggccgaca   2220
agatcctgat cctgcacgag ggctcctctt acttttatgg cacattcagc gagctgcaga   2280
atctgcagcc tgacttcagc tccaagctga tgggctgtga ctccttttgat cagttctctg   2340
ccgagaggcg caactccatc ctgacagaga ccctgcacag attctctctg gagggcgacg   2400
cacccgtgag ctggacagag accaagaagc agtccttaa cgagaccgac gagttcgacg   2460
agaagaggaa gaattctatc ctgaacccta tcaatagcac actgcaggcc ggagaaggcc   2520
agtctgtgct gaacctgatg acccacagcg tgaaccaggg ccagaatatc cacgaaaga   2580
caaccgccag cacaaggaag gtgtccctgg cacctcaggc aaacctgacc gagctggaca   2640
tctactcccg ccggctgtct caggagaccg gactggagat ctctgaggag atcaatgagg   2700
aggatctgaa ggagtgctt ttcgacgata tggagagcat cccagccgtg acaacctgga   2760
```

```
acacatacct gcgctatatc accgtgcaca agtccctgat ctttgtgctg atctggtgtc  2820
tggtcatctt cctggcagag gtggcagcat ctctggtggt gctgtggctg ctgggcaaca  2880
cacccctgca ggacaagggc aattctaccc acagccgcaa caattcctac gccgtgatca  2940
tcacatctac ctctagctac tacgtgttct acatctatgt gggcgtggcc gatacactgc  3000
tggccatggg ctttttccgg ggcctgcccc tggtgcacac actgatcacc gtgagcaaga  3060
tcctgcacca caagatgctg cacagcgtgc tgcaggcccc tatgtccaca ctgaacaccc  3120
tgaaggccgg cggcatcctg aatcggtttt ccaaggacat cgccatcctg gacgatctgc  3180
tgcctctgac catctttgat ttcatccagc tgctgctgat cgtgatcgga gcaatcgcag  3240
tggtggccgt gctgcagcct tacatcttcg tggccacagt gccagtgatc gtggccttta  3300
tcatgctgcg cgcctatttc ctgcagacca gccagcagct gaagcagctg gagagcgagg  3360
gccggtcccc tatctttaca cacctggtga cctccctgaa gggactgtgg acactgaggg  3420
ccttcggccg gcagccatac tttgagaccc tgttccacaa ggccctgaac ctgcacacag  3480
ccaattggtt tctgtatctg agcaccctgc gctggtttca gatgcggatc gagatgatct  3540
tcgtgatctt tttcatcgcc gtgaccttca tctccatcct gacaaccgga gagggagagg  3600
gaagagtggg aatcatcctg acactggcca tgaacatcat gtctaccctg cagtgggccg  3660
tgaattcctc tatcgacgtg gatagcctga tgagatctgt gagcagggtg tttaagttca  3720
tcgacatgcc cacagagggc aagcctacaa agagcaccaa gccatacaag aacggccagc  3780
tgtccaaagt gatgatcatc gagaattctc acgtgaagaa ggacgatatc tggccatccg  3840
gaggacagat gaccgtgaag gatctgacag ccaagtatac cgagggcggc aacgccatcc  3900
tggagaatat ctccttttct atcagccctg gacagagggt gggactgctg ggacggacag  3960
gctccggcaa gtctaccctg ctgagcgcct tcctgaggct gctgaataca gagggcgaga  4020
tccagatcga cggcgtgagc tgggattcca tcacccctgc acagtggaga aaggcctttg  4080
gcgtgatccc tcagaaggtg tttatcttct ccggcacctt caggaagaac ctggacccat  4140
acgagcagtg gtctgatcag gagatctgga aggtggccga cgaagtgggc ctgagatctg  4200
tgatcgagca gtttccaggc aagctggact tcgtgctggt ggatggagga tgcgtgctga  4260
gccacggaca caagcagctg atgtgcctgg ccaggtctgt gctgagcaag gccaagatcc  4320
tgctgctgga cgagccaagc gcccacctgg atcccgtgac ataccagatc atcagaagga  4380
ccctgaagca ggcctttgcc gattgcaccg tgatcctgtg cgagcaccgc atcgaggcca  4440
tgctggagtg ccagcagttc ctggtcatcg aggagaacaa ggtgcggcag tatgacagca  4500
tccagaagct gctgaatgag cggagcctgt ttcggcaggc catctcccc tctgatcgcg  4560
tgaagctgtt ccctcaccgg aacagctcca agtgtaagtc caagcccag atcgccgccc  4620
tgaaggagga gacagaggag gaggtgcagg acaccagact gtgaaataaa acatctttat  4680
tttcattaca tctgtgtgtt ggttttttgt gtgaacaacg gccggccgga ggaaccccta  4740
gtgatggagt tggccactcc ctctctgcgc gctcgctcgc tcactgaggc cgcccggca  4800
aagcccgggc gtcgggcgac ctttggtcgc ccggcctcag tgagcgagcg agcgcgcaga  4860
gagggagtgg ccaa                                                    4874
```

ADENO-ASSOCIATED VARIANTS, FORMULATIONS AND METHODS FOR PULMONARY DELIVERY

CROSS REFERENCE TO RELATED APPLICATIONS

This application is a continuation of International Application No. PCT/US2021/029253, filed Apr. 26, 2021, which claims the priority of U.S. Provisional Patent Application No. 63/016,246 filed Apr. 27, 2020, and U.S. Provisional Patent Application No. 63/088,432 filed Oct. 6, 2020, the entire disclosures of which are incorporated herein by reference.

SEQUENCE LISTING SUBMISSION VIA EFS-WEB

A computer readable XML file, entitled "090400-5013-US-Sequence-Listing" created on or about Sep. 23, 2022, with a file size of about 112,000 bytes, contains the sequence listing for this application and is hereby incorporated by reference in its entirety.

BACKGROUND OF THE INVENTION

Gene delivery vectors based on adeno-associated viruses (AAV) have demonstrated promise in both preclinical disease models and recently in human clinical trials for several disease targets. Vectors based on AAV are extremely safe because wild-type AAV is nonpathogenic and has no etiologic association with any known diseases. In addition, AAV offers the capability for highly efficient gene delivery and sustained transgene expression in numerous tissues, including liver, muscle, lung, retina, and brain.

AAV is a single stranded DNA virus that contains two open reading frames, rep and cap. The first gene encodes four proteins necessary for genome replication (Rep78, Rep68, Rep52, and Rep40), and the second expresses three structural proteins (VP1-3) that assemble to form the viral capsid. As its name implies, AAV is dependent upon the presence of a helper virus, such as an adenovirus or herpesvirus, for active replication. In the absence of a helper it establishes a latent state in which its genome is maintained episomally or integrated into the host chromosome. Multiple homologous primate AAV serotypes and numerous nonhuman primate serotypes have been identified. AAV2 is the best characterized as a gene delivery vehicle.

As of 2010, there were 75 ongoing clinical trials that used AAV as the gene delivery vehicle. However, the high prevalence of anti-capsid neutralizing antibodies, due to widespread exposure to numerous AAV variants and serotypes within the human population, decrease the efficacy of AAV gene therapy. This pre-existing immunity, as well as the subsequent development of immunity due to vector administration, can impede the broader implementation of AAV gene therapy. For example, to date, AAV has been most successful in clinical studies involving delivery to immune privileged regions.

Recent analysis indicated that the prevalence of anti-AAV IgG antibodies in humans was highest for AAV2 (72%) and AAV1 (67%), but AAV9 (47%), AAV6 (46%), AAV5 (40%), and AAV8 (38%) antibodies were also present in a large portion of the population studied. Several studies found that humoral immunity to the AAV capsid during gene therapy could be prevented by lowering the amount of rAAV particles delivered. Unfortunately, administration of low vector doses leads to low transduction and thus low therapeutic gene expression.

There is a need in the art for the development of novel AAV variants that are resistant to neutralization by anti-AAV antibodies.

SUMMARY OF THE INVENTION

In some embodiments, provided herein is a recombinant adeno-associated virus (rAAV) vector comprising (i) a capsid comprising a capsid protein of SEQ ID NO:12 and (ii) a nucleic acid comprising from 5' to 3': (a) an AAV2 terminal repeat (b) a promoter (c) a nucleotide sequence encoding a human cystic fibrosis transmembrane conductance regulator (CFTR) protein or a biologically active truncated CFTR protein lacking amino acids 708-759 of the human CFTR protein sequence (d) a polyadenylation sequence and (e) an AAV2 terminal repeat.

In related embodiments, the nucleotide sequence encoding human CFTR or a biologically active portion thereof encodes a native human CFTR protein and has the following sequence or a sequence at least 80%, at least 85%, at least 90%, at least 95%, at least 97%, at least 98% or at least 99% identical thereto:

(SEQ ID NO: 42)
ATGCAGAGGTCGCCTCTGGAAAAGGCCAGCGTTGT

CTCCAAACTTTTTTTCAGCTGGACCAGACCAATTT

TGAGGAAAGGATACAGACAGCGCCTGGAATTGTCA

GACATATACCAAATCCCTTCTGTTGATTCTGCTGA

CAATCTATCTGAAAAATTGGAAAGAGAATGGGATA

GAGAGCTGGCTTCAAAGAAAAATCCTAAACTCATT

AATGCCCTTCGGCGATGTTTTTTCTGGAGATTTAT

GTTCTATGGAATCTTTTTATATTTAGGGGAAGTCA

CCAAAGCAGTACAGCCTCTCTTACTGGGAAGAATC

ATAGCTTCCTATGACCCGGATAACAAGGAGGAACG

CTCTATCGCGATTTATCTAGGCATAGGCTTATGCC

TTCTCTTTATTGTGAGGACACTGCTCCTACACCCA

GCCATTTTTGGCCTTCATCACATTGGAATGCAGAT

GAGAATAGCTATGTTTAGTTTGATTTATAAGAAGA

CTTTAAAGCTGTCAAGCCGTGTTCTAGATAAAATA

AGTATTGGACAACTTGTTAGTCTCCTTTCCAACAA

CCTGAACAAATTTGATGAAGGACTTGCATTGGCAC

ATTTCGTGTGGATCGCTCCTTTGCAAGTGGCACTC

CTCATGGGGCTAATCTGGGAGTTGTTACAGGCGTC

TGCCTTCTGTGGACTTGGTTTCCTGATAGTCCTTG

CCCTTTTTCAGGCTGGGCTAGGGAGAATGATGATG

AAGTACAGAGATCAGAGAGCTGGGAAGATCAGTGA

AAGACTTGTGATTACCTCAGAAATGATTGAAAATA

TCCAATCTGTTAAGGCATACTGCTGGGAAGAAGCA

-continued

ATGGAAAAAATGATTGAAAACTTAAGACAAACAGA
ACTGAAACTGACTCGGAAGGCAGCCTATGTGAGAT
ACTTCAATAGCTCAGCCTTCTTCTTCTCAGGGTTC
TTTGTGGTGTTTTTATCTGTGCTTCCCTATGCACT
AATCAAAGGAATCATCCTCCGGAAAATATTCACCA
CCATCTCATTCTGCATTGTTCTGCGCATGGCGGTC
ACTCGGCAATTTCCCTGGGCTGTACAAACATGGTA
TGACTCTCTTGGAGCAATAAACAAAATACAGGATT
TCTTACAAAAGCAAGAATATAAGACATTGGAATAT
AACTTAACGACTACAGAAGTAGTGATGGAGAATGT
AACAGCCTTCTGGGAGGAGGGATTTGGGGAATTAT
TTGAGAAAGCAAAACAAAACAATAACAATAGAAAA
ACTTCTAATGGTGATGACAGCCTCTTCTTCAGTAA
TTTCTCACTTCTTGGTACTCCTGTCCTGAAAGATA
TTAATTTCAAGATAGAAAGAGGACAGTTGTTGGCG
GTTGCTGGATCCACTGGAGCAGGCAAGACTTCACT
TCTAATGGTGATTATGGGAGAACTGGAGCCTTCAG
AGGGTAAAATTAAGCACAGTGGAAGAATTTCATTC
TGTTCTCAGTTTTCCTGGATTATGCCTGGCACCAT
TAAAGAAAATATCATCTTTGGTGTTTCCTATGATG
AATATAGATACAGAAGCGTCATCAAAGCATGCCAA
CTAGAAGAGGACATCTCCAAGTTTGCAGAGAAAGA
CAATATAGTTCTTGGAGAAGGTGGAATCACACTGA
GTGGAGGTCAACGAGCAAGAATTTCTTTAGCAAGA
GCAGTATACAAAGATGCTGATTTGTATTTATTAGA
CTCTCCTTTTGGATACCTAGATGTTTTAACAGAAA
AAGAAATATTTGAAAGCTGTGTCTGTAAACTGATG
GCTAACAAAACTAGGATTTTGGTCACTTCTAAAAT
GGAACATTTAAAGAAAGCTGACAAAATATTAATTT
TGCATGAAGGTAGCAGCTATTTTTATGGGACATTT
TCAGAACTCCAAAATCTACAGCCAGACTTTAGCTC
AAAACTCATGGGATGTGATTCTTTCGACCAATTTA
GTGCAGAAAGAAGAAATTCAATCCTAACTGAGACC
TTACACCGTTTCTCATTAGAAGGAGATGCTCCTGT
CTCCTGGACAGAAACAAAAAAACAATCTTTTAAAC
AGACTGGAGAGTTTGGGGAAAAAAGGAAGAATTCT
ATTCTCAATCCAATCAACTCTATACGAAAATTTTC
CATTGTGCAAAAGACTCCCTTACAAATGAATGGCA
TCGAAGAGGATTCTGATGAGCCTTTAGAGAAGG
CTGTCCTTAGTACCAGATTCTGAGCAGGGAGAGGC

-continued

GATACTGCCTCGCATCAGCGTGATCAGCACTGGCC
CCACGCTTCAGGCACGAAGGAGGCAGTCTGTCCTG
AACCTGATGACACACTCAGTTAACCAAGGTCAGAA
CATTCACCGAAAGACAACAGCATCCACACGAAAAG
TGTCACTGGCCCCTCAGGCAAACTTGACTGAACTG
GATATATATTCAAGAAGGTTATCTCAAGAAACTGG
CTTGGAAATAAGTGAAGAAATTAACGAAGAAGACT
TAAAGGAGTGCTTTTTTGATGATATGGAGAGCATA
CCAGCAGTGACTACATGGAACACATACCTTCGATA
TATTACTGTCCACAAGAGCTTAATTTTTGTGCTAA
TTTGGTGCTTAGTAATTTTTCTGGCAGAGGTGGCT
GCTTCTTTGGTTGTGCTGTGGCTCCTTGGAAACAC
TCCTCTTCAAGACAAAGGGAATAGTACTCATAGTA
GAAATAACAGCTATGCAGTGATTATCACCAGCACC
AGTTCGTATTATGTGTTTTACATTTACGTGGGAGT
AGCCGACACTTTGCTTGCTATGGGATTCTTCAGAG
GTCTACCACTGGTGCATACTCTAATCACAGTGTCG
AAAATTTTACACCACAAAATGTTACATTCTGTTCT
TCAAGCACCTATGTCAACCCTCAACACGTTGAAAG
CAGGTGGGATTCTTAATAGATTCTCCAAAGATATA
GCAATTTTGGATGACCTTCTGCCTCTTACCATATT
TGACTTCATCCAGTTGTTATTAATTGTGATTGGAG
CTATAGCAGTTGTCGCAGTTTTACAACCCTACATC
TTTGTTGCAACAGTGCCAGTGATAGTGGCTTTTAT
TATGTTGAGAGCATATTTCCTCCAAACCTCACAGC
AACTCAAACAACTGGAATCTGAAGGCAGGAGTCCA
ATTTTCACTCATCTTGTTACAAGCTTAAAAGGACT
ATGGACACTTCGTGCCTTCGGACGGCAGCCTTACT
TTGAAACTCTGTTCCACAAAGCTCTGAATTTACAT
ACTGCCAACTGGTTCTTGTACCTGTCAACACTGCG
CTGGTTCCAAATGAGAATAGAAATGATTTTTGTCA
TCTTCTTCATTGCTGTTACCTTCATTTCCATTTTA
ACAACAGGAGAAGGAGAAGGAAGAGTTGGTATTAT
CCTGACTTTAGCCATGAATATCATGAGTACATTGC
AGTGGGCTGTAAACTCCAGCATAGATGTGGATAGC
TTGATGCATCTGTGAGCCGAGTCTTTAAGTTCAT
TGACATGCCAACAGAAGGTAAACCTACCAAGTCAA
CCAAACCATACAAGAATGGCCAACTCTCGAAAGTT
ATGATTATTGAGAATTCACACGTGAAGAAAGATGA
CATCTGGCCCTCAGGGGGCCAAATGACTGTCAAAG
ATCTCACAGCAAAATACACAGAAGGTGGAAATGCC

```
ATATTAGAGAACATTTCCTTCTCAATAAGTCCTGG
CCAGAGGGTGGGCCTCTTGGGAAGAACTGGATCAG
GGAAGAGTACTTTGTTATCAGCTTTTTTGAGACTA
CTGAACACTGAAGGAGAAATCCAGATCGATGGTGT
GTCTTGGGATTCAATAACTTTGCAACAGTGGAGGA
AAGCCTTTGGAGTGATACCACAGAAAGTATTTATT
TTTTCTGGAACATTTAGAAAAAACTTGGATCCCTA
TGAACAGTGGAGTGATCAAGAAATATGGAAAGTTG
CAGATGAGGTTGGGCTCAGATCTGTGATAGAACAG
TTTCCTGGGAAGCTTGACTTTGTCCTTGTGGATGG
GGGCTGTGTCCTAAGCCATGGCCACAAGCAGTTGA
TGTGCTTGGCTAGATCTGTTCTCAGTAAGGCGAAG
ATCTTGCTGCTTGATGAACCCAGTGCTCATTTGGA
TCCAGTAACATACCAAATAATTAGAAGAACTCTAA
AACAAGCATTTGCTGATTGCACAGTAATTCTCTGT
GAACACAGGATAGAAGCAATGCTGGAATGCCAACA
ATTTTTGGTCATAGAAGAGAACAAAGTGCGGCAGT
ACGATTCCATCCAGAAACTGCTGAACGAGAGGAGC
CTCTTCCGGCAAGCCATCAGCCCCTCCGACAGGGT
GAAGCTCTTTCCCCACCGGAACTCAAGCAAGTGCA
AGTCTAAGCCCCAGATTGCTGCTCTGAAAGAGGAG
ACAGAAGAAGAGGTGCAAGATACAAGGCTTTAG.
```

In preferred embodiments, the nucleotide sequence encoding human CFTR or a biologically activated truncated CFTR protein comprises the following nucleotide sequence or a sequence at least 80%, at least 85%, at least 90%, at least 95%, at least 97%, at least 98% or at least 99% identical thereto:

```
                                (SEQ ID NO: 43)
ATGCAGCGCAGCCCACTGGAGAAGGCAAGCGTGGT
GTCCAAGCTGTTCTTTTCCTGGACCAGGCCTATCC
TGAGGAAGGGATACAGGCAGCGGCTGGAGCTGAGC
GACATCTATCAGATCCCTTCTGTGGACAGCGCCGA
TAATCTGTCCGAGAAGCTGGAGAGAGAGTGGGATA
GGGAGCTGGCCTCTAAGAAGAACCCAAAGCTGATC
AATGCCCTGCGGAGATGCTTCTTTTGGCGGTTCAT
GTTCTACGGCATCTTCCTGTATCTGGGCGAGGTGA
CCAAGGCCGTGCAGCCACTGCTGCTGGGCAGAATC
ATCGCCTCTTACGACCCCGATAACAAGGAGGAGAG
GAGCATCGCCATCTATCTGGGCATCGGCCTGTGCC
TGCTGTTTATCGTGAGGACACTGCTGCTGCACCCA
GCCATCTTCGGCCTGCACCACATCGGCATGCAGAT
GAGAATCGCCATGTTCAGCCTGATCTACAAGAAGA
CCCTGAAGCTGAGCTCCAGGGTGCTGGACAAGATC
TCCATCGGCCAGCTGGTGTCCCTGCTGTCTAACAA
TCTGAACAAGTTTGATGAGGGACTGGCCCTGGCAC
ACTTCGTGTGGATCGCACCACTGCAGGTGGCCCTG
CTGATGGGCCTGATCTGGGAGCTGCTGCAGGCAAG
CGCCTTTTGCGGACTGGGCTTCCTGATCGTGCTGG
CCCTGTTCCAGGCAGGACTGGGACGCATGATGATG
AAGTACAGAGACCAGAGGGCCGGCAAGATCTCTGA
GCGGCTGGTCATCACCAGCGAGATGATCGAGAACA
TCCAGTCCGTGAAGGCCTATTGTTGGGAGGAGGCC
ATGGAGAAGATGATCGAGAATCTGCGCCAGACAGA
GCTGAAGCTGACCAGAAAGGCCGCCTACGTGAGGT
ACTTCAACTCTAGCGCCTTCTTTTTCTCTGGCTTT
TTCGTGGTGTTCCTGAGCGTGCTGCCATACGCCCT
GATCAAGGGCATCATCCTGCGGAAGATCTTTACCA
CAATCTCCTTCTGCATCGTGCTGAGAATGGCCGTG
ACAAGGCAGTTTCCCTGGGCCGTGCAGACCTGGTA
TGACTCTCTGGGCGCCATCAATAAGATCCAGGATT
TCCTGCAGAAGCAGGAGTACAAGACACTGGAGTAT
AACCTGACCACAACCGAGGTGGTCATGGAGAATGT
GACCGCCTTCTGGGAGGAGGGCTTTGGCGAGCTGT
TCGAGAAGGCCAAGCAGAACAATAACAATCGCAAG
ACATCTAACGGCGACGATAGCCTGTTTTTTCAGCAA
TTTTTCCCTGCTGGGCACCCCCGTGCTGAAGGACA
TCAACTTCAAGATCGAGAGGGGACAGCTGCTGGCA
GTGGCAGGCTCCACAGGCGCCGGCAAGACCTCTCT
GCTGATGATGATCATGGGCGAGCTGGAGCCAAGCG
AGGGCAAGATCAAGCACTCCGGCCGGATCTCTTTT
TGCAGCCAGTTCTCCTGGATCATGCCCGGCACCAT
CAAGGAGAATATCATCTTTGGCGTGTCCTACGATG
AGTACAGATATAGGTCTGTGATCAAGGCCTGTCAG
CTGGAGGAGGACATCAGCAAGTTCGCCGAGAAGGA
TAACATCGTGCTGGGCGAGGGCGGCATCACACTGA
GCGGAGGACAGAGGGCAAGGATCTCCCTGGCCAGA
GCCGTGTACAAGGACGCCGATCTGTATCTGCTGGA
CAGCCCCTTTGGCTATCTGGATGTGCTGACCGAGA
AGGAGATCTTCGAGTCCTGCGTGTGCAAGCTGATG
GCCAATAAGACAAGGATCCTGGTGACCTCTAAGAT
GGAGCACCTGAAGAAGGCCGACAAGATCCTGATCC
```

```
TGCACGAGGGCTCCTCTTACTTTTATGGCACATTC

AGCGAGCTGCAGAATCTGCAGCCTGACTTCAGCTC

CAAGCTGATGGGCTGTGACTCCTTTGATCAGTTCT

CTGCCGAGAGGCGCAACTCCATCCTGACAGAGACC

CTGCACAGATTCTCTCTGGAGGGCGACGCACCCGT

GAGCTGGACAGAGACCAAGAAGCAGTCCTTTAAGC

AGACCGGCGAGTTCGGCGAGAAGAGGAAGAATTCT

ATCCTGAACCCTATCAATAGCACACTGCAGGCCCG

GAGAAGGCAGTCTGTGCTGAACCTGATGACCCACA

GCGTGAACCAGGGCCAGAATATCCACAGAAAGACA

ACCGCCAGCACAAGGAAGGTGTCCCTGGCACCTCA

GGCAAACCTGACCGAGCTGGACATCTACTCCCGCC

GGCTGTCTCAGGAGACCGGACTGGAGATCTCTGAG

GAGATCAATGAGGAGGATCTGAAGGAGTGCTTTTT

CGACGATATGGAGAGCATCCCAGCCGTGACAACCT

GGAACACATACCTGCGCTATATCACCGTGCACAAG

TCCCTGATCTTTGTGCTGATCTGGTGTCTGGTCAT

CTTCCTGGCAGAGGTGGCAGCATCTCTGGTGGTGC

TGTGGCTGCTGGGCAACACACCCCTGCAGGACAAG

GGCAATTCTACCCACAGCCGCAACAATTCCTACGC

CGTGATCATCACATCTACCTCTAGCTACTACGTGT

TCTACATCTATGTGGGCGTGGCCGATACACTGCTG

GCCATGGGCTTTTTCCGGGGCCTGCCCCTGGTGCA

CACACTGATCACCGTGAGCAAGATCCTGCACCACA

AGATGCTGCACAGCGTGCTGCAGGCCCCTATGTCC

ACACTGAACACCCTGAAGGCCGGCGGCATCCTGAA

TCGGTTTTCCAAGGACATCGCCATCCTGGACGATC

TGCTGCCTCTGACCATCTTTGATTTCATCCAGCTG

CTGCTGATCGTGATCGGAGCAATCGCAGTGGTGGC

CGTGCTGCAGCCTTACATCTTCGTGGCCACAGTGC

CAGTGATCGTGGCCTTTATCATGCTGCGCGCCTAT

TTCCTGCAGACCAGCCAGCAGCTGAAGCAGCTGGA

GAGCGAGGGCCGGTCCCCTATCTTTACACACCTGG

TGACCTCCCTGAAGGGACTGTGGACACTGAGGGCC

TTCGGCCGGCAGCCATACTTTGAGACCCTGTTCCA

CAAGGCCCTGAACCTGCACACAGCCAATTGGTTTC

TGTATCTGAGCACCCTGCGCTGGTTTCAGATGCGG

ATCGAGATGATCTTCGTGATCTTTTTCATCGCCGT

GACCTTCATCTCCATCCTGACAACCGGAGAGGGAG

AGGGAAGAGTGGGAATCATCCTGACACTGGCCATG

AACATCATGTCTACCCTGCAGTGGGCCGTGAATTC

CTCTATCGACGTGGATAGCCTGATGAGATCTGTGA

GCAGGGTGTTTAAGTTCATCGACATGCCCACAGAG

GGCAAGCCTACAAAGAGCACCAAGCCATACAAGAA

CGGCCAGCTGTCCAAAGTGATGATCATCGAGAATT

CTCACGTGAAGAAGGACGATATCTGGCCATCCGG
```

SEQ ID NO:43 is a nucleotide sequence that has been codon optimized for expression in humans and encodes a biologically active truncated human CFTR protein lacking amino acids 708-759. In some embodiments, provided herein is an isolated nucleic acid comprising the nucleotide sequence of SEQ ID NO:43 or a sequence at least 80%, at least 85%, at least 90%, at least 95%, at least 97%, at least 98% or at least 99% identical thereto, optionally wherein the nucleotide sequence is operably linked to an expression control sequence. Also provided herein are plasmids and vectors comprising the nucleic acid sequence of SEQ ID NO:43 or a sequence at least or a sequence at least 80%, at least 85%, at least 90%, at least 95%, at least 97%, at least 98% or at least 99% identical thereto and host cells comprising such plasmids and vectors. Also provided herein is the use of a nucleic acid comprising the nucleotide sequence of SEQ ID NO:43 or a sequence at least 80%, at least 85%, at least 90%, at least 95%, at least 97%, at least 98% or at least 99% identical thereto, optionally wherein the nucleotide sequence is operably linked to an expression control sequence, for the treatment of cystic fibrosis or a lung disease associated therewith as herein described, or for use in the manufacture of a medicament for treating cystic fibrosis or a lung disease associated therewith.

In some aspects, the promoter is a constitutive promoter, optionally a truncated cytomegalovirus immediate/early (CMVie) enhancer/promoter and is operably linked to the nucleotide sequence encoding the human CFTR or biologically active portion thereof.

In other aspects, the promoter is a tissue specific promoter, preferably wherein the promoter directs preferential expression of the nucleic acid in a lung cell, and is operably linked to the nucleotide sequence encoding the human CFTR or biologically active portion thereof.

In preferred embodiments, the promoter is a truncated CMVie promoter and is operably linked to the nucleotide sequence encoding human CFTR or a biologically active portion thereof. In a particularly preferred embodiment, the CMVie promoter is CMV173 having the following sequence or a sequence at least 90%, at least 95%, at least 98% or at least 99% identical thereto:

```
                                      (SEQ ID NO: 44)
ACTCACGGGGATTTCCAAGTCTCCACCCCATTGAC

GTCAATGGGAGTTTGTTTTGGCACCAAAATCAACG

GGACTTTCCAAAATGTCGTAATAACCCCGCCCCGT

TGACGCAAATGGGCGGTAGGCGTGTACGGTGGGAG

GTCTATATAAGCAGAGCTCGTTTAGTGAACCGT
```

In a particularly preferred embodiment, the rAAV vector comprises (i) a capsid comprising a capsid protein of SEQ ID NO:12 and (ii) a nucleic acid comprising from 5' to 3': (a) an AAV2 terminal repeat (b) a promoter (c) a nucleotide sequence encoding a human cystic fibrosis transmembrane conductance regulator (CFTR) protein or a biologically active truncated CFTR protein lacking amino acids 708-759 of the human CFTR protein sequence (d) a polyadenylation sequence and (e) an AAV2 terminal repeat, wherein the nucleic acid comprises from 5' to 3' the following sequence or a sequence at least 80%, at least 85%, at least 90%, at least 95%, at least 97%, at least 98%, or at least 99% identical thereto:

```
(SEQ ID NO: 45)
TTGGCCACTCCCTCTCTGCGCGCTCGCTCGCTCAC

TGAGGCCGGGCGACCAAAGGTCGCCCGACGCCCGG

GCTTTGCCCGGGCGGCCTCAGTGAGCGAGCGAGCG

CGCAGAGAGGGAGTGGCCAACTCCATCACTAGGGG

TTCCTGCGGCCGCACTCACGGGGATTTCCAAGTCT

CCACCCCATTGACGTCAATGGGAGTTTGTTTTGGC

ACCAAAATCAACGGGACTTTCCAAAATGTCGTAAT

AACCCCGCCCCGTTGACGCAAATGGGCGGTAGGCG

TGTACGGTGGGAGGTCTATATAAGCAGAGCTCGTT

TAGTGAACCGTCAGAATTCTCGAGTGATCGAAAGA

GCCTGCTAAAGCAAAAAAGAAGTCACCATGCAGCG

CAGCCCACTGGAGAAGGCAAGCGTGGTGTCCAAGC

TGTTCTTTTCCTGGACCAGGCCTATCCTGAGGAAG

GGATACAGGCAGCGGCTGGAGCTGAGCGACATCTA

TCAGATCCCTTCTGTGGACAGCGCCGATAATCTGT

CCGAGAAGCTGGAGAGAGAGTGGGATAGGGAGCTG

GCCTCTAAGAAGAACCCAAAGCTGATCAATGCCCT

GCGGAGATGCTTCTTTTGGCGGTTCATGTTCTACG

GCATCTTCCTGTATCTGGGCGAGGTGACCAAGGCC

GTGCAGCCACTGCTGCTGGGCAGAATCATCGCCTC

TTACGACCCCGATAACAAGGAGGAGAGGAGCATCG

CCATCTATCTGGGCATCGGCCTGTGCCTGCTGTTT

ATCGTGAGGACACTGCTGCTGCACCCAGCCATCTT

CGGCCTGCACCACATCGGCATGCAGATGAGAATCG

CCATGTTCAGCCTGATCTACAAGAAGACCCTGAAG

CTGAGCTCCAGGGTGCTGGACAAGATCTCCATCGG

CCAGCTGGTGTCCCTGCTGTCTAACAATCTGAACA

AGTTTGATGAGGGACTGGCCCTGGCACACTTCGTG

TGGATCGCACCACTGCAGGTGGCCCTGCTGATGGG

CCTGATCTGGGAGCTGCTGCAGGCAAGCGCCTTTT

GCGGACTGGGCTTCCTGATCGTGCTGGCCCTGTTC

CAGGCAGGACTGGGACGCATGATGATGAAGTACAG

AGACCAGAGGGCCGGCAAGATCTCTGAGCGGCTGG

TCATCACCAGCGAGATGATCGAGAACATCCAGTCC

GTGAAGGCCTATTGTTGGGAGGAGGCCATGGAGAA
```

```
-continued
GATGATCGAGAATCTGCGCCAGACAGAGCTGAAGC

TGACCAGAAAGGCCGCCTACGTGAGGTACTTCAAC

TCTAGCGCCTTCTTTTTCTCTGGCTTTTTCGTGGT

GTTCCTGAGCGTGCTGCCATACGCCCTGATCAAGG

GCATCATCCTGCGGAAGATCTTTACCACAATCTCC

TTCTGCATCGTGCTGAGAATGGCCGTGACAAGGCA

GTTTCCCTGGGCCGTGCAGACCTGGTATGACTCTC

TGGGCGCCATCAATAAGATCCAGGATTTCCTGCAG

AAGCAGGAGTACAAGACACTGGAGTATAACCTGAC

CACAACCGAGGTGGTCATGGAGAATGTGACCGCCT

TCTGGGAGGAGGGCTTTGGCGAGCTGTTCGAGAAG

GCCAAGCAGAACAATAACAATCGCAAGACATCTAA

CGGCGACGATAGCCTGTTTTTCAGCAATTTTTCCC

TGCTGGGCACCCCCGTGCTGAAGGACATCAACTTC

AAGATCGAGAGGGGACAGCTGCTGGCAGTGGCAGG

CTCCACAGGCGCCGGCAAGACCTCTCTGCTGATGA

TGATCATGGGCGAGCTGGAGCCAAGCGAGGGCAAG

ATCAAGCACTCCGGCCGGATCTCTTTTTGCAGCCA

GTTCTCCTGGATCATGCCCGGCACCATCAAGGAGA

ATATCATCTTTGGCGTGTCCTACGATGAGTACAGA

TATAGGTCTGTGATCAAGGCCTGTCAGCTGGAGGA

GGACATCAGCAAGTTCGCCGAGAAGGATAACATCG

TGCTGGGCGAGGGCGGCATCACACTGAGCGGAGGA

CAGAGGGCAAGGATCTCCCTGGCCAGAGCCGTGTA

CAAGGACGCCGATCTGTATCTGCTGGACAGCCCCT

TTGGCTATCTGGATGTGCTGACCGAGAAGGAGATC

TTCGAGTCCTGCGTGTGCAAGCTGATGGCCAATAA

GACAAGGATCCTGGTGACCTCTAAGATGGAGCACC

TGAAGAAGGCCGACAAGATCCTGATCCTGCACGAG

GGCTCCTCTTACTTTTATGGCACATTCAGCGAGCT

GCAGAATCTGCAGCCTGACTTCAGCTCCAAGCTGA

TGGGCTGTGACTCCTTTGATCAGTTCTCTGCCGAG

AGGCGCAACTCCATCCTGACAGAGACCCTGCACAG

ATTCTCTCTGGAGGGCGACGCACCCGTGAGCTGGA

CAGAGACCAAGAAGCAGTCCTTTAAGCAGACCGGC

GAGTTCGGCGAGAAGAGGAAGAATTCTATCCTGAA

CCCTATCAATAGCACACTGCAGGCCCGGAGAAGGC

AGTCTGTGCTGAACCTGATGACCCACAGCGTGAAC

CAGGGCCAGAATATCCACAGAAAGACAACCGCCAG

CACAAGGAAGGTGTCCCTGGCACCTCAGGCAAACC
```

```
TGACCGAGCTGGACATCTACTCCCGCCGGCTGTCT
CAGGAGACCGGACTGGAGATCTCTGAGGAGATCAA
TGAGGAGGATCTGAAGGAGTGCTTTTTCGACGATA
TGGAGAGCATCCCAGCCGTGACAACCTGGAACACA
TACCTGCGCTATATCACCGTGCACAAGTCCCTGAT
CTTTGTGCTGATCTGGTGTCTGGTCATCTTCCTGG
CAGAGGTGGCAGCATCTCTGGTGGTGCTGTGGCTG
CTGGGCAACACACCCCTGCAGGACAAGGGCAATTC
TACCCACAGCCGCAACAATTCCTACGCCGTGATCA
TCACATCTACCTCTAGCTACTACGTGTTCTACATC
TATGTGGGCGTGGCCGATACACTGCTGGCCATGGG
CTTTTTCCGGGGCCTGCCCCTGGTGCACACACTGA
TCACCGTGAGCAAGATCCTGCACCACAAGATGCTG
CACAGCGTGCTGCAGGCCCCTATGTCCACACTGAA
CACCCTGAAGGCCGGCGGCATCCTGAATCGGTTTT
CCAAGGACATCGCCATCCTGGACGATCTGCTGCCT
CTGACCATCTTTGATTTCATCCAGCTGCTGCTGAT
CGTGATCGGAGCAATCGCAGTGGTGGCCGTGCTGC
AGCCTTACATCTTCGTGGCCACAGTGCCAGTGATC
GTGGCCTTTATCATGCTGCGCGCCTATTTCCTGCA
GACCAGCCAGCAGCTGAAGCAGCTGGAGAGCGAGG
GCCGGTCCCCTATCTTTACACACCTGGTGACCTCC
CTGAAGGGACTGTGGACACTGAGGGCCTTCGGCCG
GCAGCCATACTTTGAGACCCTGTTCCACAAGGCCC
TGAACCTGCACACAGCCAATTGGTTTCTGTATCTG
AGCACCCTGCGCTGGTTTCAGATGCGGATCGAGAT
GATCTTCGTGATCTTTTTCATCGCCGTGACCTTCA
TCTCCATCCTGACAACCGGAGAGGGAGAGGGAAGA
GTGGGAATCATCCTGACACTGGCCATGAACATCAT
GTCTACCCTGCAGTGGGCCGTGAATTCCTCTATCG
ACGTGGATAGCCTGATGAGATCTGTGAGCAGGGTG
TTTAAGTTCATCGACATGCCCACAGAGGGCAAGCC
TACAAAGAGCACCAAGCCATACAAGAACGGCCAGC
TGTCCAAAGTGATGATCATCGAGAATTCTCACGTG
AAGAAGGACGATATCTGGCCATCCGGAGGACAGAT
GACCGTGAAGGATCTGACAGCCAAGTATACCGAGG
GCGGCAACGCCATCCTGGAGAATATCTCCTTTTCT
ATCAGCCCTGGACAGAGGGTGGGACTGCTGGACG
GACAGGCTCCGGCAAGTCTACCCTGCTGAGCGCCT
TCCTGAGGCTGCTGAATACAGAGGGCGAGATCCAG
ATCGACGGCGTGAGCTGGGATTCCATCACCCTGCA
GCAGTGGAGAAAGGCCTTTGGCGTGATCCCTCAGA
AGGTGTTTATCTTCTCCGGCACCTTCAGGAAGAAC
CTGGACCCATACGAGCAGTGGTCTGATCAGGAGAT
CTGGAAGGTGGCCGACGAAGTGGGCCTGAGATCTG
TGATCGAGCAGTTTCCAGGCAAGCTGGACTTCGTG
CTGGTGGATGGAGGATGCGTGCTGAGCCACGGACA
CAAGCAGCTGATGTGCCTGGCCAGGTCTGTGCTGA
GCAAGGCCAAGATCCTGCTGCTGGACGAGCCAAGC
GCCCACCTGGATCCCGTGACATACCAGATCATCAG
AAGGACCCTGAAGCAGGCCTTTGCCGATTGCACCG
TGATCCTGTGCGAGCACCGCATCGAGGCCATGCTG
GAGTGCCAGCAGTTCCTGGTCATCGAGGAGAACAA
GGTGCGGCAGTATGACAGCATCCAGAAGCTGCTGA
ATGAGCGGAGCCTGTTTCGGCAGGCCATCTCCCCC
TCTGATCGCGTGAAGCTGTTCCCTCACCGGAACAG
CTCCAAGTGTAAGTCCAAGCCCCAGATCGCCGCCC
TGAAGGAGGAGACAGAGGAGGAGGTGCAGGACACC
AGACTGTGAAATAAAACATCTTTATTTTCATTACA
TCTGTGTGTTGGTTTTTTGTGTGAACAACGGCCGG
CCGGAGGAACCCCTAGTGATGGAGTTGGCCACTCC
CTCTCTGCGCGCTCGCTCGCTCACTGAGGCCGCCC
GGGCAAAGCCCGGGCGTCGGGCGACCTTTGGTCGC
CCGGCCTCAGTGAGCGAGCGAGCGCGCAGAGAGGG
AGTGGCCAA
```

A nucleic acid having the nucleotide sequence of SEQ ID NO:45 comprises from 5' to 3': (a) an AAV2 terminal repeat (b) a CMV173 promoter of SEQ ID NO:44 (c) a codon optimized nucleotide sequence encoding a biologically active truncated human CFTR protein lacking amino acids 708-759 of SEQ ID NO:43 (d) a polyadenylation sequence and (e) an AAV2 terminal repeat.

Also provided herein are methods for treating cystic fibrosis in a subject in need thereof, comprising administering to the subject a therapeutically effective amount of an infectious rAAV comprising (i) a capsid comprising a capsid protein of SEQ ID NO:12 and (ii) a nucleic acid comprising a nucleotide sequence encoding a human cystic fibrosis transmembrane conductance regulator (CFTR) protein or a biologically active truncated CFTR protein lacking amino acids 708-759 of the human CFTR protein sequence operably linked to a promoter. In preferred embodiments, the nucleotide sequence encoding CFTR has the sequence of SEQ ID NO: 43 and/or the promoter has the sequence of SEQ ID NO: 44 and/or the nucleic acid comprises the sequence of SEQ ID NO:45. In some aspects, the subject is administered an amount of the rAAV effective to ameliorate one or more characteristics of cystic fibrosis, nonlimiting examples of which include upper and lower airway inflammation, aberrant epithelia cytokine signaling and elevated IgE levels.

In other aspects, provided herein are methods for treating lung disease associated with cystic fibrosis, including but not limited to upper airway disease, lower airway disease, nasopharyngeal disease, sinusitis and/or salivary disease associated with cystic fibrosis, comprising administering to the subject a therapeutically effective amount of an infectious rAAV comprising (i) a capsid comprising a capsid protein of SEQ ID NO:12 and (ii) a nucleic acid comprising a nucleotide sequence encoding a human cystic fibrosis transmembrane conductance regulator (CFTR) protein or a biologically active truncated CFTR protein lacking amino acids 708-759 of the human CFTR protein sequence operably linked to a promoter. In preferred embodiments, the nucleotide sequence encoding CFTR has the sequence of SEQ ID NO: 43 and/or the promoter has the sequence of SEQ ID NO: 44 and/or the nucleic acid comprises the sequence of SEQ ID NO:45.

rAAV gene therapy vectors of the present invention comprising a capsid comprising a capsid protein of SEQ ID NO:12 and nucleic acid sequences encoding CFTR or a biologically active portion thereof (e.g. comprising a nucleic acid comprising the nucleotide sequence of SEQ ID NO: 43 optionally linked to a promoter of SEQ ID NO: 44 and/or comprising the nucleotide sequence of SEQ ID NO:45) may be administered to a patient by a variety of means to achieve and maintain a therapeutically effective level of CFTR or a portion thereof for the treatment of cystic fibrosis or lung disease associated therewith.

In some aspects, the infectious rAAV is administered to a subject with cystic fibrosis in one or more dosages, each dosage comprising between about $1\times10^{13}$ to about $1\times10^{15}$ vector genomes (vg), about $1\times10^{13}$ to about $1\times10^{14}$ vg, between about $1\times10^{14}$ and about $1\times10^{15}$ vg, or between about $1\times10^{15}$ and about $5\times10^{15}$ vg. In some preferred aspects, each dosage comprises about $1\times10^{14}$ vg or about $1\times10^{15}$ vg of the rAAV.

In some aspects, the treatment comprises no more than a single dose administration to the subject and is effective to achieve a durable and maintained therapeutic concentration of CFTR or biologically active portion thereof. In related aspects, the treatment comprises no more than a single dose administration by inhalation of about $1\times10^{13}$ to about $1\times10^{15}$ plaque forming units (pfu), virus particles (vp) or virus genomes (vg) of rAAV comprising a capsid protein of SEQ ID NO:12 and a nucleic acid of SEQ ID NO:45 to a human with cystic fibrosis. In other aspects, the dosage treatment may be a multiple dose schedule.

Methods pertaining to the administration of AAV vectors to humans have been previously described by Kay et al. (2000, Nat Genet 24:257-261), the entire content of which is incorporated herein by reference. In some preferred embodiments, the infectious rAAV is administered to the subject by pulmonary, endobronchial, intranasal, intratracheal, and/or intrabronchial administration. In some preferred embodiments, the infectious rAAV is administered using a nebulizer.

In related aspects, provided herein is an infectious rAAV comprising (i) a capsid comprising a capsid protein of SEQ ID NO:12 and (ii) a nucleic acid comprising a nucleotide sequence encoding a human cystic fibrosis transmembrane conductance regulator (CFTR) protein or a biologically active truncated CFTR protein lacking amino acids 708-759 of the human CFTR protein sequence operably linked to a promoter for use in the treatment of cystic fibrosis or for use in the manufacture of a medicament for the treatment of cystic fibrosis. In some preferred embodiments, the nucleotide sequence encoding the human CFTR protein comprises or consists of the sequence of SEQ ID NO:43 or a sequence at least 80%, at least 85%, at least 90%, at least 95%, at least 97%, at least 98% or at least 99% identical thereto, operably linked to a promoter comprising the sequence of SEQ ID NO:44 or a sequence at least 80%, at least 85%, at least 90%, at least 95%, at least 97%, at least 98% or at least 99% identical thereto. In particularly preferred embodiments, the rAAV comprises a nucleic acid comprising or consisting of the nucleotide sequence of SEQ ID NO:45.

In other embodiments, provided herein is a pharmaceutical composition suitable for inhalation comprising (i) an rAAV infectious rAAV comprising (a) a capsid comprising a capsid protein of SEQ ID NO:12 and (b) a nucleic acid comprising a nucleotide sequence encoding one or more gene product(s) in (ii) a buffer comprising about 10 mM to about 50 mM citrate, about 70 mM to about 150 mM NaCl and optionally a surfactant, preferably a non-ionic surfactant such as Pluronic F-68, more preferably about 0.005% Pluronic F68, and having pH of between 5 and 7, preferably having a pH of about 6.0. In some preferred aspects, the pharmaceutical composition comprises about 20 mM to about 50 mM citrate, about 85 mM to about 125 mM NaCl and about 0.005% Pluronic F68 and has a pH of about 6.0. In some particularly preferred aspects, the pharmaceutical composition comprises about 20 mM citrate, about 125 mM NaCl and about 0.005% Pluronic F68 and has a pH of about 6.0. In preferred embodiments, the pharmaceutical composition comprises an rAAV comprising (a) a capsid comprising a capsid protein of SEQ ID NO:12 and (b) a nucleic acid comprising a nucleotide sequence encoding a human cystic fibrosis transmembrane conductance regulator (CFTR) protein or a biologically active truncated CFTR protein lacking amino acids 708-759 of the human CFTR protein sequence operably linked to a promoter. In related embodiments, the rAAV comprises a nucleic acid comprising or consisting of the nucleotide sequence of SEQ ID NO:45.

In some aspects, the pharmaceutical composition comprises between from $10^{11}$ to $10^{14}$ vector genomes (vg) per ml. In some preferred embodiments, the pharmaceutical composition comprises from about $1\times10^{13}$ to about $9\times10^{13}$ vg/ml, preferably from about $2\times10^{13}$ to $6\times10^{13}$ vg/ml. In other preferred embodiments, the pharmaceutical comprises about $1\times10^{13}$ vg/ml, about $2\times10^{13}$ vg/ml, about $3\times10^{13}$ vg/ml, about $4\times10^{13}$ vg/ml, about $5\times10^{13}$ vg/ml, about $6\times10^{13}$ vg/ml, about $7\times10^{13}$ vg/ml, about $8\times10^{13}$ vg/ml, or about $9\times10^{13}$ vg/ml. In a particularly preferred embodiment, the pharmaceutical composition comprises about $2\times10^{13}$ vg/ml to about $5\times10^{13}$ vg/ml.

In some embodiments, the pharmaceutical composition is formulated as a liquid/suspension suitable for aerosolized delivery. In related embodiments, the pharmaceutical composition is formulated as an aerosol and/or is an inhaled dosage form.

Also provided herein are methods of delivering a heterologous nucleic acid to a lung cell comprising contacting the lung cell with an rAAV virion comprising (i) a capsid comprising a capsid protein of SEQ ID NO:12 and (ii) a heterologous nucleic acid comprising a nucleotide sequence encoding one or more gene products. In some embodiments, the heterologous nucleic acid encodes a protein and/or short interfering RNA. In some preferred embodiments, the lung cell is any cell of the lung or trachea. In other preferred embodiments, the lung cell is an airway epithelial cell, including but not limited to an alveolar epithelium cell, a bronchial (primary, secondary or tertiary) epithelial cell or a tracheal epithelial cell. In some preferred aspects, the lung cell is a ciliated airway epithelial cell. In some preferred aspects, the lung cell is a lung alveolar epithelial type 1 (AECI) or type 2 (AECII) cell. In other embodiments, the lung cell is a smooth muscle or endothelial cell. In other embodiments, the lung cell is a basal cell, goblet cell or oocyte. In particularly preferred embodiments, the rAAV comprises a nucleic acid comprising or consisting of the nucleotide sequence of SEQ ID NO:45.

Also provided herein are methods of delivering a heterologous nucleic acid to the lung of a subject (e.g. a human subject) comprising administering to the subject an rAAV virion comprising (i) a capsid comprising a capsid protein of SEQ ID NO:12 and (ii) a heterologous nucleic acid comprising a nucleotide sequence encoding one or more gene products. In some embodiments, the heterologous nucleic acid encodes a protein and/or short interfering RNA. In related embodiments, methods of delivering a heterologous nucleic acid to the upper airway, nasopharynx, sinuses, mouth/buccal region and/or salivary glands of a subject (e.g. a human subject) comprising administering to the subject an rAAV virion comprising (i) a capsid comprising a capsid protein of SEQ ID NO:12 and (ii) a heterologous nucleic acid comprising a nucleotide sequence encoding one or more gene products. In related aspects the rAAV or pharmaceutical composition comprising same is administered to the subject by pulmonary, endobronchial, intranasal, intratracheal, and/or intrabronchial administration. In particularly preferred embodiments, the rAAV comprises a nucleic acid comprising or consisting of the nucleotide sequence of SEQ ID NO:45.

Also provided herein are methods for treating a pulmonary disease, comprising administering to a subject in need thereof, a therapeutically effective amount of a recombinant AAV (rAAV) comprising (i) a capsid comprising a capsid protein of SEQ ID NO:12 and (ii) a heterologous nucleic acid comprising nucleotide sequence encoding one or more gene products, the one or more gene products operably linked to a promoter. In some aspects, the heterologous nucleic acid comprises nucleotide sequence encoding multiple gene products, in which case expression of the multiple (e.g. 2) gene products can be mediated by multiple (e.g. 2) independent promoters or may be mediated by a single promoter, with the multiple transgenes separated by an internal ribosome entry site (IRES) or a 2A peptide sequence. In preferred embodiments, the heterologous nucleic acid encodes a therapeutic protein and/or a therapeutic short interfering RNA. In related aspects, the gene product(s) delivered by the rAAV decreases the level of a hindering gene product and/or introduces or supplements the level of a supporting gene product. In particularly preferred embodiments, the rAAV comprises a nucleic acid comprising or consisting of the nucleotide sequence of SEQ ID NO:45. In other preferred embodiments, the rAAV comprises a nucleic acid comprising nucleotide sequence encoding an alpha-1-antitrypsin.

In some aspects, the pulmonary disease is selected from pulmonary arterial hypertension, pulmonary hypertension, lung cancer (primary, secondary and metastatic), surfactant deficiency, viral and/or bacterial infection, cystic fibrosis, acute bronchitis, pneumonia (including viral, bacterial, and fungal pneumonia), respiratory tract infections (including pharyngitis, croup, *aspergillus*, coocidiomycosis, hantavirus pulmonary syndrome, and histoplasmosis), chemical and hypersensitivity pneumonitis, tuberculosis and other mycobacterial infections (including but not limited to *Mycobacterium avium*), sarcoidosis, respiratory syncytial virus, pulmonary edema, acute respiratory distress syndrome (ARDS), pneumoconiosis (including black lung disease, asbestosis, and silicosis), interstitial lung disease (including sarcoidosis and autoimmune disease), pulmonary embolism, pleural effusion, pleuritis, mesothelioma, pneumothorax, acute bronchitis, bronchiolitis (including bronchiolitis obliterans), sudden infant death syndrome, sleep apnoea, bronchiectasis, bronchopulmonary dysplasia, cryptogenic organizing pneumonia, E-cigarette or vaping use associated lung injury (EVALI), Middle Eastern Respiratory Syndrome (MERS), primary ciliary dyskinesia, Severe Acute Respiratory Syndrome (SARS), alpha-1-antitrypsin deficiency, asthma, interstitital lung disease, and COVID-19 (Coronavirus Disease 2019). In other aspects, the pulmonary disease is chronic obstructive pulmonary disease (COPD) or idiopathic pulmonary fibrosis (IPF). In related aspects, a method of treating COVID-19 is provided comprising administering to a subject in need thereof, a therapeutically effective amount of a recombinant AAV (rAAV) comprising (i) a capsid comprising a capsid protein of SEQ ID NO:12 and (ii) a heterologous nucleic acid comprising a nucleotide sequence encoding one or more gene products operably linked to one or more promoters or a pharmaceutical composition comprising the rAAV, wherein the gene product(s) knocks-down, modifies and/or overexpresses a viral gene product or host cell gene to reduce or eliminate viral pathogenicicty or replication in either the lung or nasopharyx and/or expresses a neutralizing antibody against an epitope on the virus.

In some aspects, genes that may be targeted for the treatment of IPF include, but are not limited to, SFTPA1 (surfactant A1) and Caveolin-1. Genes that may be targeted for the treatment of COPD include, but are not limited to alpha-1-antitrypsin, alpha-1-antichymotrypsin, alpha-1-macroglobulin, matrix metalloproteinase 1 (MMP1), matrix metalloproteinase 12 (MMP12), microsomal epoxide hydrolyase, CYP1A1, Glutathione S-transferase, heme oxygenase-1, TGF-beta-1, TNF-alpha, IL-1 complex, IL-8, IL-13, human leukocyte antigen (HLA-B7 and Bw16), vitamin D binding protein, and beta-2-adrenergic receptor.

In related aspects, the rAAV or pharmaceutical composition is administered by pulmonary, endobronchial, intranasal, intratracheal, and/or intrabronchial administration to treat a pulmonary disease in a subject need thereof. In some preferred embodiments, the infectious rAAV is administered using a nebulizer.

In other aspects, at least one dose of about $10^{12}$ to $10^{14}$ vector genomes (vg)/kg of the rAAV is administered to the subject to treat a pulmonary disease. In related aspects, the subject is administered about $1\times10^{11}$ to about $1\times10^{14}$ vg/kg, about $1\times10^{12}$ to about $9\times10^{13}$ vg/kg, about $1\times10^{12}$ vg/kg to about $9\times10^{12}$ vg/kg, preferably about $2\times10^{12}$ vg/kg to about $3\times10^{12}$ vg/kg, more preferably about $2.6\times10^{12}$ vg/kg, about $2.7\times10^{12}$ vg/kg, about $2.8\times10^{12}$ vg/kg, about $2.9\times10^{12}$ vg/kg about $3.0\times10^{12}$ vg/kg or about $3.1\times10^{12}$ vg/kg. In preferred embodiments, the subject is administered one or more doses of in one or more dosages, each dosage comprising between about $1\times10^{13}$ to about $1\times10^{15}$ vector genomes (vg), about $1\times10^{13}$ to about $1\times10^{14}$ vg, between about $1\times10^{14}$ and about $1\times10^{15}$ vg, or between about $1\times10^{15}$ and about $5\times10^{15}$ vg of the rAAV. In some preferred aspects, each dosage comprises about $1\times10^{14}$ vg or about $1\times10^{15}$ vg of the rAAV.

The present disclosure further provides infectious recombinant adeno-associated virus (rAAV) virions that comprise a variant capsid protein and a heterologous nucleic acid. The present disclosure further provides the variant adeno-associated virus (AAV) capsid proteins (and/or a nucleic acid encoding the variant AAV capsid proteins), which confer to an infectious rAAV virion an increased resistance to human AAV neutralizing antibodies. The present disclosure further provides host cells comprising an infectious rAAV virion and/or a nucleic acid encoding a subject variant AAV capsid protein. The present disclosure further provides libraries of the above virions, capsid proteins, nucleic acids, and/or host cells; where the variant AAV capsid protein of at least one member of the library comprises an amino acid sequence having at least one amino acid substitution relative to the amino acid sequence set forth in one of SEQ ID NOs: 10-13 and 26-33.

The present disclosure further provides methods of delivering a heterologous nucleic acid to a target cell where the target cell is contacted with a subject infectious rAAV virion. The present disclosure further provides methods of delivering a gene product to an individual, the methods generally involving administering an effective amount of a subject rAAV virion to an individual in need thereof. Also provided herein are compositions and kits for practicing the subject methods.

Features of the present disclosure include an infectious recombinant adeno-associated virus (rAAV) virion comprising (a) a variant adeno-associated virus (AAV) capsid protein comprising an amino acid sequence having at least about 90% amino acid sequence identity to the amino acid sequence set forth in one of SEQ ID NOs: 11-13 and 26-33; and (b) a heterologous nucleic acid. In some cases, the variant AAV capsid protein comprises an amino acid sequence having at least about 95% amino acid sequence identity to the amino acid sequence set forth in one of SEQ ID NOs: 11-13 and 26-33. In some cases, the variant AAV capsid protein comprises the amino acid sequence set forth in one of SEQ ID NOs: 11-13 and 26-33.

Features of the present disclosure include an infectious recombinant adeno-associated virus (rAAV) virion comprising (a) a variant adeno-associated virus (AAV) capsid protein that comprises an amino acid sequence having at least about 95% amino acid sequence identity to the amino acid sequence set forth in SEQ ID NO: 10, and includes the amino acid substitutions N312K, N449D, D472N, N551S, I698V, and L735Q relative to SEQ ID NO: 2; and (b) a heterologous nucleic acid. In some cases, the variant AAV capsid protein comprises the amino acid sequence set forth in SEQ ID NO: 10. In some cases, the rAAV exhibits increased resistance to human AAV neutralizing antibodies compared to the resistance exhibited by AAV2 (wild type AAV serotype 2). In some cases, the rAAV exhibits at least about 1.5-fold (e.g., at least about 3-fold, at least about 5-fold, at least about 10-fold, at least about 30-fold, etc.) greater resistance to human AAV neutralizing antibodies than the resistance exhibited by AAV2. In some cases, the rAAV exhibits increased transduction of mammalian cells in the presence of human AAV neutralizing antibodies compared to the transduction of mammalian cells exhibited by wild type AAV serotype 2 (AAV2). In some cases, the mammalian cells are liver cells, pancreatic cells, skeletal muscle cells, heart muscle cells, fibroblasts, retinal cells, synovial joint cells, lung cells, T cells, neurons, glial cells, stem cells (e.g., hematopoietic stem cells, hematopoietic progenitor cells, neural stem cells, neural progenitor cells, neural crest stem cells, embryonic stem cells, induced pluripotent stem cells (iPS cells), mesenchymal stem cells, mesodermal stem cells, liver stem cells, pancreatic stem cells, pancreatic progenitor cells, muscle stem cells, retinal stem cells, and the like), endothelial cells, or cancer cells. In some cases, the heterologous nucleic acid comprises an RNA interfering agent. In some cases, the heterologous nucleic acid comprises a nucleotide sequence encoding a polypeptide.

Features of the present disclosure include an isolated nucleic acid comprising a nucleotide sequence that encodes a variant adeno-associated virus (AAV) capsid protein comprising an amino acid sequence having at least about 90% amino acid sequence identity to the amino acid sequence set forth in one of SEQ ID NOs: 11-13 and 26-33. In some cases, the encoded variant AAV capsid protein comprises an amino acid sequence having at least about 95% amino acid sequence identity to the amino acid sequence set forth in one of SEQ ID NOs: 11-13 and 26-33. In some cases, the encoded variant AAV capsid protein comprises the amino acid sequence set forth in one of SEQ ID NOs: 11-13 and 26-33.

Features of the present disclosure include an isolated nucleic acid comprising a nucleotide sequence that encodes a variant adeno-associated virus (AAV) capsid protein that comprises an amino acid sequence having at least about 95% amino acid sequence identity to the amino acid sequence set forth in SEQ ID NO: 10, and includes the amino acid substitutions N312K, N449D, D472N, N551S, I698V, and L735Q relative to SEQ ID NO: 2.

In some cases, the encoded variant AAV capsid protein (encoded by an isolated nucleic acid) confers to an infectious recombinant adeno-associated virus (rAAV) virion an increased resistance to human AAV neutralizing antibodies compared to the resistance exhibited by AAV2 (wild type AAV serotype 2). In some cases, increased resistance is at least about 1.5-fold (e.g., at least about 3-fold, at least about 5-fold, at least about 10-fold, at least about 30-fold, etc.) greater than the resistance exhibited by AAV2. In some cases, the encoded variant AAV capsid protein (encoded by an isolated nucleic acid) confers to an infectious recombinant adeno-associated virus (rAAV) virion an increased transduction of mammalian cells in the presence of human AAV neutralizing antibodies compared to the transduction exhibited by AAV2.

Features of the present disclosure include an isolated host cell comprising a subject nucleic acid as described above. In some cases, the host cell is stably transfected with the nucleic acid. In some cases, the host cell further comprises a nucleic acid comprising a nucleotide sequence encoding an AAV rep protein. In some cases, the host cell further comprises a recombinant AAV vector.

Features of the present disclosure include a method of delivering a heterologous nucleic acid to a target cell, comprising contacting the target cell with a subject virion (described above). In some cases, the target cell is a liver cell, a pancreatic cell, a skeletal muscle cell, a heart muscle cell, a fibroblast, a retinal cell, a synovial joint cell, a lung cell, a T cell, a neuron, a glial cell, a stem cell (e.g., a hematopoietic stem cell, a hematopoietic progenitor cell, a neural stem cell, a neural progenitor cell, a neural crest stem cell, an embryonic stem cell, an induced pluripotent stem cell (iPS cell), a mesenchymal stem cell, a mesodermal stem cell, a liver stem cell, a pancreatic stem cell, a pancreatic progenitor cell, a muscle stem cell, or a retinal stem cell, and the like), an endothelial cell, or a cancer cell. In some cases, the target cell is in vitro. In some cases, the target cell is in vivo.

Features of the present disclosure include a method of delivering a gene product to an individual in need thereof, the method comprising administering to the individual an effective amount of a subject infectious recombinant adeno-associated virus (rAAV) virion (described above). In some cases, the heterologous nucleic acid of the rAAV virion comprises an RNA interfering agent. In some cases, the heterologous nucleic acid of the rAAV virion comprises a nucleotide sequence encoding a polypeptide. In some cases, the administering step comprises the indirect delivery of the infectious rAAV virion. In some cases, the administering step comprises the direct delivery of the infectious rAAV virion.

Features of the present disclosure include a variant adeno-associated virus (AAV) capsid protein comprising an amino acid sequence having at least about 90% amino acid sequence identity to the amino acid sequence set forth in one of SEQ ID NOs: 11-13 and 26-33. In some cases, the AAV capsid protein comprises an amino acid sequence having at least about 95% amino acid sequence identity to the amino acid sequence set forth in one of SEQ ID NOs: 11-13 and 26-33. In some cases, the AAV capsid protein comprises the amino acid sequence set forth in one of SEQ ID NOs: 11-13 and 26-33.

Features of the present disclosure include a variant adeno-associated virus (AAV) capsid protein that comprises an amino acid sequence having at least about 95% amino acid sequence identity to the amino acid sequence set forth in SEQ ID NO: 10, and includes the amino acid substitutions N312K, N449D, D472N, N551S, 1698V, and L735Q relative to SEQ ID NO: 2. In some cases, the variant AAV capsid protein comprises the amino acid sequence set forth in SEQ ID NO: 10. In some cases, the variant AAV capsid protein confers to an infectious recombinant adeno-associated virus (rAAV) virion an increased resistance to human AAV neutralizing antibodies compared to the resistance exhibited by AAV2. In some cases, the increased resistance is at least about 1.5-fold (e.g., at least about 3-fold, at least about 5-fold, at least about 10-fold, at least about 30-fold, etc.) greater than the resistance exhibited by AAV2. In some cases, the variant AAVcapsid protein confers to an infectious recombinant adeno-associated virus (rAAV) virion an increased transduction of mammalian cells in the presence of human AAV neutralizing antibodies compared to the transduction exhibited by AAV2.

Features of the present disclosure include a library comprising at least one of: (i) two or more infectious rAAV virions, each comprising a variant adeno-associated virus (AAV) capsid protein and a heterologous nucleic acid; (ii) two or more isolated nucleic acids, each comprising a nucleotide sequence that encodes a variant AAV capsid protein; (iii) two or more host cells, each comprising a nucleic acid that comprises a nucleotide sequence that encodes a variant AAV capsid protein; and (iv) two or more variant AAV capsid proteins; wherein the variant AAV capsid protein of at least one member of the library comprises an amino acid sequence having at least one amino acid substitution relative to the amino acid sequence set forth in one of SEQ ID NOs: 10-13 and 26-33.

Features of the present disclosure include a method of generating and identifying a modified infectious rAAV virion that exhibits an altered property of infection relative to a starter (parent) virion comprising a starter capsid protein, the method comprising: (a) generating variant adeno-associated virus (AAV) capsid proteins from the starter capsid protein, wherein the starter capsid protein comprises the amino acid sequence set forth in one of SEQ ID NOs: 10-13 and 26-33, and wherein each variant AAV capsid protein comprises at least one amino acid substitution relative to the starter capsid protein; (b) generating variant AAV virions, each comprising a variant capsid AAV protein generated in step (a); and (c) assaying variant AAV virions generated in step (b) for the altered property of infection to identify the modified infectious rAAV virion. In some cases, the generation of the library of variant AAV capsid proteins comprises a method of mutagenesis selected from the group consisting of: polymerase chain reaction mutagenesis, oligonucleotide-directed mutagenesis, saturation mutagenesis, loop-swapping mutagenesis, fragment shuffling mutagenesis, and a combination thereof. In some cases, the altered property of infection is an increased resistance to human neutralizing AAV antibodies compared to the resistance exhibited by the starter virion. In some cases, the altered property of infection is an increased transduction of mammalian cells in the presence of human AAV neutralizing antibodies compared to the transduction exhibited by the starter virion. In some cases, the modified infectious rAAV virion comprises a modified AAV capsid protein comprising an amino acid sequence having at least about 90% amino acid sequence identity to the starter capsid protein.

Features of the present disclosure include a method of generating a variant AAV capsid protein from a starter capsid protein, the method comprising: subjecting a nucleic acid that comprises a nucleotide sequence encoding the starter capsid protein to a type of mutagenesis selected from the group consisting of: polymerase chain reaction mutagenesis, oligonucleotide-directed mutagenesis, saturation mutagenesis, loop-swapping mutagenesis, fragment shuffling mutagenesis, and a combination thereof; wherein the starter capsid protein comprises the amino acid sequence set forth in one of SEQ ID NOs: 10-13 and 26-33.

DESCRIPTION OF THE DRAWINGS

FIGS. 2A-B depict the neutralization profiles of antibody evading variants using human IVIG.

FIGS. 4A-B depict the amino acid sequences of loop-swap/shuffle and saturation mutagenesis clones.

FIG. 5 demonstrates the in vitro tropism of AAV variants.

FIGS. 6A-B show in vivo localization and neutralization of novel AAV variants.

FIGS. 7A-D demonstrate the generation of human antibody evaders.

FIGS. 8A-I depict the capsid protein sequence of Shuffle 100-1 (SEQ ID NO: 11) aligned with the wild type capsid protein sequences of AAV1-9 (SEQ ID NOs: 1-9).

FIGS. 9A-I depict the capsid protein sequence of Shuffle 100-3 (SEQ ID NO: 12) aligned with the wild type capsid protein sequences of AAV1-9 (SEQ ID NOs: 1-9).

FIGS. 10A-I depict the capsid protein sequence of Shuffle 100-7 (SEQ ID NO: 13) aligned with the wild type capsid protein sequences of AAV1-9 (SEQ ID NOs: 1-9).

FIG. 11 shows the neutralizing antibody titers of library clones and parent serotypes in immunized mouse sera.

FIG. 12 illustrates the directed evolution process utilized to identify capsid variant "A101" (comprising a capsid protein of SEQ ID NO:12) with enhanced gene delivery to the lung in the presence of human neutralizing antibodies.

FIGS. 13A-B FIG. 13A illustrates estimated genetic diversity of the capsid libraries used for the directed evolution process. The total diversity of the libraries is >1 billion genetic variants. FIG. 13B illustrates productivity of the capsid libraries. All capsid libraries were manufactured at a level sufficient to produce material for the in vivo Therapeutic Vector Evolution program study. The viral genomes (vg) administered represent the target dose, not accounting for losses associated with the delivery device and route of administration.

Figure 14A:
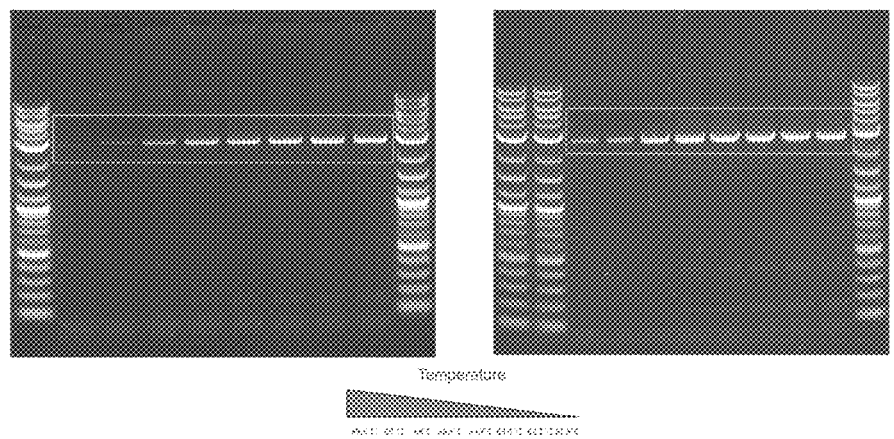
Figure 14B:
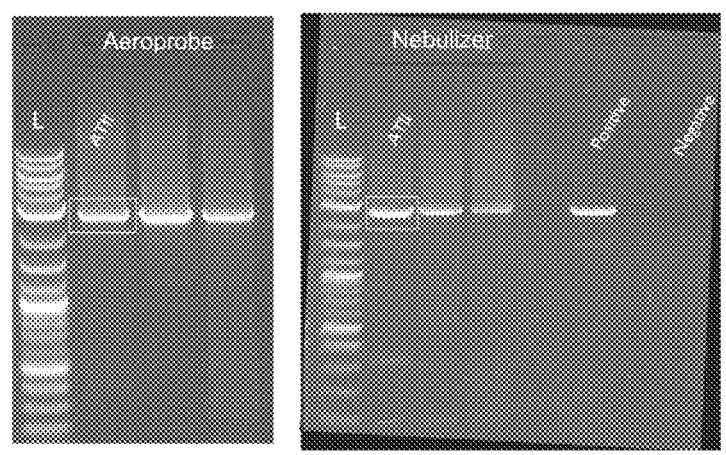

FIGS. 14A-B FIG. 14A illustrates external PCR amplification of viral genomes from the isolated AT II cells following a) AeroProbe® administration or b) nebulizer administration from the first round of selection. Bands within blue boxes represent successful amplification of viral genomes. Temperature gradient represents annealing temperatures used during PCR corresponding to each lane of the gel. FIG. 14B illustrates Internal PCR amplification of viral genomes from the isolated AT II cells following a) AeroProbe® administration or b) nebulizer administration from the first round of selection. Bands within blue boxes represent successful amplification of viral genomes.

Figure 15A:
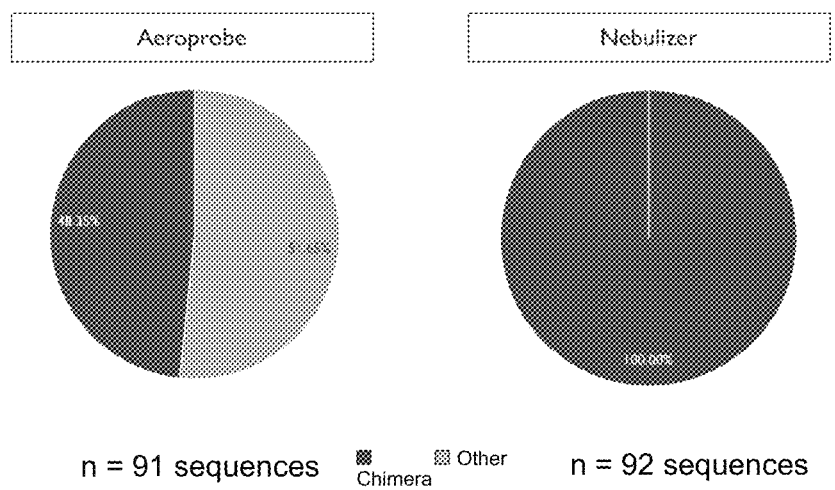
Figure 15B:
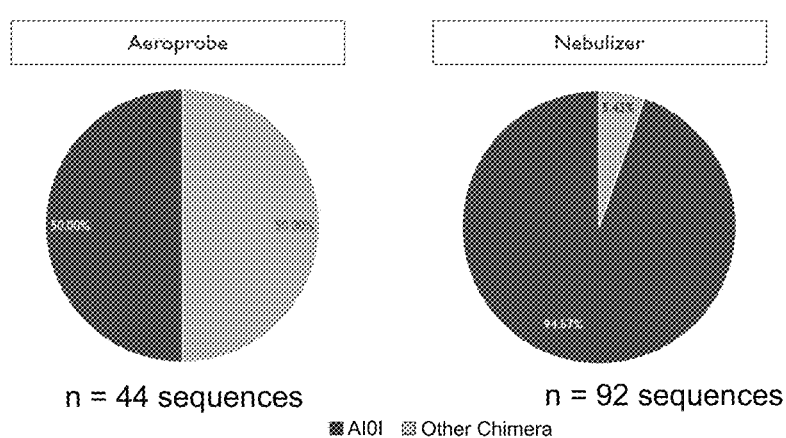

FIGS. 15A-15B FIG. 15A illustrates frequency of chimera motif within sequencing analysis for the study. Sequencing analysis is based on total frequency within sequenced population for both AeroProbe and Nebulizer delivery devices. FIG. 15B illustrates frequency of A101 variant within chimera motif for the study. Sequencing analysis based on total frequency within sequenced population for both AeroProbe and Nebulizer delivery devices.

Figure 16:
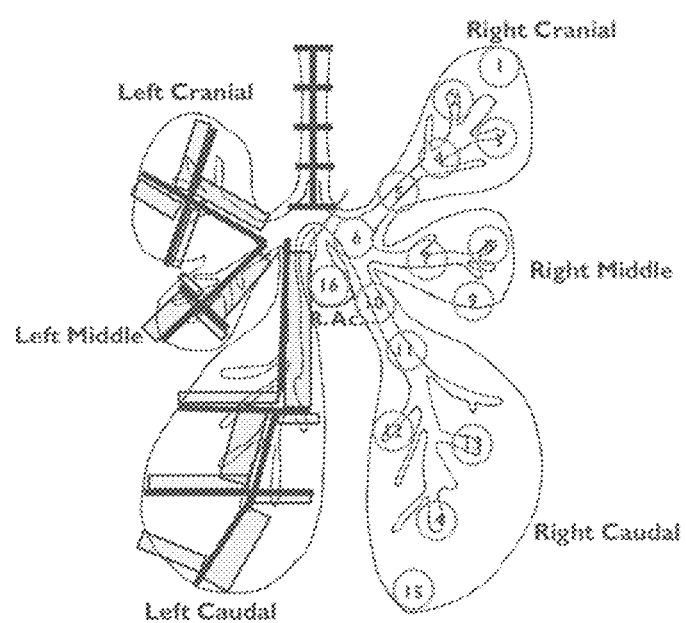

FIG. 16 Lung Sampling Schematic (Examples 3 and 7). Schematic representation of trachea and lung sampling. Circles in right lung represent adjacent samples obtained for DNA and protein isolation. Samples oriented along the long and short axis for tissue sectioning are represented by squares.

Figure 17:
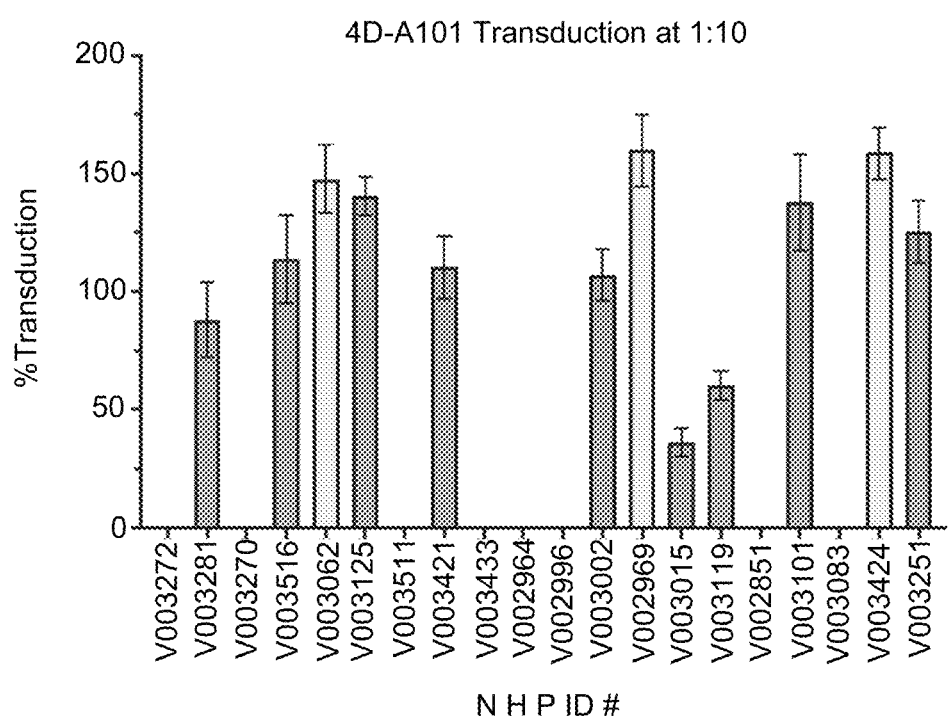

FIG. 17 Variant Capsid (comprising a capsid protein of SEQ ID NO:12) Transduction with NHP Serum Samples at 1:10 Serum Dilution. Serum samples from NHPs eligible for study inclusion were analyzed for the presence of anti-AAV neutralizing antibodies. Transduction in the presence of a 1:10 serum dilution (compared to transduction in the absence of serum) is reported for all NHP. NHP selected for study inclusion are denoted by yellow bars. Error bars=Standard Deviation, n=3 (internal replicates).

Figure 18:
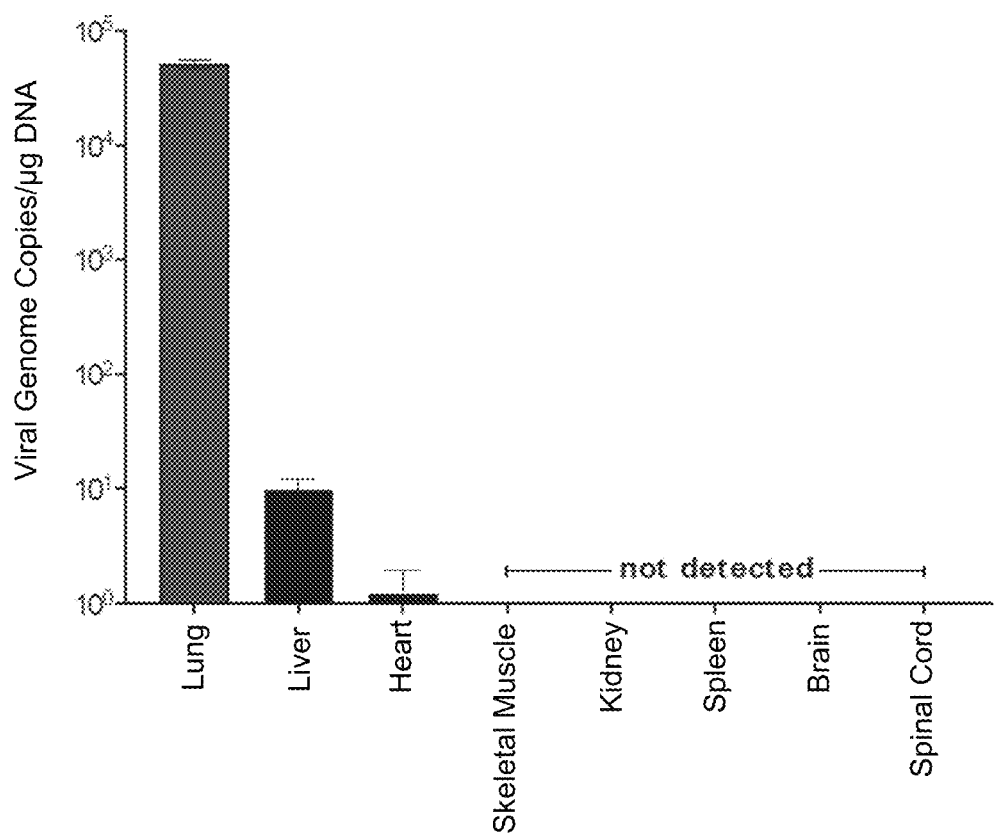

FIG. 18 Variant Capsid-Mediated Genome Biodistribution. Quantification of viral genomes in the lung and additional systemic organs by qPCR using primers and probe against the EGFP transgene. Viral genomes were detected in all 48 samples (n=16 samples per NHP; n=3 NHP). All samples tested from skeletal muscle (triceps brachii, vastus lateralis), diaphragm, kidney, spleen, brain and spinal cord were below the lower limit of quantification. Mean±standard error; n=3 NHP (n=16 biopsy sites per lung per NHP, n=10 biopsy sites per liver per NHP, n=15 biopsy sites per heart per NHP, n=9 biopsy sites per skeletal muscle per NHP, n=2 samples per kidney per NHP, n=1 sample per spleen per NHP, n=8 biopsy sites per brain per NHP, n=3 biopsy sites per spinal cord per NHP).

Figure 19:
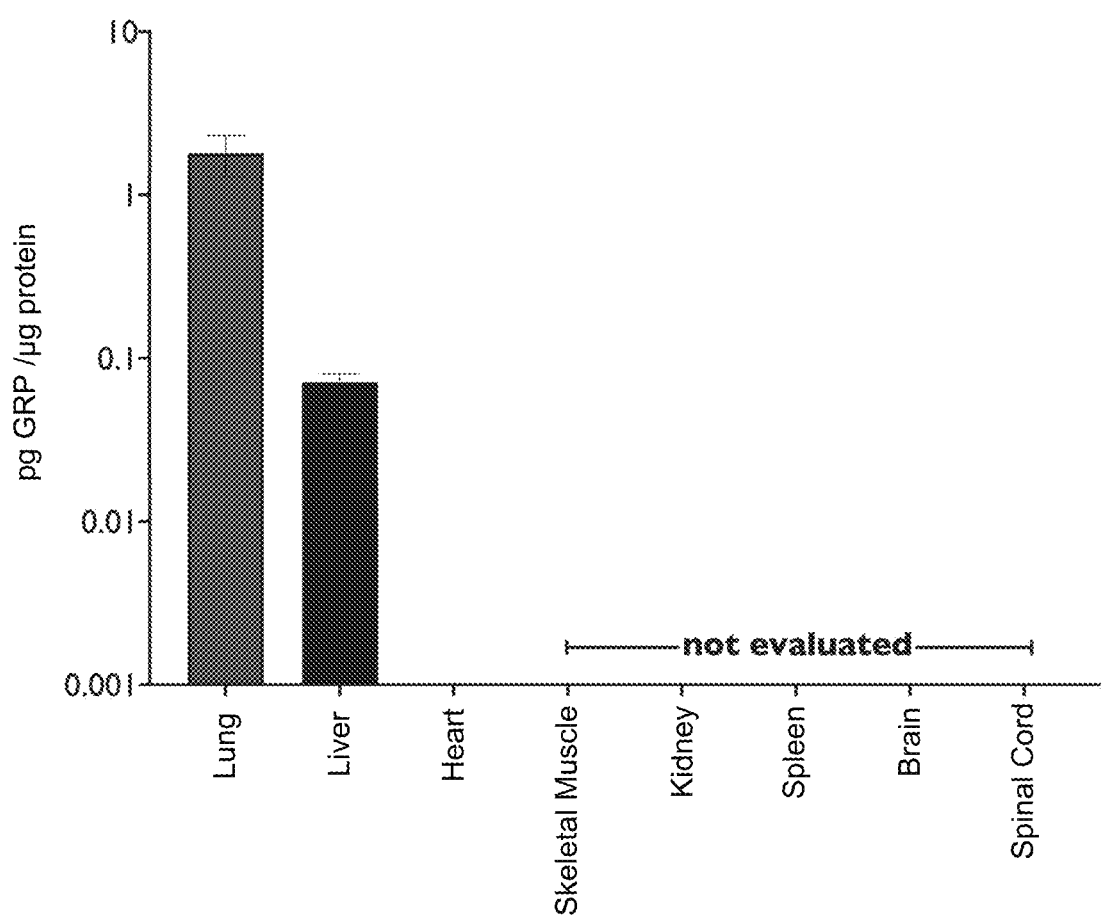

FIG. 19 Variant Capsid-Mediated Protein Expression in Lungs. Quantification of EGFP protein expression in the lung by ELISA against the EGFP protein. EGFP expression was observed in all 48 lung samples (n=16 samples per NHP; n=3 NHP). EGFP expression was observed in 10 liver samples that were positive for viral genomes (n=10 samples per NHP; n=3 NHP). Mean±standard error.

FIG. 20 Variant Capsid-Mediated Protein Localization in Lung. Representative images of EGFP expression in the trachea (a-b), bronchi (c, e, g), and alveoli (d, f, h) of NHP V002969. Sections denoted by white boxes in trachea (b), alveoli (d), and bronchi (e) are provided as magnified images in i, j, and k, respectively. Approximate locations of images are denoted by magenta boxes on the schematic diagram. EGFP expression is detected by an anti-GFP antibody (red) in all images. Nuclei were counterstained with DAPI (blue).

Figure 21A:
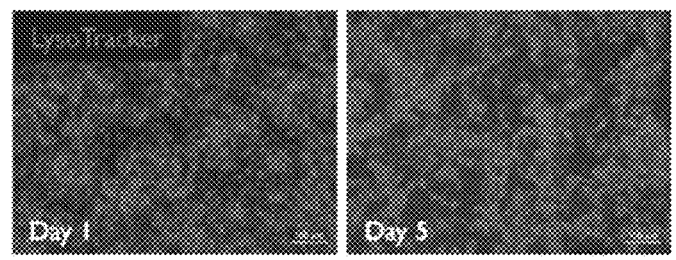
Figure 21B:
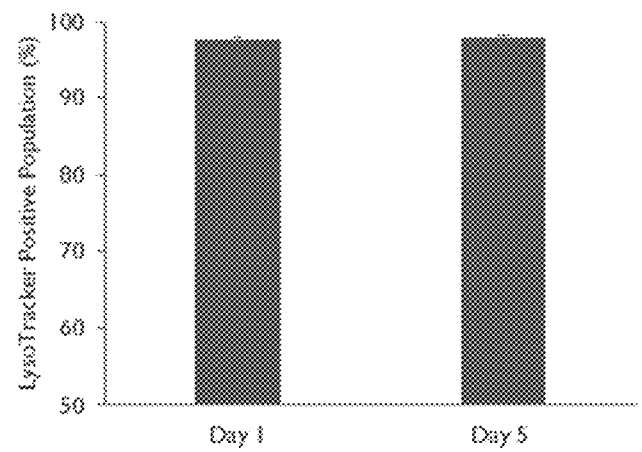
Figure 21C:
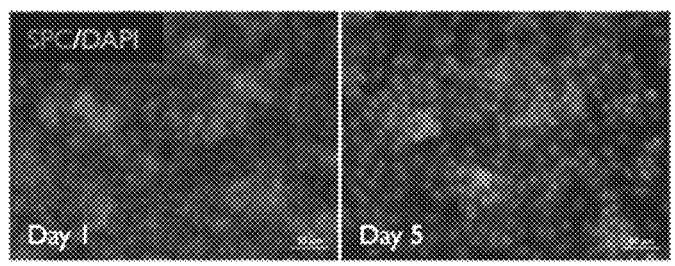
Figure 21D:
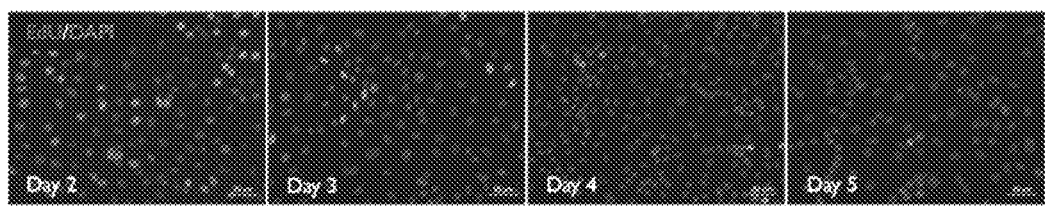

FIGS. 21A-21D. Alveolar Epithelial Type 2 Non-Human Primate Cell Characterization. NHP AECII cells were over 90% LysoTracker positive, shown by fluorescent microscopy (FIG. 17A) and quantified by flow cytometry (FIG. 21B). Surfactant protein C, a mature marker of AECII cells was evident on day 1 and day 5 after seeding (FIG. 21C). AECII cells decreased their proliferation rate over time in culture shown by EdU incorporation (FIG. 21D). EdU=5-Ethynyl-2'-deoxyuridine, Error bars=Standard Deviation, n=3 internal replicates.

Figure 22A:
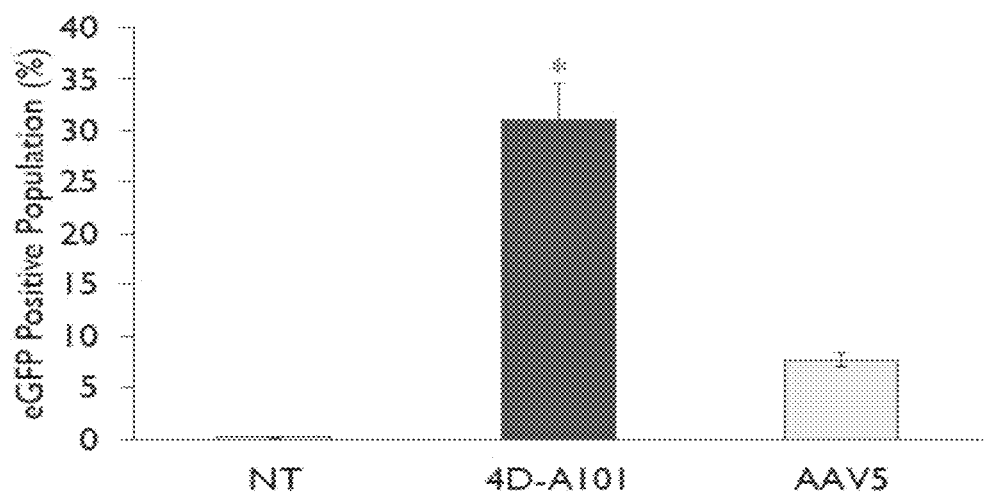
Figure 22B:
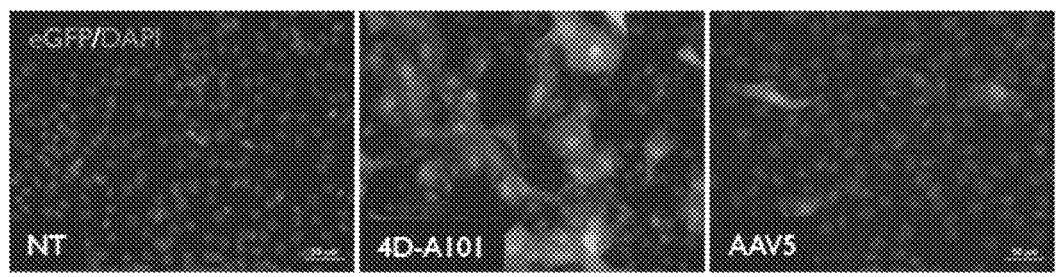

FIGS. 22A-22B. Non-Human Primate Alveolar Epithelial Type 2 Cell Vector Characterization. The rAAV with capsid comprising capsid protein of SEQ ID NO:12 (4D-A101) capsid showed a higher transduction rate than the AAV5 capsid, both carrying CAG-eGFP in ALI cultures of AECII NHP cells. Quantification of eGFP positive cells by flow cytometry (FIG. 22A). Representative ICC images of eGFP positive cells (FIG. 22B). Post-infection time of 3 days, 5 total days in culture. Error bars=Standard Deviation, n=3 internal replicates. Student's t-test, p<0.05 compared to AAV5.

Figure 23A:
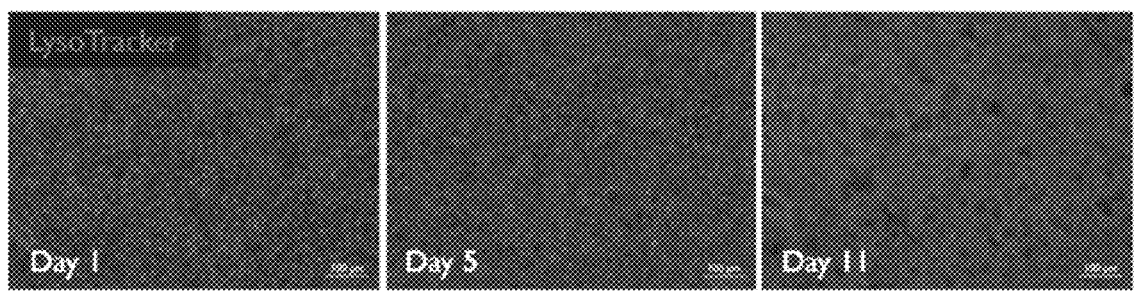
Figure 23B:
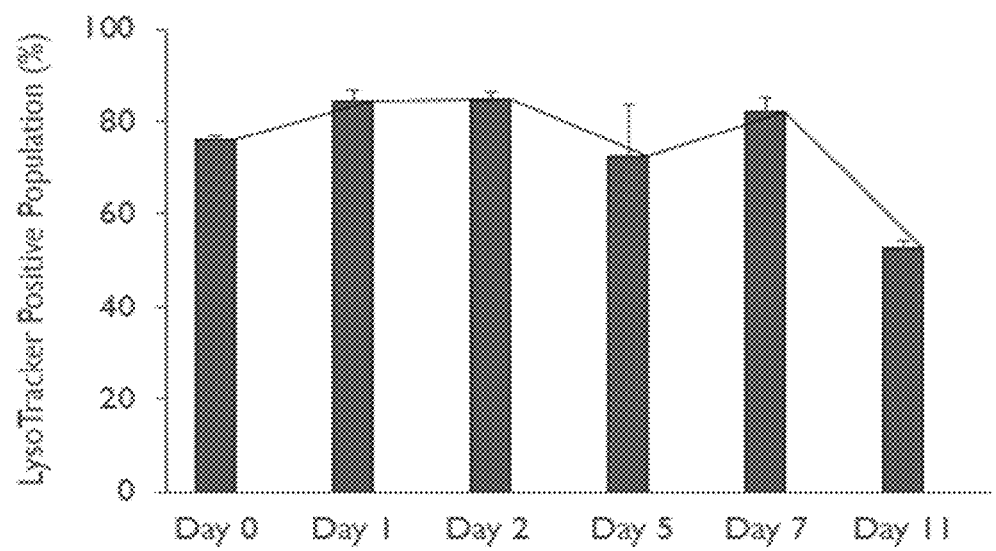
Figure 23C:
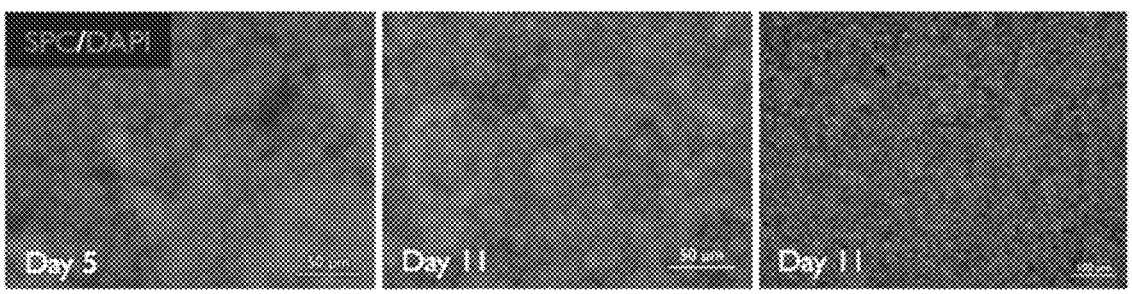
Figure 23D:
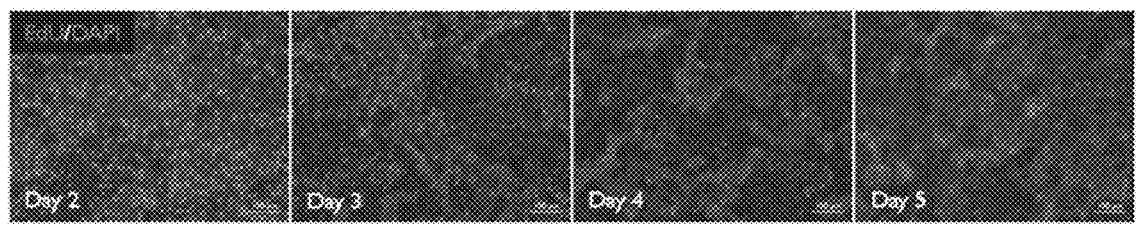

FIGS. 23A-23D. Alveolar Epithelial Type 2 Human Cell Characterization. Human AECII cells were around 80% LysoTracker positive until day 11 in culture when they decreased to 50%, shown by fluorescent microscopy (FIG. 23A) and quantified by flow cytometry (FIG. 23B). Surfactant protein C, a mature marker of AECII cells was evident on day 5 and day 11 after seeding (FIG. 23C). AECII cells decreased their proliferation rate over time in culture shown by EdU incorporation (FIG. 23D). EdU=5-Ethynyl-2'-deoxyuridine, Error bars=Standard Deviation, n=3 internal replicates.

Figure 24:
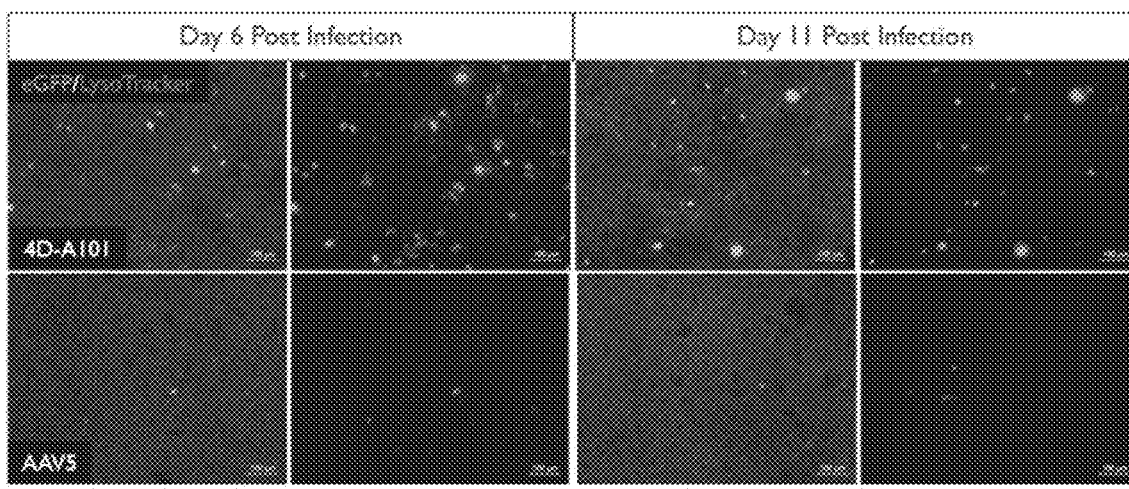

FIG. 24 Human Alveolar Epithelial Type 2 Cell Vector Characterization. Capsid comprising a capsid protein of SEQ ID NO:12 (4D-A101) showed a higher transduction rate than the AAV5 capsid, both carrying CAG-eGFP in ALI cultures of AECII human cells. Representative ICC images of eGFP positive cells. Post-infection time of 6 and 10 days, 7 and 11 total days in culture.

Figure 25:
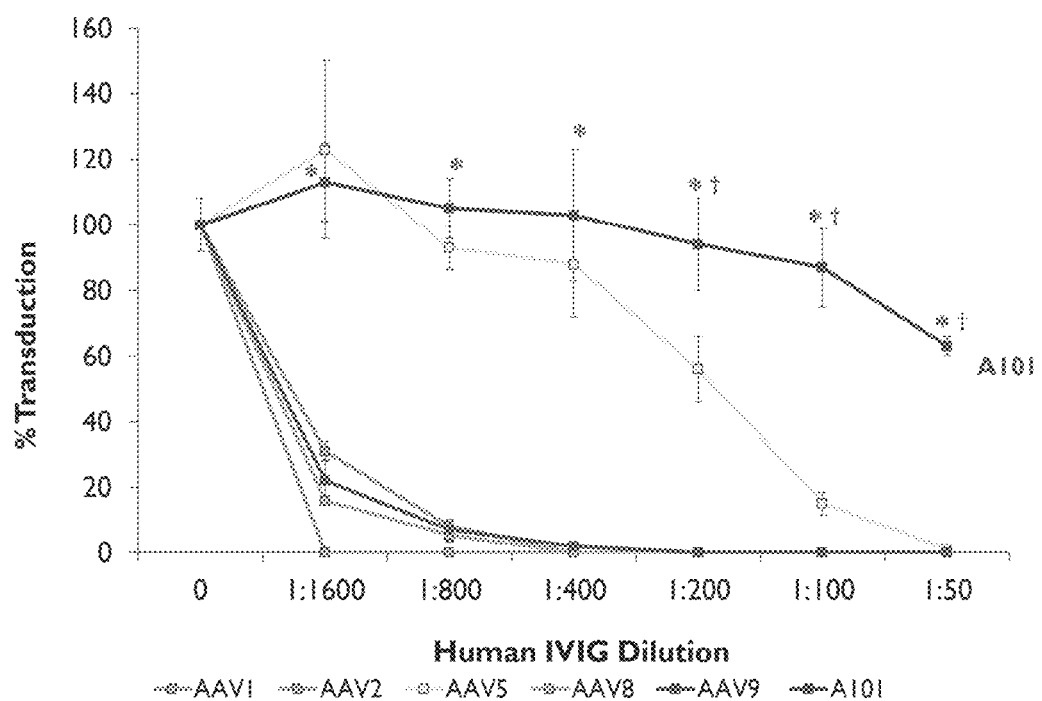

FIG. 25 In Vitro Neutralization Profiles of Wild-Type AAV1, AAV2, AAV5, AAV8, AAV9 and rAAV comprising capsid comprising capsid protein of SEQ ID NO:12 (4D-A101). rAAV comprising capsid comprising capsid protein of SEQ ID NO:12 showed superior ability to avoid AAV neutralizing antibodies in human IVIG compared to wild type AAV. AAV.CAG.Luciferase vectors were incubated with dilutions of IVIG prior to infection of 2V6.11 cells at a MOI of 1,000. Vectors capable of evading antibodies transduced the cells, and luciferase activity was measured 48 hours post infection. IVIG=intravenous immunoglobin, Error bars=Standard Deviation, n=3, internal replicates. * $p<0.05$ for 4D-A101 vs AAV1, AAV2, AAV8, and AAV9, t $p<0.05$ for 4D-A101 vs AAV5.

Figure 26:
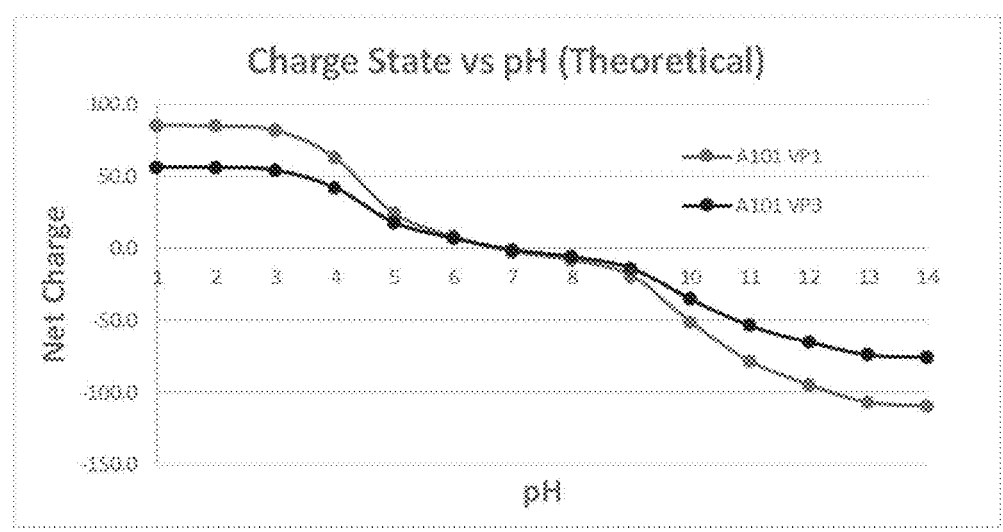

FIG. 26 Graph of net charge vs. pH for A101 VP1 and VP3 capsid proteins.

Figure 27:
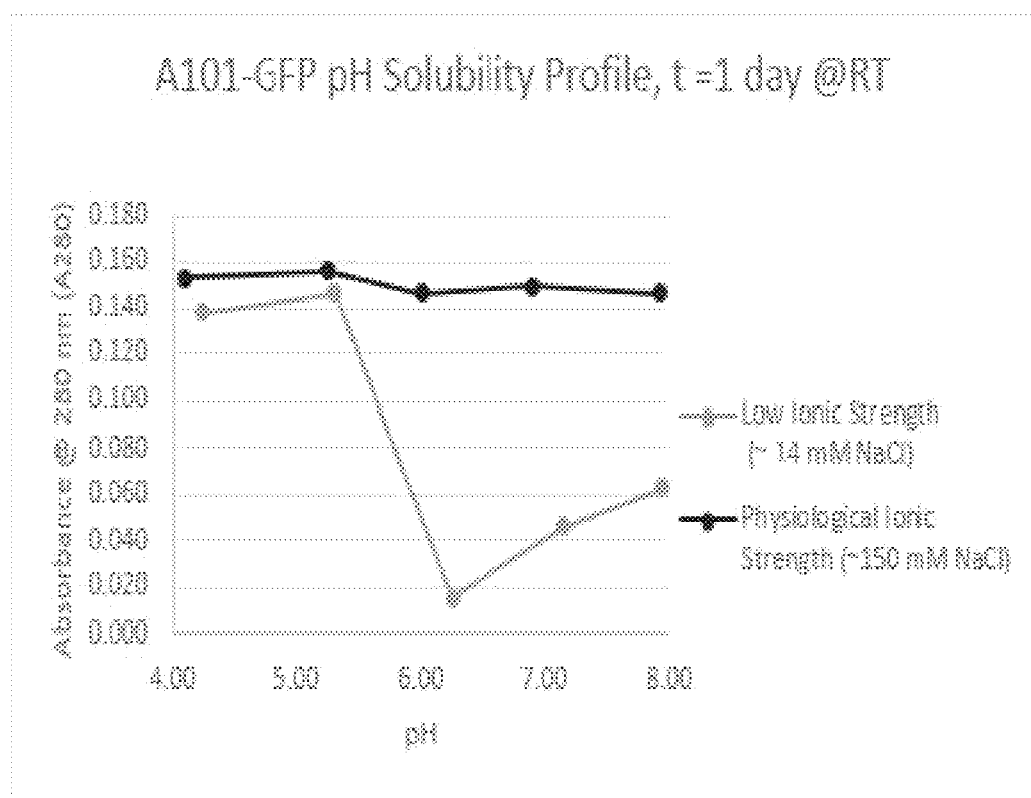

FIG. 27 Graph of A101-GFP pH Solubility After 1-day Storage at Room Temperature.

Figure 28A:
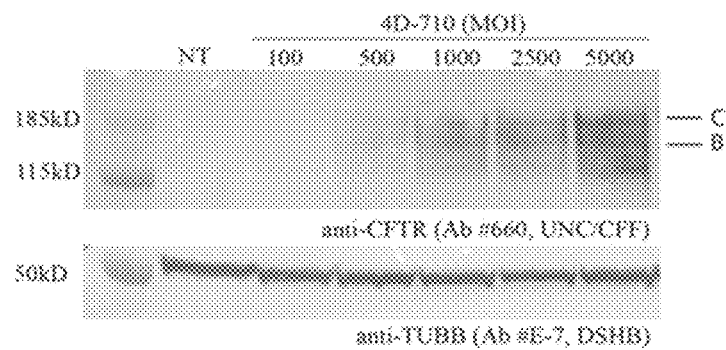
Figure 28B:
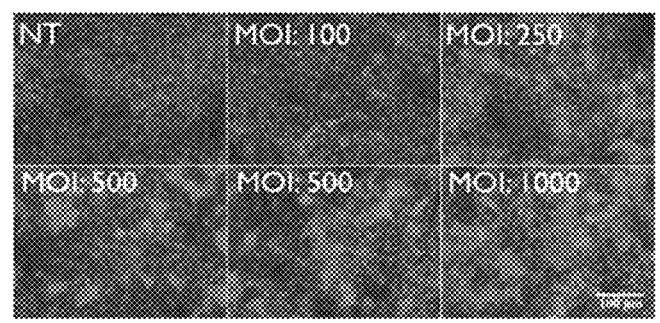
Figure 28C:
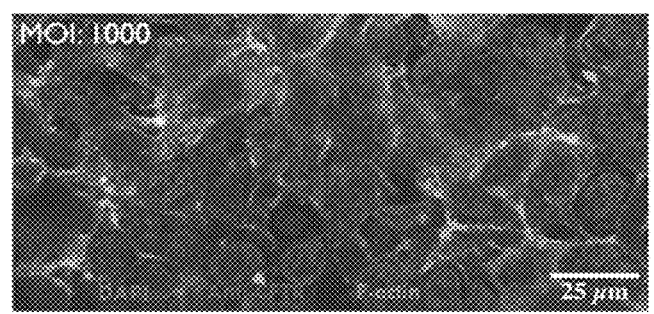

FIGS. 28A-C. Transduction Leads to Robust Protein Expression and Membrane Localization in HEK2v6.11 Cells. HEK2v6.11 were transduced with 4D-710 and probed by western blot (FIG. 28A) with anti-CFTR antibody (FIG. 28A). Representative images (FIG. 28B) show cells analyzed by immunocytochemistry, anti-CFTR (red), F-actin (green), DAPI, nuclear (Blue). Scale bars are 100 µM (FIG. 28B) and 25 µM (FIG. 28C).

Figure 29A:
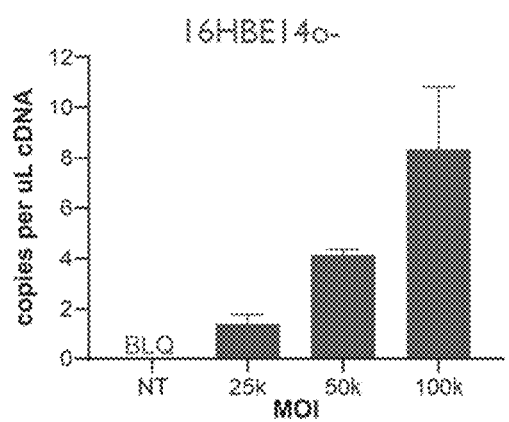
Figure 29B:
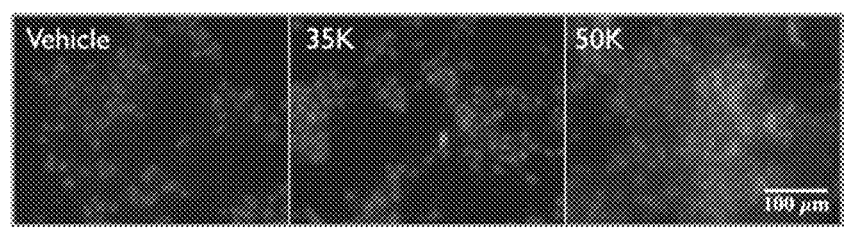

FIGS. 29A-B Transduction of 16HBE14o-G542X cells with 4D-710. Reverse transcription-ddPCR (RT-ddPCR) digital droplet PCR (ddPCR) was performed on RNA extracted from the HBE cultures following 4D-710 transduction at increasing MOIs (FIG. 29A). Exogenous CFTRΔR transcript levels were determined and quantified as copies/4 above a set threshold and plotted on a linear scale. BLQ, below the limit of quantification. NT, nontransduced.

Immunocytochemistry of HBE cultures following transduction at MOIs of 35,000 and 50,000 (FIG. 29B). Blue is DAPI and red is CFTR protein. Scale is 100 µm.

Figure 30:
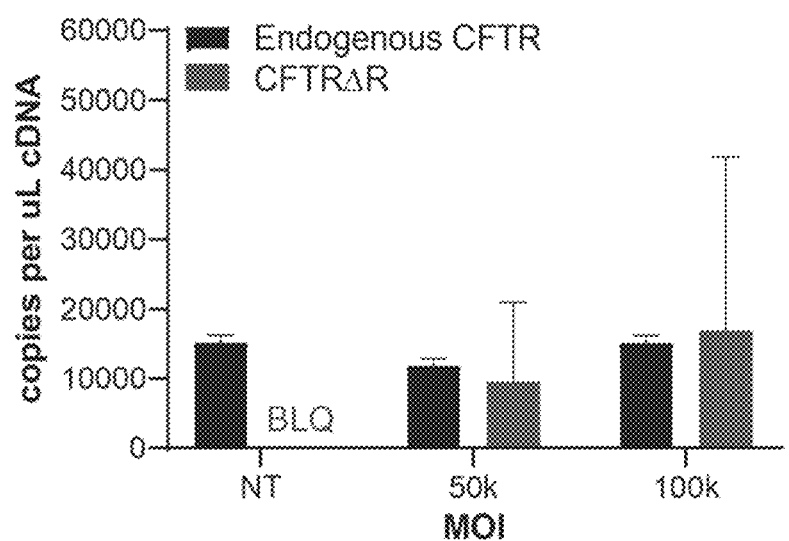

FIG. 30 Transduction of healthy ex vivo ALI lung cultures with 4D-710. ddPCR was performed on cDNA prepared from RNA extracted from the cultures following 4D-710 transduction. Two primer/probe sets were created to specifically differentiate the codon optimized human CFTRΔR transgene from the endogenous human CFTR gene. Quantification analyzed the number of droplets, above the set threshold, containing the transcript of the primer/probe set examined. BLQ, below the limit of quantification. NT, nontransduced.

Figure 4A:
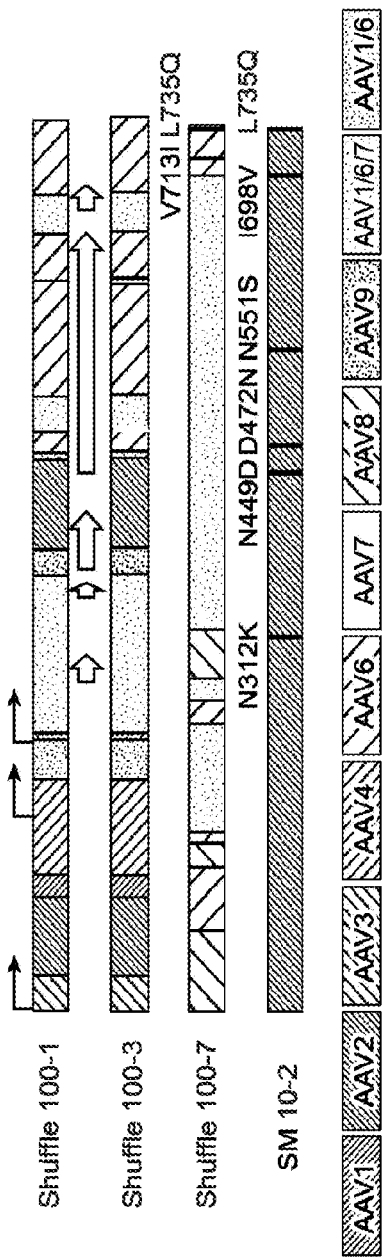
Figure 31:
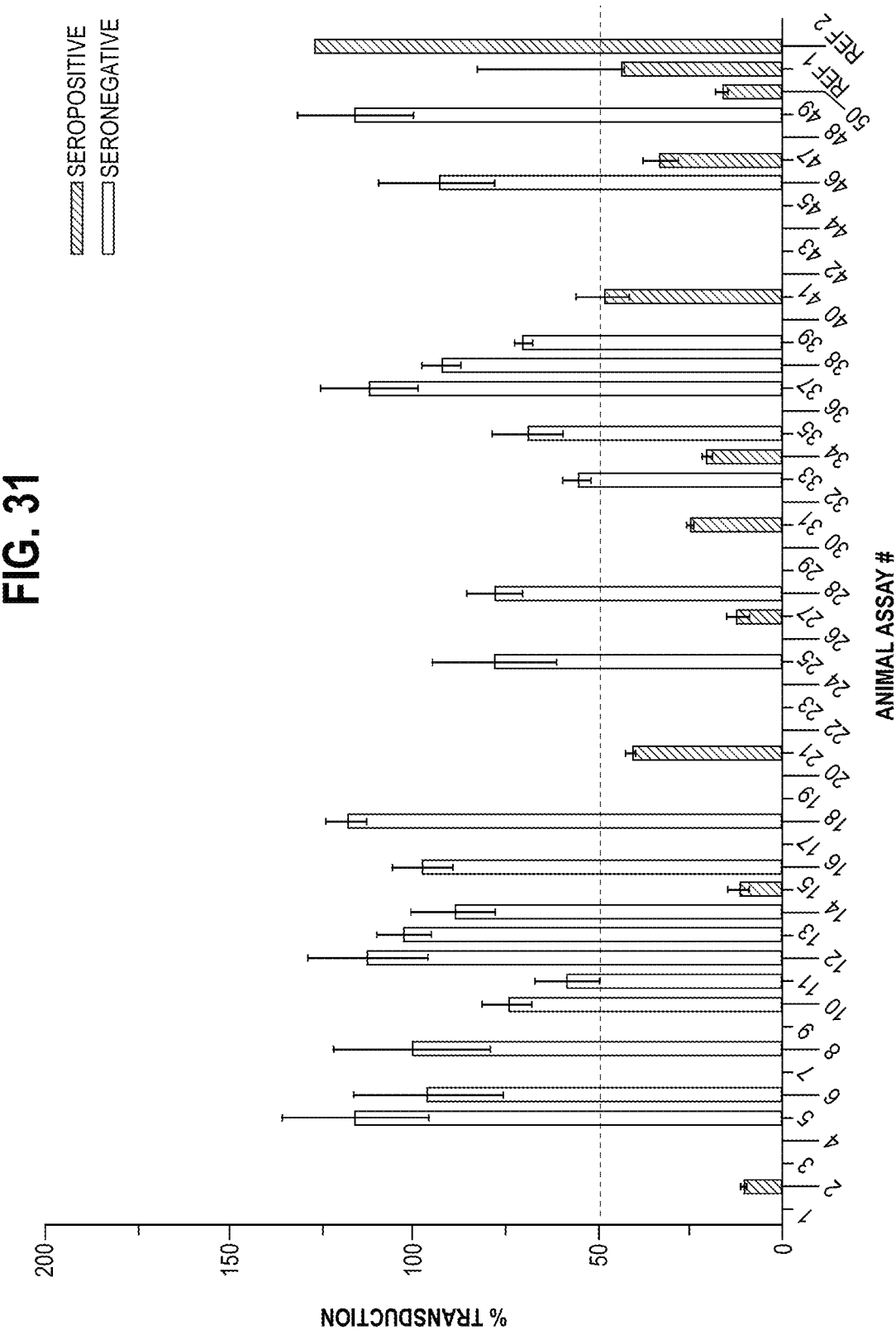

FIG. 31 4D-A101 Transduction with NHP Serum Samples at 1:10 Serum Dilution. Serum samples from NHP eligible for study inclusion were analyzed for the presence of anti-AAV neutralizing antibodies to the capsid of 4D-710 (4D-A101, comprising a capsid protein of SEQ ID NO:12). Transduction in the presence of a 1:10 serum dilution (compared to transduction in the absence of serum) is reported for all NHP. Error bars=Standard Deviation, n=3 (internal replicates).

Figure 32A:
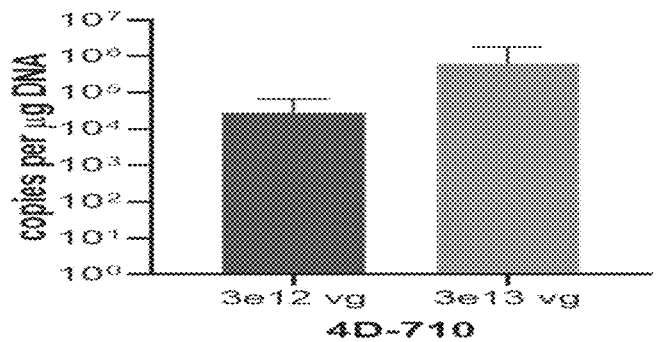
Figure 32B:
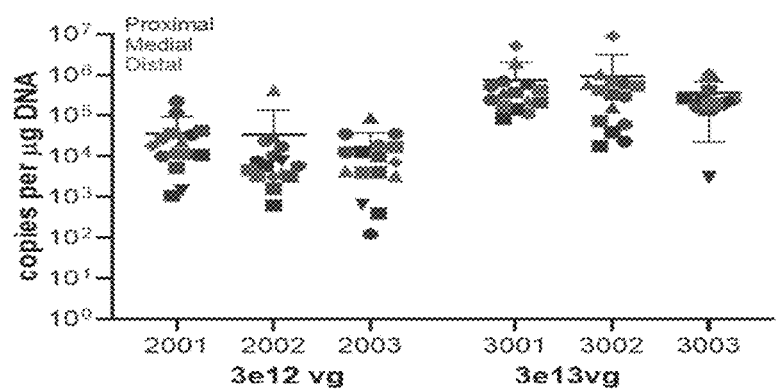
Figure 32C:
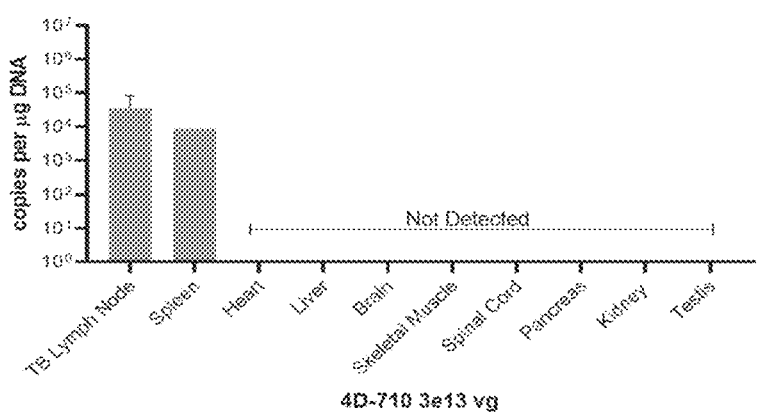

FIGS. 32A-C. Quantification of viral genomes by qPCR using primers and probe against the CFTRΔR transgene. FIG. 32A, viral genomes were robustly detected in lung samples distributed throughout the right lung. FIG. 32B, individual animal lung samples are denoted by approximate region and lung lobe: alveoli (green), primary/secondary bronchi (blue), tertiary/lower bronchi (red), cranial lobe (circle), middle lobe (square), caudal lobe (triangle), accessory lobe (diamond). FIG. 32C, viral genomes quantified in $3 \times 10^{13}$ vg dosed animals demonstrate that all samples tested from heart, liver, brain, skeletal muscle (triceps brachii, vastus lateralis, diaphragm), spinal cord, pancreases, kidney, and testis were below the lower limit of quantification. All three animals had detectable viral genomes in the tracheobronchial (TB) lymph node, and one animal had detectable viral genomes in the spleen. Mean±SD.

Figure 33A:
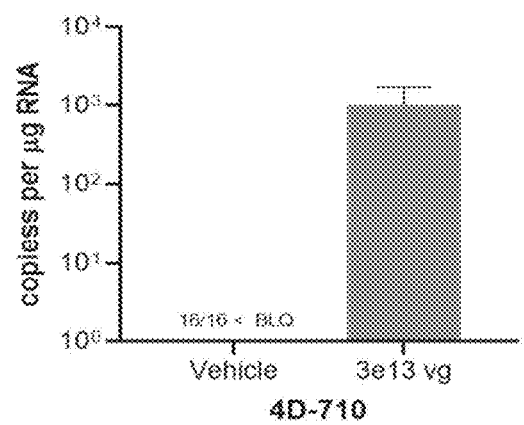
Figure 33B:
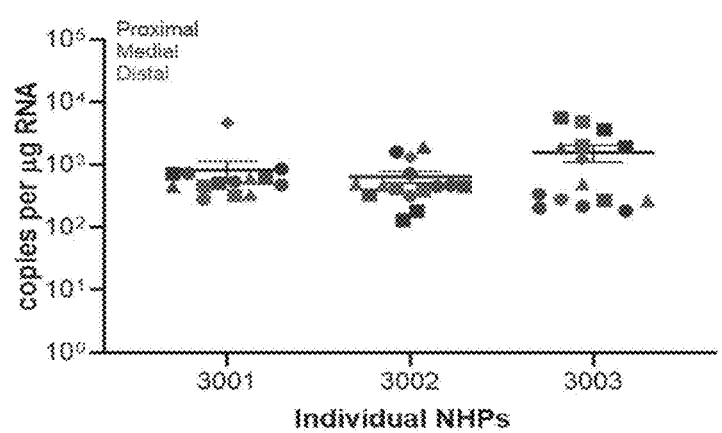

FIGS. 33A-B 4D-710 Transgene Transcript Expression in Lungs. Quantification of CFTRΔR transcript by RT-qPCR using primers and probe against the 4D-710 transgene. FIG. 33A, transcripts were detected in the right lung samples distributed throughout the lobes in $3 \times 10^{13}$ vg dosed animals, all vehicle animals were BLQ. FIG. 33B, individual animal lung samples dosed with $3 \times 10^{13}$ vg are denoted by approximate region and lung lobe: alveoli (green), primary/secondary bronchi (blue), tertiary/lower bronchi (red), cranial lobe (circle), middle lobe (square), caudal lobe (triangle), accessory lobe (diamond). Mean±SD.

Figure 34A:
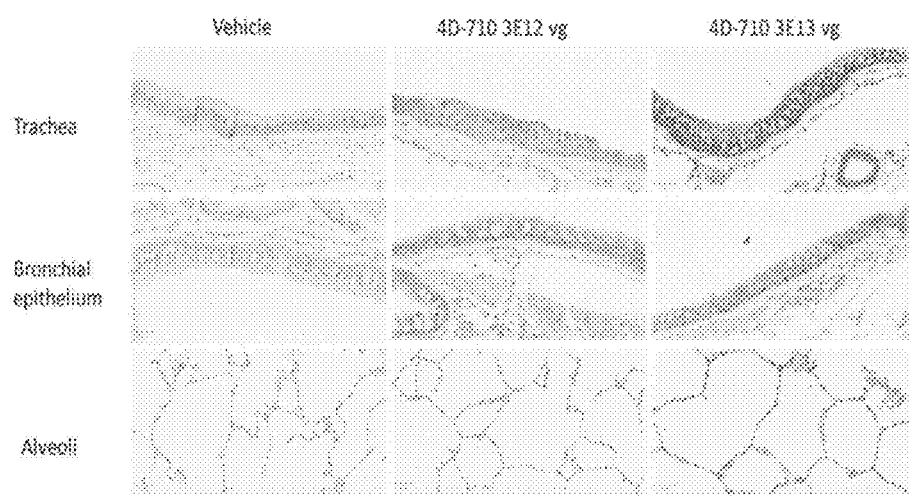
Figure 34B:
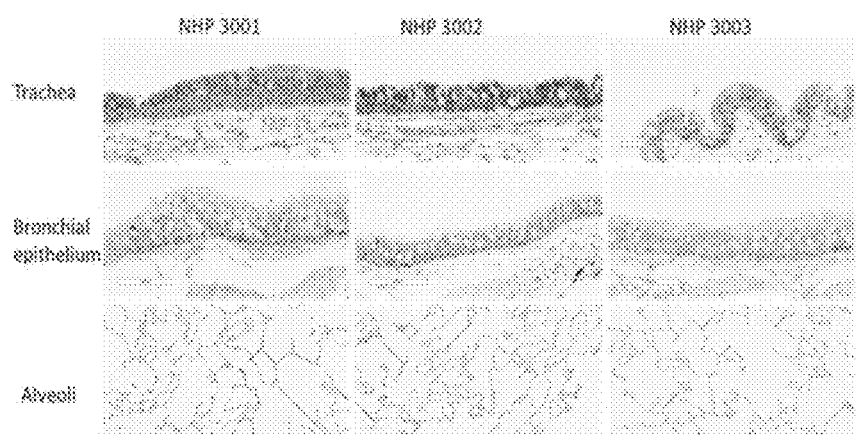

FIGS. 34A-B 4D-710 Protein Expression in Lungs. CFTR protein expression in the lung by immunohistochemistry staining. FIG. 34A, CFTR expression in tracheal epithelium, bronchial epithelium, and alveoli sections of each treatment group, representative images. FIG. 34B, CFTR protein expression in the tracheal epithelium, bronchial epithelium, and alveoli sections of $3 \times 10^{13}$ vg treated animals (individual animals shown), representative images.

Figure 35:
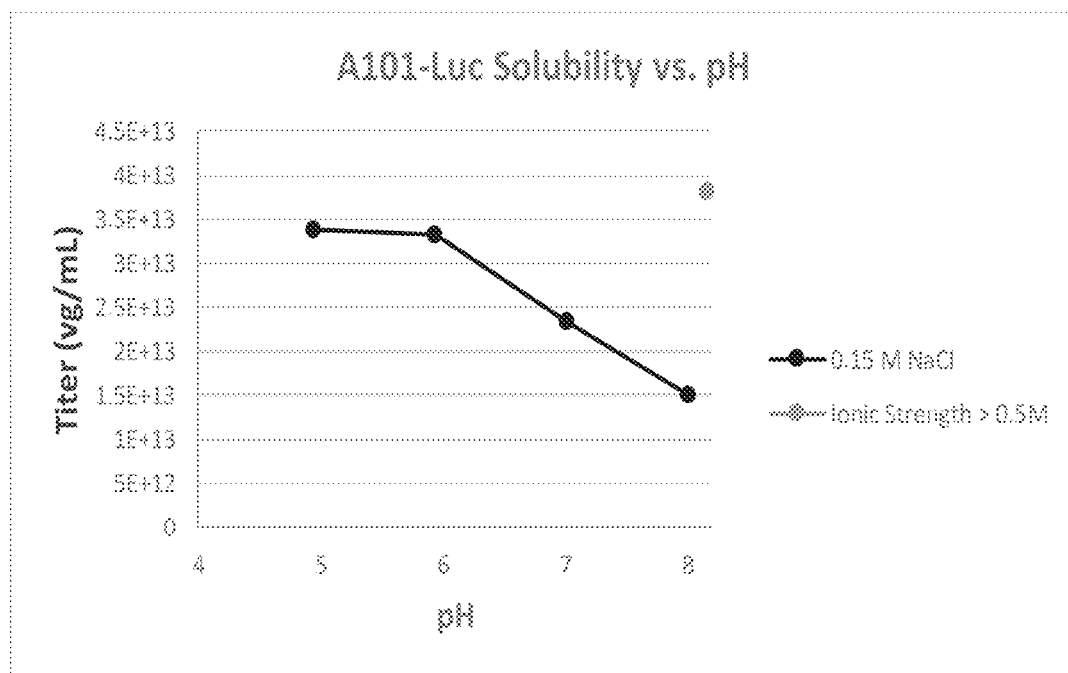

FIG. 35 Graph of A101-Luc Solubility vs. pH

DETAILED DESCRIPTION OF THE INVENTION

Definitions

Adeno-associated virus is a nonpathogenic parvovirus composed of a 4.7 kb single-stranded DNA genome within a non-enveloped, icosahedral capsid. "AAV" is an abbreviation for adeno-associated virus, and may be used to refer to the virus itself or derivatives thereof. The genome contains three open reading frames (ORF) flanked by inverted terminal repeats (ITR) that function as the viral origin of replication and packaging signal. The rep ORF encodes four nonstructural proteins that play roles in viral replication, transcriptional regulation, site-specific integration, and virion assembly. The cap ORF encodes three structural proteins (VP1-3) that assemble to form a 60-mer viral capsid. Finally, an ORF present as an alternate reading frame within the cap gene produces the assembly-activating protein (AAP), a viral protein that localizes AAV capsid proteins to the nucleolus and functions in the capsid assembly process.

There are several naturally occurring serotypes and over 100 variants of AAV, each of which differs in amino acid sequence, particularly within the hypervariable regions of the capsid proteins, and thus in their gene delivery properties. No AAV has been associated with any human disease, making recombinant AAV attractive for clinical applications.

The term "AAV" as used herein covers all subtypes and both naturally occurring and recombinant forms, except where required otherwise. The term "AAV" includes AAV type 1 (AAV-1 or AAV1), AAV type 2 (AAV-2 or AAV2), AAV type 3 (AAV-3 or AAV3), AAV type 4 (AAV-4 or AAV4), AAV type 5 (AAV-5 or AAV5), AAV type 6 (AAV-6 or AAV6), AAV type 7 (AAV-7 or AAV7), AAV type 8 (AAV-8 or AAV8), AAV type 9 (AAV-9 or AAV9), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

The term "4D-A101" or "A101" as used herein refers to an AAV capsid comprising a capsid protein of SEQ ID NO:12.

The term "4D-710" as used herein refers to a recombinant AAV comprising (i) a capsid comprising a capsid protein of SEQ ID NO:12 and (ii) a heterologous nucleic acid comprising the nucleotide sequence of SEQ ID NO:45.

The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers NC_002077.1 (AAV-1), AF063497.1 (AAV-1), NC_001401.2 (AAV-2), AF043303.1 (AAV-2), J01901.1 (AAV-2), U48704.1 (AAV-3), NC_001729.1 (AAV-3), NC_001829.1 (AAV-4), U89790.1 (AAV-4), NC_006152.1 (AAV-5), AF085716.1 (AAV-5), AF028704.1 (AAV-6), NC_006260.1 (AAV-7), AF513851.1 (AAV-7), AF513852.1 (AAV-8) NC_006261.1 (AAV-8), and AY530579.1 (AAV-9); the disclosures of which are incorporated by reference herein for teaching AAV nucleic acid and amino acid sequences. See also, e.g., Srivistava et al. (1983) *J. Virology* 45:555; Chiorini et al. (1998) *J. Virology* 71:6823; Chiorini et al. (1999) *J. Virology* 73:1309; Bantel-Schaal et al. (1999) *J. Virology* 73:939; Xiao et al. (1999) *J. Virology* 73:3994; Muramatsu et al. (1996) *Virology* 221:208; Shade et al., (1986) *J. Virol.* 58:921; Gao et al. (2002) *Proc. Nat. Acad. Sci. USA* 99:11854; Moris et al. (2004) *Virology* 33:375-383; international patent publications WO 00/28061, WO 99/61601, WO 98/11244; and U.S. Pat. No. 6,156,303.

The sequences of naturally existing cap (capsid) proteins associated with AAV serotypes are known in the art and include: AAV1 (SEQ ID NO: 1), AAV2 (SEQ ID NO: 2), AAV3 (SEQ ID NO: 3), AAV4 (SEQ ID NO: 4), AAV5 (SEQ ID NO: 5), AAV6 (SEQ ID NO: 6), AAV7 (SEQ ID NO: 7), AAV8 (SEQ ID NO: 8), and AAV9 (SEQ ID NO: 9). The term "variant AAV capsid protein" is a an AAV capsid protein comprising an amino acid sequence that includes at least one substitution (including deletion, insertion, etc.) relative to one of the naturally existing AAV capsid protein sequences set forth in SEQ ID NOs:1-9.

An "AAV virion" or "AAV viral particle" refers to a viral particle composed of at least one AAV capsid protein and an encapsidated AAV polynucleotide.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

If an AAV virion comprises a heterologous polynucleotide (i.e. a polynucleotide other than a wild-type AAV genome, e.g., a transgene to be delivered to a target cell, an RNAi agent or CRISPR agent to be delivered to a target cell, etc.), it is typically referred to as a "recombinant AAV (rAAV) virion" or an "rAAV viral particle." In general, the heterologous polynucleotide is flanked by at least one, and generally by two, AAV inverted terminal repeat sequences (ITRs).

The term "rAAV vector" encompasses rAAV virions (i.e., rAAV viral particles) (e.g., an infectious rAAV virion), which by definition include an rAAV polynucleotide; and also encompasses polynucleotides encoding rAAV (e.g., a single stranded polynucleotide encoding rAAV (ss-rAAV); a double stranded polynucleotide encoding rAAV (ds-rAAV), e.g., plasmids encoding rAAV; and the like).

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans. For example, a plasmid or other expression vector comprising nucleotide sequences encoding one or more adenoviral proteins is transfected into a producer cell along with an rAAV vector.

An "infectious" virus or viral particle is one that comprises a competently assembled viral capsid and is capable of delivering a polynucleotide component into a cell for which the viral species is tropic. The term does not necessarily imply any replication capacity of the virus. Assays for counting infectious viral particles are described elsewhere in this disclosure and in the art. Viral infectivity can be expressed as the ratio of infectious viral particles to total viral particles. Methods of determining the ratio of infectious viral particle to total viral particle are known in the art. See, e.g., Grainger et al. (2005)*Mol. Ther.* 11:S337 (describing a TCID50 infectious titer assay); and Zolotukhin et al. (1999) *Gene Ther.* 6:973. See also the Examples.

The term "tropism" as used herein refers to the preferential targeting of specific host species or specific cell types within a host species by a virus (e.g., an AAV). For example, a virus that can infect cells of the heart, lung, liver, and muscle has a broader (i.e., increased) tropism relative to a virus that can infect only lung and muscle cells. Tropism can also include the dependence of a virus on particular types of cell surface molecules of the host. For example, some viruses can infect only cells with surface glycosaminoglycans, while other viruses can infect only cells with sialic acid (such dependencies can be tested using various cells lines deficient in particular classes of molecules as potential host cells for viral infection). In some cases, the tropism of a virus describes the virus's relative preferences. For example, a first virus may be able to infect all cell types but is much more successful in infecting those cells with surface glycosaminoglycans. A second virus can be considered to have a similar (or identical) tropism as the first virus if the second virus also prefers the same characteristics (e.g., the second virus is also more successful in infecting those cells with surface glycosaminoglycans), even if the absolute transduction efficiencies are not similar. For example, the second virus might be more efficient than the first virus at infecting every given cell type tested, but if the relative preferences are similar (or identical), the second virus can still be considered to have a similar (or identical) tropism as the first virus. In some embodiments, the tropism of a virion comprising a subject variant AAV capsid protein is not altered relative to a naturally occurring virion. In some embodiments, the tropism of a virion comprising a subject variant AAV capsid protein is expanded (i.e., broadened) relative to a naturally occurring virion. In some embodiments, the tropism of a virion comprising a subject variant AAV capsid protein is reduced relative to a naturally occurring virion.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment herein that comprises a polynucleotide encompasses both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970)

A "gene" refers to a polynucleotide that performs a function of some kind in the cell. For example, a gene can contain an open reading frame that is capable of encoding a particular protein after being transcribed and translated. On the other hand a gene can encode a functional RNA product that is not translated (e.g., an aptamer, an interfering RNA, a ribosomal RNA (rRNA), a transfer RNA (tRNA), etc.).

A "gene expression product" or "gene product" is a molecule resulting from expression of a particular gene, as defined above. Gene expression products include, e.g., a polypeptide, an aptamer, an interfering RNA, a messenger RNA (mRNA), an rRNA, a tRNA, a non-coding RNA (ncRNA), and the like.

An "RNA interfering agent" or "RNAi agent" encompasses any agent (or a polynucleotide encoding such an agent) that can be used to change the expression of a gene (as defined above). Examples of RNAi agents known to one of ordinary skill in the art include, but are not limited to, (i) siRNA agents; (ii) antisense RNA; (iii) CRISPR agents; (iv) Zinc finger nuclease agents, and (v) Transcription activator-like effector nuclease (TALEN) agents.

(i) an siRNA agent ("small interfering" or "short interfering RNA" (or siRNA)) is an RNA duplex of nucleotides that is targeted to a gene interest (a "target gene"). An "RNA duplex" refers to the structure formed by the complementary pairing between two regions of a RNA molecule, forming a region of double stranded RNA (dsRNA). siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. siRNA agents that contain a hairpin can also be referred to as "shRNA (short hairpin RNA) agents." In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length. In general, the level of expression product (e.g., mRNA, polypeptide, etc.) of a target gene is reduced by an siRNA agent (e.g., an siRNA, an shRNA, etc.) that contains specific double stranded nucleotide sequences that are complementary to at least a 19-25 nucleotide long segment (e.g., a 20-21 nucleotide sequence) of the target gene transcript, including the 5' untranslated (UT) region, the ORF, or the 3' UT region. In some embodiments, short interfering RNAs are about 19-25 nt in length. See, e.g., PCT applications WO0/44895, WO99/32619, WO01/75164, WO01/92513, WO01/29058, WO01/89304, WO02/16620, and WO02/29858; and U.S. Patent Publication No. 20040023390 for descriptions of siRNA technology. The siRNA and/or shRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

(ii) antisense RNA is RNA that is complementary to a gene expression product. For example, an antisense RNA targeted to a specific mRNA is an RNA-based agent (or can be a modified RNA) that is complementary to the mRNA, where hybridization of the antisense RNA to the mRNA alters the expression of the mRNA (e.g., via altering the stability of the RNA, altering the translation of the RNA, etc.). Also included in "antisense RNA" are nucleic acids encoding an antisense RNA.

(iii) CRISPR agents. CRISPR (Clustered regularly interspaced short palindromic repeats)/CRISPR-associated (Cas) systems provide bacteria and archaea with adaptive immunity against viruses and plasmids by using CRISPR RNAs (crRNAs) to guide the silencing of invading nucleic acids. The Cas 9 protein (or functional equivalent and/or variant thereof, i.e., Cas9-like protein) naturally contains DNA endonuclease activity that depends on association of the protein with two naturally occurring or synthetic RNA molecules called crRNA and tracrRNA (also called guide RNAs). In some cases, the two molecules are covalently linked to form a single molecule (also called a single guide RNA ("sgRNA")). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence. If the Cas9 or Cas9-like protein retains its natural enzymatic function, it will cleave target DNA to create a double-strand break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Cas9-like proteins with decreased DNA-cleavage activity (even no DNA-cleaving activity) can still be guided to a target DNA and can block RNA polymerase activity. Thus enzymatically inactive Cas9-like proteins can be targeted to a specific location in a target DNA by a DNA-targeting RNA in order to block transcription of the target DNA. Detailed information regarding CRISPR agents can be found, for example in (a) Jinek et. al., Science. 2012 Aug. 17; 337(6096):816-21: "A programmable dual-RNA-guided DNA endonuclease in adaptive bacterial immunity"; (b) Qi et al., Cell. 2013 Feb. 28; 152(5):1173-83: "Repurposing CRISPR as an RNA-guided platform for sequence-specific control of gene expression", and (c) U.S. patent application Ser. No. 13/842,859 and PCT application number PCT/US13/32589; all of which are hereby incorporated by reference in their entirety. Thus, the term "CRISPR agent" as used herein encompasses any agent (or nucleic acid encoding such an agent), comprising naturally occurring and/or synthetic sequences, that can be used in the Cas9-based system (e.g., a Cas9 or Cas9-like protein; any component of a DNA-targeting RNA, e.g., a crRNA-like RNA, a tracrRNA-like RNA, a single guide RNA, etc.; a donor polynucleotide; and the like).

(iv) Zinc finger nuclease (ZFN) agents. Zinc-finger nucleases (ZFNs) are artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double strand breaks. For more information on the use of ZFNs, see, for example: Asuri et al., Mol Ther. 2012 February; 20(2):329-38; Bibikova et al. Science. 2003 May 2; 300(5620):764; Wood et al. Science. 2011 Jul. 15; 333(6040):307; Ochiai et al. Genes Cells. 2010 August; 15(8):875-85; Takasu et. al., Insect Biochem Mol Biol. 2010 October; 40(10):759-65; Ekker et al, Zebrafish 2008 Summer; 5(2):121-3; Young et al, Proc Natl Acad Sci USA. 2011 Apr. 26; 108(17):7052-7; Goldberg et al, Cell. 2010 Mar. 5; 140(5):678-91; Geurts et al, Science. 2009 Jul. 24; 325(5939):433; Flisikowska et al, PLoS One. 2011; 6(6):e21045. doi: 10.1371/joumal.pone.0021045. Epub 2011 Jun. 13; Hauschild et al, Proc Natl Acad Sci USA. 2011 Jul. 19; 108(29):12013-7; and Yu et al, Cell Res. 2011 November; 21(11):1638-40; all of which are herein incorporated by reference for their teachings related to ZFNs. The term "ZFN agent" encompasses a zinc finger nuclease and/or a polynucleotide comprising a nucleotide sequence encoding a zinc finger nuclease.

(v) Transcription activator-like effector nuclease (TALEN) agents. Transcription activator-like effector nucleases (TALENs) are artificial DNA endonucleases generated by fusing a TAL (Transcription activator-like) effector DNA binding domain to a DNA cleavage domain. TALENS can be quickly engineered to bind practically any desired DNA sequence and when introduced into a cell, TALENs can be used to edit target DNA in the cell (e.g., the cell's genome) by inducing double strand breaks. For more information on the use of TALENs, see, for example: Hockemeyer et al. Nat Biotechnol. 2011 Jul. 7; 29(8):731-4; Wood et al. Science. 2011 Jul. 15; 333(6040):307; Tesson et al. Nat Biotechnol. 2011 Aug. 5; 29(8):695-6; and Huang et. al., Nat Biotechnol. 2011 Aug. 5; 29(8):699-700; all of which are herein incorporated by reference for their teachings related to TALENs. The term "TALEN agent" encompasses a TALEN and/or a polynucleotide comprising a nucleotide sequence encoding a TALEN.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

A "2A peptide" refers to "self-cleaving" peptides of about 20 amino acids that produce equimolar levels of multiple genes from the same mRNA and may be used in place of IRES elements in multicistronic vectors. Non-limiting examples include T2A, P2A, E2A and F2A peptides sequences.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

A cell has been "genetically modified" or "transformed" or "transfected" by exogenous DNA (e.g. via a recombinant virus), when such DNA has been introduced inside the cell. The presence of the exogenous DNA results in permanent or transient genetic change. The transforming DNA may or may not be integrated (covalently linked) into the genome of the cell. A "clone" is a population of cells derived from a single cell or common ancestor by mitosis. A "cell line" is a clone of a primary cell that is capable of stable growth in vitro for many generations.

A cell is said to be "stably" altered, transduced, genetically modified, or transformed with a genetic sequence if the sequence is available to perform its function during extended culture of the cell in vitro and/or for an extended period of time in vivo. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

An "isolated" plasmid, nucleic acid, vector, virus, virion, host cell, protein, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this disclosure are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease (and/or symptoms caused by the disease) from occurring in a subject which may be predisposed to the disease or at risk of acquiring the disease but has not yet been diagnosed as having it; (b) inhibiting the disease (and/or symptoms caused by the disease), i.e., arresting its development; and (c) relieving the disease (and/or symptoms caused by the disease), i.e., causing regression of the disease (and/or symptoms caused by the disease).

The terms "individual," "host," "subject," and "patient" are used interchangeably herein, and refer to a mammal, including, but not limited to, humans; non-human primates, including simians; mammalian sport animals (e.g., horses); mammalian farm animals (e.g., sheep, goats, etc.); mammalian pets (dogs, cats, etc.); and rodents (e.g., mice, rats, etc.).

In some embodiments, the individual is a human who has previously been naturally exposed to AAV and as a result harbors anti-AAV antibodies (i.e., AAV neutralizing antibodies). In some embodiments, the individual is a human who has previously been administered an AAV vector (and as a result may harbor anti-AAV antibodies) and needs re-administration of vector for treatment of a different condition or for further treatment of the same condition. Based on positive results in clinical trials involving AAV gene delivery to, for example, liver, muscle, and retina—all tissues affected by neutralizing antibodies against this vehicle—there are many such therapeutic applications/disease targets.

The term "effective amount" as used herein is an amount sufficient to effect beneficial or desired clinical results. An effective amount can be administered in one or more administrations. For purposes of this disclosure, an effective amount of a compound (e.g., an infectious rAAV virion) is an amount that is sufficient to palliate, ameliorate, stabilize, reverse, prevent, slow or delay the progression of (and/or symptoms associated with) a particular disease state (e.g., cancer). Accordingly, an effective amount of an infectious rAAV virion is an amount of the infectious rAAV virion that is able to evade the neutralizing activity of an individual's anti-AAV antibodies, thus effectively delivering the heterologous nucleic acid to a target cell (or target cells) of the individual.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an infectious recombinant adeno-associated virus (rAAV) virion" includes a plurality of such virions and reference to "the infectious recombinant adeno-associated virus (rAAV) virion" includes reference to one or more such virions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present disclosure provides infectious recombinant adeno-associated virus (rAAV) virions that comprise a variant capsid protein and a heterologous nucleic acid. The present disclosure further provides the variant adeno-associated virus (AAV) capsid proteins (and/or a nucleic acid encoding the variant AAV capsid proteins), which confer to an infectious rAAV virion an increased resistance to human AAV neutralizing antibodies. The present disclosure further provides host cells comprising an infectious rAAV virion and/or a nucleic acid encoding a subject variant AAV capsid protein. The present disclosure further provides libraries of the above virions, capsid proteins, nucleic acids, and/or host cells; where the variant AAV capsid protein of at least one member of the library comprises an amino acid sequence having at least one amino acid substitution relative to the amino acid sequence set forth in one of SEQ ID NOs:10-13 and 26-33.

The present disclosure further provides methods of delivering a heterologous nucleic acid to a target cell where the target cell is contacted with a subject infectious rAAV virion. The present disclosure further provides methods of delivering a gene product to an individual, the methods generally involving administering an effective amount of a subject rAAV virion to an individual in need thereof. Also provided herein are compositions and kits for practicing the subject methods. In many embodiments, a subject infectious rAAV virion, a subject nucleic acid, a subject variant AAV capsid protein, a subject host cell, etc., is isolated.

Variant AAV Capsid Polypeptides

A subject variant AAV capsid polypeptide (or the variant AAV capsid protein encoded by a subject nucleic acid) confers to an infectious rAAV virion comprising the variant AAV capsid polypeptide an increased resistance to human AAV neutralizing antibodies compared to the resistance exhibited by a wild type AAV (e.g., AAV2 (wild type AAV serotype 2)) or an AAV comprising a wild-type capsid protein. In some embodiments, the increased resistance is at least about 1.5-fold (e.g., at least about 1.5-fold, at least about 2-fold, at least about 3-fold, at least about 4-fold, at least about 5-fold, at least about 7.5-fold, at least about 10-fold, at least about 12-fold, at least about 15-fold, at least about 17-fold, at least about 20-fold, at least about 25-fold, at least about 30-fold, at least about 40-fold, at least about 50-fold, at least about 75-fold, at least about 100-fold, at least about 150-fold, at least about 200-fold, at least about 250-fold, at least about 300-fold, etc.) greater than the resistance exhibited by a wild type AAV (e.g., AAV2 (wild type AAV serotype 2)) or an AAV comprising a wild-type capsid protein.

A subject variant AAV capsid protein (or the variant AAV capsid protein encoded by a subject nucleic acid) can be said to confer to an infectious rAAV virion an increased transduction of mammalian cells in the presence of human AAV neutralizing antibodies compared to the transduction exhibited by a wild type AAV (e.g., AAV2 (wild type AAV serotype 2)) or an AAV comprising a wild-type capsid protein. In some embodiments, the increased transduction is at least about 1.5-fold (e.g., at least about 1.5-fold, at least about 2-fold, at least about 3-fold, at least about 4-fold, at least about 5-fold, at least about 7.5-fold, at least about 10-fold, at least about 12-fold, at least about 15-fold, at least about 17-fold, at least about 20-fold, at least about 25-fold, at least about 30-fold, at least about 40-fold, at least about 50-fold, at least about 75-fold, at least about 100-fold, at least about 150-fold, at least about 200-fold, at least about 250-fold, at least about 300-fold, etc.) greater than the transduction exhibited by a wild type AAV (e.g., AAV2 (wild type AAV serotype 2)) or an AAV comprising a wild-type capsid protein.

In some embodiments, a subject variant AAV capsid protein (or the variant AAV capsid protein encoded by a subject nucleic acid) exhibits decreased binding to a neutralizing antibody that binds a wild-type AAV capsid protein. For example, a subject variant AAV capsid protein can exhibit at least about 1.5-fold (e.g., at least about 1.5-fold, at least about 2-fold, at least about 3-fold, at least about 4-fold, at least about 5-fold, at least about 7.5-fold, at least about 10-fold, at least about 12-fold, at least about 15-fold, at least about 17-fold, at least about 20-fold, at least about 25-fold, at least about 30-fold, at least about 40-fold, at least about 50-fold, at least about 75-fold, at least about 100-fold, at least about 150-fold, at least about 200-fold, at least about 250-fold, at least about 300-fold, etc.) reduced binding (e.g., reduced affinity) to a neutralizing antibody that binds a wild-type capsid AAV protein, compared to the binding affinity of the antibody to wild-type AAV capsid protein.

In some embodiments, an anti-AAV neutralizing antibody binds to a subject variant AAV capsid protein (or the variant AAV capsid protein encoded by a subject nucleic acid) with an affinity of less than about $10^{-7}$M, less than about $5\times10^{-6}$ M, less than about $10^{-6}$ M, less than about $5\times10^{-5}$M, less than about $10^{-5}$ M, less than about $10^{-4}$ M, or lower.

The term "variant capsid protein" does not encompass wild type AAV capsid proteins. A "variant AAV capsid protein" does not comprise an amino acid sequence present in a naturally occurring AAV capsid protein. For example, a subject variant capsid protein does not comprise an amino acid sequence having 100% sequence identity to any of the sequences set forth in SEQ ID NOs:1-9. In other words, a subject variant capsid protein does not comprise an amino acid sequence as set forth in any of SEQ ID NOs:1-9. A variant capsid protein can differ in amino acid sequence from a "starter" or "parental" AAV capsid protein, which parental AAV capsid protein may be a wild-type AAV capsid protein or non-wild-type AAV capsid protein.

In some embodiments a subject variant AAV capsid protein (or the variant AAV capsid protein encoded by a subject nucleic acid) comprises an amino acid sequence having at least about 90% (e.g., at least about 92%, at least about 95%, at least about 96%, at least about 97%, at least about 98%, at least about 99%, at least about 99.5%, or 100%) amino acid sequence identity to amino acids 203-736 of the amino acid sequence set forth in one of SEQ ID NOs:10-13 and 26-33.

In some embodiments a subject variant AAV capsid protein (or the variant AAV capsid protein encoded by a subject nucleic acid) comprises an amino acid sequence having at least about 90% (e.g., at least about 92%, at least about 95%, at least about 96%, at least about 97%, at least about 98%, at least about 99%, at least about 99.5%, or 100%) amino acid sequence identity to the amino acid sequence set forth in one of SEQ ID NOs:10-13 and 26-33.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to amino acids 203-736 of the amino acid sequence set forth in SEQ ID NO:10, and includes the amino acid substitutions N312K, N449D, D472N, N551S, I698V, and L735Q relative to the AAV capsid protein of AAV2 (e.g., SEQ ID NO: 2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to the amino acid sequence set forth in SEQ ID NO:10, and includes the amino acid substitutions N312K, N449D, D472N, N551S, I698V, and L735Q relative to the AAV capsid protein of AAV2 (e.g., SEQ ID NO: 2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to amino acids 203-736 of the amino acid sequence set forth in SEQ ID NO:31, and includes the amino acid substitutions N312K, N449D, N551S, and I698V relative to the AAV capsid protein of AAV2 (e.g., SEQ ID NO:2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to the amino acid sequence set forth in SEQ ID NO:31, and includes the amino acid substitutions N312K, N449D, N551S, and I698V relative to the AAV capsid protein of AAV2 (e.g., SEQ ID NO:2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to amino acids 203-736 of the amino acid sequence set forth in SEQ ID NO:32, and includes the amino acid substitutions D180N, N312K, Q385R, N449D, N551S, I698V, and S721T relative to the AAV capsid protein of AAV2 (e.g., SEQ ID NO:2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to the amino acid sequence set forth in SEQ ID NO:32, and includes the amino acid substitutions D180N, N312K, Q385R, N449D, N551S, I698V, and S721T relative to the AAV capsid protein of AAV2 (e.g., SEQ ID NO:2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to amino acids 203-736 of the amino acid sequence set forth in SEQ ID NO:33, and includes the amino acid substitutions N312K, N449D, T450A, N551S, and I698V relative to the AAV capsid protein of AAV2 (e.g., SEQ ID NO:2), or the corresponding positions in another AAV parental serotype.

In some embodiments a subject variant AAV capsid protein (or the variant AAV capsid protein encoded by a subject nucleic acid) comprises an amino acid sequence having at least about 95% (e.g., at least about 96%, at least about 97%, at least about 98%, at least about 99%, at least about 99.5%, or 100%) amino acid sequence identity to the amino acid sequence set forth in SEQ ID NO:33, and includes the amino acid substitutions N312K, N449D, T450A, N551S, and I698V relative to the AAV capsid protein of AAV2 (e.g., SEQ ID NO:2), or the corresponding positions in another AAV parental serotype.

Figure 8I:
Figure 9F:
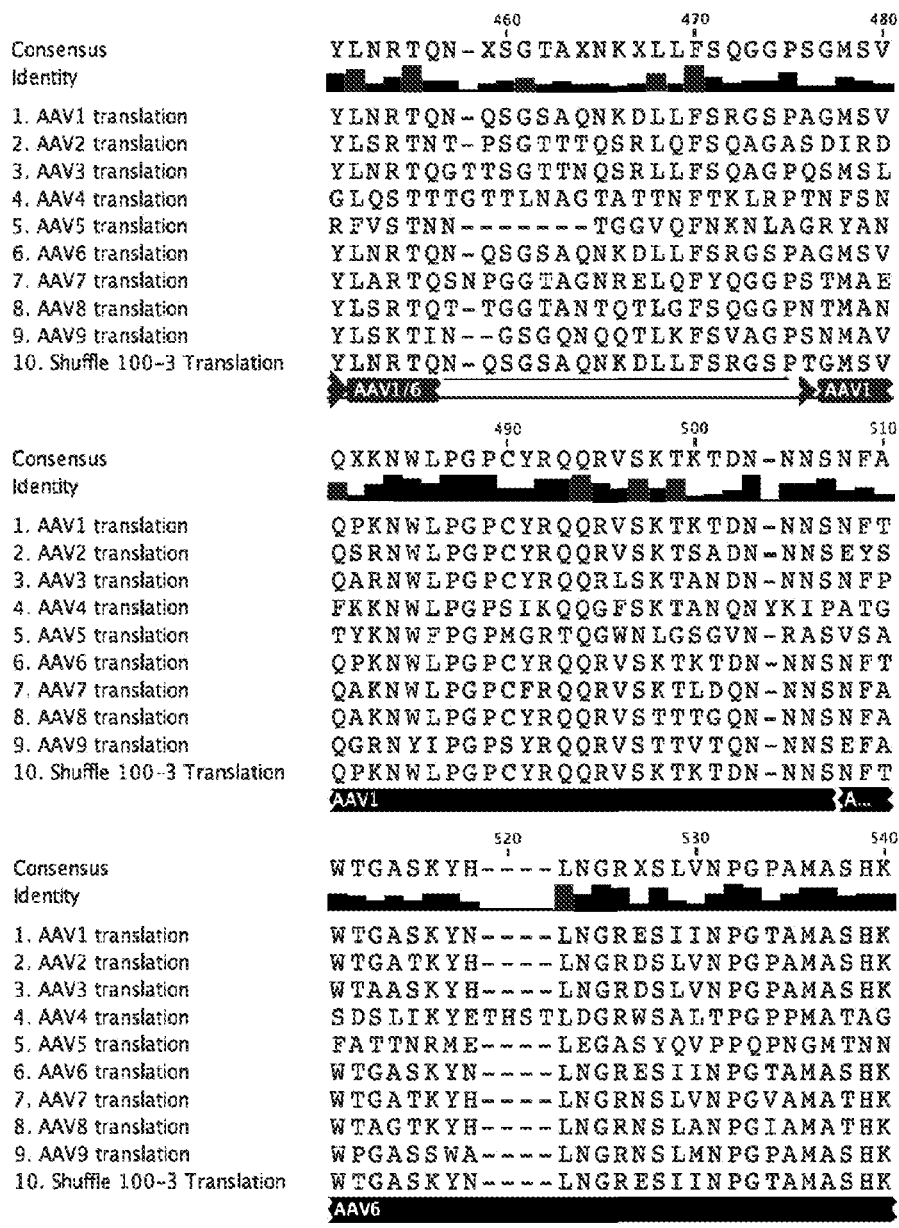

Exemplary variant AAV capsid proteins include, but are not limited to (see FIGS. 8-10 for selected exemplary sequence alignments):

SM 10-2 (amino acid sequence)(SEQ ID NO:10); SM 10-2 (nucleotide sequence)(SEQ ID NO:22); Shuffle 100-1 (amino acid sequence) (SEQ ID NO: 11); Shuffle 100-1 (nucleotide sequence) (SEQ ID NO: 23);

```
Shuffle 100-3 (amino acid sequence)
(SEQ ID NO: 12):
MAADGYLPDWLEDTLSEGIRQWWKLKPGPPPPKPA

ERHKDDSRGLVLPGYKYLGPFNGLDKGEPVNEADA

AALEHDKAYDQQLKAGDNPYLKYNHADAEFQQRLQ

GDTSFGGNLGRAVFQAKKRVLEPLGLVEQAGETAP

GKKRPLIESPQQPDSSTGIGKKGKQPAKKRLNFGQ

TGDSESVPDPQPLGEPPATPAAVGPTTMASGGGAP

MADNNEGADGVGNASGNWHCDSTWLGDRVITTSTR

TWALPTYNNHLYKQISSASTGASNDNHYFGYSTPW

GYFDFNRFHCHFSPRDWQRLINNNWGFRPKRLNFK

LFNIQVKEVTTNDGVTTIANNLTSTVQVFSDSDYQ

LPYVLGSAHEGCLPPFPADVFMVPQYGYLTLNNGS

QAVGRSSFYCLEYFPSQMLRTGNNFTFSYTFEDVP

FHSSYAHSQSLDRLMNPLIDQYLYYLNRTQNQSGS

AQNKDLLFSRGSPTGMSVQPKNWLPGPCYRQQRVS

KTKTDNNNSNFTWTGASKYNLNGRESIINPGTAMA

SHKDDKDKFFPMSGVMIFGKESAGASNTALDNVMI

TDEEEIKATNPVATERFGTVAVNLQSSSTDPATGD

VHAMGALPGMVWQDRDVYLQGPIWAKIPHTDGHFH

PSPLMGGFGLKNPPPQILIKNTPVPANPPAEFSAT

KFASFITQYSTGQVSVEIEWELQKENSKRWNPEVQ

YTSNYAKSANVDFTVDNNGLYTEPRPIGTRYLTRP

L;

Shuffle 100-3 (nucleotide sequence)
(SEQ ID NO: 24):
atggctgctgatggttatcttccagattggctcga ggacactctctctgaaggaataagacagtggtgga agctcaaacctggcccaccaccaccaaagcccgca gagcggcataaggacgacagcaggggtcttgtgct tcctgggtacaagtacctcggacccttcaacggac tcgacaagggagagccggtcaacgaggcagacgca gcggccctcgagcacgacaaggcctacgaccagca gctcaaggccggtgacaacccctacctcaagtaca accacgccgacgcggagttccagcagcggcttcag ggcgacacatcgtttgggggcaacctcggcagagc agtcttccaggccaaaaagagggttcttgaacctc ttggtctggttgagcaagcgggtgagacggctcct
```

```
ggaaagaagagaccgttgattgaatcccccagca gcccgactcctccacgggtatcggcaaaaaggca agcagccggctaaaaagagactcaattttggtcag actggcgactcagagtcagtccccgacccacaacc tctcggagaacctccagcaaccccgctgctgtgg gacctactacaatggcttcaggtggtggcgcacca atggcagacaataacgaaggcgccgacggagtggg taatgcctcaggaaattggcattgcgattccacat ggctgggcgacagagtcatcaccaccagcacccgc acctgggccttgcccacctacaataaccacctcta caagcaaatctccagtgcttcaacgggggccagca acgacaaccactacttcggctacagcacccctgg gggtattttgacttcaacagattccactgccactt tcaccacgtgactggcagcgactcatcaacaaca attggggattccggcccaagagactcaacttcaaa ctcttcaacatccaagtcaaggaggtcacgacgaa tgatggcgtcacaaccatcgctaataaccttacca gcacggttcaagtcttctcggactcagactatcag ctcccgtacgtgctcgggtcggctcacgagggctg cctcccgccgttcccagcagacgtcttcatggtgc cacagtatggatacctcaccctgaacaacgggagt caggcaggacgtcttcattttactgcctgga gtactttccttctcagatgctgcgtaccggaaaca actttaccttcagctacacttttgaggacgttcct ttccacagcagctacgctcacagccagagtctgga ccgtctcatgaatcctctcatcgaccagtacctgt attacctgaacagaactcagaatcagtccggaagt gcccaaaacaaggacttgctgtttagccgggggtc tccaactggcatgtctgttcagcccaaaaactggc tacctggaccctgttatcggcagcagcgcgtttct aaaacaaaaacagacaacaacaacagcaactttac ctggactggtgcttcaaaatataaccttaatgggc gtgaatctataatcaaccctggcactgctatggcc tcacacaaagacgacaaagacaagttctttcccat gagcggtgtcatgattttggaaaggagagcgccg gagcttcaaacactgcattggacaatgtcatgatc acagacgaagaggaaatcaaagccactaaccccgt ggccactgaaagatttgggactgtggcagtcaatc tccagagcagcagcacagaccctgcgaccggagat gtgcatgccatgggagccttacctggaatggtgtg
```

```
            -continued
gcaagacagagacgtatacctgcagggtcctattt gggccaaaattcctcacacggatggacactttcac ccgtctcctctcatgggcggctttggactcaagaa cccgcctcctcagatcctcatcaaaaacacgcctg ttcctgcgaatcctccggcggagttttcagctaca aagtttgcttcattcatcacccagtattccacagg acaagtgagcgtggagattgaatgggagctgcaga aagaaaacagcaaacgctggaatcccgaagtgcag tatacatctaactatgcaaaatctgccaacgttga tttcactgtggacaacaatggactttatactgagc ctcgcccattggcacccgttacctcacccgtccc ctgtaa;
```

Shuffle 100-7 (amino acid sequence) (SEQ ID NO: 13); Shuffle 100-7 (nucleotide sequence) (SEQ ID NO: 25); Shuffle 10-2 (amino acid sequence) (SEQ ID NO: 26); Shuffle 10-2 (nucleotide sequence) (SEQ ID NO: 34); Shuffle 10-6 (amino acid sequence) (SEQ ID NO: 27); Shuffle 10-6 (nucleotide sequence) (SEQ ID NO: 35); Shuffle 10-8 (amino acid sequence) (SEQ ID NO: 28); Shuffle 10-8 (nucleotide sequence) (SEQ ID NO: 36); Shuffle 100-2 (amino acid sequence) (SEQ ID NO: 29); Shuffle 100-2 (nucleotide sequence) (SEQ ID NO: 37); SM 10-1 (amino acid sequence) (SEQ ID NO: 30); SM 10-1 (nucleotide sequence) (SEQ ID NO: 38); SM 10-8 (amino acid sequence) (SEQ ID NO: 31); SM 10-8 (nucleotide sequence) (SEQ ID NO: 39); SM 100-3 (amino acid sequence) (SEQ ID NO: 32); SM 100-3 (nucleotide sequence) (SEQ ID NO: 40); SM 100-10 (amino acid sequence) (SEQ NO: 33); and SM 100-10 (nucleotide sequence) (SEQ ID NO: 41).

Nucleic Acids and Host Cells

The present disclosure provides nucleic acids comprising nucleotide sequences encoding a variant AAV capsid protein (as described above), as well as host cells comprising a subject nucleic acid. The nucleic acids and host cells are useful for generating rAAV virions (as described below).

The present disclosure provides host cells, e.g., isolated host cells, comprising a subject nucleic acid. A subject host cell can be referred to as a "genetically modified host cell" and is typically an isolated cell, e.g., a cell in in vitro culture. A subject host cell is useful for producing a subject rAAV virion, as described below. Where a subject host cell is used to produce a subject rAAV virion, it is referred to as a "packaging cell." In some embodiments, a subject host cell is stably genetically modified (i.e., stably transfected) with a subject nucleic acid. In other embodiments, a subject host cell is transiently genetically modified (i.e., transiently transfected) with a subject nucleic acid.

A subject nucleic acid is introduced stably or transiently into a host cell, using established techniques, including, but not limited to, electroporation, calcium phosphate precipitation, liposome-mediated transfection, and the like. For stable transformation, a subject nucleic acid will generally further include a selectable marker, e.g., any of several well-known selectable markers such as neomycin resistance, and the like.

A subject host cell is generated by introducing a subject nucleic acid into any of a variety of cells, e.g., mammalian cells, including, e.g., murine cells, and primate cells (e.g., human cells). Suitable mammalian cells include, but are not limited to, primary cells and cell lines, where suitable cell lines include, but are not limited to, 293 cells, COS cells, HeLa cells, Vero cells, 3T3 mouse fibroblasts, C3H10T1/2 fibroblasts, CHO cells, and the like.

In some embodiments, a subject host cell includes, in addition to a nucleic acid comprising a nucleotide sequence encoding a mutant capsid protein, a nucleic acid that comprises a nucleotide sequence encoding one or more AAV rep proteins. In other embodiments, a subject host cell further comprises an rAAV vector, as described below. As described in more detail below, an rAAV virion is generated using a subject host cell.

Infectious rAAV Virions

A subject infectious rAAV virion comprises a variant AAV capsid protein and a heterologous nucleic acid (described in greater detail below), and exhibits an increased resistance to human AAV neutralizing antibodies compared to the resistance exhibited by a wild type AAV (e.g., AAV2 (wild type AAV serotype 2)) or an AAV comprising a wild-type capsid protein. By "increased resistance" it is meant that a subject infectious rAAV virion exhibits an increased infectivity in the presence of human anti-AAV antibodies. As described above, viral infectivity can be expressed as the ratio of infectious viral particles to total viral particles. Thus in increased infectivity means an increased ratio of infectious viral particles to total viral particles. To determine resistance of an AAV to human anti-AAV antibodies, infectivity of the AAV is measured in the presence of various concentrations of human anti-AAV antibodies in order to obtain the antibody concentration (e.g., serum concentration, IVIG concentration, etc.) (mg/mL) required to reduce gene delivery efficiency (i.e., infectivity) to 50% of that in the absence of human anti-AAV antibodies. A virus that requires a higher antibody concentration to reduce gene delivery efficiency to 50% of that in the absence of human anti-AAV antibodies is said to have increased resistance to antibody neutralization. Thus, a two-fold increase in resistance means a two-fold increase in the antibody concentration required to reduce gene delivery efficiency to 50% of that in the absence of human anti-AAV antibodies. In some embodiments, a subject infectious rAAV virion exhibits at least about 1.5-fold (e.g., at least about 1.5-fold, at least about 2-fold, at least about 3-fold, at least about 4-fold, at least about 5-fold, at least about 7.5-fold, at least about 10-fold, at least about 12-fold, at least about 15-fold, at least about 17-fold, at least about 20-fold, at least about 25-fold, at least about 30-fold, at least about 40-fold, at least about 50-fold, at least about 75-fold, at least about 100-fold, at least about 150-fold, at least about 200-fold, at least about 250-fold, at least about 300-fold, etc.) greater resistance to human AAV neutralizing antibodies than the resistance exhibited by a wild type AAV (e.g., AAV2 (wild type AAV serotype 2)) or an AAV comprising a wild-type capsid protein.

A subject infectious rAAV virion can be said to exhibit increased transduction of mammalian cells in the presence of human AAV neutralizing antibodies. In some embodiments, a subject infectious rAAV virion exhibits at least about 1.5-fold (e.g., at least about 1.5-fold, at least about 2-fold, at least about 3-fold, at least about 4-fold, at least about 5-fold, at least about 7.5-fold, at least about 10-fold, at least about 12-fold, at least about 15-fold, at least about 17-fold, at least about 20-fold, at least about 25-fold, at least about 30-fold, at least about 40-fold, at least about 50-fold, at least about 75-fold, at least about 100-fold, at least about 150-fold, at least about 200-fold, at least about 250-fold, at least about 300-fold, etc.) greater transduction of mammalian cells in the presence of human AAV neutralizing antibodies than the transduction exhibited by a wild type AAV (e.g., AAV2 (wild type AAV serotype 2)) or an AAV comprising a wild-type capsid protein.

In some embodiments, a subject infectious rAAV virion exhibits decreased binding to a neutralizing antibody that binds a wild-type AAV capsid protein. For example, a subject infectious rAAV virion can exhibit at least about 1.5-fold (e.g., at least about 1.5-fold, at least about 2-fold, at least about 3-fold, at least about 4-fold, at least about 5-fold, at least about 7.5-fold, at least about 10-fold, at least about 12-fold, at least about 15-fold, at least about 17-fold, at least about 20-fold, at least about 25-fold, at least about 30-fold, at least about 40-fold, at least about 50-fold, at least about 75-fold, at least about 100-fold, at least about 150-fold, at least about 200-fold, at least about 250-fold, at least about 300-fold, etc.) reduced binding (e.g., reduced affinity) to a neutralizing antibody that binds a wild-type capsid AAV protein, compared to the binding affinity of the antibody to wild-type AAV capsid protein.

In some embodiments, an anti-AAV neutralizing antibody binds to a subject infectious rAAV virion with an affinity of less than about $10^{-7}$M, less than about $5 \times 10^{-6}$M, less than about $10^{-6}$ M, less than about $5 \times 10^{-5}$M, less than about $10^{-5}$ M, less than about $10^{-4}$ M, or lower.

In some embodiments, a subject infectious rAAV virion exhibits increased in vivo residence time compared to a wild-type AAV. For example, a subject infectious rAAV virion exhibits a residence time that is at least about 10%, at least about 25%, at least about 50%, at least about 100%, at least about 3-fold, at least about 5-fold, at least about 10-fold, at least about 25-fold, at least about 50-fold, at least about 100-fold, or more, longer than the residence time of a wild-type AAV.

Whether a given subject infectious rAAV virion exhibits reduced binding to a neutralizing antibody and/or increased resistance to neutralizing antibody can be determined using any convenient assay known to one of ordinary skill in the art.

In some embodiments, a subject infectious rAAV virion comprises wild-type Rep78, Rep68, Rep52, and Rep40 proteins. In other embodiments, a subject infectious rAAV virion comprises, in addition to one or more variant capsid proteins, one or more mutations in one or more of Rep78, Rep68, Rep52, and Rep40 proteins.

Heterologous Nucleic Acids

A suitable heterologous DNA molecule (also referred to herein as a "heterologous nucleic acid") for use in a subject rAAV vector (e.g., a subject infectious rAAV virion) can be any heterologous nucleic acid. In some embodiments, the heterologous nucleic acid comprises a nucleotide sequence encoding a polypeptide (e.g., a protein that imparts some desired characteristic to the target cell, e.g., a fluorescent protein that allows for cell tracking, an enzyme that provides an activity missing or altered in the target cell, etc.). In some embodiments, the heterologous nucleic acid comprises an RNA interfering agent (as defined above).

A subject heterologous nucleic acid will generally be less than about 5 kilobases (kb) in size and will include, for example, a gene (a nucleotide sequence) that encodes a protein that is defective or missing from a recipient individual or target cell; a gene that encodes a protein having a desired biological or therapeutic effect (e.g., an antibacterial, antiviral or antitumor/anti-cancer function); a nucleotide sequence that encodes an RNA that inhibits or reduces production of a deleterious or otherwise undesired protein (e.g., a nucleotide sequence that encodes an RNA interfering agent, as defined above); and/or a nucleotide sequence that encodes an antigenic protein.

Suitable heterologous nucleic acids include, but are not limited to, those encoding proteins used for the treatment of endocrine, metabolic, hematologic, cardiovascular, neurologic, musculoskeletal, urologic, pulmonary and immune disorders, including such disorders as inflammatory diseases, autoimmune, chronic and infectious diseases, such as acquired immunodeficiency syndrome (AIDS), cancer, hypercholestemia, lysosomal storage diseases such as Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, I-Cell disease/Mucolipidosis II, Infantile Free Sialic Acid Storage Disease/ISSD, Juvenile Hexosaminidase A Deficiency, Krabbe disease, Lysosomal acid lipase deficiency, Metachromatic Leukodystrophy, Mucopolysaccharidoses disorders (including Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, and Mucolipidosis type IV), Multiple sulfatase deficiency, Niemann-Pick Disease, Neuronal Ceroid Lipofuscinoses, Pompe disease/Glycogen storage disease type II, Pycnodysostosis, Sandhoff disease/Adult Onset/GM2 Gangliosidosis, Sandhoff disease/GM2 gangliosidosis—Infantile, Sandhoff disease/GM2 gangliosidosis—Juvenile, Schindler disease, Salla disease/Sialic Acid Storage Disease, Tay-Sachs/GM2 gangliosidosis, and Wolman disease, insulin disorders such as diabetes, growth disorders, various blood disorders including various anemias, thalassemias and hemophilia; genetic defects such as cystic fibrosis, Gaucher's Disease, Hurler's Disease, adenosine deaminase (ADA) deficiency, emphysema, or the like.

Suitable heterologous nucleic acids include, but are not limited to, those encoding any of a variety of proteins, including, but not limited to: an interferon (e.g., IFN-γ, IFN-α, IFN-β, IFN-ω; IFN-τ); an insulin (e.g., Novolin, Humulin, Humalog, Lantus, Ultralente, etc.); an erythropoietin ("EPO"; e.g., Procrit®, Eprex®, or Epogen® (epoetin-α); Aranesp® (darbepoietin-α); NeoRecormon®, Epogin® (epoetin-β); and the like); an antibody (e.g., a monoclonal antibody) (e.g., Rituxan® (rituximab); Remicade® (infliximab); Herceptin® (trastuzumab); Humira™ (adalimumab); Xolair® (omalizumab); Bexxar® (tositumomab); Raptiva™ (efalizumab); Erbitux™ (cetuximab); Avastin® (bevacizumab); and the like), including an antigen-binding fragment of a monoclonal antibody (e.g., Lucentis® (ranibizumab)); a blood factor (e.g., Activase® (alteplase) tissue plasminogen activator; NovoSeven® (recombinant human factor VIIa); Factor VIIa; Factor VIII (e.g., Kogenate®); Factor IX; β-globin; hemoglobin; and the like); a colony stimulating factor (e.g., Neupogen® (filgrastim; G-CSF); Neulasta (pegfilgrastim); granulocyte colony stimulating factor (G-CSF), granulocyte-monocyte colony stimulating factor, macrophage colony stimulating factor, megakaryocyte colony stimulating factor; and the like); a growth hormone (e.g., a somatotropin, e.g., Genotropin®, Nutropin®, Norditropin®, Saizen®, Serostim®, Humatrope®, etc.; a human growth hormone; and the like); an interleukin (e.g., IL-1; IL-2, including, e.g., Proleukin®; IL-3, IL-4, IL-5, IL-6, IL-7, IL-8, IL-9; etc.); a growth factor (e.g., Regranex® (beclapermin; PDGF); Fiblast® (trafermin; bFGF); Stemgen® (ancestim; stem cell factor); keratinocyte growth factor; an acidic fibroblast growth factor, a stem cell factor, a basic fibroblast growth factor, a hepatocyte growth factor; and the like); a soluble receptor (e.g., a TNF-α-binding soluble receptor such as Enbrel® (etanercept); a soluble VEGF receptor; a soluble interleukin receptor; a soluble γ/δ T cell receptor; and the like); an enzyme (e.g., α-glucosidase; Cerazyme® (imiglucarase; β-glucocerebrosidase, Ceredase® (alglucerase); an enzyme activator (e.g., tissue plasminogen activator); a chemokine (e.g., IP-10; Mig; Groa/IL-8, RANTES; MIP-1α; MIP-1β; MCP-1; PF-4; and the like); an angiogenic agent (e.g., vascular endothelial growth factor (VEGF); an anti-angiogenic agent (e.g., a soluble VEGF receptor); a protein vaccine; a neuroactive peptide such as bradykinin, cholecystokinin, gastrin, secretin, oxytocin, gonadotropin-releasing hormone, beta-endorphin, enkephalin, substance P, somatostatin, prolactin, galanin, growth hormone-releasing hormone, bombesin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, an insulin-like growth factor, a luteinizing hormone, a macrophage activating factor, tumor necrosis factor, a neutrophil chemotactic factor, a nerve growth factor a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); an ion channel, e.g., cystic fibrosis transmembrane conductance regulator (CFTR); dystrophin; utrophin, a tumor suppressor; lysosomal enzyme acid α-glucosidase (GAA); and the like. Suitable nucleic acids also include those that encode a functional fragment of any of the aforementioned proteins; and nucleic acids that encode functional variants of any of the aforementioned proteins.

Suitable heterologous nucleic acids also include those that encode antigenic proteins. A subject rAAV vector that comprises a heterologous nucleic acid that encodes an antigenic protein is suitable for stimulating an immune response to the antigenic protein in a mammalian host. The antigenic protein is derived from an autoantigen, an allergen, a tumor/cancer-associated antigen, a pathogenic virus, a pathogenic bacterium, a pathogenic protozoan, a pathogenic helminth, or any other pathogenic organism that infects a mammalian host. As used herein, the term "a nucleic acid encoding an antigenic protein derived from" includes nucleic acids encoding wild-type antigenic proteins, e.g., a nucleic acid isolated from a pathogenic virus that encodes a viral protein; synthetic nucleic acids generated in the laboratory that encode antigenic proteins that are identical in amino acid sequence to a naturally-occurring antigenic protein; synthetic nucleic acids generated in the laboratory that encode antigenic proteins that differ in amino acid sequence (e.g., by from one amino acid to about 15 amino acids) from a naturally-occurring antigenic protein, but that nonetheless induce an immune response to the corresponding naturally-occurring antigenic protein; synthetic nucleic acids generated in the laboratory that encode fragments of antigenic proteins (e.g., fragments of from about 5 amino acids to about 50 amino acids, which fragments comprises one or more antigenic epitopes), which fragments induce an immune response to the corresponding naturally-occurring antigenic protein; etc.

Similarly, an antigenic protein "derived from" an autoantigen, an allergen, a tumor/cancer-associated antigen, a pathogenic virus, a pathogenic bacterium, a pathogenic protozoan, a pathogenic helminth, or any other pathogenic organism that infects a mammalian host, includes proteins that are identical in amino acid sequence to a naturally-occurring antigenic protein, and proteins that differ in amino acid sequence (e.g., by from one amino acid to about 15 amino acids) from a naturally-occurring antigenic protein, but that nonetheless induce an immune response to the corresponding naturally-occurring antigenic protein; and fragments of antigenic proteins (e.g., fragments of from about 5 amino acids to about 100 amino acids, e.g., from about 5 to about 50 amino acids, which fragments comprises one or more antigenic epitopes), which fragments induce an immune response to the corresponding naturally-occurring antigenic protein.

In some embodiments, an immune response to an antigenic protein encoded by a subject rAAV vector will stimulate a protective immune response to a pathogenic organism that displays the antigenic protein or antigenic epitope (or a protein or an epitope that is cross-reactive with the rAAV-encoded antigenic protein or antigenic epitopes) in the mammalian host. In some embodiments, a cytotoxic T lymphocyte (CTL) response to the rAAV-encoded antigenic protein will be induced in the mammalian host. In other embodiments, a humoral response to the rAAV-encoded antigenic protein will be induced in the mammalian host, such that antibodies specific to the antigenic protein are generated. In many embodiments, a TH1 immune response to the rAAV-encoded antigenic protein will be induced in the mammalian host. Suitable antigenic proteins include tumor/cancer-associated antigens, viral antigens, bacterial antigens, and protozoal antigens; and antigenic fragments thereof. In some embodiments, the antigenic protein is derived from an intracellular pathogen. In other embodiments, the antigenic protein is a self-antigen. In yet other embodiments, the antigenic protein is an allergen.

Tumor/cancer-specific antigens include, but are not limited to, any of the various MAGEs (Melanoma-Associated Antigen E), including MAGE 1 (e.g., GenBank Accession No. M77481), MAGE 2 (e.g., GenBank Accession No. U03735), MAGE 3, MAGE 4, etc.; any of the various tyrosinases; mutant ras; mutant p53 (e.g., GenBank Accession No. X54156 and AA494311); and p97 melanoma antigen (e.g., GenBank Accession No. M12154). Other tumor/cancer-specific antigens include the Ras peptide and p53 peptide associated with advanced cancers, the HPV 16/18 and E6/E7 antigens associated with cervical cancers, MUCI1-KLH antigen associated with breast carcinoma (e.g., GenBank Accession No. J03651), CEA (carcinoembryonic antigen) associated with colorectal cancer (e.g., GenBank Accession No. X98311), gp100 (e.g., GenBank Accession No. 573003) or MART1 antigens associated with melanoma, and the PSA antigen associated with prostate cancer (e.g., GenBank Accession No. X14810). The p53 gene sequence is known (See e.g., Harris et al. (1986) Mol. Cell. Biol., 6:4650-4656) and is deposited with GenBank under Accession No. M14694. Thus, subject proteins, nucleic acids, and/or virions can be used as immunotherapeutics for cancers including, but not limited to, cervical, breast, colorectal, prostate, lung cancers, and for melanomas.

Viral antigens are derived from known causative agents responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Japanese encephalitis (e.g., GenBank Accession No. E07883), dengue (e.g., GenBank Accession No. M24444), hantavirus, and human immunodeficiency virus (e.g., GenBank Accession No. U18552).

Suitable bacterial and parasitic antigens include those derived from known causative agents responsible for diseases including, but not limited to, diphtheria, pertussis (e.g., GenBank Accession No. M35274), tetanus (e.g., GenBank Accession No. M64353), tuberculosis, bacterial and fungal pneumonias (e.g., *Haemophilus influenzae, Pneumocystis carinii*, etc.), cholera, typhoid, plague, shigellosis, *salmonellosis* (e.g., GenBank Accession No. L03833), Legionnaire's Disease, Lyme disease (e.g., GenBank Accession No. U59487), malaria (e.g., GenBank Accession No. X53832), hookworm, onchocerciasis (e.g., GenBank Accession No. M27807), schistosomiasis (e.g., GenBank Accession No. L08198), trypanosomiasis, leshmaniasis, giardiasis (e.g., GenBank Accession No. M33641), amoebiasis, filariasis (e.g., GenBank Accession No. J03266), borreliosis, and trichinosis.

Suitable heterologous nucleic acids that encode heterologous gene products include non-translated RNAs, such as an RNAi agent (as described in greater detail above) (e.g., an antisense RNA; an siRNA; an shRNA; a double stranded RNA (dsRNA); a CRISPR agent, e.g., a Cas9 or Cas9-like protein, a crRNA-like RNA, a tracrRNA-like RNA, a single guide RNA, and/or a donor polynucleotide; and the like), a ribozyme, etc. RNAi agents can be used to inhibit gene expression. Some RNAi agents provide a tool that can be subsequently used to inhibit gene expression (e.g., a CRISPR agent such as a cas9 or cas9-like protein).

Target genes include any gene encoding a target gene product (RNA or protein) that is deleterious (e.g., pathological), for example, a target gene product that is malfunctioning (e.g., due to a mutation in the encoded protein sequence, due to a mutation in the non-coding sequences that control the steady state level of the gene product, etc.). Target gene products include, but are not limited to, huntingtin; hepatitis C virus; human immunodeficiency virus; amyloid precursor protein; tau; a protein that includes a polyglutamine repeat; a herpes virus (e.g., varicella zoster); any pathological virus; and the like.

As such a subject rAAV that includes a heterologous nucleic acid encoding an RNAi agent is useful for treating a variety of disorders and conditions, including, but not limited to, neurodegenerative diseases, e.g., a trinucleotide-repeat disease, such as a disease associated with polyglutamine repeats, e.g., Huntington's disease, spinocerebellar ataxia, spinal and bulbar muscular atrophy (SBMA), dentatorubropallidoluysian atrophy (DRPLA), etc.; an acquired pathology (e.g., a disease or syndrome manifested by an abnormal physiological, biochemical, cellular, structural, or molecular biological state) such as a viral infection, e.g., hepatitis that occurs or may occur as a result of an HCV infection, acquired immunodeficiency syndrome, which occurs as a result of an HIV infection; cancer; and the like.

In many embodiments, a heterologous nucleic acid encoding an RNAi agent is operably linked to a promoter. Suitable promoters are known those skilled in the art and include the promoter of any protein-encoding gene, e.g., an endogenously regulated gene or a constitutively expressed gene. For example, the promoters of genes regulated by cellular physiological events, e.g., heat shock, oxygen levels and/or carbon monoxide levels, e.g., in hypoxia, may be operably linked to an siRNA-encoding nucleic acid.

The selected heterologous nucleotide sequence, such as EPO-encoding or nucleic acid of interest, is operably linked to control elements that direct the transcription or expression thereof in the nucleotide sequence in vivo. Such control elements can comprise control sequences normally associated with the selected gene (e.g., endogenous cellular control elements). Alternatively, heterologous control sequences can be employed. Useful heterologous control sequences generally include those derived from sequences encoding mammalian or viral genes. Examples include, but are not limited to, the SV40 early promoter, mouse mammary tumor virus long terminal repeat (LTR) promoter; adenovirus major late promoter (Ad MLP); a herpes simplex virus (HSV) promoter, an endogenous cellular promoter that is heterologous to the gene of interest, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In some embodiments, cell type-specific or tissue-specific promoter will be operably linked to the heterologous nucleic acid encoding the heterologous gene product, such that the gene product is produced selectively or preferentially in a particular cell type(s) or tissue(s). In some embodiments, an inducible promoter will be operably linked to the heterologous nucleic acid.

For example, muscle-specific and inducible promoters, enhancers and the like, are useful for delivery of a gene product to a muscle cell. Such control elements include, but are not limited to, those derived from the actin and myosin gene families, such as from the myoD gene family; the myocyte-specific enhancer binding factor MEF-2; control elements derived from the human skeletal actin gene and the cardiac actin gene; muscle creatine kinase sequence elements and the murine creatine kinase enhancer (mCK) element; control elements derived from the skeletal fast-twitch troponin C gene, the slow-twitch cardiac troponin C gene and the slow-twitch troponin I gene; hypoxia-inducible nuclear factors; steroid-inducible elements and promoters, such as the glucocorticoid response element (GRE); the fusion consensus element for RU486 induction; and elements that provide for tetracycline regulated gene expression.

The AAV expression vector which harbors the DNA molecule of interest (the heterologous DNA) bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993);

Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Alternatively, AAV ITRs can be excised from the viral genome or from an AAV vector containing the same and fused 5' and 3' of a selected nucleic acid construct that is present in another vector using any convenient method known to one of ordinary skill in the art. For example, one suitable approach uses standard ligation techniques, such as those described in Sambrook et al., supra. For example, ligations can be accomplished in 20 mM Tris-Cl pH 7.5, 10 mM MgCl$_2$, 10 mM DTT, 33 µg/ml BSA, 10 mM-50 mM NaCl, and either 40 µM ATP, 0.01-0.02 (Weiss) units T4 DNA ligase at 0° C. to 16° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. Preferred codons for expression of the chimeric gene sequence in mammalian muscle cells can be used. The complete chimeric sequence is assembled from overlapping oligonucleotides prepared by standard methods. See, e.g., Edge, Nature (1981) 292:756; Nambair et al. Science (1984) 223:1299; Jay et al. J. Biol. Chem. (1984) 259:6311.

Generation of Subject Infectious rAAV Virions

By way of introduction, it is typical to employ a host or "producer" cell for rAAV vector replication and packaging. Such a producer cell (usually a mammalian host cell) generally comprises or is modified to comprise several different types of components for rAAV production. The first component is a recombinant adeno-associated viral (rAAV) vector genome (or "rAAV pro-vector") that can be replicated and packaged into vector particles by the host packaging cell. The rAAV pro-vector will normally comprise a heterologous polynucleotide (or "transgene"), with which it is desired to genetically alter another cell in the context of gene therapy (since the packaging of such a transgene into rAAV vector particles can be effectively used to deliver the transgene to a variety of mammalian cells). The transgene is generally flanked by two AAV inverted terminal repeats (ITRs) which comprise sequences that are recognized during excision, replication and packaging of the AAV vector, as well as during integration of the vector into a host cell genome.

A second component is a helper virus that can provide helper functions for AAV replication. Although adenovirus is commonly employed, other helper viruses can also be used as is known in the art. Alternatively, the requisite helper virus functions can be isolated genetically from a helper virus and the encoding genes can be used to provide helper virus functions in trans. The AAV vector elements and the helper virus (or helper virus functions) can be introduced into the host cell either simultaneously or sequentially in any order.

The final components for AAV production to be provided in the producer cell are "AAV packaging genes" such as AAV rep and cap genes that provide replication and encapsidation proteins, respectively. Several different versions of AAV packaging genes can be provided (including rep-cap cassettes and separate rep and/or cap cassettes in which the rep and/or cap genes can be left under the control of the native promoters or operably linked to heterologous promoters. Such AAV packaging genes can be introduced either transiently or stably into the host packaging cell, as is known in the art and described in more detail below.

1. rAAV Vector

A subject rAAV virion, including the heterologous DNA of interest (where "heterologous DNA of interest" is also referred to herein as "heterologous nucleic acid"), can be produced using standard methodology, known to those of skill in the art. The methods generally involve the steps of (1) introducing a subject rAAV vector into a host cell; (2) introducing an AAV helper construct into the host cell, where the helper construct includes AAV coding regions capable of being expressed in the host cell to complement AAV helper functions missing from the AAV vector; (3) introducing one or more helper viruses and/or accessory function vectors into the host cell, wherein the helper virus and/or accessory function vectors provide accessory functions capable of supporting efficient recombinant AAV ("rAAV") virion production in the host cell; and (4) culturing the host cell to produce rAAV virions. The AAV expression vector, AAV helper construct and the helper virus or accessory function vector(s) can be introduced into the host cell, either simultaneously or serially, using standard transfection techniques.

AAV expression vectors are constructed using known techniques to at least provide as operatively linked components in the direction of transcription, control elements including a transcriptional initiation region, the DNA of interest and a transcriptional termination region. The control elements are selected to be functional in a mammalian muscle cell. The resulting construct which contains the operatively linked components is bounded (5' and 3') with functional AAV ITR sequences.

The nucleotide sequences of AAV ITR regions are known. See, e.g., Kotin, R. M. (1994) Human Gene Therapy 5:793-801; Berns, K. I. "Parvoviridae and their Replication" in Fundamental Virology, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAV-7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell. ITRs allow replication of the vector sequence in the presence of an appropriate mixture of Rep proteins. ITRs also allow for the incorporation of the vector sequence into the capsid to generate an AAV particle.

In order to produce rAAV virions, an AAV expression vector is introduced into a suitable host cell using known techniques, such as by transfection. A number of transfection techniques are generally known in the art. See, e.g., Graham et al. (1973) Virology, 52:456, Sambrook et al. (1989) Molecular Cloning, A Laboratory Manual, Cold Spring Harbor Laboratories, New York, Davis et al. (1986) Basic Methods in Molecular Biology, Elsevier, and Chu et al. (1981) Gene 13:197. Particularly suitable transfection methods include calcium phosphate co-precipitation (Graham et al. (1973) Virol. 52:456-467), direct micro-injection into cultured cells (Capecchi, M. R. (1980) Cell 22:479-488), electroporation (Shigekawa et al. (1988) BioTechniques 6:742-751), liposome mediated gene transfer (Mannino et al. (1988) BioTechniques 6:682-690), lipid-mediated transduction (Feigner et al. (1987) Proc. Natl. Acad. Sci. USA 84:7413-7417), and nucleic acid delivery using high-velocity microprojectiles (Klein et al. (1987) Nature 327:70-73).

For the purposes of this disclosure, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" for producing rAAV virions generally refers to a cell which has been transfected with an exogenous DNA sequence. Cells from the stable human cell line, 293 (readily available through, e.g., the American Type Culture Collection under Accession Number ATCC CRL1573) are used in many embodiments. Particularly, the human cell line 293 is a human embryonic kidney cell line that has been transformed with adenovirus type-5 DNA fragments (Graham et al. (1977) J. Gen. Virol. 36:59), and expresses the adenoviral E1a and E1b genes (Aiello et al. (1979) Virology 94:460). The 293 cell line is readily transfected, and provides a particularly convenient platform in which to produce rAAV virions.

2. AAV Helper Functions

Host cells containing the above-described AAV expression vectors must be rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs, namely the rep and cap coding regions, or functional homologues thereof. In the context of the instant disclosure, the cap functions include one or more mutant capsid proteins, wherein at least one capsid protein comprises at least one mutation, as described above.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) Current Topics in Microbiol. and Immunol. 158:97-129; and Kotin, R. M. (1994) Human Gene Therapy 5:793-801. Suitable homologues of the AAV rep coding region include the human herpesvirus 6 (HHV-6) rep gene which is also known to mediate AAV-2 DNA replication (Thomson et al. (1994) Virology 204:304-311).

AAV cap proteins include VP1, VP2, and VP3, wherein at least one of VP1, VP2, and VP3 comprises at least one mutation, as described above.

AAV helper functions are introduced into the host cell by transfecting the host cell with an AAV helper construct either prior to, or concurrently with, the transfection of the AAV expression vector. AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) J. Virol. 63:3822-3828; and McCarty et al. (1991) J. Virol. 65:2936-2945. A number of other vectors have been described which encode Rep and/or Cap expression products. See, e.g., U.S. Pat. No. 5,139,941.

Both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in practicing methods of the disclosure include the hygromycin B resistance gene (encoding Aminoglycoside phosphotranferase (APH)) that allows selection in mammalian cells by conferring resistance to hygromycin; the neomycin phosphotranferase gene (encoding neomycin phosphotransferase) that allows selection in mammalian cells by conferring resistance to G418; and the like. Other suitable markers are known to those of skill in the art.

3. AAV Accessory Functions

The host cell (or packaging cell) must also be rendered capable of providing non AAV derived functions, or "accessory functions," in order to produce rAAV virions. Accessory functions are non AAV derived viral and/or cellular functions upon which AAV is dependent for its replication. Thus, accessory functions include at least those non AAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

Particularly, accessory functions can be introduced into and then expressed in host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents. See, e.g., Buller et al. (1981) J. Virol. 40:241-247; McPherson et al. (1985) Virology 147:217-222; Schlehofer et al. (1986) Virology 152:110-117.

Alternatively, accessory functions can be provided using an accessory function vector. Accessory function vectors include nucleotide sequences that provide one or more accessory functions. An accessory function vector is capable of being introduced into a suitable host cell in order to support efficient AAV virion production in the host cell.

Accessory function vectors can be in the form of a plasmid, phage, transposon, cosmid, or another virus. Accessory vectors can also be in the form of one or more linearized DNA or RNA fragments which, when associated with the appropriate control elements and enzymes, can be transcribed or expressed in a host cell to provide accessory functions.

Nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. See, e.g., Carter, B. J. (1990) "Adeno-Associated Virus Helper Functions," in CRC Handbook of Parvoviruses, vol. I (P. Tijssen, ed.), and Muzyczka, N. (1992) Curr. Topics. Microbiol. and Immun. 158:97-129. Specifically, early adenoviral gene regions E1a, E2a, E4, VAI RNA and, possibly, E1b are thought to participate in the accessory process. Janik et al. (1981) Proc. Natl. Acad. Sci. USA 78:1925-1929. Herpesvirus-derived accessory functions have been described. See, e.g., Young et al. (1979) Prog. Med. Virol. 25:113. Vaccinia virus-derived accessory functions have also been described. See, e.g., Carter, B. J. (1990) supra., Schlehofer et al. (1986) Virology 152:110-117.

As a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest, e.g., the heterologous nucleic acid) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the host cell using a variety of conventional purification methods, such as CsCl gradients, affinity chromatography, and ion-exchange chromatography. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile.

The resulting rAAV virions are then ready for use for DNA delivery, such as in gene therapy applications, or for the delivery of a gene product to a mammalian host.

Delivering a Heterologous Nucleic Acid

The present disclosure further provides methods of delivering a heterologous nucleic acid to a target cell and/or to an individual in need thereof. In some embodiments, an individual in need thereof is a human who has previously been naturally exposed to AAV and as a result harbors anti-AAV antibodies (i.e., AAV neutralizing antibodies). Based on positive results in clinical trials involving AAV gene delivery to, for example, liver, muscle, and retina—all tissues affected by neutralizing antibodies against this vehicle—there are many such therapeutic applications/disease targets.

A subject method generally involves: (i) administering an effective amount of a subject rAAV virion to an individual, and/or (ii) contacting a target cell with a subject virion. Generally, rAAV virions are administered to a subject using either in vivo ("direct") or in vitro ("indirect") transduction techniques. If transduced in vitro ("indirectly"), a desired recipient cell (i.e., "target cell") can be removed from the individual, transduced with rAAV virions and reintroduced into the individual. Alternatively, syngeneic or xenogeneic cells can be used where those cells will not generate an inappropriate immune response in the individual.

Suitable methods for the delivery and introduction of transduced target cells into an individual have been described. For example, cells can be transduced in vitro by combining recombinant AAV virions with cells e.g., in appropriate media, and screening for those cells harboring the DNA of interest using conventional techniques such as Southern blots and/or PCR, or by using selectable markers. Transduced cells can then be formulated into pharmaceutical compositions, described more fully below, and the composition introduced into the subject by various techniques, such as by intramuscular, intravenous, subcutaneous and intraperitoneal injection.

For in vivo (i.e., "direct") delivery, the rAAV virions will be formulated into pharmaceutical compositions and will generally be administered parenterally (e.g., administered via an intramuscular, subcutaneous, intratumoral, transdermal, intrathecal, intravenous, etc.) route of administration.

Pharmaceutical compositions will comprise sufficient genetic material to produce a therapeutically effective amount of the gene expression product of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins Pharmaceutical Dosage Forms and Drug Delivery Systems (1999) H. C. Ansel et al., eds., $7^{th}$ ed., Lippincott, Williams, & Wilkins and Handbook of Pharmaceutical Excipients (2000) A. H. Kibbe et al., eds., $3^{rd}$ ed. Amer. Pharmaceutical Assoc.

Appropriate doses will depend on the mammal being treated (e.g., human or nonhuman primate or other mammal), age and general condition of the subject to be treated, the severity of the condition being treated, the particular therapeutic protein in question, its mode of administration, among other factors. An appropriate effective amount can be readily determined by one of skill in the art.

Thus, a "therapeutically effective amount" will fall in a relatively broad range that can be determined through clinical trials. For example, for in vivo injection, i.e., injection directly to skeletal or cardiac muscle, a therapeutically effective dose will be on the order of from about $10^6$ to about $10^{15}$ of the rAAV virions, e.g., from about $10^8$ to $10^{12}$ rAAV virions. For in vitro transduction, an effective amount of rAAV virions to be delivered to cells will be on the order of from about $10^8$ to about $10^{13}$ of the rAAV virions. Other effective dosages can be readily established by one of ordinary skill in the art through routine trials establishing dose response curves.

Dosage treatment may be a single dose schedule or a multiple dose schedule. Moreover, the subject may be administered as many doses as appropriate. One of skill in the art can readily determine an appropriate number of doses.

The cells of interest (i.e., "target cells") are typically mammalian, where the term refers to any animal classified as a mammal, including humans, domestic and farm animals, and zoo, laboratory, sports, or pet animals, such as dogs, horses, cats, cows, mice, rats, rabbits, etc. In some embodiments, the target cell is a human cell.

Target cells of interest include any cell susceptible to infection by a subject rAAV virion. In some cases, e.g., when the method is a method of delivering a heterologous nucleic acid to a target cell, the target cell can be a cell removed from an individual (e.g., a "primary" cell), or the target cell can be a tissue culture cell (e.g., from an established cell line).

Exemplary target cells include, but are not limited to, liver cells, pancreatic cells (e.g., islet cells: alpha cells, beta cells, delta cells, gamma cells, and/or epsilon cells), skeletal muscle cells, heart muscle cells, fibroblasts, retinal cells, synovial joint cells, lung cells, T cells, neurons, glial cells, stem cells, hematopoietic progenitor cells, neural progenitor cells, endothelial cells, and cancer cells. Exemplary stem cell target cells include, but are not limited to, hematopoietic stem cells, neural stem cells, neural crest stem cells, embryonic stem cells, induced pluripotent stem cells (iPS cells), mesenchymal stem cells, mesodermal stem cells, liver stem cells, pancreatic stem cells, muscle stem cells, and retinal stem cells.

The term "stem cell" is used herein to refer to a mammalian cell that has the ability both to self-renew, and to generate differentiated progeny (see, e.g., Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. As is appreciated by one of ordinary skill in the art, "progenitor cells" differ from stem cells in that they typically do not have the extensive self-renewal capacity, and often can generate a more restricted subset of the lineages in the tissue from which they derive, for example only lymphoid, or erythroid lineages in a hematopoietic setting. As used herein, the term "stem cell" encompasses both "stem cells" and "progenitor cells" as defined above.

Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

Suitable stem cells of interest include, but are not limited to: hematopoietic stem cells and progenitor cells derived therefrom (U.S. Pat. No. 5,061,620); neural crest stem cells (see Morrison et al. (1999) Cell 96:737-749); neural stem cells and neural progenitor cells; embryonic stem cells; mesenchymal stem cells; mesodermal stem cells; liver stem cells, muscle stem cells, retinal stem cells, induced pluripotent stem cells (iPS cells), etc. Other hematopoietic "progenitor" cells of interest include cells dedicated to lymphoid lineages, e.g. immature T cell and B cell populations.

Purified populations of stem or progenitor cells may be used. For example, human hematopoietic stem cells may be positively selected using antibodies specific for CD34, thy-1; or negatively selected using lineage specific markers which may include glycophorin A, CD3, CD24, CD16, CD14, CD38, CD45RA, CD36, CD2, CD19, CD56, CD66a, and CD66b; T cell specific markers, tumor/cancer specific markers, etc. Markers useful for the separation of mesodermal stem cells include FcγRII, FcγRIII, Thy-1, CD44, VLA-4a, LFA-113, HSA, ICAM-1, CD45, Aa4.1, Sca-1, etc. Neural crest stem cells may be positively selected with antibodies specific for low-affinity nerve growth factor receptor (LNGFR), and negatively selected for the markers sulfatide, glial fibrillary acidic protein (GFAP), myelin protein Po, peripherin and neurofilament. Human mesenchymal stem cells may be positively separated using the markers SH2, SH3 and SH4.

Target cells which are employed may be fresh, frozen, or have been subject to prior culture. They may be fetal, neonate, adult. Hematopoietic cells may be obtained from fetal liver, bone marrow, blood, particularly G-CSF or GM-CSF mobilized peripheral blood, or any other conventional source. The manner in which stem cells are separated from other cells of the hematopoietic or other lineage is not critical to this disclosure. As described above, a substantially homogeneous population of stem or progenitor cells may be obtained by selective isolation of cells free of markers associated with differentiated cells, while displaying epitopic characteristics associated with the stem cells.

Nucleic acids that can be delivered to an individual include any of the above defined heterologous nucleic acids. Proteins that can be delivered using a subject method also include a functional fragment of any of the aforementioned proteins; and functional variants of any of the aforementioned proteins.

In some embodiments, a therapeutically effective amount of a protein is produced in the mammalian host. Whether a therapeutically effective amount of a particular protein is produced in the mammalian host using a subject method is readily determined using assays appropriate to the particular protein. For example, where the protein is EPO, hematocrit is measured.

Where the rAAV encodes an antigenic protein, suitable antigenic proteins that can be delivered to an individual using a subject method include, but are not limited to, tumor/cancer-associated antigens, autoantigens ("self" antigens), viral antigens, bacterial antigens, protozoal antigens, and allergens; and antigenic fragments thereof. In some embodiments, a cytotoxic T lymphocyte (CTL) response to the rAAV-encoded antigenic protein will be induced in the mammalian host. In other embodiments, a humoral response to the rAAV-encoded antigenic protein will be induced in the mammalian host, such that antibodies specific to the antigenic protein are generated. In many embodiments, a TH1 immune response to the rAAV-encoded antigenic protein will be induced in the mammalian host. Whether an immune response to the antigenic protein has been generated is readily determined using well-established methods. For example, an enzyme-linked immunosorbent assay can be used to determine whether antibody to an antigenic protein has been generated. Methods of detecting antigen-specific CTL are well known in the art. For example, a detectably labeled target cell expressing the antigenic protein on its surface is used to assay for the presence of antigen-specific CTL in a blood sample.

Whether a therapeutically effective amount of a heterologous nucleic acid (e.g., a nucleic acid encoding a polypeptide, an RNAi agent, etc.) has been delivered to a mammalian host using a subject method is readily determined using any appropriate assay. For example, where the gene product is an RNAi agent that inhibits HIV, viral load can be measured.

Methods of Generating and Identifying Modified rAAV Virions

The present disclosure provides a method of generating and identifying a modified infectious recombinant adeno-associated virus (rAAV) virion that comprises a variant capsid protein comprising an amino acid sequence with at least one amino acid substitution (including deletions, insertions, etc.) compared to a starter AAV capsid protein. A starter AAV capsid protein comprises an amino acid sequence set forth in one of SEQ ID NOs: 10-13 and 26-33.

The method generally involves generating a mutant rAAV virion library; and selecting the library for modified rAAV virions with altered properties relative to a starter rAAV virion. The starter rAAV virion comprises a variant AAV capsid protein that comprises an amino acid sequence set forth in one of SEQ ID NOs: 10-13 and 26-33. The present disclosure further provides libraries and compositions comprising the libraries.

In some embodiments, a given selection step is repeated two, three, four, or more times to enrich a subject AAV library for altered virion properties. In some embodiments, following selection of an AAV library, individual clones are isolated and sequenced.

Generation of a Mutant AAV Library

A mutant AAV library is generated that comprises one or more mutations relative to a starter AAV cap gene. A starter cap gene is a cap comprising a nucleotide sequence that encodes a variant AAV capsid protein that comprises an amino acid sequence set forth in one of SEQ ID NOs: 10-13 and 26-33. Mutations in the rAAV cap gene are generated using any known method. Suitable methods for mutagenesis of a starter AAV cap gene include, but are not limited to, a polymerase chain reaction (PCR)-based method, oligonucleotide-directed mutagenesis, saturation mutagenesis, loop-swapping mutagenesis, fragment shuffling mutagenesis (i.e., DNA shuffling), and the like. Methods for generating mutations are well described in the art. See, e.g., Zhao et al. Nat Biotechnol. 1998 March; 16(3):234-5; Koerber et. al.; Mol Ther. 2008 October; 16(10):1703-9; Koerber et. al.; Mol Ther. 2009 December; 17(12):2088-95; U.S. Pat. Nos. 6,579,678; 6,573,098; and 6,582,914; all of which are hereby incorporated by reference for their teachings related to mutagenesis.

In some embodiments, a mutant AAV library comprising mutations in the cap gene will be generated using a staggered extension process. The staggered extension process involves amplification of the cap gene using a PCR-based method. The template cap gene is primed using specific PCR primers, followed by repeated cycles of denaturation and very short annealing/polymerase-catalyzed extension. In each cycle, the growing fragments anneal to different templates based on sequence complementarity and extend further. The cycles of denaturation, annealing, and extension are repeated until full-length sequences form. The resulting full-length sequences include at least one mutation in the cap gene compared to a wild-type AAV cap gene.

The PCR products comprising AAV cap sequences that include one or more mutations are inserted into a plasmid containing a wild-type AAV genome. The result is a library of AAV cap mutants. Thus, the present disclosure provides a mutant AAV cap gene library comprising from about 10 to about $10^{10}$ members, and comprising mutations in the AAV cap gene. A given member of the library has from about one to about 50 mutations in the AAV cap gene. A subject library comprises from 10 to about $10^9$ distinct members, each having a different mutation(s) in the AAV cap gene.

Once a cap mutant library is generated, viral particles are produced that can then be selected on the basis of altered capsid properties. Library plasmid DNA is transfected into a suitable host cell (e.g., 293 cells), followed by introduction into the cell of helper virus. Viral particles produced by the transfected host cells (rAAV library particles) are collected.

Library Selection

Once a library is generated, it is selected for a particular virion property (i.e., an altered property of infection). Viral particles are generated as discussed above (thus producing a library of modified rAAV virions), and subjected to one or more selection steps to identify a modified rAAV virion with an altered property of infection (relative to an infectious rAAV virion comprising a variant capsid protein that comprises an amino acid sequence set forth in one of SEQ ID NOs: 10-13 and 26-33). Properties of infection that are selected for can include, but are not limited to: 1) altered binding (e.g., decreased binding) to AAV neutralizing antibodies; 2) increased evasion of AAV neutralizing antibodies; 3) increased infectivity of a cell that is resistant to infection with AAV; and 4) altered heparin binding.

1. Selection for Reduced Binding to AAV Neutralizing Antibodies

In some embodiments, a subject AAV library is selected for altered (e.g., reduced) binding to neutralizing antibodies that bind to and neutralize wild-type AAV virions, compared to the binding of such antibodies to wild-type AAV virions and neutralization of wild-type AAV virions (or relative to an infectious rAAV virion comprising a variant capsid protein that comprises an amino acid sequence set forth in one of SEQ ID NOs: 10-13 and 26-33). AAV library particles (AAV library virion) are contacted with neutralizing antibodies and the ability of the AAV library particles to infect a permissive host cell is tested. Typically, AAV library particles are contacted with various concentrations of neutralizing antibodies. The higher the concentration of neutralizing antibodies that is required to reduce infectivity of the AAV library particles, the more resistant the AAV particles are to neutralization. Any convenient assay known to one of ordinary skill in the art may be used to directly measure the binding (e.g., measure the binding affinity) of an AAV library virion to neutralizing anti-AAV antibodies.

2. Selection for Increased Evasion of AAV Neutralizing Antibodies

In some embodiments, a subject AAV library is selected for increased evasion of neutralizing antibodies (i.e. increased resistance to human neutralizing AAV antibodies) relative to an infectious rAAV virion comprising a variant capsid protein that comprises an amino acid sequence set forth in one of SEQ ID NOs: 10-13 and 26-33. AAV library particles are contacted with targets cells in the presence of neutralizing AAV antibodies (usually human neutralizing anti-AAV antibodies). After a suitable amount of time to allow for infection of the cells with AAV library particles, helper virus is added, and AAV library particles that successfully infected the cell(s) are harvested. In some embodiments, infectivity is measured (e.g., as described above) for those virions exhibiting successful infection. In some embodiments, the cycle of infection, addition of helper virus, and harvesting of AAV particles is repeated one, two, three, or more times. The selection can occur with varying amounts (concentrations) of neutralizing AAV antibodies to select for various degrees of evasion (e.g., each repeated round can utilize an increased concentration of antibodies relative to the previous round).

3. Selection for Increased Infectivity of Non-Permissive Cells

In some embodiments, a subject AAV library is selected for increased infectivity of non-permissive cells (relative to an infectious rAAV virion comprising a variant capsid protein that comprises an amino acid sequence set forth in one of SEQ ID NOs: 10-13 and 26-33). AAV library particles are contacted with a non-permissive cell (e.g., a population of non-permissive cells). After a suitable amount of time to allow for infection of the cells with AAV library particles, helper virus is added, and AAV library particles that successfully infected the non-permissive cell(s) are harvested. In some embodiments, the cycle of infection, addition of helper virus, and harvesting of AAV particles is repeated one, two, three, or more times.

4. Selection for Altered Heparin Binding

In some embodiments, a subject library is selected for altered heparin binding, including increased heparin binding and decreased heparin binding relative to wild-type AAV virion heparin binding (or relative to an infectious rAAV virion comprising a variant capsid protein that comprises an amino acid sequence set forth in one of SEQ ID NOs: 10-13 and 26-33). AAV library particles are contacted with a heparin affinity matrix. For example, AAV library particles are loaded onto a heparin affinity column under conditions that permit binding of the AAV library particles to the heparin. Exemplary conditions include equilibration of the column with 0.15 M NaCl and 50 mM Tris at pH 7.5. After allowing the AAV library particle to bind to the heparin affinity matrix, the AAV library particle/heparin affinity matrix complex is washed with volumes of buffer containing progressively increasing concentrations of NaCl, and at each NaCl concentration, eluted AAV library particles are collected. For example, after binding the AAV library particle/heparin affinity matrix complex is washed with a volume of 50 mM Tris buffer, pH 7.5, containing 200 mM NaCl, and eluted AAV library particles are collected. The elution step is repeated with a 50 mM Tris buffer, pH 7.5, containing about 250 mM NaCl, about 300 mM NaCl, about 350 mM, about 400 mM NaCl, about 450 mM NaCl, about 500 mM NaCl, about 550 mM NaCl, about 600 mM NaCl, about 650 mM NaCl, about 700 mM NaCl, or about 750 mM NaCl.

AAV library particles that elute at NaCl concentrations lower than about 450 mM NaCl exhibit decreased heparin binding properties relative to wild-type AAV. AAV library particles that elute at NaCl concentrations higher than about 550 mM NaCl exhibit increased heparin binding properties relative to wild-type AAV.

In some embodiments, eluted AAV library particles are amplified by co-infection of permissive cells with a helper virus, and are re-fractionated on heparin affinity matrix. This step can be repeated a number of times to enrich for AAV library particles with altered heparin binding properties.

In the present methods, one or more selection steps may follow generation of AAV library particles. For example, in some embodiments, the method comprises selecting for increased heparin binding, followed by selecting for decreased binding to neutralizing antibodies. In other embodiments, the method comprises selecting for decreased binding to neutralizing antibodies, followed by selecting for increased heparin binding. In other embodiments, the method comprises selecting for decreased heparin binding, followed by selecting for decreased binding to neutralizing antibodies. In other embodiments, the method comprises selecting for decreased binding to neutralizing antibodies, followed by selecting for decreased heparin binding. In other embodiments, the method comprises selecting for decreased binding to neutralizing antibodies, followed by selecting for increased infectivity of a stem cell. In other embodiments, the method comprises selecting for decreased binding to neutralizing antibodies, followed by selecting for increased evasion of neutralizing antibodies. In other embodiments, the method comprises selecting for increased evasion of neutralizing antibodies, followed by selecting for decreased binding to neutralizing antibodies.

Thus, the present disclosure provides an adeno-associated virus (AAV) library that includes a plurality of nucleic acids, each of which nucleic acid includes a nucleotide sequence that encodes a variant AAV capsid protein. The encoded variant AAV capsid protein includes at least one amino acid substitution relative to a sequence set forth in one of SEQ ID NOs: 10-13 and 26-33. The present disclosure provides a library of mutant adeno-associated virus (AAV) particles, including a plurality of AAV particles each of which includes an AAV capsid protein that includes at least one amino acid substitution relative to a sequence set forth in one of SEQ ID NOs: 10-13 and 26-33. Nucleic acids encoding mutant AAV capsid proteins are described above, as are the properties of the encoded mutant AAV capsid proteins.

The present disclosure further provides a library comprising at least one of: (i) two or more infectious rAAV virions, each comprising a variant adeno-associated virus (AAV) capsid protein and a heterologous nucleic acid; (ii) two or more isolated nucleic acids, each comprising a nucleotide sequence that encodes a variant AAV capsid protein; (iii) two or more host cells, each comprising a nucleic acid that comprises a nucleotide sequence that encodes a variant AAV capsid protein; and (iv) two or more variant AAV capsid proteins; where the variant AAV capsid protein of at least one member of the library comprises an amino acid sequence having at least one amino acid substitution relative to the amino acid sequence set forth in one of SEQ ID NOs: 10-13 and 26-33.

Compositions and Kits

Also provided are compositions and kits for use in the methods of the present disclosure. The subject compositions and kits include at least one of: a subject infectious rAAV virion, a subject rAAV vector, a subject nucleotide acid comprising a nucleotide sequence encoding a subject variant AAV capsid protein, an isolated host cell comprising a subject nucleic acid (i.e., a subject genetically modified host cell comprising a nucleic acid that comprises a nucleotide sequence encoding a subject variant AAV capsid protein); a subject library (e.g., any of the above described libraries); and a subject variant AAV capsid protein. A composition or kit can include any convenient combination of the above. A composition or kit can also include helper virus and/or a nucleic acid comprising a nucleotide sequence that encodes a helper virus. A kit may also include reagents for the generation of nucleic acids (i.e., "mutant" nucleic acids) encoding modified variant AAV capsid proteins.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

The invention now being fully described, it will be apparent to one of ordinary skill in the art that various changes and modifications can be made without departing from the spirit or scope of the invention.

EXAMPLES

Example 1

Adeno-associated virus (AAV) gene therapy vectors have demonstrated considerable promise in several clinical trials to date. However, circulating anti-AAV antibodies, resulting from childhood exposure or prior administration of an AAV vector, have prevented the implementation of AAV gene therapy for many potential patients. We have isolated novel AAV variants that are capable of enhanced anti-AAV antibody evasion, both in vitro and in vivo. The stringent pressure resulting from selections using low and high potency human sera pools and human IVIG evolved AAV variants capable of evasion of antibody neutralization from individual human sera, human IVIG, and mouse sera, the most broadly evasive variants to date.

Materials and Methods

Cell Lines

Cell lines were cultured at 37° C. and 5% $CO_2$, and unless otherwise mentioned, were obtained from the American Type Culture Collection (Manassas, Va.). HEK293T, HeLa, and HT1080 cells were cultured in Dulbecco's modified Eagle's medium supplemented with 10% fetal bovine serum (Gibco, Carlsbad, Calif.) and 1% penicillin/streptomycin (Invitrogen, Carlsbad, Calif.). CHO K1 and CHO pgsA cells were cultured in F-12K medium (ATCC) supplemented with 10% fetal bovine serum (Gibco) and 1% penicillin/streptomycin (Invitrogen). Pro5 and Lec1 cells were cultured in MEM-alpha medium (Gibco) supplemented with 10% fetal bovine serum (Gibco) and 1% penicillin/streptomycin (Invitrogen).

Human Sera Pools for Selection

Eighteen individual human serum samples were obtained from Innovative Research, Inc. (Southfield, Mich.) and the neutralizing antibody titer for wild type AAV2 was determined for each sample (Table 2). Since individual samples likely possess variations in both the affinities and epitope specificities of the antibodies, three potent sera pools (α=A+F+G, β=B+H+M, and γ=I+J+N) were generated by mixing equal volumes of individual serum samples. Selection in the presence of these variations of antibodies should result in a general enhancement of resistance to many pre-existing human antibodies. Later selections were performed in the presence of Gamimune N, 10% Human IVIG (Bayer, Elkhart Ind.) to select for resistance to an even broader range of antibodies.

Table 2: Neutralizing Antibody Titers of Individual Human Serum Samples

Neutralizing antibody (NAb) titers for each sample are reported as the reciprocal of the volume fraction of serum necessary to reduce infectivity to 37% of the value measured in the absence of serum. Three sera pools (α=A+F+G, β=B+H+M, and γ=I+J+N) were then generated by mixing equivolume amounts of three individual serum samples.

TABLE 2

| Human Serum~NAB | |
|---|---|
| Sample | titer |
| A | 500 |
| B | 275 |
| C | 200 |
| D | <75 |
| E | <75 |
| F | 350 |
| G | 425 |
| H | 450 |
| I | 200 |
| J | 500 |
| K | 172 |
| L | <75 |
| M | 2200 |
| N | 5000 |
| O | <75 |
| P | <75 |
| Q | <75 |
| R | 120 |

Library Generation and Viral Production

To create the saturation mutagenesis library, an AAV2 cap library was generated by error-prone PCR followed by the staggered extension process described by Zhao et al. using 5'-GCGGAAGCTTCGATCAACTACGC-3' (SEQ ID NO: 14) and 5'-GGGGCGGCCGCAATTACAGATTACGAGTCAGGTATCTGGTG-3' (SEQ ID NO: 15) as forward and reverse primers, respectively. Selections using pooled individual human sera revealed a variant containing four point mutations (described in the results section) that served as the basis for the saturation mutagenesis library. The cap gene for this variant was subjected to further mutagenesis by changing the amino acids at specific sites. Primer 5'-catt<u>NNK</u>gaccagtctaggaactgg-3'(SEQ ID NO: 16) and the corresponding reverse complement primer were used to mutagenize the R471 amino acid site. Primer 5' gccacaaggacgatgaagaa <u>NNK</u>tttttcctcagagcggggttctcatattgggaagcaaggctca <u>NNK</u>aaaaca agt gtggacattg-3'(SEQ ID NO: 17) and the corresponding reverse complement primer were used to mutagenize the K532 and E548 amino acid sites. Primer 5'-ccaacctccagagaggc<u>NNK</u>agacaagcagctacc-3' (SEQ ID NO: 18) and the corresponding reverse complement primer were used to mutagenize the N587 amino acid site. Primer 5'-ccaactacaacaagtct<u>NNK</u>aatgtggactttactgtggac <u>NNK</u>aatggcgtgtatt-3'(SEQ ID NO: 19) and the corresponding reverse complement primer were used to mutagenize the V708 and T716 amino acid sites. A library consisting of AAV2 containing randomized cap loop regions and a library containing shuffled DNA from the wild type AAV1, AAV2, AAV4, AAV5, AAV6, AAV8, AAV9 cap genes were packaged and pooled for initial selection steps (Koerber et. al.; Mol Ther. 2008 October; 16(10):1703-9; and Koerber et. al.; Mol Ther. 2009 December; 17(12):2088-95; both of which are hereby incorporated by reference in their entirety).

For the second and third rounds of evolution, random mutagenesis libraries were generated by subjecting cap genes from the Loop-Swap/Shuffle library and the Saturation Mutagenesis library to error-prone PCR using 5'-CATGGGAAAGGTGCCAGACG-3' (SEQ ID NO: 20) and 5'-ACCATCGGCAGCCATACCTG-3'(SEQ ID NO: 21) as forward and reverse primers, respectively, as previously described. The replication competent AAV libraries and recombinant AAV vectors expressing GFP under the control of a CMV promoter were packaged using HEK293T cells (ATCC) using the calcium phosphate transfection method, and the viruses were purified by iodixonal gradient centrifugation. Recombinant AAV vectors expressing GFP or luciferase under the control of a CMV promoter for use in vivo were further purified by Amicon filtration. DNase-resistant genomic titers were determined via quantitative PCR. (Excoffon et. al, Proc Natl Acad Sci USA. 2009 Mar. 10; 106(10):3865-70; and Maheshri et al., Nat Biotechnol. 2006 February; 24(2):198-204; both of which are hereby incorporated by reference in their entirety).

Library Selection and Evolution

One round of selection is defined as HEK293T cell infection using the AAV starting library (incubated for 30 minutes at room temperature for the pooled individual human sera or for 1 hour at 37° C. with heat inactivated IVIG prior to infection), followed by adenovirus rescue and harvest of successful variants. Each round of evolution consists of mutagenesis of the cap gene to create the starting library and three rounds of selection. Three rounds of evolution were performed with each library, with clonal analysis performed between each round of evolution. The starting libraries for each round of evolution were generated as described above. Following the third round of selection, AAV cap genes were isolated from the pool of successful AAV variants and amplified via PCR. Cap genes were inserted into the pXX2 recombinant AAV packaging plasmid using NotI and HindIII. Cap genes were then sequenced at the University of California, Berkeley DNA sequencing facility, and analyzed using Geneious software (Biomatters, Auckland, New Zealand). Three-dimensional models of the AAV2 capsid (Protein Databank accession number 1LP3) were rendered in Pymol (DeLano Scientific, San Carlos, Calif.).

In Vitro Transduction Analysis of Antibody-Evading Variants

HEK293T were plated at a density of $3\times10^4$ cells/well 24 hours prior to infection. Variants were incubated at 37° C. for 1 hour with heat inactivated IVIG, individual human sera, or individual mouse sera prior to infection, and cells were then infected with rAAV-GFP at a genomic MOI of 2000. The percentage of GFP positive cells was assessed 48 hours post infection using an ImageXpress Micro Cellular Imaging and Analysis System (Molecular Devices, Sunnyvale, Calif.) and MetaXpress Image Analysis Software, version 3.1.0, Multi Wavelength Cell Scoring Application Module (Molecular Devices).

In Vitro Transduction Analysis

To determine the relative transduction efficiencies the selected mutants compared to parental wild-type AAV serotypes, HEK293T, CHO K1, CHO pgsA (lacking all surface glycosaminoglycans), CHO Pro5 (the parental line for several glycosylation mutants, including Lec1 cells), CHO Lec1 (glycosylation defective), HeLa, and HT1080 cells (a human fibrosarcoma cell line) were plated at a density of $2.5\times10^4$ cells per well 24 hours prior to infection. Cells were infected with rAAV1-GFP, rAAV2-GFP, rAAV6-GFP, Shuffle 100.1-GFP, Shuffle 100.3-GFP, SM 10.2-GFP, or Shuffle 100.7-GFP at a range of MOI of 100-1000. The percentage of GFP positive cells was assessed 48 hours post infection using a Beckman-Coulter Cytomics FC500 flow cytometer (Beckman-Coulter, Brea, Calif.).

In Vivo Analysis of Antibody-Evading Variants

For analysis of gene expression in vivo, eight week old, female, Balb/c mice were primed with 4 mg IVIG per mouse or phosphate buffered saline (for control mice) via tail vein injection 24 hours prior to administration of recombinant Shuffle 100-3 (see SEQ ID NO: 12), SM 10-2 (see SEQ ID NO: 10), or AAV2 vectors. Mice were infected with $10^{11}$ viral genomes of recombinant AAV vectors encoding luciferase under the control of a CMV promoter via tail vein injection. For bioluminescence imaging, mice were anesthetized with 2% isofluorane and oxygen. D-luciferin substrate (GOLD Biotechnology, St. Louis, Mo.) was injected intraperitoneally, at a dose of 500 µg/g of body weight. Images were generated using a VivoVision IVIS Lumina imager (Xenogen, Alameda, Calif.). For each mouse, ventral images were taken 7-10 minutes after the substrate injection, every week for four weeks. Five weeks post-infection, serum was collected via cardiac puncture and mice were then perfused with 0.9% saline solution. Heart, liver, lungs, kidney, spleen, brain, spinal cord, and hind limb muscle were harvested and frozen. Frozen tissue samples were homogenized and resuspended in reporter lysis buffer (Promega, Mannheim, Germany) for in vitro luciferase analysis. Lysate containing luciferase was clarified by centrifugation for 10 minutes at 10,000 g. To assay the samples, 20 µL of the lysate was added to 100 µL of the luciferase assay buffer, mixed, incubated for 5 minutes, and placed in the luminometer. The signal was integrated for 30 seconds with a 2 second delay and was reported in Relative Light Units (RLU) detected by a TD 20/20 luminometer (Turner Designs, Sunnyvale, Calif.). The luciferase signal was normalized to the total protein content determined by a bicinchoninic acid assay (Pierce).

Results

Our results demonstrate that AAV can evolve to significantly overcome neutralization by anti-AAV antibodies, both in vitro and in vivo. Novel AAV variants were isolated that required 2- to 35-fold higher neutralizing antibody titers (using human IVIG) than wild-type AAV in vitro. The antibody neutralization properties also translated to enhanced transduction in vivo in the presence of neutralizing antibodies. The isolation of such novel clones resistant to anti-AAV antibodies allows for the broader implementation of treatments based on AAV as a nucleic acid delivery vector (including individuals with high antibody titers that are currently ineligible for AAV gene therapy).

AAV Library Generation and Selection Through Directed Evolution

Figure 1A:
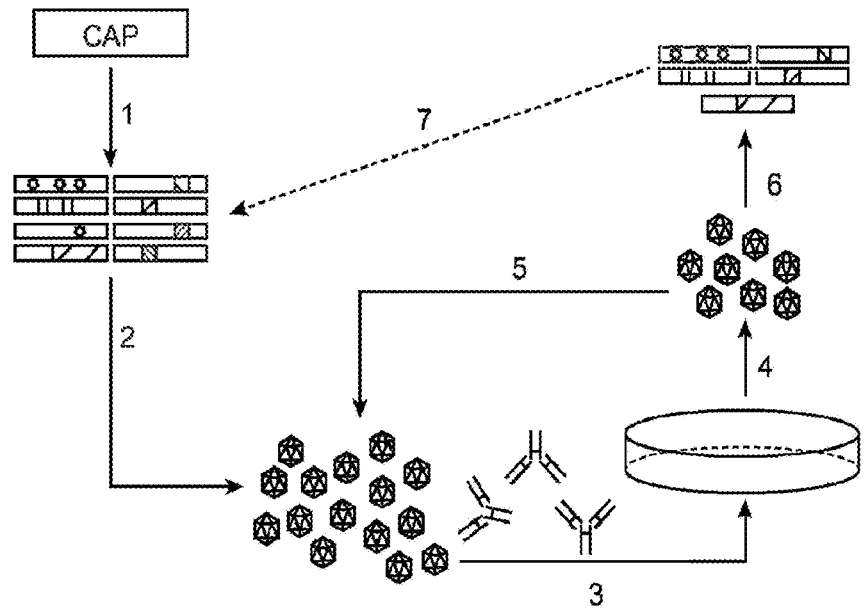
FIGS. 1A-B depict directed Evolution of AAV for Enhanced Antibody Evasion.

FIG. 1a shows a schematic of the directed evolution approach used to isolate novel AAV variants capable of evading human antibody neutralization. Libraries of viruses were created using the DNA mutagenesis techniques described in the following paragraphs (FIG. 1a, steps 1 and 2). During initial selections, pools of viral libraries developed from error-prone PCR mutations to AAV2 cap genes were incubated with various dilutions of the low potency a human sera pool for 30 minutes at room temperature prior to infection of HEK293T cells (step 3). Following three rounds of selection against the low potency a human sera pool (FIG. 1a, steps 4 and 5), several variants with enhanced resistance to this neutralizing sera pool were obtained (FIG. 1a, step 6, FIG. 7a). Variant 1.45, contained two point mutations (N312K, N449D), which resulted in >10-fold more resistance to neutralization by the α pool compared to wild type AAV2.

The cap gene from variant 1.45 was subjected to additional random mutagenesis and the resulting library was selected for three additional rounds of selection against the β and γ pools, in parallel. As only minor improvements in antibody evasion were observed (data not shown), the recovered cap genes were pooled and subjected to additional diversification via DNA shuffling and EP PCR. Three more rounds of selection against increasing amounts of sera from both the β and γ pools resulted in substantial enrichment in the amount of recovered virus from the viral library compared to wild type AAV2 (FIG. 7b, c). Sequencing of the successful cap genes from both pools revealed several low frequency mutants and a single dominant mutant, variant γ4.3, which contained four point mutations (N312K, N449D, N551S, and 1698V), present within both libraries. In the presence of human IVIG, variant 1.45 demonstrated a modest 1.2-fold enhanced resistance to neutralization, whereas γ4.3 demonstrated 3.1-fold enhanced resistance to neutralization (FIG. 7d). This observation confirms the hypothesis that pools of individual human sera can be used to isolate AAV variants capable of enhanced evasion of antibodies present in the general human population.

Figure 1B:
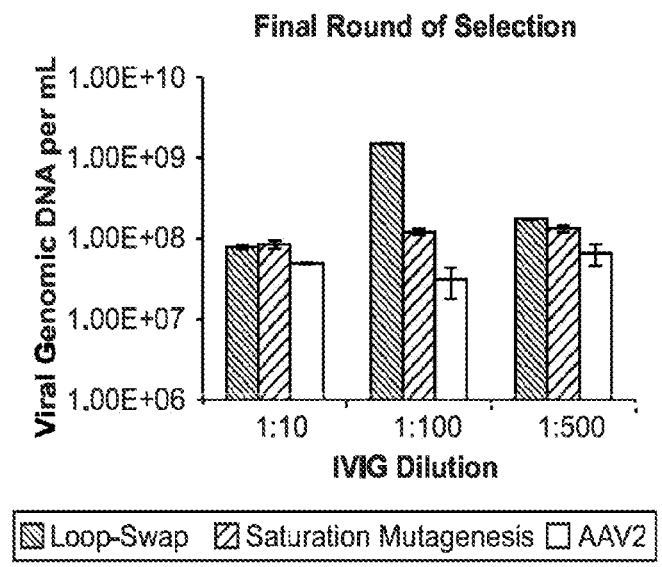

The moderate success of variant γ4.3 in resisting neutralization by anti-AAV antibodies prompted the development of a library based on the γ4.3 cap gene. Amino acid sites R471, K532, E548, N587, V708, T716, previously determined to be immunogenic sites on the AAV2 capsid, were subjected to saturation mutagenesis in an attempt to find amino acid mutations that may improve upon the antibody resistance of γ4.3. This "saturation mutagenesis" library, along with a "shuffled" library composed of random cap chimeras of 7 parent AAV serotypes and a "loop-swap" library composed of AAV2 cap with substituted loop regions were subjected to three additional rounds of selection, in which the pools of viral libraries were incubated with various dilutions of human IVIG for one hour at 37° C. prior to infection of HEK293T cells. Following infection with AAV libraries, and amplification of the infectious AAV variants through adenovirus superinfection, the number of viral genomes, or viral titer, from each library condition was quantified and compared to titers of wild-type AAV2 as a method for determining the success of the selection (FIG. 1B). For each round of selection using the saturation mutagenesis and loop-swap/shuffled libraries, viral pools from the 1:10 and 1:100 IVIG dilution conditions that produced higher viral titers than wild-type AAV2 were used as the starting point for the subsequent round of selection. After three rounds of selection, the successful viral cap genes were isolated and tested individually to determine the virus with the most efficient gene delivery. In addition, the cap genes isolated from the third round of selection were subjected to additional rounds of error-prone PCR mutagenesis, and the process was repeated to iteratively increase the fitness of the virus.

FIG. 1 depicts directed Evolution of AAV for Enhanced Antibody Evasion. (a) Schematic of Directed Evolution. 1) A viral library is created by genetically diversifying the cap gene using several complementary approaches. 2) Viruses are packaged in HEK293T cells using plasmid transfection, then harvested and purified. 3) The viral library is incubated with human IVIG at several concentrations and introduced to HEK293T cells in vitro. 4) Successful viruses are amplified and recovered via adenovirus superinfection. 5) Successful clones are enriched through repeated selections at lower MOIs. 6) Isolated viral DNA reveals successful cap genes. 7) Successful cap genes are mutated again to serve as a new starting point for selection. (b) Selection of Antibody Evading Mutants from Loop-Swap/Shuffled, and Saturation Mutagenesis libraries. HEK293T cells were infected with viral libraries for 24 hours. Viral particles that productively infected cells were amplified by adenovirus infection, and the rescued AAV was quantified by qPCR (quantitative polymerase chain reaction). A 1:10 dilution of IVIG corresponds to a concentration of 10 mg IVIG/mL. Error bars indicate the standard deviation (n=3).

FIG. 7 demonstrates the generation of human antibody evaders based on AAV2. (a) Four viral clones selected after three rounds of selection against the low stringency α pool demonstrate enhanced resistance to 1 μL of a serum at MOI of 1. Two additional rounds of diversification (i.e. mutagenesis and DNA shuffling) and selection (3 rounds of increasing serum amounts) resulted in significantly enhanced viral recovery in the presence of large amounts of highly potent (b) β and (c) γ pools. (d) Additionally, two viral clones (1.45 and γ4.3) demonstrate 1.23- and 3.10-fold enhanced resistances to a highly diverse pool of pre-existing antibodies present with pooled human intravenous immunoglobulin (IVIg) from ~100,000 individuals compared to wild-type AAV2.

Increased Antibody Evasion of the Novel Evolved AAV Variants In Vitro

Figure 2A:
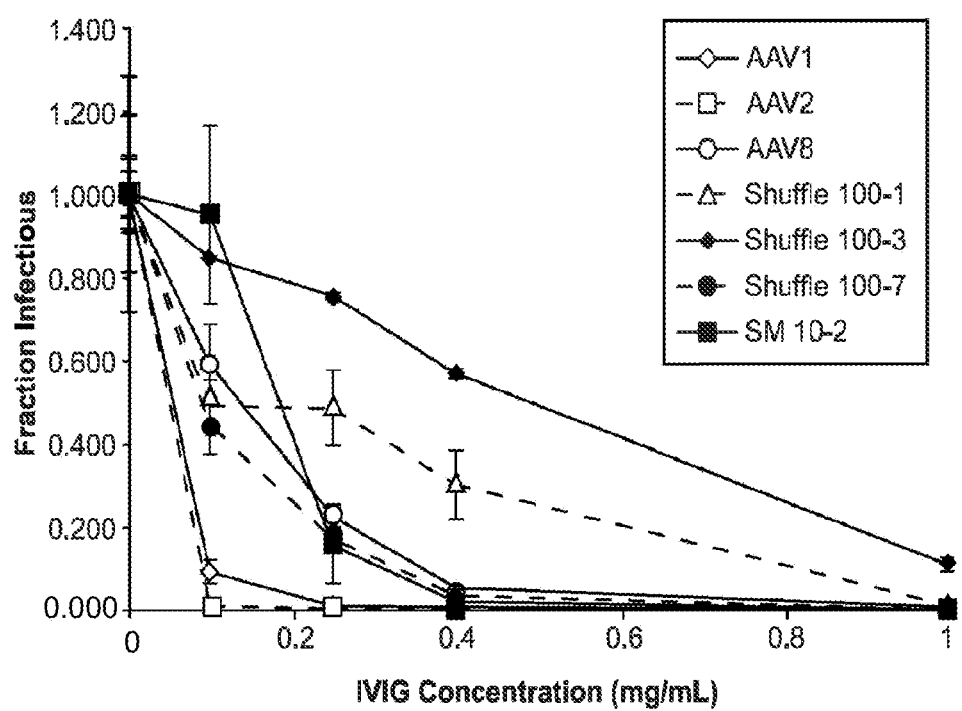
Figure 2B:
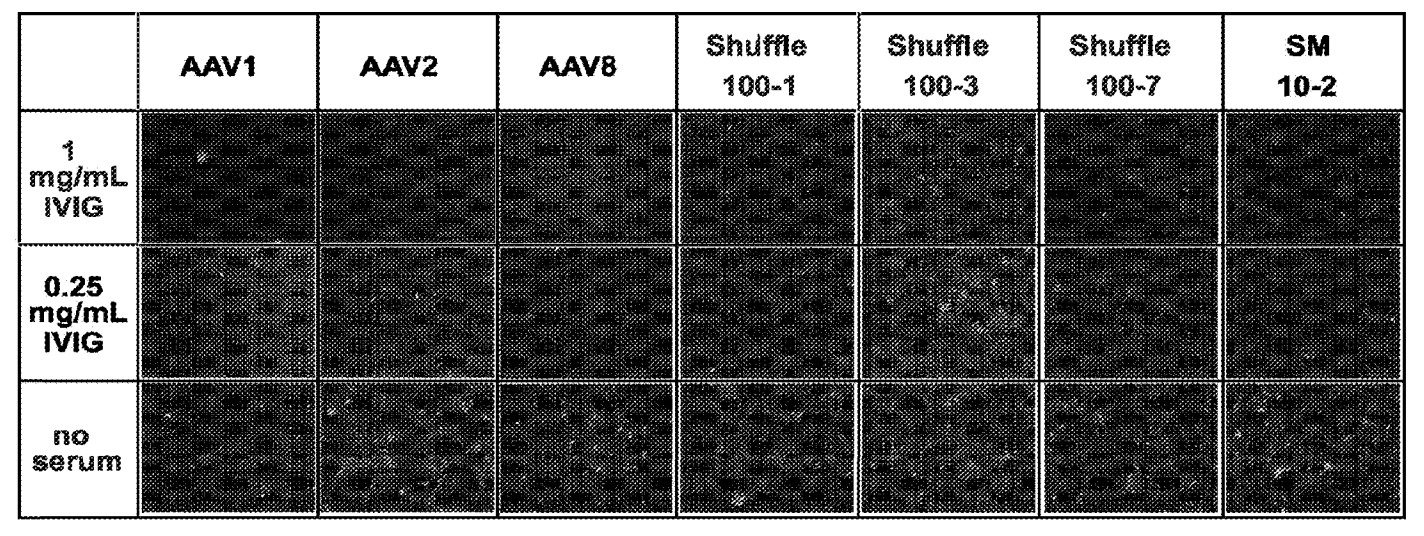

Of the twelve clones selected and packaged for individual analysis from the saturation mutagenesis and loop-swap/shuffled libraries after nine rounds screening against human IVIG, all twelve required higher neutralizing antibody titers than both wild-type AAV1 and AAV2 (FIG. 2a and Table 1). Variant Shuffle 100-3 (see SEQ ID NO: 12), which required a 35-fold higher in vitro IVIG concentration for neutralization than wild-type AAV2, was still capable of transducing approximately 10% of cells in the presence of 1 mg/mL IVIG (FIG. 2b). In addition, variant SM 10-2 from the AAV2 saturation mutagenesis library required a 7.5-fold higher in vitro WIG concentration for neutralization than wild-type AAV2. Furthermore, variants Shuffle 100-3 and SM 10-2 (see SEQ ID NO: 10) showed enhanced transduction in the presence of sera samples from individual patients excluded from a hemophilia B clinical trial (FIG. 3) (Nathwani et al., N Engl J Med. 2011 Dec. 22; 365(25):2357-65).

FIG. 2 depicts the neutralization profiles of antibody evading variants. The cap genes of antibody evading mutants isolated after three rounds of evolution were used to package recombinant AAV encoding GFP and incubated with human IVIG before infection of HEK293T cells. The fraction of remaining infectious particles was determined using high content fluorescence imaging and normalized to the infectious titer in the absence of IVIG. Two clones from each library with resistance to IVIG are shown. Data for the other clones analyzed are displayed in Table 1. (a) Neutralization curves. Error bars indicate the standard deviation (n=3). (b) Representative fluorescence images from several IVIG dilutions show that mutants are capable of HEK293T transduction in the presence of high concentrations of neutralizing antibodies.

Figure 3A:
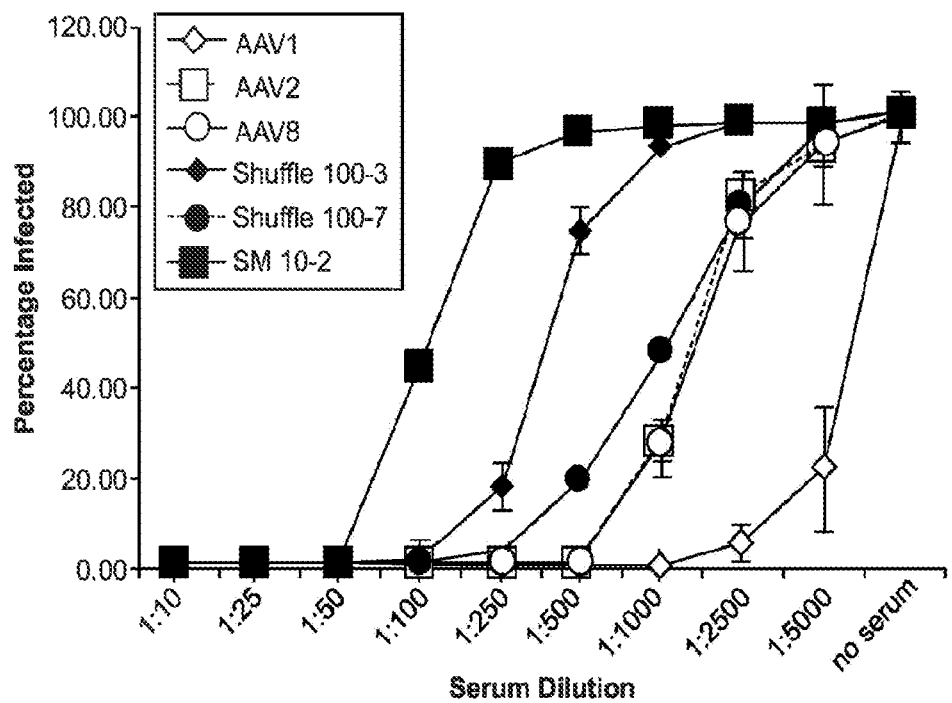
FIGS. 3A-C depict the neutralization profiles of antibody evading variants using human sera acquired from individuals that were excluded from hemophilia B clinical trials due to the presence of high neutralizing antibody titers against AAV.
Figure 3B:
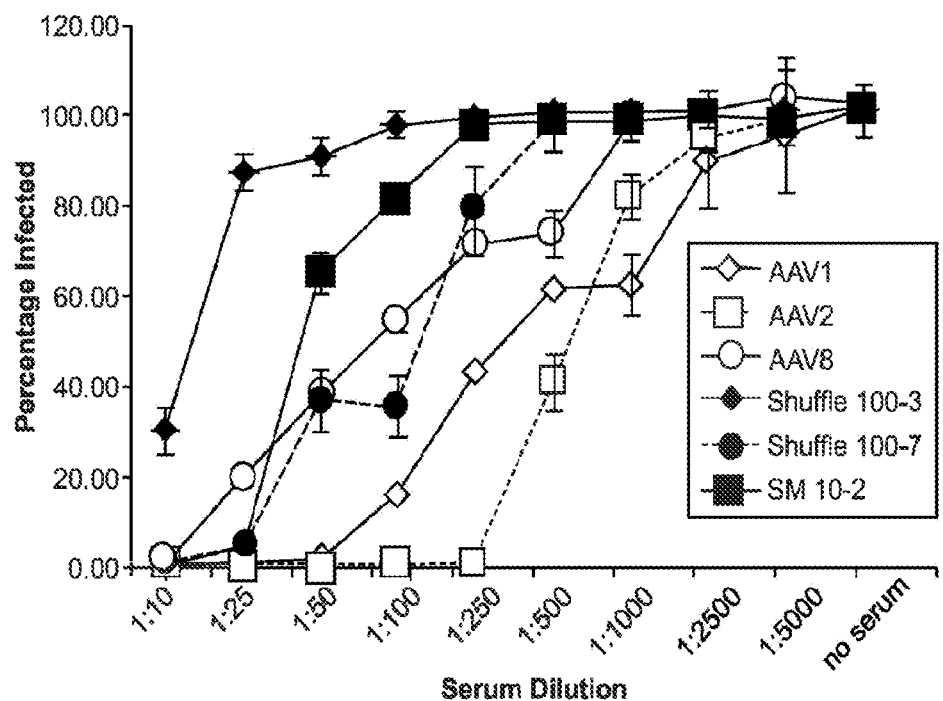
Figure 3C:
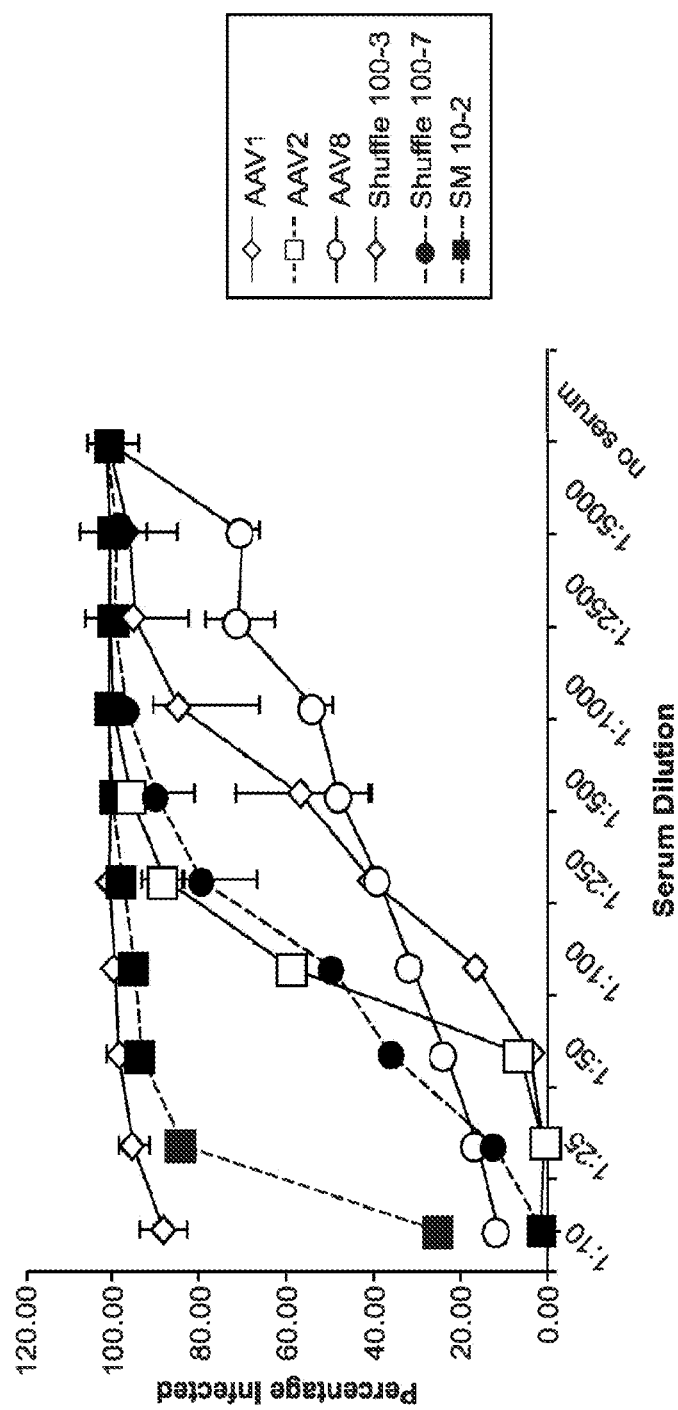

FIG. 3 depicts the neutralization profiles of antibody evading variants. Human sera were acquired from individuals that were excluded from hemophilia B clinical trials due to the presence of high neutralizing antibody titers against AAV. Recombinant AAV encoding GFP was incubated with individual human serum samples before infection of HEK293T cells. The fraction of remaining infectious particles was determined using fluorescence microscopy and normalized to the infectious titer in the absence of human sera. Error bars indicate the standard deviation (n=3).

Figure 4B:
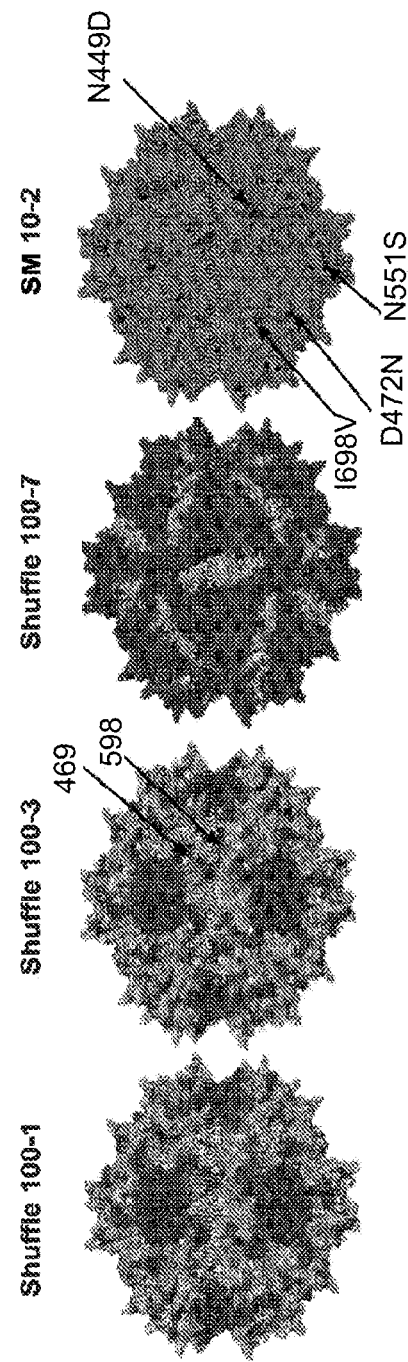

Sequence analysis of the twelve clones revealed that the two variants with the highest neutralizing antibody resistance, Shuffle 100-3 (see SEQ ID NO: 12) and Shuffle 100-1 (see SEQ ID NO: 11), are almost identical shuffled capsids containing fragments of AAV1-4, AAV6, and AAV9 (FIG. 4). Differences in amino acids 469 (AAV6 residue to AAV7 residue) and 598 (AAV6 residue to AAV1 residue) between the two variants translate to almost a 3-fold increase in neutralizing antibody titer for Shuffle 100-3 (see SEQ ID NO: 12) (Table 1). Variant Shuffle 100-7 (see SEQ ID NO: 13), which had the fourth highest neutralizing antibody resistance (Table 1), is also a shuffled capsid containing fragments of AAV1, AAV6, and AAV8 (FIG. 4), which agrees well with reported data showing that wild-type AAV1 and AAV8 are effective at evading anti-AAV2 antibodies. Interestingly, variant SM 10-2 (SEE SEQ ID NO: 10) retained the point mutations acquired by variant γ4.3 and also retained wild type residues at the saturation mutagenesis sites. Variant SM 10-2 (SEE SEQ ID NO: 10) did acquire additional point mutations at surface residue D472N and internal residue L735Q. FIG. 4 depicts the amino acid sequences of loop-swap/shuffle and saturation mutagenesis clones. (a) Schematics of the capsid protein are shown for the two clones from each library with the highest neutralizing IVIG concentrations. Each region is shaded according to the parent serotype from which it is derived. Black arrows denote (from left to right) the start codons of VP1, VP2, and VP3 capsid proteins. Gray arrows denote (from left to right) surface loop regions I, II, III, IV, and V based on the AAV2 capsid. (b) Molecular models of the full AAV2 capsid, based on the solved structure, are shown for the two clones from each library with the highest neutralizing IVIG concentrations. Each region is shaded according to the parent serotype from which it is derived. For variant Shuffle 100-3 (see SEQ ID NO: 12), black arrows indicate differences from variant Shuffle 100-1 (see SEQ ID NO: 11). For variant SM 10-2 (SEE SEQ ID NO: 10), mutations N449D, D472N, N551S, and I698V are surface mutations (black).

Table 1: IVIG Neutralizing Antibody Titers of Library Clones and Parent Serotypes Human IVIG was used to neutralize recombinant AAV-GFP vectors with capsids from wild-type AAV1, AAV2, AAV8, and variants recovered from the loop-swap/shuffled and saturation mutagenesis libraries. The IVIG concentration (mg/mL) required to reduce gene delivery efficiency to 50% of that in the absence of IVIG is shown, and compared to the concentration required to reduce delivery of AAV2. All variants analyzed required higher concentrations of IVIG than wild-type AAV1 and AAV2. The neutralizing antibody titer was determined by fitting the curves in FIG. 2 to an exponential curve. SEQ ID NOs are listed as "amino acid, nucleotide."

TABLE 1

| Clone | SEQ ID NO: | Neutralizing IVIG concentration mg/ml | Fold Resistance Relative to AAV2 |
| --- | --- | --- | --- |
| AAV1 | 1 | 0.026 | 1.757 |
| AAV2 | 2 | 0.015 | 1.000 |
| AAV8 | 8 | 0.092 | 6.113 |
| Shuffle 10-2 | 26, 34 | 0.037 | 2.443 |
| Shuffle 10-6 | 27, 35 | 0.028 | 1.842 |
| Shuffle 10-8 | 28, 36 | 0.084 | 5.583 |
| Shuffle 100-1 | 11, 23 | 0.183 | 12.178 |
| Shuffle 100-2 | 29, 37 | 0.073 | 4.831 |
| Shuffle 100-3 | 12, 24 | 0.529 | 35.227 |
| Shuffle 100-7 | 13, 25 | 0.090 | 6.025 |
| SM 10-1 | 30, 38 | 0.071 | 4.732 |
| SM 10-2 | 10, 22 | 0.113 | 7.519 |
| SM 10-8 | 31, 39 | 0.051 | 3.409 |
| SM 100-3 | 32, 40 | 0.074 | 4.941 |
| SM 100-10 | 33, 41 | 0.066 | 4.393 |

Figure 5:
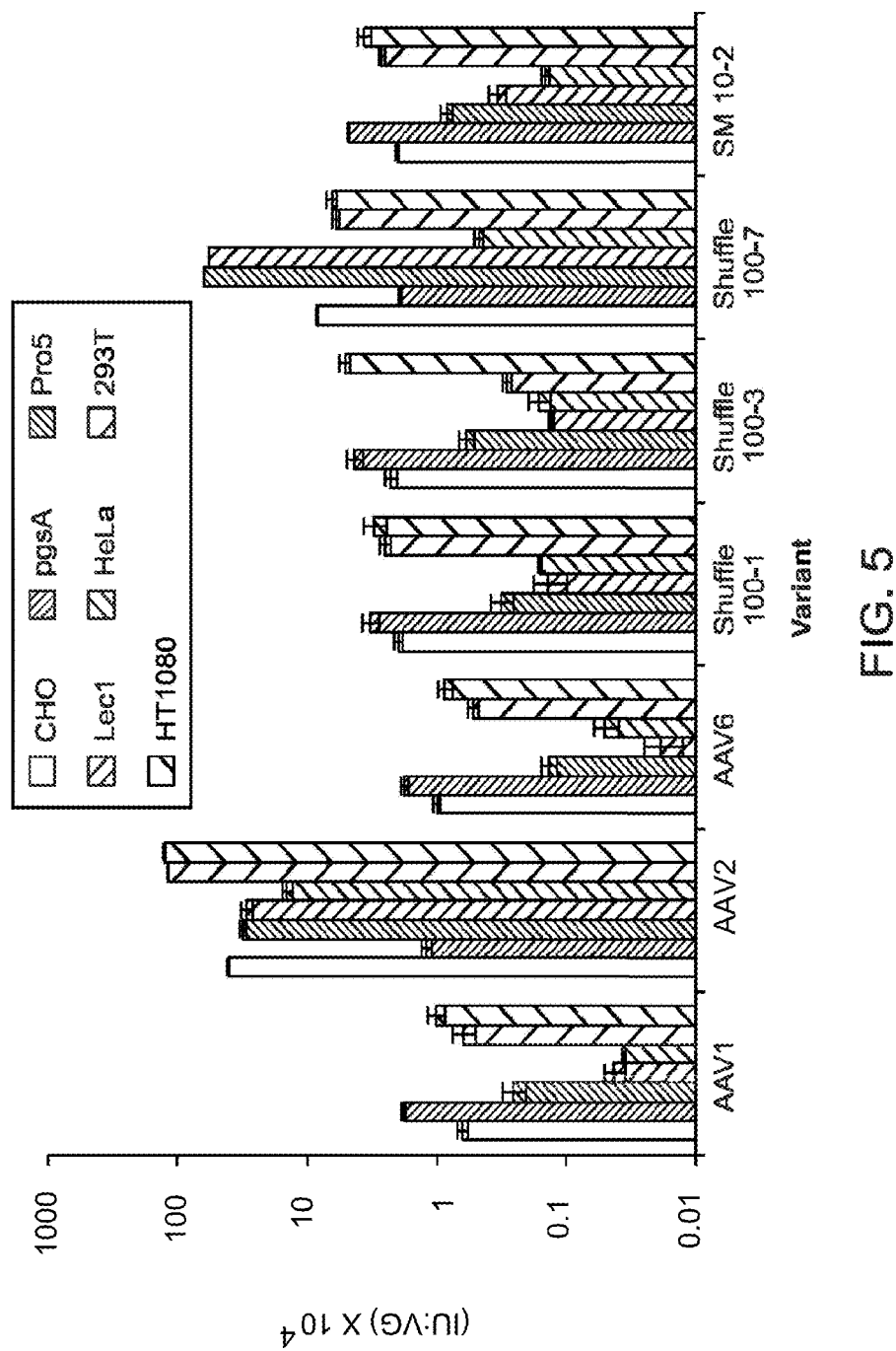

Variants Shuffle 100-3 (see SEQ ID NO: 12), Shuffle 100-1 (see SEQ ID NO: 11), and Shuffle 100-7 (see SEQ ID NO: 13) have transduction profiles that mimic the transduction profiles of parent serotypes AAV1 and AAV6 (FIG. 5). In addition, the mutations in SM 10-2 (see SEQ ID NO: 10) do not prevent a heparin dependence (as seen in parent serotype AAV2) leading to a profile similar to AAV2 (FIG. 5).

FIG. 5 demonstrates the in vitro tropism of novel aav variants. Recombinant AAV vectors expressing green fluorescent protein were used to transduce a panel of cell lines: CHO, pgsA (lacking all surface glycosaminoglycans), Pro5, Lec1 (lacking sialic acid), HEK293T, HeLa, and HT1080 (human fibrosarcoma cell line) to profile the transduction properties of the new AAV variants. Error bars indicate the standard deviation (n=3).

Increased Antibody Evasion of the Novel Evolved AAV Variants In Vivo

Figure 6A:
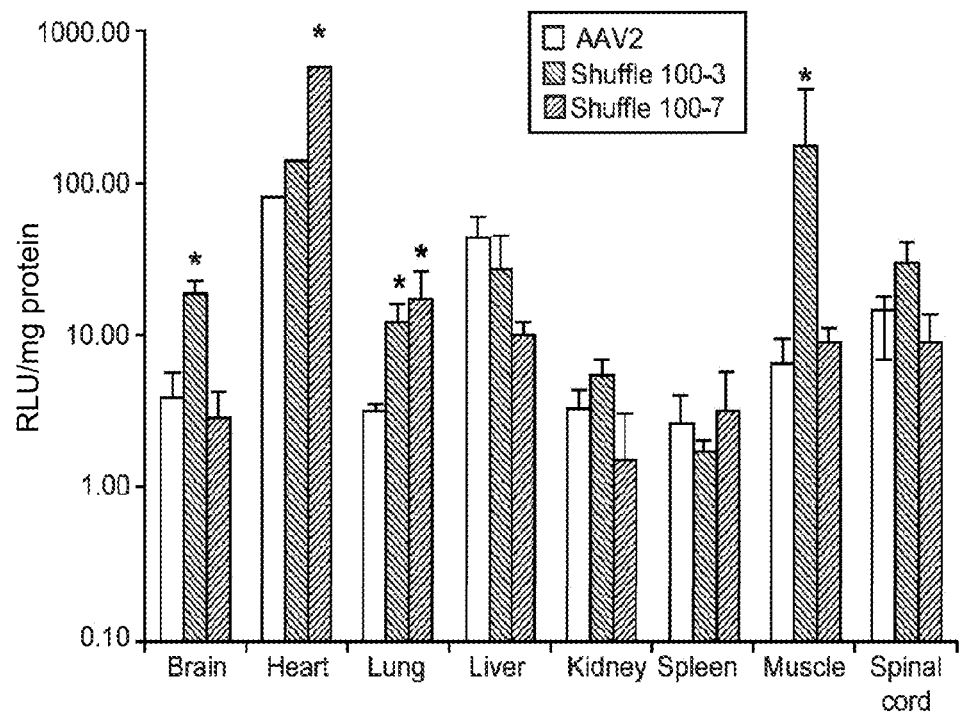

To determine the localization pattern of variants Shuffle 100-3 and Shuffle 100-7, luciferase enzyme activity was examined in various tissues of naïve mice injected with AAV2, Shuffle 100-3, or Shuffle 100-7 (FIG. 6a). Variant Shuffle 100-7 displayed similar in vivo tropism to AAV2, except for 7-fold higher transduction of the heart, 5-fold higher transduction of the lungs, and 4.5-fold lower transduction of the liver. The Shuffle 100-3 variant exhibited over 4-fold higher transduction of the brain, over 3-fold higher transduction of the lungs, and 27-fold higher transduction of muscle than AAV2. Analysis of the serum from these mice showed that variant Shuffle 100-3 required equal or higher in vitro serum concentrations for neutralization than AAV1 and AAV8 for serum from mice given AAV1, AAV2, AAV8 or Shuffle 100-3 gene delivery vectors (FIG. 11). Shuffle 100-7 required equal or higher in vitro serum concentrations for neutralization than AAV1 for serum from mice given AAV1, AAV2, AAV8, Shuffle 100-3, or SM 10-2 gene delivery vectors (FIG. 11). Furthermore, both variants were less neutralized by serum from mice given AAV2 gene delivery vectors than all wild-type AAV serotypes tested. Interestingly, variant Shuffle 100-3 was also less neutralized by serum of mice immunized against it than any of the other serotypes or variants tested (FIG. 11). This data illustrates the possibility that these variants could be used in combination with wild-type AAV serotypes or the other variant in applications requiring multiple vector administrations.

FIG. 11 shows the neutralizing antibody titers of library clones and parent serotypes in immunized mouse sera. Sera from mice administered library clones or wild-type AAV was used to neutralize recombinant AAV-GFP vectors with capsids from wild-type AAV1, AAV2, AAV8, and variants recovered from the loop-swap/shuffled and saturation mutagenesis libraries. The serum dilution required to reduce gene delivery efficiency to 50% of that in the absence of serum is shown.

Figure 6B:
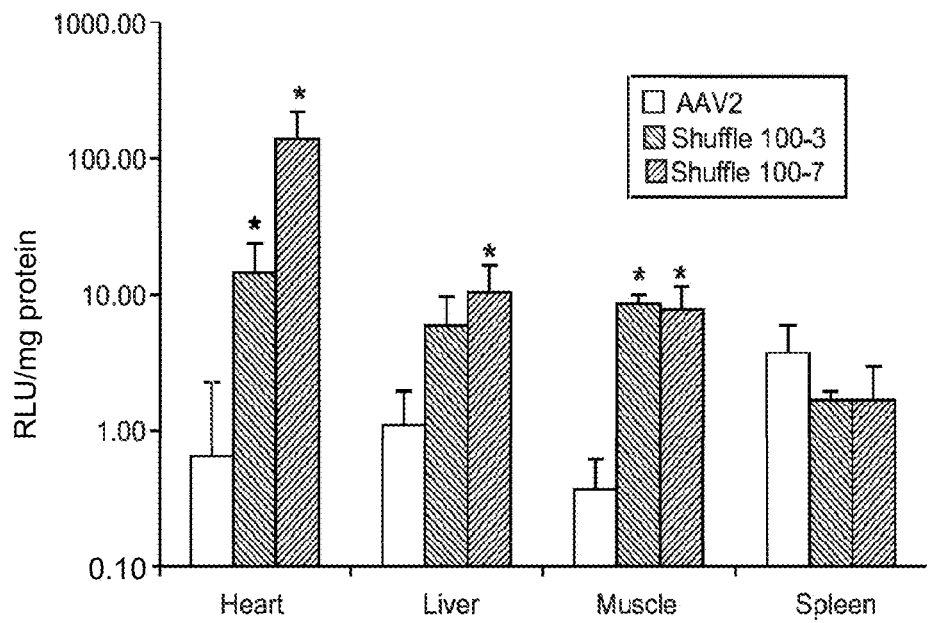

To determine the ability of variants Shuffle 100-7 and Shuffle 100-3 to evade antibody neutralization in vivo, mice were passively immunized with human IVIG prior to AAV injection. Variant Shuffle 100-7 had significantly higher heart, liver, and muscle transduction than AAV2, as measured by luciferase enzyme activity (FIG. 6b). Variant Shuffle 100-3 had significantly higher heart and muscle transduction compared to AAV2 (FIG. 6b).

FIG. 6 shows the in vivo localization and neutralization of novel AAV variants. (a) Recombinant AAV vectors encoding luciferase were administered via tail vein injection to female BALB/c mice. After 5 weeks, levels of luciferase activity were determined and normalized to total protein for each sample analyzed. (b) Recombinant AAV vectors expressing luciferase were administered via tail vein injection to female BALB/c mice 24 hours after tail vein injection of 4 mg of human IVIG. After 5 weeks, levels of luciferase expression were normalized to total protein for each sample analyzed. Error bars indicate the standard deviation (n=3), *=p<0.05. RLU, relative luciferase unit.

Variant γ4.3, isolated from an AAV2-based error-prone library selected against a pool of individual human sera, contained four point mutations (N312K, N449D, N551S, and I698V). Interestingly, two of these positions (N449 and N551) were previously identified as immunogenic residues using other pools of human serum, demonstrating that antigenic epitopes involving these sites are targeted by many different neutralizing antibodies. Thus, these sites are interesting and valuable targets for mutation. Pairing directed evolution and rational design in the saturation mutagenesis library resulted in the isolation of variant SM 10-2, which was capable of higher antibody resistance than both AAV1 and AAV2 in vitro. Variant SM 10-2 incorporates two additional point mutations (D472N and L735Q) to those found on variant γ4.3. The D472N mutation was previously shown to increase the level of capsid synthesis in HEK293 cells. Similarly, the replacement of the positively charged lysine side chain at amino acid position 735 with the uncharged glutamine side chain may function to stabilize the capsid, as it is also present in variant Shuffle 100-7 despite being located within the interior of the assembled capsid (FIG. 4).

The creation of chimeric AAV capsids allows for the creation of viral variants that can merge desirable properties from multiple AAV serotypes. Although AAV8 and AAV9 have also been shown to be much more resistant to neutralization by IVIG than AAV2, amino acids specific to these capsids were only present in small spans on the surface of the shuffled variants isolated during our selections (FIG. 4). The variant displaying the more efficient evasion of antibody neutralization in vitro, Shuffle 100-3, displayed similar in vitro tropism to its parental serotypes AAV1 and AAV6, but at a higher rate of infectivity than either wild-type serotype. Differences in amino acids 469 and 598 between variants Shuffle 100-1 and Shuffle 100-3 translate to almost a 3-fold increase in neutralizing antibody titer for Shuffle 100-3. A study by Lochrie et al. reported that the immunogenic residues recognized by human sera and IVIG are different, suggesting that different humans can produce various neutralizing antibodies to different sets of epitopes on the AAV capsid and complete escape from neutralization is not easy (Lochrie et al., J Virol. 2006 January; 80(2):821-34). Our work demonstrates that the use of multiple rounds of directed evolution using several different serum pools containing various amounts and potencies of anti-AAV antibodies will result in the isolation of novel AAV variants that are capable of enhanced cellular transduction, both in vitro and in vivo, in the presence of multiple anti-AAV antibody pools.

Adaptive immune responses to AAV vector components in animals and humans often prevent re-administration of AAV vectors of the same serotype, making gene delivery applications requiring multiple vector administrations difficult. In vitro neutralization assays using the serum from the mice used in the biodistribution studies demonstrate that the variants are less neutralized by these sera than wild-type AAV (FIG. 11), which may be useful for gene therapy strategies in which vector readministration is necessary. For example, Shuffle 100-3 was not neutralized by serum from mice injected with AAV2, and AAV2 was not neutralized by serum from mice injected with Shuffle 100-3, suggesting this variant can be used in combination with wild-type AAV serotypes or in applications requiring multiple vector administrations. In conclusion, we have used directed evolution to isolate novel AAV variants that are capable of reduced neutralization by anti-AAV antibodies derived from individual human patients, pooled human serum, and mouse serum, both in vitro and in vivo.

Example 2

Identification of a Capsid Variant Suitable for Use in Gene Therapy to the Primate Lung Introduction A directed evolution strategy was used to identify AAV Capsid Variants with enhanced gene delivery efficiency to non-human primate (NHP) lung alveolar epithelial type II (AT II) cells following intratracheal aerosol administration in the presence of human neutralizing antibodies (NAbs). Briefly, wild-type adeno-associated virus (AAV) cap genes were diversified by several approaches to create large genetic libraries that were packaged to generate libraries of viral particles, and selective pressure was then applied to isolate novel variants that can overcome gene delivery barriers, including but not limited to anti-capsid immune responses, limited transduction of certain tissues, and inability for targeted delivery to specific cell types.

Methods

Cell Lines and Library Production

HEK293T cells were obtained from the American Type Culture Collection (Manassas, VA). Cells were cultured at 37° C. and 5% $CO_2$ in Dulbecco's modified Eagle's medium supplemented with 10% fetal bovine serum (Gibco, Carlsbad, CA) and 1% penicillin/streptomycin (Invitrogen, Carlsbad, CA). Viral libraries were produced in HEK293T cells using triple transfection, and viruses were purified by iodixanol gradient centrifugation and Amicon filtration. DNase-resistant genomic titers were determined via quantitative PCR (qPCR).

Intratracheal Injection and Tissue Harvesting

For each delivery device used in the selection, a single male cynomolgus macaque (*Macaca fascicularis*) between 4-6 years of age and weighing between 5.5-6.0 kg was dosed. The animals were anesthetized with 10 mg/kg ketamine and 15 μg/kg dexmedetomidine delivered intramuscularly (IM). Five mL of the library was pre-complexed with 1.75 mg/mL of human intravenous immunoglobulin (IVIG) and administered as described below. Each animal was intubated with a 5 mm endotracheal tube, with the tip of the tube positioned at the level of the clavicle (approximately 5 cm above the carina), and its position confirmed by fluoroscopy.

The nebulizer device was connected to the distal end of the endotracheal tube, and a bird respirator was used to deliver breaths at a rate of 15±1 breaths/minute with a pressure of 20 cm H2O. The AeroProbe® catheter (Trudell Medical International) was fitted with a piece of 0.144 inch star tubing to facilitate proper location within the endotracheal tube. The tip of the catheter was positioned just above the tip of the endotracheal tube. The AeroProbe® catheter was connected to the AeroProbe Catheter Control System, and a ventilator (Harvard Appartatus) was used to deliver breaths at a rate of 20 breaths/minute with a pressure of 18-20 cm H2O. Following the completion of dosing, each animal was extubated and received 0.15 mg/kg atipamezole IM to reverse sedation. The animals were visually monitored until fully recovered from anesthesia prior to returning to their home cages.

Euthanasia was performed by trained veterinary staff using 100 mg/kg pentobarbital sodium delivered intravenously on day 15±1. The lungs, including the trachea, were removed and dissected as detailed below. DNA was isolated from the AT II cells and stored at −20° C. until viral genome amplification.

Alveolar Epithelial Type II (AT II) Cell Isolation

AT II cells were isolated from non-human primate lungs, as described by Fang et al., Measurement of Protein Permeability and Fluid Transport of Human Alveolar Epithelial Type II Cells Under Pathological Conditions. Humana Press, New York, NY, 2018, pp 121-128. Briefly, lungs were flushed with 500 mL of PBS containing 5 mM EDTA and 5 mM EGTA using a syringe placed within the trachea. Lungs were then filled with 250 mL of a 1.2 mg/mL elastase solution and incubated for 1 hour at 37° C. Lungs were homogenized to release cells lining the lungs, and the airways were discarded. AT II cells were isolated following a series of inclusion and exclusion steps, including a Percoll gradient and CD14/CD45 Dynabeads. AT II cells were plated on collagen IV-coated inserts for 24 hours prior to DNA isolation. Characterization was done examining Lysotracker and surfactant protein C by flow cytometry and immunocytochemistry to insure purity of the cell isolate.

Therapeutic Vector Evolution

Figure 12:
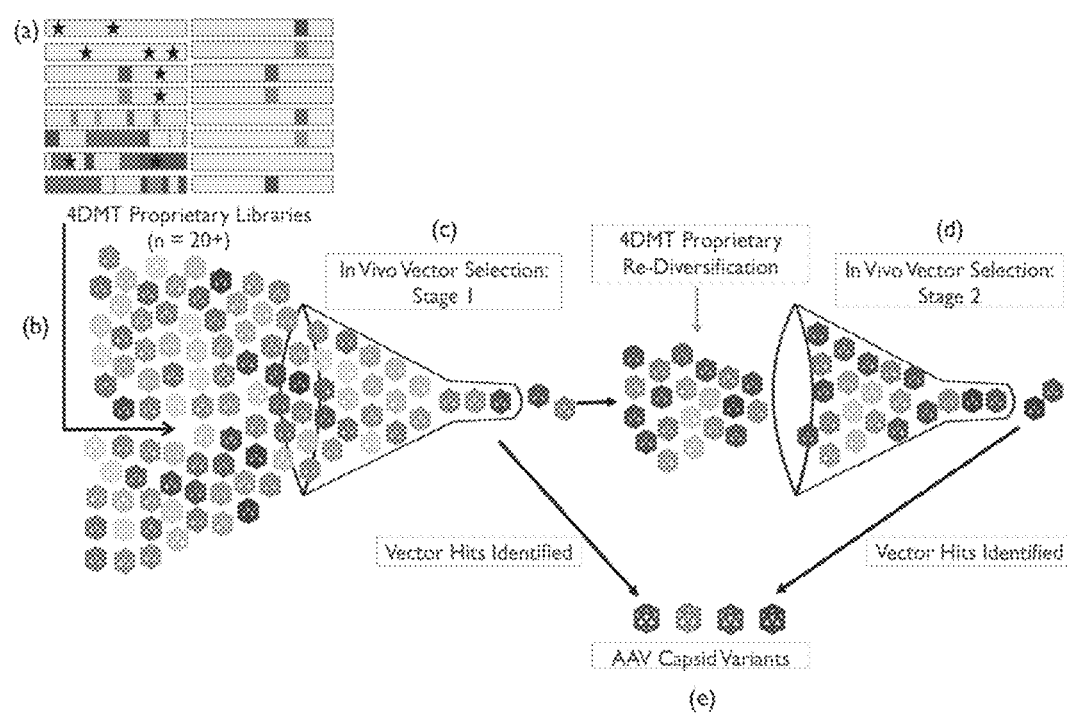

The Vector Evolution process employed is shown in FIG. 12. Briefly, a viral capsid library comprising proprietary combinations of DNA mutation techniques and cap genes was created (a). Viruses were then packaged (b) such that each particle is composed of a mutant capsid surrounding the cap gene encoding that capsid and purified. The capsid library was placed under selective pressure in vivo. The tissue or cell type of interest was harvested to isolate AAV variants that have successfully localized to the target. Successful viruses were recovered by PCR amplification. Successful clones were enriched through repeated selection (Stage I—(c)). Selected cap genes then underwent proprietary re-diversification and were enriched through further selection steps to iteratively increase viral fitness (Stage 2—(d)). Variants identified as hits during Vector Selection Stages 1 and 2 were assessed to identify capsid variants with the desired properties (e).

Motifs were declared "Hits" when the following criteria were met: 1) a motif represents approximately 5% of the sequenced population in two or more consecutive rounds of the selection; or 2) a motif representing at least 10% of the sequenced population in one or more rounds of the selection.

Results

Pilot Studies for Delivery Device Parameters and AT II Cell Isolation

Two delivery devices, an AeroProbex catheter (Trudell Medical International) and CRO's in-house nebulizer, were employed to enable downstream compatibility with multiple clinically translatable devices. Both delivery devices were evaluated in pilot studies delivering Evans blue dye to ensure that ventilation parameters resulted in adequate distribution to all lung lobes and the alveolar sacs. Both delivery devices demonstrated good distribution to all lobes, including the alveolar compartment, with more intense dye observed in the dependent lobes.

The AT II cell isolation protocol was optimized using a total of 6 NHP lungs. The protocol optimization resulted in high yield and purity of AT II cells isolated from both NHP lungs used during Therapeutic Vector Evolution.

Therapeutic Vector Evolution

Figure 13A:
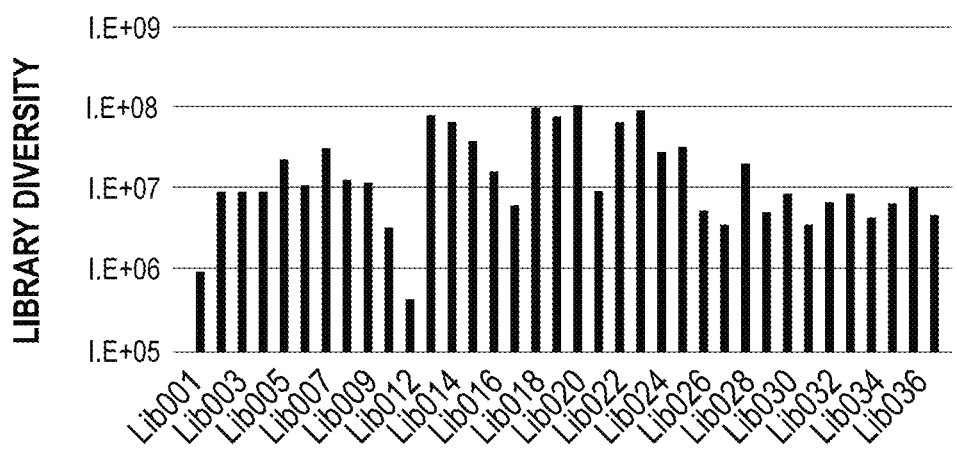
Figure 13B:
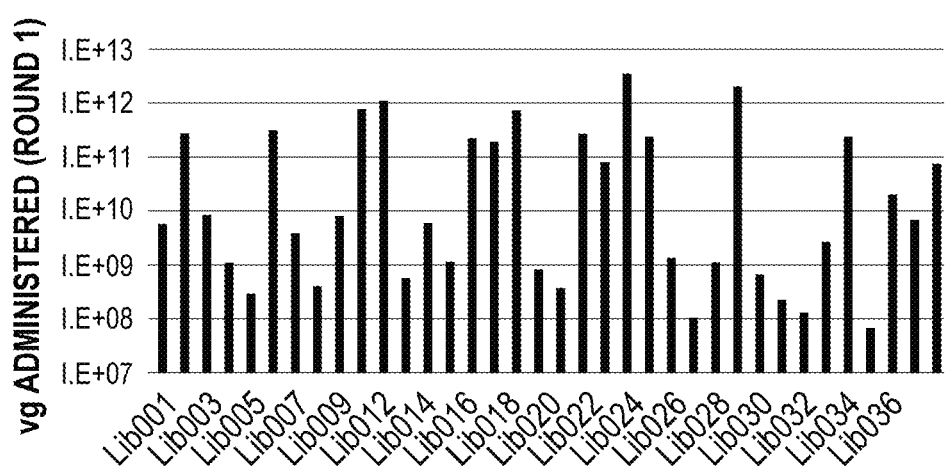

Prior to initiation of Round 1 of the Therapeutic Vector Evolution program, 37 vector libraries were synthesized, manufactured, and characterized. As shown in FIG. 13A, the diversity of the plasmid libraries is estimated to include approximately $1 \times 10^6$ to $>1 \times 10^8$ individual unique variants per library. This represents a high quality, highly diverse starting library of AAV variants. Next, production of each individual library was completed in order to generate enough material for the first round of selection. As shown in FIG. 13B, all libraries manufactured at a level sufficient to produce material for an in vivo Therapeutic Vector Evolution selection.

All 37 libraries were combined and successfully administered to both NHPs via a single dose aerosol administration using either the AeroProbe® or nebulizer. Prior to administration, the libraries were incubated with 1.75 mg/mL human intravenous immunoglobulin. This represents a high, yet physiologically-relevant lung mucus concentration of human NAbs. The library dose of $1.7\times10^{12}$ vg per NHP represents a dose that is approximately 10-fold lower than the current maximum feasible dose based on manufacturing considerations. Therefore, this represents stringent selective pressure to enable discovery of a vector capable of transducing AT II cells in the alveolar space in the presence of NAbs. The NHP lungs were harvested two weeks post-administration. AT II cells were isolated from the lungs, and DNA was isolated from the AT II cells.

Successful Amplification of AAV Capsid Genomes

Amplification of capsid genes from tissue represents successful localization of library vectors into the cell type of interest. The capsids amplified from each delivery device (FIGS. 14A-B) were cloned into an AAV library packaging plasmid for sequence analysis and to initiate the subsequent round of selection (if necessary).

Sequencing Analysis

Sequencing was performed on individual clones within the library to determine the frequency of variants within the population. Sequencing on a minimum of 90 clones from each delivery device was performed. Variants were evaluated for the presence of motifs within the sequencing data. Variants were grouped into motifs based on the presence of a unifying variation (for example, a specific point mutation or specific peptide insertion sequence in a consistent location within the capsid) that occurred in multiple sequences. A motif was progressed for further evaluation only if it represents at least 5% of the sequenced population in two or more consecutive rounds of the selection or at least 10% of the sequenced population in one or more rounds of the selection. The motif that met the latter criterion is represented in FIG. 15A-B. The selection was considered complete following the first round, as strong convergence to the A101 variant (comprising a capsid protein of SEQ ID NO:12) was observed using both delivery devices.

Based on the ranking criteria above, A101 capsid variant comprising a capsid protein of SEQ ID NO:12 was identified as conferring enhanced gene delivery efficiency to the primate lung following intratracheal aerosol administration in the presence of human neutralizing antibodies (NAbs). A101 is a chimera consisting primarily of AAV1 but also including amino acids from AAV2, AAV4, AAV6 and AAV9.

Example 3

Although initial attempts at developing AAV-based gene therapy for the lung demonstrated clinical safety, the use of the AAV2 vector ultimately did not efficiently transduce lung cells to show clinical benefit in cystic fibrosis. More recently, additional AAV serotypes, including AAV1 and AAV5, have demonstrated improved, but still not optimal, transduction of primate lungs following aerosolized administration. The experimental data below confirms the surprising suitability of rAAV comprising a capsid comprising a capsid protein of SEQ ID NO:12 as a vehicle in which to efficiently deliver transgenes such as human CFTR throughout the primate lung in the presence of human neutralizing antibodies.

Gene delivery of recombinant AAV (rAAV) comprising (i) a capsid comprising a capsid protein of SEQ ID NO:12 and (ii) a nucleic acid comprising a nucleotide sequence encoding reporter transgene (GFP or EGFP) operably linked to a CAG promoter was characterized (including evaluation of histopathology) following aerosol administration to three non-human primates (NHP). Nebulized delivery of the rAAV resulted in robust delivery of viral genomes to all regions of the lung, including the peripheral (bronchioalveolar regions), with minimal systemic biodistribution, and the rAAV mediates protein expression to all regions of the lung, including the alveoli.

Materials and Methods

Neutralizing Antibody Assay

HEK2v6.11 cells (obtained from John Hopkins University) were plated on black opaque 96 well plates at a cell density of 30,000 cells/well in Dulbecco's modified Eagle medium (DMEM; Corning) with 1% heat inactivated fetal bovine serum (FBS; GE Healthcare Life Sciences) and 1% penicillin/streptomycin (Invitrogen). Cells were allowed to adhere to the plate for 24 hours prior starting the experiment.

Each NHP serum sample was assayed at dilutions of 1:10, 1:25, 1:50. Each plate contained positive and negative controls for transduction. NHP serum samples were incubated with rAAV comprising (i) a capsid comprising a capsid protein of SEQ ID NO:12 and (ii) a nucleic acid comprising a CAG promoter operably linked to a lucerifase gene at an MOI of 1,000 at 37 C for 1 hour. Following a 1 hour incubation, each NHP serum sample dilution plus the rAAV was added to individual wells of black opaque 96 well plates containing 2V6.11 cells. Luciferase was detected by ONE-Glo EX Luciferase assay kit (Promega) 48 hours post-transduction. With the addition of the ONE-Glo EX, cells were lysed, and luciferase substrate was added to the cells in a single step. Luminescence was read using a Cytation 3 microplate reader (BioTek).

Coefficients of variation (CV) and standard deviations were calculated for all NHP serum sample dilutions and each point of the standard curve. NHP serum samples were normalized to the positive transduction control. Each NHP was assigned a neutralizing antibody titer. The neutralizing antibody titer for each NHP serum sample was defined as the lowest serum dilution at which #50% transduction was observed. NHPs for which #50% transduction at 1:10 serum dilution was observed were considered for inclusion in the study.

Test System & Immunosuppression

Three male cynomolgus macaques were included in the study. Animals ranged in age from 4 years, 10 months to 9 years, 8 months and ranged in weight from 4.73 kg to 7.09 kg. Animals received methylprednisolone (20 mg/kg, intramuscular) immunosuppression once weekly starting on day −7.

Test Article Preparation and Administration

Test article lots of rAAV comprising (i) a capsid comprising a capsid protein of SEQ ID NO:12 and (ii) a nucleic acid comprising a CAG promoter operably linked to a EGFP were thawed on ice, pooled together, and diluted in formulation buffer to deliver a final dose of $2.80\times10^{12}$ vg/kg in 5 mL to each NHP. The test article dilutions for each animal are provided in Table 3. Animals were sedated with Ketamine and Dexmedetomidine. Animals were intubated with the tip of the intubation tube located approximately 5 cm above the carina. Animals were placed in a chair in a seated position for administration. For each animal, 5 mL of diluted test article was loaded into the AeroEclipseII nebulizer reservoir (Trudell Medical). During dosing, pressure was adjusted to 15-20 cm H2O. Test article was administered at a rate of 12-24 breaths/minute until no visible mist was generated for 10 pulses (animals were dosed continuously for <40 minutes). Following the completion of dosing, animals were extubated, and sedation was reversed.

TABLE 3

Test: Article Dose Preparation

| NHP ID | Lot | Weight (kg) | Total Dose (vg) | Dose Solution (vg/mL) | Final Dose Prep Volume (mL) | Stock Virus (mL) | Formulation Buffer (mL) |
|---|---|---|---|---|---|---|---|
| V002969 | 4DER000040.01<br>4DER000043.01 | 5.41 | 1.51E+13 | 3.03E+12 | 5.25 | 2.048 | 3.202 |
| V003424 | 4DER000040.01<br>4DER000043.01 | 4.73 | 1.32E+13 | 2.65E+12 | 5.25 | 1.791 | 3.459 |
| V003062 | 4DER000040.01<br>4DER000043.01 | 7.09 | 1.99E+13 | 3.97E+12 | 5.25 | 2.685 | 2.565 |

In-Life, Necropsy, and Tissue Harvesting

Cage-side observations were performed twice daily by CRO staff from Day −7 to necropsy. Body weights were assessed weekly, and blood samples were collected at defined timepoints for hematology and clinical chemistry. Euthanasia was performed on Day 57±1 by trained veterinary staff using by intravenous injection of pentobarbital sodium (100 mg/kg) followed by bilateral thoracotomy and transcardial perfusion with heparinized phosphate buffered saline. Following perfusion, the lungs (including trachea), brain, spinal cord (cervical, thoracic, and lumbar regions), heart (ventricle and atrial regions), liver, spleen, skeletal muscle (triceps brachii, vastus lateralis), diaphragm, and kidney were collected. Samples of tissue were collected and flash frozen for subsequent DNA and protein isolation. Additional samples were collected and fixed in 4% paraformaldehyde (for lung and neural tissues) or 10% neutral buffered formalin (for peripheral tissues) for subsequent paraffin embedding and sectioning for immunofluorescence.

The trachea and lungs were sampled extensively to provide multiple samples for each analysis process. The lungs were harvested and clamped as superior on the trachea as possible. The right lung was clamped twice, approximately 1 mm apart, on the mainstem bronchi. The right lung was removed by cutting between the clamps. Sixteen samples each for DNA and protein isolation were collected from regions of the right lung encompassing the primary/secondary bronchi, tertiary bronchi, and alveoli, as described in FIG. 16. The trachea and left lung were inflated with 4% paraformaldehyde and fixed in a 10× volume of 4% paraformaldehyde. The trachea and left lung were then sectioned to encompass samples of the trachea, primary/secondary bronchi, tertiary bronchi, and alveoli, as described in FIG. 16.

Viral Genome Biodistribution

Viral genome biodistribution was performed by the Mattawan site of Charles River Laboratories using a qualified assay for AAV viral genomes containing the EGFP transgene sequence. Total DNA was extracted from tissue samples using a QIAsymphony (Qiagen) and associated DSP DNA mini kit. qPCR reactions were performed on 96-well plates, with each plate containing a standard curve, a set of QC samples, and study samples. Duplicate QC samples were prepared at high, medium, and low copies/reaction in a background of 1,000 ng NHP matrix DNA per reaction. When possible, the tissue DNA samples were tested at 1,000 ng per reaction. If it was not possible to load the amounts specified above for a specific sample (because the DNA concentration was too low or the sample volume was limiting), a smaller amount of sample DNA was analyzed.

All sample reactions were run in triplicate, and the third reaction was spiked with 200 copies of pAAV-CAG-EGFP-SV40 DNA to evaluate potential qPCR inhibition. If qPCR inhibition was observed as shown by the measured value in the third spiked well at less than 110 copies of the target DNA, the sample DNA were reanalyzed at lower amount.

Protein Expression Biodistribution

Total protein was extracted from tissue samples using a gentleMACS tissue dissociator (Miltenyi Biotec) and associated reagents. EGFP was quantified using a GFP ELISA kit (Abcam), and total protein was quantified using a Pierce BCA protein assay kit (ThermoFisher). For both GFP and total protein, reactions were performed in triplicate, and each kit contained a standard curve.

Immunofluorescence Imaging

Tissue was processed to paraffin blocks using a Sakura VIP 5, using a standard program for canine, NHP, and porcine tissues by Seventh Wave Laboratory. Slides were cut at 10 mm thickness by Seventh Wave Laboratory stored at 4° C. Immunohistochemistry was performed on 6 sections of lung (including alveolar and bronchial regions) and 2 sections of trachea from each study animal (n=3) and an additional control animal. Paraffin slides were dehydrated using standard paraffin antibody staining protocol. Briefly, sections were deparaffinized with xylene and rehydrated with decreasing concentrations of ethanol in water (100%, 90%, 70%, 50% and 30%) followed by PBS wash. Antigen retrieval was performed prior to staining with antibody using a combination of heat-induced epitope retrieval (HEIR) and pressure. Slides were incubated for 10 minutes in boiling sodium citrate buffer, then incubated for 3 minutes under pressure. Slides were cooled to room temperature prior to antibody staining. Following antigen retrieval, slides were stained using a primary chicken polyclonal anti-GFP antibody (Abcam #13970) at 1:1000 dilution, a secondary goat anti-chicken IgY antibody (Abcam #175779) at 1:1000 dilution, and DAPI. Fluorescence imaging was performed using a Zeiss AxioObserver microscope. Anti-GFP signal was acquired in the far-red channel (647 nm) at 1000 ms. DAPI signal was detected in blue channel (355 nm) at 100 ms. All images were processed using the Zeiss ZenPro software using the same parameters and pixel intensity values in the anti-GFP channel.

Histopathology Assessment

Tissue trimming, embedding, sectioning, and H&E staining performed by Seventh Wave Laboratory. Tissue was processed to paraffin blocks using a Sakura VIP 5, using a standard program for canine, NHP, and porcine tissues. Slides were cut at 4 mm thickness and stained for hematoxylin and eosin (H&E) using a Leica XL Autostainer. A histopathology assessment was performed on 16 sections of lung, 4 sections of trachea, and 1 section of carina from each study animal (n=3) and an additional control animal, with the histopathologist blinded to treatment condition. Slides scored for the nature and severity of the findings using standard assessment scale.

Computerized Systems

For serum neutralizing antibody screening, data was generated and analyzed using the Cytation 3 microplate reader (Biotek), Gen5plus software version 3.03.14, and Microsoft Excel version 15.32.

For quantification of viral genomes within tissue samples, data was generated and analyzed using the QuantStudio 7 Flex Real-Time PCR System, QuantStudio Real Time PCR Software v1.4, Microsoft Excel, and GraphPad Prism version 8.1.2.

For quantitation of EGFP expression within tissue samples, data was generated and analyzed using the Cytation 3 microplate reader (Biotek), Gen5plus software version 3.03.14, Microsoft Excel version 15.32, and GraphPad Prism version 8.1.2.

For representative immunofluorescent imaging, images were acquired using a Zeiss Axio Observer z1 microscope and ZenPro software. Images were processed using ZenPro software. Images were transferred into Microsoft PowerPoint version 15.32 for presentation.

All data analysis and compilation were carried out on a Macbook Pro running OSX (10.12.6).

Results and Discussion

Anti-AAV Neutralizing Antibody Screen Identifies NHP for Study Inclusion

A neutralizing antibody assay was used in order to assess levels of neutralizing antibodies against AAV capsid having a capsid protein of SEQ ID NO:12 in non human primate (NHP) serum. Each NHP serum sample was assigned a neutralizing antibody titer. An animal was considered seronegative and passed the study inclusion criteria if #50% transduction was observed at a 1:10 serum dilution.

In total, 20 NHP serum samples were evaluated across four 96-well plates. Assay acceptance criteria was set for 1) the coefficient of variance (CV) of the standard curve, 2) CV of the unknown serum samples, and 3) percent deviation from actual input protein for the standard curve. Acceptable CVs for the standard curve were defined as <25%, but actual CVs did not exceed 5%. Acceptable CVs for the unknown serum samples within the limit of quantification were defined as <30%, but actual CVs did not exceed 19%. Acceptable percent deviation from input protein for the standard curve was defined as <25%, but actual percent deviation did not exceed 19%. All plates met all assay acceptance criteria, and the data from these plates were used for evaluation. Overall, 11 (55%) NHP serum samples evaluated were seronegative for capsid having a capsid protein of SEQ ID NO:12 (FIG. 17). The NHPs with the top three highest percent transductions at the 1:10 serum dilution were selected for study inclusion. All selected NHPs demonstrated transduction above the transduction observed in the absence of NHP serum. This observation has been noted in previous studies and is likely a result of favorable interactions with an unknown serum protein. The selected NHP IDs and the percent transduction at the 1:10 serum dilution are reported in Table 4.

TABLE 4

NHPs Included in Study

| NHP ID # | % Transduction at 1:10 |
|---|---|
| V003272 | BLQ |
| V003281 | 88 |
| V003270 | BLQ |
| V003516 | 113 |
| V003062 | 147 |
| V003125 | 140 |
| V003511 | BLQ |
| V003421 | 110 |
| V003433 | BLQ |
| V002964 | BLQ |
| V002996 | BLQ |
| V003002 | 107 |
| V002969 | 160 |
| V003015 | 36 |
| V003119 | 60 |
| V002851 | BLQ |
| V003101 | 137 |
| V003083 | BLQ |
| V003424 | 160 |
| V003251 | 124 |

Nebulized Delivery of Variant Capsid Comprising a Capsid Protein of SEQ ID NO:12 is Well-Tolerated in NHP The study design is summarized in Table 5. All animals recovered normally following test article administration and survived to the scheduled necropsy dates. No significant clinical findings were reported in any animal at any point during the in-life portion of the study. Minor changes outside the references ranges for hematology and clinical chemistry findings were noted in some animals at some timepoints, but these variations were interpreted as normal physiological variations. No major findings were reported during gross examination at necropsy.

TABLE 5

Study Design Summary

| # | Route & Dose | Dose | In-Life | Tissue Collection | Analysis |
|---|---|---|---|---|---|
| 3 | Aerosolized (AeroEclipse II) | $2.80 \times 10^{12}$ vg/kg | 8 weeks | Lung<br>Heart<br>Liver<br>Skeletal Muscle (triceps, quadriceps, diaphragm)<br>Kidney<br>Spleen<br>CNS (brain, spinal cord) | qPCR<br>ELISA (lung & qPCR+ tissues)<br>IHC (lung & ELISA+ tissues) |

Variant Capsid Comprising a Capsid Protein of SEQ ID NO:12 Mediates Robust Gene Delivery to All Regions of Lung Viral genomes were quantified by qPCR for all samples obtained during necropsy to determine the genomic biodistribution of rAAV comprising a variant capsid (comprising a capsid protein of SEQ ID NO:12) and a nucleic acid comprising an EGFP transgene operably linked to a CAG promoter.

A high quantity of viral genomes, ranging from approximately $10^4$-$10^5$ vg/μg was observed in all 48 lung samples (n=16 samples per NHP; n=3 NHP), which represented samples from the alveolar sacs, tertiary bronchi, and primary/secondary bronchi (FIG. 18). For all three animals, no significant differences in the quantity of viral genomes within different lung lobes or different lung regions were noted. A small number of heart and liver samples, 3 (out of 15) heart samples from NHP V003424 and 10 (out of 10) liver samples from NHP V002969, had detectable viral genomes present. However, the quantity of viral genomes present per μg of DNA was 1,000- to 10,000-fold less than the quantity of viral genomes present in the lungs. All samples tested from skeletal muscle (triceps brachii, vastus lateralis), diaphragm, kidney, spleen, brain and spinal cord were below the lower limit of quantification (BLQ). Therefore, nebulized delivery of the rAAV results in robust delivery of viral genomes to all regions of the lung, with minimal systemic exposure.

Variant Capsid (Comprising a Capsid Protein of SEQ ID NO:12) Mediates Protein Expression to all Regions of Lung and Transduces Multiple Cell Types EGFP protein expression was quantified for all samples for which qPCR demonstrated presence of viral genomes above the lower limit of quantitation of the assay. This sample set included all lung samples from all three NHPs, 3 (out of 15) heart samples from NHP V003424, and 10 (out of 10) liver samples from NHP V002969. EGFP expression was observed in all 48 lung samples (n=16 samples per NHP; n=3 NHP), which represented samples from the alveolar sacs, tertiary bronchi, and primary/secondary bronchi (FIG. 19). Expression was highest for animal V002969 across all regions and all lung lobes. For all three animals, no significant differences in the amount of EGFP protein expression within different lung lobes were noted. In general, samples from alveolar regions contained average or above average quantities of EGFP, but this trend was not significant. The qPCR+ liver samples from NHP V002969 did result in detectable EGFP protein expression, but expression levels were multiple orders of magnitude lower than expression levels in the lungs.

These results are consistent with genome biodistribution data demonstrating that genome localization to the liver was multiple orders of magnitude lower than genome localization to the lungs (FIG. 18). The qPCR+ heart samples from NHP V003424 did not contain any detectable EGFP protein expression. These results demonstrate that nebulized delivery of rAAV comprising a capsid with a capsid protein of SEQ ID NO:12 and a nucleic acid encoding a transgene, mediates protein expression to all regions of the lung.

Immunofluorescent imaging was performed to further define the extent of transduction within different regions of the lung. Slides representing 6 sections of lung (including alveolar and bronchial regions) and 2 sections of trachea from each study animal (n=3) and an additional control animal were scanned, and representative images were acquired for each region. In general, EGFP expression was highest for animal V002969 across all regions and all lung lobes, which corresponds to the observed relative expression across animals as determined by ELISA. Within the trachea and bronchi, EGFP expression was observed primarily in cells of the ciliated epithelial layer (FIG. 20). Within the alveoli, broad EGFP expression was observed (FIG. 20), but ATI and ATII cells cannot be determined without the use of specific cell markers. These results demonstrate that nebulized delivery of rAAV comprising a capsid comprising a capsid protein of SEQ ID NO:12 and a nucleic acid encoding a transgene mediates protein expression to all regions of the lung.

Administration of rAAV Comprising a Capsid Comprising a Capsid Protein of SEQ ID NO:12 is Safe and does not Result in Inflammation in Lung Tissue Cageside observations were performed twice daily throughout the in-life portion of the study, beginning one week prior to dosing. No significant clinical signs were observed in any of the animals throughout the study in-life portion of the study. Hematology and clinical chemistry analyses of blood samples were performed biweekly throughout the in-life portion of the study and one week prior to dosing. Although some individual hematology and/or clinical chemistry values fell outside of the reference range, these values were largely interpreted as physiological variations.

Following necropsy, a histopathology assessment was performed on lung tissue and compared to a control (non-administered) animal. Focal hemorrhage, black pigment and minimal mononuclear cell infiltrates in the alveolar spaces were observed in all animals and are common incidental findings in monkeys. In addition, the submucosal lymphoid infiltrates in the trachea and inflammation on the mucosal surface of the carina are also likely incidental findings and unrelated to test article administration. None of the observations were considered adverse. No findings in the treated animals were different or of greater severity than those observed in the control animal.

Conclusions rAAV comprising a capsid with a variant capsid protein of SEQ ID NO:12 and a nucleic acid encoding a reporter transgene (EGFP), was characterized by aerosol delivery of a reporter gene to cynomolgus macaques. Sera was prescreened to identify animals that were seronegative for pre-existing neutralizing antibodies to the test article capsids. Animals (n=3) received the maximum feasible dose of rAAV, delivered using the AeroEclipseII device, a clinically relevant actuated nebulizer.

A high quantity of viral genomes (by qPCR) and resulting EGFP expression (by ELISA and immunostaining) was observed in all lung samples across all 3 NHPs in the study, which represented samples from the alveolar sacs, tertiary bronchi, and primary/secondary bronchi. A small number of heart and liver samples had low but detectable viral genomes present, and all samples from all other tissues showed no detectable viral genomes. These data demonstrate that nebulized delivery of the rAAV results in robust delivery of viral genomes to all regions of the lung, with minimal systemic biodistribution, and the rAAV mediates protein expression to all regions of the lung, including the alveoli. rAAV delivery and EGFP expression was consistent among animals, with even distribution across multiple bronchial levels and alveoli and even distribution across cranial, middle and caudal sections. The protein expression data are consistent with the genome biodistribution data demonstrating that genome localization to the liver was multiple orders of magnitude lower than genome localization to the lungs.

Additional experiments are performed to determine the efficiency and specificity for AECII cells in the primate lung. If further specificity is desirable beyond what is inherent to the rAAV comprising a capsid comprising a capsid protein of SEQ ID NO:12, the use of a cell-specific promoter is used to drive expression of the transgene of interest. The experiments described herein indicate that rAAV comprising a capsid protein of SEQ ID NO:12 can be used to safely and effectively deliver CFTR transgene to the lungs of subjects with cystic fibrosis and to deliver therapeutic genes to treat other pulmonary disorders.

Example 4

Summary

A cell culture model of lung alveolar epithelial type 2 (AECII) cells from freshly isolated non-human primate lungs and human donor lungs rejected for transplant was established. This model was used in the characterization of rAAV comprising capsid comprising a variant capsid protein of SEQ ID NO:12 identified to target AECII cells. The rAAV, and natural serotype AAV5 were evaluated for transduction efficiency in AECII cell air liquid interface (ALI) culture. rAAV comprising a capsid comprising a variant capsid protein of SEQ ID NO:12, following apical transduction with a multiplicity of infection (MOI) of 35,000, showed enhanced transduction of AECII cells compared to AAV5. The rAAV also demonstrated strong resistance to human anti-AAV antibodies.

To confirm that the rAAV capsid targets AECII cells and that infectivity translates to human AECII, AECII cells were isolated from NHP lungs and human donor lungs, rejected from transplant, and cultured in air liquid interface to mimic the lung environment. rAAV transduction efficiency was determined through reporter enhanced green fluorescent protein (eGFP) expression driven by the CAG promoter at multiple time points following infection and compared to AAV5.CAG-eGFP. This data demonstrates that rAAV variants comprising a capsid comprising a variant capsid protein of SEQ ID NO:12 are more infectious than naturally occurring serotypes (i.e. are superior transducers than AAV5 capsid), potentially providing improved treatments for genetic diseases.

One general challenge in pre-clinical and clinical gene therapy studies with AAV is that pre-existing neutralizing antibodies can inhibit successful transduction. To understand the ability of rAAV comprising a capsid comprising a variant capsid protein of SEQ ID NO:12 to evade neutralizing antibodies within the human population in comparison to wild-type AAVs, the rAAV and wild-type AAV1, AAV2, AAV5, AAV8, and AAV9 were analyzed against human IVIG in an in vitro luciferase assay. The data provided here reports that rAAV comprising a capsid comprising a variant capsid protein of SEQ ID NO:12 has neutralizing antibody resistance when exposed to human IVIG (4-fold over AAV5 and 32-fold over AAV2), a critical component for treatment via aerosol delivery and a selective pressure applied during the Therapeutic Vector Evolution process.

Materials and Methods

Lung Alveolar Epithelial Type 2 Cell Isolation

Non-human primate (NHP, Cynomolgus macaque, CRO) or human donor lungs rejected for transplant (Donor Network West, Donor ID: AGES430) were used to isolate alveolar epithelial type 2 cells (AECII) according to Fang et al[1,2]. For NHP cell isolation, the entire lung was utilized; for human donor lungs, the right middle lobe was dissected out and used for cell isolation. The bronchi were flushed with PBS without Calcium or Magnesium (ThermoFisher) containing EDTA (Sigma) and EGTA (Sigma) followed by inflation with elastase (Worthington Chemicals). The tissue was incubated for 1 hour at 37° C. The lung was homogenized, and the trachea and bronchi removed. The cell homogenate was passed through layers of gauze to eliminate large remaining pieces. The cells were sequentially passed through 100 μm and 20 μm strainers. The cells were loaded onto a two-step Percoll (ThermoFisher) density gradient, (70% and 30%), and centrifuged at 1800 rpm for 20 minutes. The intermediate layer was removed, centrifuged, and washed twice with PBS without Calcium or Magnesium. The monocytes and macrophages were removed using CD14 and CD45 Dynabeads (ThermoFisher). The remaining cells were incubated overnight at 37° C. on IgG coated plates to remove T cells. The following day, the non-adherent cells were collected from the plates, centrifuged and subjected to hypotonic solution to lyse red blood cells (ACK Lysis Buffer 1:10, ThermoFisher). Resulting cells were plated on human collagen IV coated inserts (Sigma, human placental collagen IV, 18-24 hours at 25° C.) at a density of $1.5 \times 10^6$ cells/cm$^2$ and incubated at 37° C., 5% $CO_2$. Cells were cultured in Airway Epithelial Cell Basal Medium (ATCC) with commercial supplements, Fetal Bovine Serum (10%, HyClone, ThermoFisher) and insulin, transferrin, and selenium (1:200, ThermoFisher). One day after seeding, the inserts were washed twice with PBS to remove non-adherent cells. The top of the insert was maintained dry to ensure the formation of an air liquid interface (ALI).

LysoTracker Staining

Cells achieving ALI were examined for LysoTracker staining in culture. LysoTracker (ThermoFisher) is an indicator dye that gets absorbed by highly acidic components of live cells, such as lysosomes and the lamellar bodies of AECII cells. It is routinely used to mark AECII cells.

LysoTracker on Adherent Cells and Microscopy

Cells on inserts identified for staining were washed twice with PBS. LysoTracker concentrate was diluted in media (1:1000). One hundred microliters of diluted LysoTracker was added to the insert for live cell staining. Cells were incubated for 5 minutes at 37° C. Following incubation, the insert was washed three times with PBS and imaged on a Zeiss Axio Observer D.1 fluorescent microscope. A non-stained well was used as a control and to set exposure.

LysoTracker on Cell Suspension and Flow Cytometry

Cells are incubated with Trypsin-EDTA 0.05% (ThermoFisher) for 10 minutes at 37° C. Trypsin was deactivated with Defined Trypsin Inhibitor (ThermoFisher), and cells were collected from the inserts and centrifuged at 300×g for 4 minutes. LysoTracker concentrate was diluted in media (1:1000). One hundred microliters of diluted LysoTracker was added to each cell pellet and vortexed at half speed to mix. A non-stained cell sample was used as a control and to set flow cytometry gates. Cells were incubated for 5 minutes at 37° C. Following incubation, cells were centrifugated and washed twice with PBS. Cells were resuspended in PBS and run on a BD Accuri C6 Plus Flow Cytometer. The LysoTracker positive population was identified as a right shifting population from the unstained control.

EdU Incorporation

Cell proliferation was determined using a Click-iT EdU Alexa Fluor Kit (ThermoFisher) according to manufacturer's instructions. Briefly, cells were pulsed for 2 hours with EdU, washed twice with PBS and fixed with 4% paraformaldehyde (15 minutes at 4° C.). The Click-iT reaction cocktail including an Alexa Fluor azide was prepared and incubated with the cells for 30 minutes at 25° C. Following the reaction, the cells were washed twice with PBS and counterstained with DAPI for 10 minutes at 25° C. Cells were imaged on a Zeiss Axio Observer D.1 fluorescent microscope.

Vector Transduction

NHP AECII cells were transduced two days after seeding. Human AECII cells were transduced one day after seeding. On the day of transduction, three inserts were incubated with Trypsin-EDTA 0.05% (ThermoFisher) for 10 minutes at 37° C. Trypsin was deactivated with Defined Trypsin Inhibitor (ThermoFisher). Cells were collected from the insert and counted on a hemocytometer. An average cell number was determined per insert and used to calculate total viral genomes required per insert. A multiplicity of infection (MOI) of 35,000 was used for all experiments in a total volume of 100 μl per insert. Cells were exposed apically for 48 hours with rAAV comprising capsid with capsid protein of SEQ ID NO:12 and a GFP gene operably linked to a CAG promoter or native AAV of serotype 5 comprising a GFP gene operably linked to a CAG promoter. Two days post-infection, virus was removed from the insert to regain air liquid interface. Three days post-infection, NHP cells were harvested for analysis, a total of five days in culture. Six- and ten-days post-infection, human cells were harvested for analysis, a total of seven and eleven days in culture.

Immunocytochemistry (ICC)

Cells were washed twice with PBS and fixed with 4% paraformaldehyde (15 minutes at 4° C.). Cells were blocked with 5% goat serum and 2% bovine serum albumin (BSA) in 0.2% Triton X-100 in PBS for 30 minutes. Cells were incubated with Surfactant Protein C antibody or IgG control (MilliporeSigma, 1:100) for 2 hours at 25° C. Primary antibody was washed three times with 0.2% Triton in PBS, followed by secondary antibody incubation (Goat anti-Rabbit Alexa Fluor 555, 1:500) for 30 minutes at 25° C. Cells were counterstained with DAPI for 10 minutes at 25° C. and washed three times with PBS. Cells were imaged on a Zeiss Axio Observer D.1 fluorescent microscope using IgG control to set exposure.

Flow Cytometry

Post-transduction cells were lifted with Trypsin-EDTA 0.05% (ThermoFisher) for 10 minutes at 37° C. Trypsin was deactivated with Defined Trypsin Inhibitor (ThermoFisher), and cells were collected from the inserts and centrifuged at 300×g for 4 minutes. Cells were resuspended in PBS and run on a BD Accuri C6 Plus Flow Cytometer. The transduced (eGFP positive) cells were identified as a right shifting population from the non-transduced control.

Neutralizing Antibody Resistance Assay

HEK 2V6.11 (obtained from John Hopkins University) cells were plated onto 96-well plates at a density of $3 \times 10^4$ cells per well. Twenty-four hours after seeding, rAAV comprising (i) capsid comprising capsid protein of SEQ ID NO:12 ("A101") and (ii) a luciferase transgene operably linked to a CAG promoter and wild-type AAVs (serotypes AAV1, AAV2, AAV5, AAV8, and AAV9, all carrying a luciferase reporter transgene) were incubated at 37° C. for 1 hour with five dilutions 1:50, 1:100, 1:200, 1:400, 1:800, 1:1600 of human intravenous immunoglobins (IVIG) prior to infection. Cells were then infected with the rAAV and the wild-type AAV at a MOI of 1,000. Each plate contained positive and negative controls for transduction. The positive control was either the rAAV or wild-type AAV in the absence of IVIG. The negative control for transduction was media without serum or AAV.CAG-Luciferase. Luciferase activity was measured 48 hours post infection using a Cytation 3 (Biotek) plate reader.

Computerized Systems

FloJo, LLC Software was used to analyze flow cytometry data.

Microsoft Excel was used to calculate averages and standard deviations from FloJo outputs and make histograms.

For serum neutralizing antibody screening, data was generated and analyzed using the Cytation 3 microplate reader (Biotek), Gen5plus software version 3.03.14, and Microsoft Excel.

Results and Discussion

Non-Human Primate AECII ALI Culture Characterization

Lung alveolar epithelial type 2 cells (AECII) were isolated from a non-human primate (NHP) lung and cultured in air liquid interface (ALI). Cells were cultured on collagen coated inserts and analyzed for AECII specific markers, LysoTracker dye and Surfactant Protein-C(SPC). Cells at day 1 and day 5 contained over 90% LysoTracker positive cells, shown by ICC and quantified by flow cytometry (FIGS. 21A and 21B). AECII cultured cells were also examined for SPC, a mature AECII marker at day 1 and day 5 in culture. Cells expressed SPC by ICC at the time-points analyzed (FIG. 21C). To further characterize the AECII culture system, cell mitosis was examined over time. Mitosis was monitored through EdU incorporation followed by a Click-iT reaction with an azide linked fluorescent dye.

Mitosis was examined day 2 through day 5 and reported by fluorescent microscopy and nuclei staining (FIG. 21D). Mitosis was highest two days after seeding; as cells were maintained in culture the number of cells undergoing mitosis decreased, as evidenced by a lack of EdU incorporation in the nuclei.

Characterization of rAAV Comprising Capsid with Variant Capsid Protein of SEQ ID NO:12 in a Non-Human Primate AECII ALI Culture System Two days after seeding NHP isolated AECII cells, they were transduced with rAAV comprising capsid with variant capsid protein of SEQ ID NO:12 and GFP transgene under the control of CAG promoter or AAV comprising a wild type AAV5 capsid and GFP transgene under the control of CAG promoter at an MOI of 35,000. Three days post infection, five days total in culture, cells were analyzed for eGFP expression by ICC and Flow Cytometry. rAAV comprising capsid comprising capsid protein of SEQ ID NO:12 yielded a significantly higher percentage of eGFP positive cells (~30%) compared to AAV5 (~8%) indicating a better transduction efficiency (FIGS. 22A and 22B).

Human AECII ALI Culture Characterization

The right middle lobe of a human lung, obtained from Donor Network West, (Donor ID: AGES430) was dissected from the remaining lung set and the AECII cells were isolated. Cells were grown on collagen coated inserts and ALI was achieved. To determine purity, two AECII markers were examined, LysoTracker and SPC protein expression. LysoTracker was monitored over time, from the fresh isolate (Day 0) to 11 days in culture. LysoTracker positive cells were around 80% until Day 7. The LysoTracker positive cell population declined to around 50% at Day 11, as AECII transdifferentiate into AECI (FIGS. 23A and 23B). Cells also showed strong SPC expression at the time-points analyzed (FIG. 23C).

Mitosis was monitored over time as in the NHP AECII system. A similar result was observed, where the largest number of cells undergoing mitosis occurred within the first three days in culture and decreased over time (FIG. 23D).

Characterization of 4D-A101 in a Human AECII ALI Culture System

One day after seeding, human AECII cells were infected with rAAV comprising a capsid comprising capsid protein of SEQ ID NO:12 or AAV5 containing an eGFP transgene at a MOI of 35,000. Six- and ten-days post infection, cells were imaged for eGFP expression a surrogate for transduction efficiency. The rAAV comprising capsid comprising capsid protein of SEQ ID NO:12 at both day 6 and day 10 post infection showed a higher level of eGFP positive cells compared to AAV5 (FIG. 24). Cells maintained LysoTracker staining indicating an AECII cell phenotype.

Neutralizing Antibody Resistance Assay

The Relative Light Units (RLUs) of each AAV luciferase vector at each IVIG dilution was normalized to the positive transduction control, AAV luciferase vector alone. Following normalization each vector at each IVIG dilution was converted and expressed as a percent transduction. High percent transduction correlates with low neutralization and low percent transduction correlates with high neutralization. Each AAV luciferase vector was then assigned a neutralizing antibody titer defined as the lowest dilution at which it reaches greater than 50% transduction. Overall, 4D-A101 demonstrated an improvement in resisting neutralizing antibodies versus each wild-type AAV tested (FIG. 25, illustrating percent transduction of HEK2v6.11 cells in the presence of human IVIG). 4D-A101 demonstrated a greater than 32-fold increase in antibody evasion compared to wild-type AAV1, AAV2, AAV8, and AAV9 and was 4-fold better at antibody evasion compared to wild-type AAV5 (Table 6).

TABLE 6

Neutralizing Antibody Titers of Wild-Type AAV1, AAV2, AAV5, AAV8, AAV9 and 4D-A101. The IVIG dilution required to reduce luciferase activity to 50% of that in the absence of IVIG is shown.

| AAV | Neutralizing IVIG Dilution | Fold Increase Relative to AAV2 |
| --- | --- | --- |
| AAV1 | >1:1600 | 1 |
| AAV2 | >1:1600 | — |
| AAV5 | 1:200 | 8 |
| AAV8 | >1:1600 | 1 |
| AAV9 | >1:1600 | 1 |
| A101 | 1:50 | 32 |

Conclusions

AECII cells were isolated and cultured in ALI and maintained a high purity determined by Lysotracker staining and SPC expression. rAAV comprising a capsid comprising a capsid protein of SEQ ID NO:12 showed superior transduction efficiency compared to AAV5 in both NHP and human AECII ALI culture systems.

The ability of rAAV comprising a capsid comprising a capsid protein of SEQ ID NO:12 to evade neutralizing antibodies in human pooled IVIG, enhances its therapeutic promise for patients, was demonstrated. Based on these results, it is likely that a much smaller portion of the target patient population will be excluded from treatment based on the presence of pre-existing neutralizing antibodies.

Example 5

Formulation screening studies were undertaken to select and characterize optimal formulation buffers for solubility, delivery, and storage of recombinant AAV particles comprising a capsid comprising a VP1 capsid protein of SEQ ID NO:12, a VP2 capsid protein comprising amino acids 138-736 of SEQ ID NO:12 and a VP3 capsid comprising amino acids 203-736 of SEQ ID NO:12 and a nucleic acid encoding a transgene (e.g. a reporter gene such as luciferase or green fluorescent protein or a therapeutic transgene such as CFTR).

All studies were performed with capsids (comprising VP1 of SEQ ID NO:12), purified by affinity (AVB) and anion-exchange (CIMQA) chromatography. Initial studies were conducted with purified material previously formulated in DPBS (Dulbecco's Phosphate Buffered Saline) with 0.005% Pluronic. These lots were either diluted or buffer-exchanged into relevant buffer systems. Later studies were conducted with lots which were buffer exchanged directly into appropriate buffer systems immediately following CIMQA purification.

Freeze-Thaw Stability

Small sample aliquots (≤100 uL), containing ~2-3×10$^{13}$ viral genomes per mL, were transferred to 1.5 mL polypropylene tubes and subjected to either 5 or 10 cycles of rapid freezing (i.e., quench cooling at −80 C) followed by thawing at room temperature until no ice crystals were visible. In a separate study, a volume ≥5-mL, containing approximately ~6×10$^{11}$ viral genomes/mL, was transferred to a 15-mL polypropylene Falcon tube and placed at −80 C for approximately 1 hour (until frozen) and then thawed for approximately 1 hour at room temperature until no ice crystals were observed upon gentle mixing. This process was repeated 2 additional times (3× FT). The sample was stored overnight at room temperature after the third freeze-thaw cycle.

5° C., Room Temperature, 37° C. and 40° C./75% RH Accelerated Stability

Various samples ranging in concentration from approximately 1×10$^{12}$-6×10$^{13}$ viral genomes per mL were aliquoted (≤100 uL) to 1.5 mL polypropylene tubes or 2.0 mL polypropylene cryo vials and stored at 5° C., Room Temperature, 37° C. and 40° C./75% RH for the predetermined time in each study protocol. Sample tubes were stored in vented storage boxes and parafilm was routinely used to minimize the effect of evaporate loss during sample storage.

Agitation Stability

Small sample aliquots (≤100 uL), containing ~2-3×10$^{13}$ viral genomes per mL, were transferred to 1.5 mL polypropylene tubes and placed inside a sample box that was secured to a vortex mixer set to 1500 rpm. Samples were agitated at room temperature 2-4 days.

Charge-State Modeling

A charge state excel based calculator (online download; Gale Rhodes, University of Southern Maine) was modified to automatically extract and quantify ionizable and labile residues. Capsid protein monomer (e.g., VP1 and VP3) net charge was determined by adding partial negative and partial positive charges for each ionizable species at each pH interval (≤1 pH unit):

Negative Charge Contribution=# of residues*−1*(10^(−(pKa−pH))/((10^(−(pKa−pH))+1)

Positive Charge Contribution=# of residues*(10^(pKa−pH)/((10^(pKa−pH))+1)

| Ionizable Group | pKa | Charge |
| --- | --- | --- |
| N-term | 8 | Positive; no charge if acetylated |
| C-term | 3.1 | Negative |
| Asp | 4.4 | Negative |
| Arg | 12 | Positive |
| Cys | 8.5 | Negative; no charge if Cys-Cys bond |
| Glu | 4.4 | Negative |
| His | 6.5 | Positive |
| Tyr | 10 | Negative |
| Lys | 9.8 | Positive |

The reported iso-electric point (pI) is the pH where net charge was mathematically determined to be closest to 0.

Extinction Coefficient@280 nm (Theoretical)

ProtParam (web.expasy.org/protparam) was used to determine the molar mass of VP1, VP2 and VP3 proteins based on known primary sequences. The molar extinction coefficient@280 nm was calculated according to the following equation: (M−1 cm−1)=(#Trp)(5,500)+(#Tyr)(1,490)+(#cystine)(125). Note: VP1, VP2 and VP3 all contain 5 cysteine residues but according to literature AAV cysteines do not form disulfide bonds (S—S=cystine). The $Abs_{280\,nm}^{0.1\%}$ (or absorbance units equal to a 1 mg/mL solution) was then calculated by dividing the molar extinction coefficient by molar mass.

|  | A101 VP1 | A101 VP3 |
| --- | --- | --- |
| Total # of Residues | 736 | 543 |
| Molar Mass (g/mol) | 81370.5 | 59560.2 |
| # of Cystine (S-S bond) | 0 | 0 |
| # of Tyrosine | 30 | 24 |
| # of Tryptophan | 15 | 12 |
| Molar Extinction Coefficient @ 280 nm (M$^{-1}$ cm$^{-1}$) | 127200 | 101760 |
| $Abs_{280nm}^{0.1\%}$ | 1.56 | 1.71 |

Absorbance at 280 nm (A280) and Turbidity by UV Spectrophotometry

Approximately 30 uL of sample (or buffer) was transferred to a 3 mm quartz cuvette and UV spectra (250-400 nm; 1 nm spacing) was collected on a NanoDrop spectrophotometer. Alternatively, multiple test articles (or buffers) were transferred to a UV Star 96-well microtiter plate and UV spectra (250-400 nm; 1 nm spacing) was collected on a Cytation plate reader. The pathlength of microtiter sample wells was empirically determined by measuring absorbance at 977 and 900 nm and applying the following equation:

$$\frac{(A_{977}-A_{900})_{sample}}{(A_{977}-A_{900})_{1.0\,cm\,water}} = \text{Pathlength of sample}$$

where ($A_{977}-A_{900}$) 1 cm water=0.18

Buffer and sample spectra were normalized to a 1-cm pathlength cell by dividing optical density (O.D.), measured at each wavelength, by the cuvette or sample well pathlength. Normalized spectra were averaged, where duplicates were run. Sample spectra was background corrected by subtracting normalized O.D. values for corresponding buffer blank. The light scattering contribution at 280 nm (LS280) was calculated using a log-log extrapolation derived from the non-absorbing UV region (~300-400 nm) and subtracted from O.D.280−LS280=A280. Light scattering corrected A280 was multiplied by sample dilution factor (where appropriate) and divided by the theoretical VP3 extinction coefficient ($Abs_{280\ nm}^{0.1\%}=1.71$) to yield estimated capsid protein concentration in mg/mL protein. However, this method was prone to overestimation of capsid protein due to the absorbance of DNA. Alternatively, A280 values are presented in this report without further conversion to avoid capsid protein overestimation due to the absorbance of DNA. O.D.350 values were initially used to semi-quantitatively monitor changes in light-scattering, or turbidity, arising from self-association. However, 350/A280 values are also presented in this report to normalize scattering to the amount of capsid in the soluble fraction.

pH

A small or large volume pH probe was used to measure sample or buffer pH, respectively. pH probes were calibrated using pH 4.01, 7.01, 10.01 prepackaged Mettler Toledo pH standards.

Osmolality by Freezing Point Depression 15 uL of reference solution (e.g., 290 mOsm/kg) or sample was transferred to the freezer chamber of an Advanced Instruments Freezing Point Depression Osmometer. The sample was supercooled until frozen and temperature was monitored until a plateau was observed. Plateau temperature was used to calculate osmolality according to the following equation: 1 mOsm of solute/kg of water=1.858 millidegrees (m° C.) ↓ in freezing point.

Hydrodynamic Size and Polydispersity by Dynamic Light Scattering

Approximately 30 uL of sample was loaded into a clean 3 mm cuvette (ZN2112) and multiple scans (n=2 or 3) were collected on a Malvern Zetasizer Ultra (dispersant=water, sample type=protein). Scans were averaged to generate plots for intensity (%) and volume (%). The former was leveraged during early formulation screening as low level, HMW species are more easily observed by intensity (LS~diameter$^6$~Mw$^2$). Scans were also averaged to generate values for polydispersity by Cumulants Fits, mean size by intensity (10-100 d·nm), mean size by volume (10-100 d·nm), % area by intensity (10-100 d·nm) and % area by volume (10-100 d·nm), where appropriate.

Subvisible Particle Sizing by Horizon Backgrounded Membrane Imaging (BMI)

Backgrounded membrane imaging (BMI) was performed on the Horizon Particle Analysis System. A blank 96-well sample plate was loaded on the Horizon system and a background image was acquired. The plate was then transferred to a vacuum manifold. Approximately 20-30 uL of sample was loaded per well. Blotting paper and a blotting paper adaptor were attached to the vacuum manifold and the sample plate repositioned at the top of the stack. Vacuum was turned on to remove any remaining liquid on the bottom of the wells. The sample plate was subsequently transferred to the Horizon instrument. Particle counts and images were collected (2-10 um, 10-25 um, >25 um and total).

Titer by Droplet Digital Polymerase Chain Reaction (ddPCR)

5-10 uL frozen aliquots were submitted for determination of AAV genome concentration by ddPCR according to SOP-AD-018. Samples of rAAV comprising a capsid protein of SEQ ID NO:12 were diluted into Dulbecco's phosphate-buffered saline with calcium and magnesium containing 0.02% Pluronic™ F-68 non-ionic surfactant (DPBS+0.02% F68), mixed with DNase I enzyme, to digest any non-encapsidated DNA, and further diluted with DPBS+0.02% F68 to bring the test article into the dynamic range of the assay. The DNAse treated sample was subsequently mixed with ddPCR Supermix and SV40 (or CFTR) primers/FAM-labeled probes. 20 μL of reaction mixture was then partitioned into droplets using a Bio-Rad QX200 Auto DG Droplet Generator, subjected to PCR, then read on the Bio-Rad QX200 Droplet Reader, which measures each droplet individually for fluorescent signal. Data was analyzed using the Bio-Rad QuantaSoft software, which uses Poisson statistical analysis of positive and negative droplets to provide absolute quantitation of target sequence(s). No-template controls were used to set the negative baseline for samples. ddPCR without DNase I enzyme treatment was also performed on select samples.

Chemical Purity by Polyacrylamide Gel Electrophoresis (PAGE)

5-10 uL frozen aliquots were submitted for chemical purity analysis according to SOP-AD-028 Rev. 00 (Determination of Capsid Purity by Krypton™ Stained SDS-PAGE) or SOP-AD-002 (Determination of Capsid Purity by Silver Stained LDS-PAGE). In short, approximately $1.00\times10^{10}$ (SOP-AD-028) or $1.00\times10^9$ (SOP-AD-002) viral genomes were mixed with 4×LDS sample buffer, 10× sample reducing agent, water and heated at 95 C for 10 minutes. A NuPAGE™ 4-12% Bis-Tris gel was secured in a gel box containing an upper chamber (1×SDS buffer+antioxidant) and a lower chamber (1×SDS buffer). Heat denatured (and reduced) reaction mixtures were loaded on the gel. The gel box cover was attached, and electrodes connected to an external power supply. Power was then applied according to manufacturer specification. The current flow was stopped when the sample dye front was ≥¾ of the length of the full gel. Gels were washed and stained according to manufacture instructions. Gel imaging was performed on a ChemiDoc MP Imager.

Functional Activity by Green Fluorescent Protein (GFP) Expression 15 uL frozen aliquots were submitted for analysis of green fluorescent protein (GFP) expression. HEK2v6.11 cells were transduced at 10,000 MOI and harvest 72 hours post-transduction. GFP expression was imaged by fluorescence microscopy and quantified by flow cytometry.

Significant loss (~50%) of rAAV having a capsid with VP1 of SEQ ID NO:12 was observed during concentration to $\geq 1\times10^{13}$ viral genomes/milliliter (vg/mL) and buffer exchange of the purified AAVs into a Dulbecco's phosphate-buffered saline-based formulation buffer (Dulbecco's phosphate-buffered saline with calcium and magnesium containing 0.05% Pluronic™ F-68 non-ionic surfactant (DPBS+0.05% F68)). The experiments described herein determined the root cause for loss and a superior formulation buffer is described.

The pI for VP1 of SEQ ID NO:12, VP2 and VP3 were estimated to be 6.7, 7.4 and 6.8, respectively. VP1 has a higher number of charged residues compared to VP2 and VP3 which and likely accounts for the theoretical differences in net charge that are observed below pH 5 and above pH 9 (FIG. 26). However, net charge between pH 5 and pH 9 appears to be largely similar for VP1 and VP3 while some subtle differences are predicted for VP2. VP1, VP2 and VP3 monomers contain aspartic acid (D), asparagine (N), methionine (M) and free cysteine (C) residues. Consequently, VP1 and VP3 monomers are assumed to be susceptible to aspartic acid shuffling at low pH, deamidation at neutral/basic pH, oxidation and disulfide shuffling at high pH.

The pH of DBPS is approximately 7.0. This is very close to the pI, or theoretical solubility minima, for the VP1 and VP3 proteins. It was, therefore, suspected that pH might play a role in the physical instability observed during concentration and buffer exchange by tangential-flow filtration.

pH vs. Solubility rAAV starting material, comprising a capsid with VP1 of SEQ ID NO:12 and a nucleic acid encoding GFP (~2×10$^{13}$ vg/mL in DPBS+0.005% Pluronic F68) was thawed and diluted 10-fold, to approximately 2×10$^{12}$ vg/mL, into various buffers (pH 4-8) at both low ionic strength (~14 mM NaCl) and physiological ionic strength (~150 mM NaCl). Low ionic strength formulations showed a pH-dependent increase in high molecular weight (HMW) species as pH was increased from 4 to 8. This pH dependence was significantly reduced in the presence of 150 mM NaCl.

Samples were subsequently stored room temperature and then evaluated by UV spectrophotometry the following day (T=1 day@RT). UV absorbance at 280 nm (A280) is plotted vs. pH in FIG. 27. Low ionic strength samples showed a very abrupt decrease in A280 signal (i.e., inferring reduced rAAV concentration) above pH 5 which was consistent with the physical instability observed by DLS. All samples containing 150 mM NaCl showed similar A280 values. These data indicate that lower pH and addition of salt seem to improve solubility. Formulation details, sample pH and A280 values (Light Scattering and Pathlength Corrected) can be found below:

| Formulation Buffer | Sample pH | A280 |
|---|---|---|
| 20 mM Acetate, pH 4 + 14 mM NaCl + 0.005% F68 | 4.24 | 0.138 |
| 10 mM Acetate, pH 5 + 14 mM NaCl + 0.005% F68 | 5.31 | 0.147 |
| 20 mM Phosphate, pH 6 + 14 mM NaCl + 0.005% F68 | 6.25 | 0.015 |
| 10 mM Phosphate, pH 7 + 14 mM NaCl + 0.005% F68 | 7.16 | 0.046 |
| 10 mM Tris, pH 8 + 14 mM NaCl + 0.005% F68 | 7.95 | 0.063 |
| 20 mM Acetate, pH 4 + 150 mM NaCl + 0.005% F68 | 4.09 | 0.153 |
| 10 mM Acetate, pH 5 + 150 mM NaCl + 0.005% F68 | 5.26 | 0.157 |
| 20 mM Phosphate, pH 6 + 150 mM NaCl + 0.005% F68 | 6.00 | 0.147 |
| 10 mM Phosphate, pH 7 + 150 mM NaCl + 0.005% F68 | 6.90 | 0.150 |

These results seemed to suggest that both ionic strength and pH influence rAAV solution-state behavior. Therefore, a follow-up study was conducted to further assess the solubility limits of rAAV, from pH 5 to 8, in the presence of sodium chloride (~0.15M ionic strength) or trisodium citrate (high ionic strength). rAAV starting material comprising a capsid with VP1 of SEQ ID NO:12 and a nucleic acid encoding luciferase (1.76×10$^{13}$ vg/mL in DPBS+0.005% Pluronic F68) was thawed, buffer-exchanged and concentrated into various buffers (Table 7) to a target of approximately 3×10$^{13}$ vg/mL. Process yields were estimated by dividing viral genomes recovered by viral genomes of starting material. Decreased recovery was observed for DPBS+0.005% F68 and 10 mM Tris, pH 8+150 mM NaCl+0.005% F68 formulations. These lower yields also seemed to correspond with a slower rate of buffer-exchange and concentration.

TABLE 7

A101-Luc pH Solubility Study Summary (After 0.2 μm Filtration)

| Formulation Buffer | Buffer pH | Titer (vg/mL) | Theoretical Recovery (%) | A280 | OD350 | 350/280 |
|---|---|---|---|---|---|---|
| 10 mM NaAcetate pH 5, 150 mM NaCl, 0.005% F68 | 4.94 | 3.38E+13 | 88% | 4.142 | 0.193 | 0.047 |
| 10 mM NaCitrate pH 6, 150 mM NaCl, 0.005%, F68 | 5.93 | 3.33E+13 | 93% | 4.095 | 0.073 | 0.018 |
| DPBS, 0.005% F68 | 7.01 | 2.34E+13 | 72% | 2.775 | 0.053 | 0.019 |
| 10 mM Tris pH 8, 150 mM NaCl, 0.005% F68 | 8.00 | 1.51E+13 | 55% | 1.897 | 0.040 | 0.021 |
| 10 mM Tris pH 8, 100 mM Trisodium Citrate, 0.005% F68 | 8.16 | 3.82E+13 | 99% | 4.629 | 0.073 | 0.016 |

A280 and OD350 have been corrected for background, dilution factor and pathlength. A280 values have also been corrected for light scattering.

Samples containing sodium chloride showed a similar pH-dependent trend, i.e., ↓ solubility with ↑ pH, by Titer and A280. The high ionic strength formulation (10 mM Tris, pH 8+100 mM Sodium Citrate+0.005% F68) showed the highest solubility of formulations tested further demonstrating the influence of ionic strength. There appeared to be a pH-dependent trend for 0.2 μm filtered samples, i.e., O.D.350 at lower pH. However, 350/A280 values were also plotted to represent physical instability relative to the amount of rAAV in the soluble fraction. 350/A280 showed instability at pH5. However, an inflection was observed at pH 6 (10 mM Citrate, pH 6+150 mM NaCl+0.005% F68), one that appears to represent a balance between high solubility and physical stability. The high ionic strength formulation showed comparable turbidity to the pH 6 formulation. As illustrated by FIG. 35 (corresponding to the data in Table 7), lower pH shows improved solubility in the presence of 0.15M NaCl (solubility is higher at pH 5 and 6 compared to pH 7 and 8 when the salt concentration is ~150 mM NaCl) and clearly demonstrates that increased ionic strength is required to "recover" solubility at higher pH. These findings ultimately led to the use of a citrate, pH 6 formulation.

DLS (dynamic light scattering) showed varied levels of HMW species in concentrated samples except for the high ionic strength formulation (10 mM Tris, pH 8+100 mM Trisodium Citrate+0.005% F68). However, HMW species were largely reduced after 0.2 μm filtration except for a persistent sub-micron species observed in the 10 mM Sodium Acetate, pH 5+150 mM NaCl+0.005% F68 formulation. This is consistent with the increased 350/A280 observed for the same sample.

The results of this study suggested that it was possible to formulate rAAV ≥3×10$^{13}$ vg/mL when the pH≤6 or when the ionic strength is increased above 0.15M. However, at low pH (e.g., pH 5) there may be a risk of soluble, HMW species and higher pH formulations may require a concentration of ionic strength modifier (e.g., sodium citrate) that is in excess of the amount found in other approved inhaled products according to the FDA's inactive ingredient database. Therefore, the next study aimed to narrow the formulation pH range (6-8) while also evaluating the impact of sodium citrate from 20-100 mM.

rAAV starting material comprising a capsid with VP1 of SEQ ID NO:12 and a nucleic acid encoding GFP (8.75×10$^{12}$ vg/mL in DPBS+0.005% Pluronic F68) was thawed, buffer-exchanged and concentrated into various buffers (Table 8; all formulations also include 0.005% F68) to a target of approximately $3 \times 10^{13}$ vg/mL. Buffer pH and osmolality (without rAAV) can be found in Table 9. Formulated samples were 0.2 μm filtered and aliquoted into polypropylene tubes. 1 aliquot of each formulation was used for T=0 measurements and then subjected to 4-day room temperature agitation@1500 rpm. Separate aliquots were used to assess the impact of freeze-thaw (5/10×FT cycles), room temperature storage (T=13 day) and 28-day storage (15 days at 2-8 C followed by 13 days at room temperature). rAAV starting material, $8.46 \times 10^{12}$ vg/mL in DPBS+0.005% F68, was evaluated under select conditions.

TABLE 8

| Formulation | [vg/mL]$_{4101}$ | pH | Buffer | [mM]$_{buffer}$ | Target [mM]$_{NaCitrate}$ | [mM]$_{NaCl}$ | [mM]$_{IonicStrength}$ |
|---|---|---|---|---|---|---|---|
| fPD_2019_006-01 | 3.00E+13 | 6 | Citrate | 20 | 0 | 125 | 221 |
| fPD_2019_006-02 | | | | 50 | 0 | 70 | 310 |
| fPD_2019_006-03 | | | | 100 | 0 | 0 | 481 |
| fPD_2019_006-04 | | | Histidine | 10 | 20 | 115 | 217 |
| fPD_2019_006-05 | | | | 10 | 50 | 55 | 307 |
| fPD_2019_006-06 | | | | 10 | 100 | 0 | 502 |
| fPD_2019_006-07 | | 7 | Potassium | 10 | 20 | 110 | 249 |
| fPD_2019_006-08 | | | Phosphate | 10 | 50 | 50 | 365 |
| fPD_2019_006-09 | | | | 10 | 100 | 0 | 608 |
| fPD_2019_006-10 | | 8 | Tris | 10 | 20 | 115 | 237 |
| fPD_2019_006-11 | | | | 10 | 50 | 55 | 357 |
| fPD_2019_006-12 | | | | 10 | 100 | 0 | 601 |

[mM]$_{NaCitrate}$ represents the concentration of trisodium citrate required for ionic strength modification; excludes the amount in base buffer ionic strength values are ballpark estimates derived from the following equation: $I = (\frac{1}{2}) \Sigma ni = 1 \, c_i z_i^2$

TABLE 9

Buffer pH and Osmolality (mOsm/kg)

| | Measured | |
|---|---|---|
| Formulation | Buffer pH | Buffer mOsm/kg |
| fPD_2019_006-01 | 6.046 | 286 |
| fPD_2019_006-02 | 6.084 | 266 |
| fPD_2019_006-03 | 6.061 | 271 |
| fPD_2019_006-04 | 6.045 | 292 |
| fPD_2019_006-05 | 5.997 | 275 |
| fPD_2019_006-06 | 6.039 | 324 |
| fPD_2019_006-07 | 7.005 | 281 |
| fPD_2019_006-08 | 7.016 | 257 |
| fPD_2019_006-09 | 7.038 | 302 |
| fPD_2019_006-10 | 8.026 | 285 |
| fPD_2019_006-11 | 8.043 | 259 |
| fPD_2019_006-12 | 8.042 | 295 |

Titer analysis by ddPCR was used sparingly due to the high number of formulations and conditions to be screened. However, T=0 sample titers ranged from ~2.3 to $2.9 \times 10^{13}$ vg/mL (Table 10). This slight variability was assumed to be related to the small process scale as most conditions appeared to meet or exceed >90% recovery. The exception being fPD_2019_006_003, fPD_2019_006_005 and fPD_2019_006_007 which all showed lower recovery. Sample titer was also measured after 28-day storage (15 days at 2-8 C followed by 13 days at room temperature). All formulations retained ≥100% titer relative to T=0

TABLE 10

T = 0 Titer and % Recovery

| | Titer (vg/ml) | Volume (mL) Recovered After Buffer Exchange/ Concentration | Total VG | Recovery (%) |
|---|---|---|---|---|
| fPD_2019_006-01 | 2.76E+13 | 250 | 6.91E+12 | 99.99% |
| fPD_2019_006-02 | 2.85E+13 | 245 | 6.97E+12 | 100.94% |

TABLE 10-continued

T = 0 Titer and % Recovery

| | Titer (vg/ml) | Volume (mL) Recovered After Buffer Exchange/ Concentration | Total VG | Recovery (%) |
|---|---|---|---|---|
| fPD_2019_006-03 | 2.30E+13 | 252 | 5.79E+12 | 83.77% |
| fPD_2019_006-04 | 2.41E+13 | 262 | 6.33E+12 | 91.55% |
| fPD_2019_006-05 | 2.25E+13 | 269 | 6.06E+12 | 87.65% |
| fPD_2019_006-06 | 2.54E+13 | 265 | 6.74E+12 | 97.60% |
| fPD_2019_006-07 | 2.43E+13 | 246 | 5.97E+12 | 86.42% |
| fPD_2019_006-08 | 2.52E+13 | 263 | 6.61E+12 | 95.74% |
| fPD_2019_006-09 | 2.34E+13 | 280 | 6.56E+12 | 94.91% |
| fPD_2019_006-10 | 2.35E+13 | 272 | 6.38E+12 | 92.42% |
| fPD_2019_006-11 | 2.39E+13 | 280 | 6.69E+12 | 96.77% |
| fPD_2019_006-12 | 2.72E+13 | 248 | 6.74E+12 | 97.49% |
| fPD_2019_006-13 | 8.46E+12 | N/A | N/A | N/A |

Little to no significant change in hydrodynamic size by % volume was observed for any of the formulations at the conditions tested. Therefore, overlays were generated for hydrodynamic size by % intensity which is typically more sensitive to the presence of low-level HMW species. fPD_2019_006-05 and fPD_2019_006-10 showed increased peak width after 4-day agitation at 1500 rpm. This could also be observed in a plot of sample polydispersity. T=0 polydispersity of the starting material (fPD_2019_006-13) was higher than any of the 12 formulations screened further suggesting improvement over the original DPBS formulation.

Table 9 includes A280 values as well % A280 remaining relative to T=0. Most formulations retained ≥95% of their respective A280 signals except for fPD_2019_006-11 and fPD_2019_006-13 (DPBS control) after 4 days agitation@1500 rpm and fPD_2019_006-03 and fPD_2019_006-08 which showed a slight drop after 28-day storage.

A significantly larger number of particles were observed for agitated samples compared to other test conditions implying the length of agitation may have been overly aggressive. However, formulations appeared to vary in their response to the different stressors applied. For example, fPD_2019_006-05 contained an elevated number of particles >10 μm after agitation while fPD_2019_006-09 and fPD_2019_006-10 showed elevated counts after 10× freeze-thaw.

The titer and physical stability results generated in study fPD_2019_006 were evaluated with a semi-quantitative weighting system and it was decided that fPD_2019_006-01 (20 mM Citrate, pH 6+125 mM NaCl+0.005% F68), fPD_2019_006-02 (50 mM Citrate, pH 6+70 mM NaCl+0.005% F68), fPD_2019_006-08 (10 mM Phosphate, pH 5+50 mM NaCl+50 mM Trisodium Citrate+0.005% F68) and fPD_2019_006-12 (10 mM Tris, pH 8+100 mM Trisodium Citrate+0.005% F68) all showed favorable characteristics which should be studied further. Subsequent to that decision remaining aliquots of 28-day samples were analyzed by Krypton stained PAGE. VP1, VP2 and VP3 were observed in all samples tested. Low molecular weight (LMW) bands were also observed in varied abundance; the most prominent being in fPD_2019_006-01. Unfortunately, T=0 was not available for comparison so it was unclear whether these LMW bands were degradation products or process impurities. Therefore, chemical stability was assessed in follow-up studies.

rAAV comprising a capsid with VP1 of SEQ ID NO:12 and a nucleic acid encoding CFTR, CIMQA pool (lot #dPD_2020_001, 7.92×10$^{11}$ vg/mL) was buffer-exchanged and concentrated directly into the 4 buffers identified in fPD_2019_006 to a target of approximately 3×10$^{13}$ vg/mL. rAAV comprising a capsid with VP1 of SEQ ID NO:12 and a nucleic acid encoding GFP (Lot #4DER000057 vg/mL), in DPBS+0.005% F68, was buffer-exchanged and concentrated into 20 mM Citrate, pH 6+125 mM NaCl+0.005% F68 to a target of approximately 6E13 vg/mL. rAAV-CFTR and rAAV-GFP formulations were subsequently aliquoted into polypropylene tubes and subjected to either 10 freeze-thaw cycles, 40-hour agitation@1500 rpm or 40-hour storage@40 C.

TABLE 11

Formulation Screening Study Design

| Formulation | Target [vg/mL]$_{A101}$ | Buffer | Virus |
|---|---|---|---|
| fPD_2020_001-01 | 3.00E+13 | 20 mM Citrate pH 6 + 125 mM NaCl + 0.005% F68 | A101-CFTR |
| fPD_2020_001-02 | | 10 mM Potassium Phosphate, pH 7 + 50 mM Citrate + 50 mM NaCl + 0.005% F68 | A101-CFTR |
| fPD_2020_001-03 | | 10 mM Tris, pH 8 + 100 mM Citrate + 0.005% F68 | A101-CFTR |
| fPD_2020_001-04 | | 50 mM Citrate pH 6 + 70 mM NaCl + 0.005% F68 | A101-CFTR |
| fPD_2020_001-05 | 6.00E+13 | 20 mM Citrate pH 6 + 125 mM NaCl + 0.005% F68 | A101-GFP | rAAV-CFTR, T=0 titers ranged from 1.7-1.9×10$^{13}$ vg/mL. This was ≥30% lower than the 3×10$^{13}$ vg/mL target but was attributed to small working volume instead of a solubility limitation. pH 7 and pH 8 formulations (fPD_2020_001-02 and fPD_2020_001-03) showed approximately 4% loss when subjected to agitation stress while no loss was observed for pH 6 formulations (fPD_2020_001-01 and fPD_2020_001-04). This stability trend was significantly magnified at 40 C as pH 7 and pH 8 formulations showed losses ≥90% while pH 6 losses were <30%. All 4 rAAV-CFTR formulations retained ≥100% titer after 10 freeze-thaw cycles. rAAV-GFP (fPD_2020_001-05, 5.3E13 vg/mL at T=0) proved incredibly stable at pH 6 with no loss during agitation and <3% loss during 40 C storage 10 freeze-thaw cycles. The difference in relative stability between rAAV-CFTR and rAAV-GFP formulated in the same buffer has been speculated to be related to transgene size. However, will require additional studies in the future.

fPD_2020_001-02 (pH 7) and fPD_2020_001-03 (pH 8) showed higher A280 signal loss compared to pH 6 samples during storage at 40 C. This is consistent with the trend observed for titer but at a reduced magnitude. This may be related to an increase in the amount of empty capsids (and free DNA) during storage at 40 C. Empty capsids and DNA would still absorb UV light, but the latter would be susceptible to DNAse treatment. A280 results for the rAAV-GFP formulation (fPD_2020_001-05) are also consistent with titer analysis; minimal to no change.

TABLE 12

| Absorbance at 280 nm (A280) | | | | |
|---|---|---|---|---|
| A280 | T = 0 | Agitation (40 hr @ 1500 rpm) | 40 C. (40 hr) | 10X FT |
| fPD_2020_001-01 | 2.504 | 2.416 | 2.234 | 2.448 |
| fPD_2020_001-02 | 2.466 | 2.417 | 2.037 | 2.137 |
| fPD_2020_001-03 | 2.603 | 2.475 | 2.131 | 2.414 |
| fPD_2020_001-04 | 2.390 | 2.208 | 2.104 | 2.188 |
| fPD_2020_001-05 | 4.427 | 4.557 | 4.468 | 4.410 |

Hydrodynamic size by intensity plots showed increase peak width for all rAAV-CFTR samples at 40 C. A low level, HMW species was detected in fPD_2020_001-01. However, significant differences in titer and UV may suggest this peak is absent in less stable formulations due to precipitation, surface adsorption or changes in empty/full capsid ratio. Size differences were less obvious by volume, but polydispersity also proved to be highly sensitive to subtle differences. Consistent with other test methods rAAV-GFP showed little to no change.

40 C. storage resulted in what appeared to be high 2-10 um particle counts for the A101-GFP formulation (fPD_2020_001-05). It was assumed that this was a concentration dependent phenomenon (i.e., rAAV-GFP titer was approximately 3-fold higher than rAAV-CFTR samples). Interestingly, this sample showed a comparatively low number of particles >10 um perhaps suggesting the formulation prevents the formation of larger aggregates. rAAV-CFTR formulated in the same buffer (fPD_2020_001-01) showed sensitivity to agitation and heat but did appear to resist formation of particles >25 um. The other rAAV-CFTR formulations showed a slight tendency toward particles >25 um.

No significant differences were observed at T=0, 40 hr A 1500 rpm or after 10× FT. However, pH 7 (fPD_2020_001-02) and pH 8 (fPD_2020_001-03) formulations showed increased LMW species and appeared to be overloaded. Conversely, fPD_2020_001-01 showed the presence of some HMW bands after 40 C. storage. It was unclear, however, if this was artifact related to sample prep or the staining procedure (e.g. silver-stain is considered non-quantitative). Fortunately, Western Blot analysis was also performed on the same samples. Western Blot clearly demonstrated that pH 7 and pH 8 40 C. samples were overloaded (loaded based on titer). This further supports the idea that the disproportionate loss in titer compared to A280 is likely attributed to increased empty capsids. No HMW bands were observed for the 40 C. fPD_2020_001-01 sample by Western Blot analysis.

A bulk of formulation screening efforts had been focused on improving the physical stability of the rAAV and to a lesser degree monitoring chemical stability. However, an important piece had still not been addressed; functional activity. Therefore, rAAV-GFP functional activity was evaluated in three of the formulations tested in study fPD_2020_001. rAAV-GFP (1.58 a $10^{13}$ vg/mL), in DPBS+0.005% F68, was buffer-exchanged and concentrated into 20 mM Citrate pH 6+125 mM NaCl+0.005% F68 (fPD_2020_002-01), 10 mM Potassium Phosphate, pH 7+50 mM Citrate+50 mM NaCl+0.005% F68 (fPD_2020_002-02) or 50 mM Citrate pH 6+70 mM NaCl+0.005% F68 (fPD_2020_002-03) to a target of approximately $3 \times 10^{13}$ vg/mL. rAAV-GFP formulations were subsequently aliquoted into polypropylene tubes and stored at room temperature for 13 days. Titer was measured at T=0 (Table 12) and values applied to both T=0 and T=13-day samples (i.e., same load volume for functional testing).

TABLE 13 fPD_2020_002: A101-GFP Functional Activity Study

| Sample | [vg/mL] @ T = 0 | Buffer |
|---|---|---|
| fPD_2020_002-01 | 2.38E+13 | 20 mM Citrate pH 6 + 125 mM NaCl + 0.005% F68 |
| fPD_2020_002-02 | 2.29E+13 | 10 mM Potassium Phosphate, pH 7 + 50 mM |

TABLE 13-continued fPD_2020_002: A101-GFP Functional Activity Study

| Sample | [vg/mL] @ T = 0 | Buffer |
|---|---|---|
| fPD_2020_002-03 | 2.51E+13 | Citrate + 50 mM NaCl + 0.005% F68 50 mM Citrate pH 6 + 70 mM NaCl + 0.005% F68 |

Hydrodynamic size was assessed at T=0. No difference was observed for the three formulations tested. No loss in A280 signal (Table 14) was observed during 13-day room temperature storage.

TABLE 14

Absorbance at 280 nm (A280)

| A280 | T = 0 | 13 dy @ RT |
|---|---|---|
| fPD = 2020_002_01 | 2.27 | 2.43 |
| fPD = 2020_002_02 | 2.16 | 2.32 |
| fPD = 2020_002_03 | 2.24 | 2.38 |

Fluorescence Microscopy and Flow Cytometry results demonstrated that all rAAV-GFP samples showed green fluorescent protein expression while no fluorescence was observed for the vehicle. Little to no difference was observed in % GFP positive cells after 13-day room temperature storage implying all three formulations preserved rAAV functional activity.

Based on the results of studies fPD_2020_001 and fPD_2020_002 the decision was made to move forward with a final assessment of two citrate, pH 6 formulations. Purified rAAV-CFTR (4D130109) formulated in 20 mM Citrate, pH 6+125 mM NaCl+0.005% F68 (fPD_2020_003-01, lot #dPD_2020_007) and 50 mM Citrate, pH 6+85 mM NaCl+0.005% F68 (fPD_2020_003-02, lot #dPD_2020_007) was thawed and aliquoted (~100 uL) into polypropylene tubes. Two aliquots of each formulation (n=2) were used for T=0 measurements. The remaining vials were placed at 40 C./75% RH and pulled after 4 hours (n=2), 20 hours (n=2) or 44 hours (n=2). The 20 mM Citrate, pH 6 formulation (fPD_2020_003-01) used the same buffer that had shown good stability in prior studies. The 50 mM Citrate formulation was similar to the 50 mM Citrate, pH 6 formulation identified in prior studies with a slight change; NaCl concentration was raised from 70 mM to 85 mM to increase the solution tonicity. Osmolality of 20 mM and 50 mM Citrate, pH 6 buffers were 289 and 295 mOsm/kg, respectively.

TABLE 15 fPD_2020_003: Final Formulation Selection Study Samples

| Sample | Target [vg/mL]$_{4101}$ | Buffer | Virus | Buffer Osmo (mOsm/kg) |
|---|---|---|---|---|
| fPD_2020_003-01 | 3.00E+13 | 20 mM Citrate pH 6 + 125 mM NaCl + 0.005% F68 | A101-CFTR | 289 |
| fPD_2020_003-02 | | 50 mM Citrate pH 6 + 85 mM NaCl + 0.005% F68 | A101-CFTR | 295 |

Titer analysis by ddPCR (n=2) was conducted plus and minus DNAase pre-treatment. A measurable difference was observed between the two methods suggesting either the presence free capsid DNA and/or DNAse susceptible capsids (e.g. perturbed or chemically damaged). However, 40 C./75% RH titer loss was comparable for the two formulations.

Increased A280 signal loss was observed for fPD_2020_003-02 (50 mM Citrate, pH 6 formulation) possibly suggesting salting out (or precipitation) of some part of the soluble fraction. Interestingly, turbidity was increased for fPD_2020_003-01 further suggesting the presence of perturbed species which was maintained in solution at lower citrate concentration.

DLS trended with turbidity results. Sample fPD_2020_003-01 showed detectable levels of a HMW species by intensity at 20 and 44 hours at 40 C./75% RH while the species appeared to be absent in fPD_2020_003-02. This peak accounts for the differences observed in Peak Area % and Polydispersity.

Samples were also analyzed for chemical purity by PAGE. Observations are as follows. Cleavage products are detected at T=0 for both formulations. Presumably these are process impurities carried through downstream purification. Low level cleavage products begin to form with prolonged time@40 C./75% RH. The chemical purity of both formulations appears to be comparable.

Based on these results, it was determined that increased citrate might confer a slight improvement in rAAV-CFTR physical stability at 40 C./75% RH. However, it was unclear if this was a true protective effect or if a concurrent loss in A280 suggested that a physically unstable species had been salted out. Furthermore, the 50 mM Citrate showed no reduction in titer loss compared to the 20 mM Citrate formulation and both formulations appeared to have similar increases in LMW species by PAGE. Therefore, it was determined that the 50 mM Citrate formulation did not offer enough improvement to warrant a higher citrate concentration that might be less tolerated in an inhaled drug product.

The 20 mM Citrate, pH 6+125 mM NaCl+0.005% F68 formulation was thus established as the lead formulation for the NHP pilot tox/dose-ranging study. Tentative pilot tox test article requirements can be found in Table 16. A study (fPD_2020_006) was conducted to assess the low-dose (~6×10$^{11}$ vg/mL) freeze-thaw stability.

additional times. After the third freeze-thaw cycle the material was stored at room temperature overnight.

Titer showed very little change through 3 freeze-thaw (3×FT) cycles while slight reduction in titer (~10%) was observed when the 3×FT sample was stored at room temperature overnight. However, this value was still within the variation of the ddPCR assay and, therefore, considered a worst-case scenario.

No significant difference in physical stability was observed for freeze-thaw samples by DLS. Smaller aliquots (~50 uL) of T=0, 2× and 3×FT samples were also measured after an additional hour storage at room temp (2 hour total thaw). No change was observed in these samples.

Example 6

In Vitro and Ex Vivo Characterization of 4D-710 in Human Cells

The ability of an rAAV comprising (i) a capsid of SEQ ID NO:12 and (ii) a heterologous nucleic acid comprising the nucleotide sequence of SEQ ID NO:45 (4D-710) to transduce human cells and deliver a codon-optimized human CFTR transgene of SEQ ID NO:43 (cohCFTRΔR, encoding a functional CFTR gene with amino acids 708-759 deleted) was assessed. The human cells were HEK2v6.11, 16HBE14o-G542X (accessed through the Cystic Fibrosis Foundation) and ex vivo ALI non-CF cultures. Protein expression, protein membrane-localization and mRNA expression of the therapeutic transgene cassette were evaluated.

Materials and Methods—SDS-PAGE and Western Blot. Cells were lysed for western blot analysis in PBS containing 1% v/v NP-40 for 30 minutes at 4° C. prior to removal of insoluble material. For western blotting, equal volumes of lysate, containing 1× loading dye and reducing agent (Thermo Bolt) were heated at 50° C. for 10 minutes, then loaded onto 4-12% bis-tris acrylamide gel (Thermo Bolt) and run at 250 V for 45 minutes. The gel was semi-dry transferred to 0.2 μM Nitrocellulose (BIO-RAD) on the "High MW" transfer setting of the BIO-RAD Trans-Blot Turbo (10 minutes, 1.3 A). The blot was then rinsed in ultrapure water briefly before being blocked in 1× iBind Flex solution (Thermo) for 10 minutes. The blot was then incubated in 1× iBindFlex solution containing anti-CFTR

TABLE 16

Tentative Test Article Requirement for NHP Pilot Tox

| | Transgene | Dose (in 5 mL) | Titer (vg/mL) | Volume (mL) | Aliquots | vg/aliquot |
|---|---|---|---|---|---|---|
| Formulation Buffer | N/A | N/A | 0 | 5.5 | 1 | 0 |
| A101-CFTR | CFTR | 3.00E+12 | 6.00E+11 | 5.5 | 3 | 3.30E+12 |
| A101-CFTR | CFTR | 3.00E+13 | 6.00E+12 | 5.5 | 3 | 3.30E+13 |
| A101-GFP | GFP | 3.00E+13 | 6.00E+12 | 5.5 | 3 | 3.30E+13 | rAAV-CFTR (4D130109, lot #4DER000060.02, ~3×10$^{13}$ vg/mL), in 20 mM Citrate, pH 6+125 mM NaCl+0.005% F68, was diluted in the same formulation buffer to a target of approximately 6×10$^{11}$ vg/mL (Low dose@5.5 mL total volume). A 100 uL aliquot was removed for T=0 titer and DLS. The remaining material was placed in a −80 C. freezer for 1 hour. The tube was removed and allowed to thaw at room temperature for 1 hour. The thawed tube was gently inverted to mix and a 100 uL aliquot was removed for DLS and titer (1× Freeze-Thaw). This process was repeated two antibody (Ab660, CFF/UNC 1:500) or anti-Tubulin antibody (E-7, DSHB 1:1000) for 2 hours at room temperature with gentle shaking. Blots were then washed with PBS (Corning) containing 0.01% Tween-20 (Sigma) for 5 minutes with shaking; this wash step was repeated two additional times. Blots were then incubated in anti-mouse-HRP secondary antibody (R&D systems, 1:5000) in 1× iBind Flex solution for 1 hour at room temperature. Washing steps with PBS-0.01% Tween-20 were then repeated. Washed blots were then coated in DuraWest HRP Detection Substrate (Thermo) for 5 minutes, and blots were then imaged on a BIO-RAD ChemiDoc Imaging System.

Materials and Methods—Immunocytochemistry. For immunocytochemistry, 2v6.11 cells were grown on poly-L-lysine-coated glass chamber slides, 16HBE14o-were grown on transwell inserts coated with both bovine collagen I and human plasma fibronectin. At two days (2v6.11) or four days (16HBE14o-) post-transduction, cells were fixed in 4% PFA for 20 minutes at room temperature in the dark. Cells were then permeabilized with 0.2% Triton-X in PBS (without calcium and magnesium) and incubated at 4° C. overnight with CFTR MM13-4 antibody (EMD Millipore, 1:100) in blocking buffer. Blocking buffer consisted of 0.2% Triton-X, 5% goat serum, and 2% bovine serum albumin in PBS. After washing out antibody with PBS-Triton, Secondary Goat anti-Mouse Alexa Fluor-647 conjugate (Invitrogen, 1:500) was added in blocking buffer for one hour at room temperature in the dark. Secondary antibody was subsequently washed out. Nuclei were stained with 4',6-diamidino-2-phenylindole (DAPI) in PBS, then cover-slipped with Prolong Gold (Invitrogen), and subsequently imaged. Cells were imaged using a Zeiss Axio Observer.D1 Fluorescent Microscope. Image processing was performed using Zeiss Zen 2 software (Carl Zeiss Microscopy LLC, White Plains, NY).

Materials and Methods—RNA extraction and Droplet Digital PCR. RNA was isolated from cells using a RNeasy Micro Qiagen Kit (Thermo Fisher Scientific) and cDNA was made using the Maxima H minus cDNA Synthesis Kit (Thermo Fisher). cDNA samples were prepared by serial dilution in 1×TE buffer (10 mM Tris, 0.1 mM EDTA pH 8.0). Samples were then plated into master mix containing ddPCR supermix and either a primer/probe set targeting CFTRΔR (SEQ ID NO:43) or the endogenous CFTR gene (Thermo Fisher). Samples were then partitioned into nanoliter droplets using the Automated Droplet Generator (BIO-RAD), subjected to endpoint PCR in a C1000 Touch Thermal Cycler (BIO-RAD), and read on the QX200 Droplet Reader (BIO-RAD) which measures each droplet individually for fluorescent signal. Data was then analyzed using BIO-RAD's QuantaSoft software, which uses Poisson statistical analysis of the positive (droplets containing fluorescent signal above threshold) and negative (droplets with fluorescent signal below threshold) droplets to provide absolute quantitation of target sequence(s). Analysis was further performed using Microsoft Excel.

Results

Initial proof-of-concept transgene expression and protein membrane-localization after transduction with 4D-710 was assessed by transducing the HEK2v6.11 cell line—a relatively simple system (compared to the more complex human air-liquid-interface cell model). HEK2v6.11 cells are derived from the human embryonic kidney line, HEK-293T, with ponasterone A-inducible expression of the human adenovirus E4 ORF6 protein. Multiple AAV serotypes are capable of high transduction efficiency in this cell line. Briefly, HEK2v6.11 were grown in DMEM (Gibco) with 10% FBS and 1% penicillin/streptomycin. Upon confluence, cells were treated at various MOIs for 48 hours. Ponasterone was added to 1 µg/ml to increase expression from the AAV vector. Cells were analyzed by western blot or by immunocytochemistry and transduced with 4D-710 for 24 hours and analyzed by Western blot or by immunocytochemistry (ICC) 48 hours post-transduction. Dose-dependent transduction of 4D-710 into HEK2v6.11 cells was demonstrated by western blot at increasing Multiplicity of Infections (MOIs) (FIG. 28A). The B band, which reflects the ER core-glycosylated form of the protein (150 kDa), and the C band, reflecting fully glycosylated mature form of CFTR (170-180 kDa), can be seen, suggesting the proper protein translation and cellular processing. Representative immunofluorescence images further demonstrate dose-dependent transduction (FIG. 28B) and cytoplasmic (FIG. 28B) and membrane (FIG. 28C) expression of CFTR protein. The nontransduced controls show that endogenous CFTR protein is not detected, indicating that the protein detected is the transduced CFTRΔR transgene. Thus, not only are the immature and mature forms of CFTRΔR made, but membrane expression of CFTRΔR protein was observed by ICC (using an anti-CFTR antibody and F-actin antibody to stain the cell membrane).

Transduction with 4D-710 of a human lung cell line was evaluated. 16HBE14o-G542X cells are an immortalized human bronchial epithelial (HBE) cell line (originally immortalized with the origin-of-replication defective SV40 plasmid) harboring a CFTR null mutation (G542X, generated using CRISPR-based gene editing) and do not express CFTR. 16HBE14o-G542X cells were cultured in MEM (Gibco 11095-072) plus 10% FBS (Gibco 26140-079) and 1% penicillin/streptomycin (Gibco 15140-122). Cells were seeded into trans-well inserts at 9,000 cells per insert. Media was added to both the top (100 µL) and bottom (500 µL). At day three post-seeding, cells were treated at various MOIs apically for 72 hours. Cells were analyzed by immunocytochemistry or reverse transcription-droplet digital polymerase chain reaction (RT-ddPCR) using primers and probe specific for codon optimized CFTRΔR mRNA (the 4D-710 transgene). To detect exogenous CFTR protein, transduction was performed in parallel with Doxorubicin treatment (1 µM) for 24 hours in culture media. To assess transcript levels of codon optimized CFTRΔR transgene following transduction of 4D-710 into human bronchial epithelia cells, 16HBE14o-G542X cultures were transduced with 4D-710 at increasing MOIs. In order to further confirm transduction of the HBEs with 4D-710, RT-ddPCR was performed to determine the number of copies of CFTRΔR mRNA. FIG. 29A shows a dose-dependent response curve for the number of copies of CFTRΔR mRNA for increasing MOIs. In the presence of Doxorubicin, transduced cells were identified through immunocytochemistry (FIG. 29B), with a greater number of cells transduced at 50,000 MOT versus 35,000 MOI. Thus, dose dependent transduction of human bronchial epithelial cells and robust expression of the CFTR transgene in these disease-relevant human cells was demonstrated.

Air-liquid-interface (ALI) cultures are from healthy (non-CF) lungs and as such have endogenous expression of CFTR. Endogenous CFTR was distinguished from expression of the truncated 4D-710 CFTR transgene using RT-ddPCR using primers and probe specific for endogenous CFTR or specific for CFTRΔR FTRΔR mRNA. Standard ALI culturing of the ex vivo non-CF lungs represents the best in vitro model of the in vivo lung system (these cultures are complex with non-homogenous cell types (like the in vivo lung)). Briefly, ex vivo human ALI non-CF lung cultures were plated on collagen type IV-coated Corning transwell inserts, cultured basally in PneumaCult ALI medium (StemCell Technologies 05040) with inclusion of pen/strep (Gibco 15140-122), gentamycin, and amphotericin B according to the manufacturer's protocol. After 30 days post-seeding when the ALI cultures are mature, cultures were treated at various MOIs apically in the presence of 0.625 uM idarubicin for 24 hours in culture media. Seven days post-transduction, cells were analyzed by RT-ddPCR using primers and probe specific for endogenous CFTR or specific for CFTRΔR mRNA. To assess transcript levels of codon optimized CFTRΔR transgene following transduction into ex vivo healthy ALI lung, ALI cultures were transduced with 4D-710 at MOIs of 50,000 and 100,000 in the presence of idarubicin. RNA was isolated seven days post transduction and cDNA was synthesized. RT-ddPCR was run on the prepared samples and transcript levels per droplet were analyzed as a copies/4 value. Quantification analyzed the number of droplets, above the set threshold, containing the transcript of the primer/probe set examined. Two primer/probe sets were created to specifically differentiate the codon optimized human CFTRΔR transgene, from the endogenous human CFTR gene. Non-transduced ALI cultures expressed below the limit of quantification levels of CFTRΔR transcript, as expected (FIG. 30). Following transduction with 4D-710, cells demonstrate a dose-dependent increase in CFTRΔR transcript (FIG. 30). At 50,000 MOI, CFTRΔR transcript level is ~80% of endogenous CFTR level (FIG. 30). At 100,000 MOI CFTRΔR transcript reaches and in some cases is increased over the endogenous CFTR level (FIG. 30). These data illustrate that 4D-710 can transduce ex vivo lung ALI cultures with dose dependent expression of the CFTRΔR transgene and that at high MOI, there is an increase in CFTRΔR mRNA over endogenous CFTR.

Conclusions—4D-710 is a recombinant AAV gene replacement therapy product designed to treat cystic fibrosis caused by CFTR mutations, a respiratory condition of the lung, preferably by single dose aerosol delivery to the lung. 4D-710 comprises a capsid protein of SEQ ID NO:12, identified by directed evolution as surprisingly useful for delivery of therapeutic gene products to the lung, and a heterologous nucleic acid comprising the nucleotide sequence of SEQ ID NO:45 (the nucleotide sequence of SEQ ID NO:45 comprises a codon optimized human cystic fibrosis gene therapy payload (SEQ ID NO:43) operably linked to a CMV173 promoter (SEQ ID NO:44)). The in vitro and ex vivo data provided herein with human cells have demonstrated that 4D-710 restores human CFTR transcript and transgene expression in human bronchial epithelia cells containing a cystic fibrosis Class I mutation and in healthy ALI lung cultures. Furthermore, the CFTR protein, expressed following transduction of 4D-710, was expressed, post-translationally glycosylated and localized to the cytoplasm and cell membrane in HEK2v6.11 cells. These data demonstrate that 4D-710 is capable of transducing a human lung cell line and delivering detectable CFTRΔR mRNA leading to dose-dependent production of CFTR protein and localization of the expressed CFTR protein to the membrane. Combined with the data of Example 3 and Example 7 demonstrating safe, robust and widespread transduction and transgene expression throughout the primate lung following aerosol delivery, with minimal systemic exposure, these data represent a significant advance over existing AAV serotypes for the development of gene therapies for cystic fibrosis and other pulmonary disorders.

Example 7

Dose Range and Pilot Safety Study for Aerosol Delivery of 4D-710 to the Lungs of Cynomolgus Monkeys An in vivo study was initiated to test safety and transduction activity of the 4D-710 therapeutic product in a pilot study in Cynomolgus monkeys to assess the ability of engineered viral vectors to transduce cells and express the CFTRΔR transgene in the airway, lungs, and other tissues following a single aerosolized administration within a range of dose levels. As discussed in Example 6, 4D-710 is an rAAV comprising a capsid protein of SEQ ID NO:12 and a heterologous nucleic acid of SEQ ID NO:45. The heterologous nucleic acid component of 4D-710 comprises the nucleotide sequence of SEQ ID NO:43—a codon optimized human CFTRΔR transgene—operably linked to the CMV173 promoter of SEQ ID NO:44. The expression and function of the intended therapeutic transgene cassette was characterized in vivo in Cynomolgus primates. Sera was pre-screened to identify animals that were seronegative for pre-existing neutralizing antibodies to the test article capsids. Animals received vehicle (formulation buffer only), $3 \times 10^{12}$ vg of 4D-710, or $3 \times 10^{13}$ vg of 4D-710, delivered endoscopically just below the larynx using the AeroEclipseII device (Trudell Medical) to ensure optimal delivery to the distal lung. After eight weeks, select tissues (lung, heart, skeletal muscles, liver, kidney, pancreas, spleen, brain, spinal cord, tracheobronchial lymph nodes, and testes) were harvested for analyses. Viral genomes were quantified via qPCR. Tissue samples that contained detectable viral genomes were assessed for CFTRΔR transcript by RT-qPCR, and lung samples were sectioned and imaged for CFTR protein expression by IHC.

The data below demonstrate that nebulized delivery of 4D-710 resulted in robust delivery of viral genomes to all regions of the lung, including the peripheral (bronchioalveolar) regions, with minimal systemic biodistribution, and 4D-710 mediated CFTRΔR transcript and protein expression to all regions of the lung. There were no reported adverse safety findings in animals dosed with vehicle, or test article 4D-710 ($3 \times 10^{12}$ and $3 \times 10^{13}$ vg).

Materials and Methods

Neutralizing Antibody Assay

HEK2v6.11 cells (obtained from John Hopkins University) were plated on black opaque 96 well plates at a cell density of 30,000 cells/well in Dulbecco's modified Eagle medium (DMEM; Corning) with 1% heat inactivated fetal bovine serum (FBS; GE Healthcare Life Sciences) and 1% penicillin/streptomycin (Invitrogen). Cells were allowed to adhere to the plate for 24 hours prior to starting the experiment.

Each non-human primate (NHP) serum sample was assayed at dilutions of 1:10, 1:25, 1:50. Each plate contained positive and negative controls for transduction. NHP serum samples were incubated with virus at 37 C for 1 hour. Each well was infected with 4D-A101.CAG-Luciferase (rAAV comprising a capsid protein of SEQ ID NO:12 and a heterologous nucleic acid encoding luciferase operably linked to a CAG promoter) at an MOI of 1,000. Following a 1 hour incubation, each NHP serum sample plus 4D-A101.CAG-Luciferase dilution was added to individual wells of black opaque 96 well plates containing HEK2v6.11 cells. Luciferase was detected by ONE-Glo EX Luciferase assay kit (Promega) 48 hours post-transduction. With the addition of the ONE-Glo EX, cells were lysed, and luciferase substrate was added to the cells in a single step. Luminescence was read using a Cytation 3 microplate reader (BioTek).

Coefficients of variation (CV) and standard deviations were calculated for all NHP serum sample dilutions and each point of the standard curve. NHP serum samples were normalized to the positive transduction control. Each NHP was assigned a neutralizing antibody titer. The neutralizing antibody titer for each NHP serum sample was defined as the lowest serum dilution at which #50% transduction was observed. NHPs for which #50% transduction at 1:10 serum dilution was observed were considered for inclusion in the study.

Test System and Immunosuppression

Seven male cynomolgus macaques were included in the study. Animals ranged in age from 4.7 years to 4.9 years and ranged in weight from 3.8 kg to 6.0 kg. Animals received methylprednisolone (10 mg/kg, intramuscular) immunosuppression once weekly starting on day −7 until one week prior to euthanasia and tissue collection (D49). Additional details are provided in the contract research organization (CRO) study report (Preclinical Study Report Pending).

Test Article Preparation and Administration

Test article (TA) lots of 4D-710 and vehicle were diluted in formulation buffer to deliver final doses of $3 \times 10^{12}$ vg and $3 \times 10^{13}$ in 5 mL. TAs were thawed at room temperature for >1 hour and tubes inverted gently 5× before adding 5 mL to the delivery device (AeroEclipseII).

The animals were anesthetized with Telazol (IM, 7-8 mg/kg) and a cuffed endotracheal tube (size 4.5) was placed in the trachea just below the larynx and secured to avoid slipping out during transport and placement in the chair. Thereafter, they were positioned in a chair in an upright position in order to connect the endotracheal tube to the aerosol generation system. Animals were covered with blankets and Bair Hugger for external heat and heart rate and 02 saturation were monitored during exposure and recovery from anesthesia.

The aerosol generation and delivery system used an AeroEclipse II Breath Actuated Nebulizer (BAN, Trudell Medical International, Canada) for aerosol generation. A total of five (5) mL of control or test article were delivered to anesthetized animals via endotracheal tube. The nebulizer was operated in continuous aerosol generation mode by switching the knob at the cap of the nebulizer. In addition, the vent holes inside the cap of the nebulizer were plugged.

Animal Observations

Twice daily cage-side observations were performed per CRO husbandry SOP Procedures for Care and Management of Indoor Nonhuman Primates. On treatment and procedure days, animals were closely observed by study personnel. Main observations included, but were not limited to signs of vomiting, lethargy, respiratory distress, and cyanosis, discoloration of mucous membranes, emesis, and irregular discharge from orifices or bloody stool/urine.

Blood Collection

Animals were fasted overnight with free access to drinking water prior to any blood collections and fed immediately thereafter. Blood samples for clinical pathology and antibody titer and immunogenicity analysis were collected by venipuncture of femoral vein. Samples (1 mL in EDTA) for hematology and complete cell count were shipped to an outside reference laboratory (IDEXX) on day of collection to be analyzed with 24 to 48 hours after collection. Samples for clinical chemistry (1 mL in SST) were analyzed by CRO's Pathology Laboratory on day of collection.

Bronchoalveolar Lavages (BAL)

Fasted animals were anesthetized with ketamine hydrochloride followed by isoflurane inhalation per SOP Anesthesia of Nonhuman Primates. A properly sized cuffed endotracheal tube was inserted just proximal to the carina to allow the insertion of a pediatric fiberoptic bronchoscope to perform BAL per SOP ACL-1536 Procedures for Conducting Lung Lavage and/or Bronchoscopy in Nonhuman Primates. Samples from both sides of the lung were collected at baseline (D-7) and 4 weeks after treatment. Three 10 mL aliquots of Dulbecco's PBS were introduced in the appropriate side of the lung through the bronchoscope and aspirated sequentially. The lavage isolates from the first wash were kept separate and the $2^{nd}$ and $3^{rd}$ wash combined during collection and kept on wet ice until processing within less than 2 hours after collection. Combined cells from all washes were counted and slides were prepared to perform differential cell counts using morphological criteria at CRO.

Euthanasia and Necropsy

For euthanasia, animals were anesthetized with ketamine (11.0 to 12.4 mg/kg, IM) followed by IV injection of euthanasia solution per CRO SOP, Large Animal Euthanasia. After confirming the death, the necropsy was performed by trained necropsy personnel per CRO SOP Necropsy Procedure for Nonrodent Species and tissues collected, weighed, preserved and examined. Tissues were processed accordingly for DNA and RNA or prepared for histopathology analysis.

Animals were perfused with heparinized saline prior to collection of any tissue. Lungs & trachea, skeletal muscle (diaphragm, triceps brachii, and vastus lateralis), heart, liver, spleen, pancreas, testes, kidney, brain, tracheobronchial lymph nodes, and spinal cord were collected. Each tissue was separated into different regions and multiple samples collected from each region. Gross necropsy examination of major peripheral organs was performed, and tissue samples collected from any identified lesions. Samples of tissue were collected and flash frozen for subsequent DNA or stored in RNALater for subsequent RNA isolation. Additional samples were collected and fixed in 10% neutral buffered formalin for subsequent paraffin embedding and sectioning for immunohistochemistry.

The trachea and lungs were sampled extensively to provide multiple samples for each analysis process. The lungs were harvested and clamped as superior on the trachea as possible. The right lung was clamped twice, approximately 1 mm apart, on the mainstem bronchi. The right lung was removed by cutting between the clamps. Sixteen samples each for DNA and RNA isolation were collected from regions of the right lung encompassing the primary/secondary bronchi, tertiary bronchi, and alveoli, as described in FIG. 16. The trachea and left lung were inflated with fixative and fixed in 10% neutral buffered formalin. The trachea and left lung were then sectioned to encompass samples of the trachea, primary/secondary bronchi, tertiary bronchi, and alveoli, as described in FIG. 16.

Viral Genome Biodistribution and Transgene Expression

A real-time quantitative Polymerase Chain Reaction (qPCR) and a reverse-transcriptase real-time quantitative Polymerase Chain Reaction (RT-qPCR) method were developed for quantification in NHP tissues. Quantification of viral genomes in the lung of NHPs from each group was performed by qPCR and RT-qPCR using primers and probes against (and specific for) the codon optimized transgene (SEQ ID NO:43). Viral titers measured in tissue is expressed as number of copies per μg of DNA (BLQ=50) and transgene transcript is expressed as number of copies per reaction of 250 ng RNA (BLQ=25).

Immunohistochemistry was performed in the trachea and left lung tissue samples encompassing samples of the trachea, primary/secondary bronchi, tertiary bronchi, and alveoli, as described in FIG. 16 from all animals. The CFTR IHC assay was performed using a Roche Discovery ULTRA autostainer and detection reagents, CC1S antigen retrieval protocol and tyramide amplification kit, and anti-CFTR mouse monoclonal antibody (Abcam ab270238 M3A7).

Results
Anti-AAV Neutralizing Antibody Screen Identifies NHP for Study Inclusion A neutralizing antibody assay was used in order to assess levels of neutralizing antibodies against the 4D-A101 capsid (comprising a capsid protein of SEQ ID NO:12) in NHP serum. Each NHP serum sample was assigned a neutralizing antibody titer. An animal was considered seronegative and passed the study inclusion criteria if #50% transduction was observed at a 1:10 serum dilution.

In total, 50 NHP serum samples were evaluated. Assay acceptance criteria was set for 1) the coefficient of variance (CV) of the standard curve, 2) CV of the unknown serum samples, and 3) percent deviation from actual input protein for the standard curve. Acceptable CVs for the standard curve were defined as <25%. Acceptable CVs for the unknown serum samples within the limit of quantification were defined as <30%. Acceptable percent deviation from input protein for the standard curve was defined as <25%. All plates met all assay acceptance criteria, and the data from these plates were used for evaluation. Overall, 19 (38%) NHP serum samples evaluated were seronegative for 4D-A101 (FIG. 31). The NHPs with the highest percent transductions at the 1:10 serum dilution and passed health screening at the vendor were selected for study inclusion. The selected NHP IDs and the percent transduction at the 1:10 dilution is reported in Table 17:

TABLE 17

NHPs Included in Study

| Assay # | NHP ID # | % Transduction at 1:10 |
|---|---|---|
| 1 | 2DRPL2-39C-B-A | BLQ |
| 2 | 2DRPL2-4C-E | 10 |
| 3 | 2DRPZ2-18C-G | BLQ |
| 4 | 2DRPZ2-26C-H | BLQ |
| 5 | 2DRPZ2-27C-F | 115 |
| 6 | 2DRPZ2-9C-I | 96 |
| 7 | 2DRPZ4-16C-B | BLQ |
| 8 | 2DRPZ6-30C-G | 100 |
| 9 | DPC15-39A-K | BLQ |

TABLE 17-continued

NHPs Included in Study

| Assay # | NHP ID # | % Transduction at 1:10 |
|---|---|---|
| 10 | DPL8-26A-L | 74 |
| 11 | DRP8BL-22K-E | 58 |
| 12 | DRPL13-9A-K | 112 |
| 13 | DRPL3-37D-B | 102 |
| 14 | DRPL4-2D-C | 89 |
| 15 | DRPL5-17D-B | 11 |
| 16 | DRPL7-31D-A | 97 |
| 17 | DRPS1-31C-G | BLQ |
| 18 | DRPS15-53B-A | 118 |
| 19 | DRPS7-11B-H | BLQ |
| 20 | DRPZ10-19B-I | BLQ |
| 21 | DRPZ11-18C-E | 40 |
| 22 | DRPZ12-21A-D-E | BLQ |
| 23 | DRPZ12-33A-L | BLQ |
| 24 | DRPZ13-44A-I | BLQ |
| 25 | DRPZ1-5D-D | 78 |
| 26 | DRPZ16-12C-A | BLQ |
| 27 | DRPZ16-20B-A-C | 12 |
| 28 | DRPZ16-2B-F | 78 |
| 29 | DRPZ2-24D-A | BLQ |
| 30 | DRPZ31-13C-G | BLQ |
| 31 | DRPZ33-36C-A | 25 |
| 32 | DRPZ34-7C-A | BLQ |
| 33 | DRPZ3-9C-H | 56 |
| 34 | DRPZ40-18C-C | 20 |
| 35 | DRPZ40-22C-C | 69 |
| 36 | DRPZ4-17B-G | BLQ |
| 37 | DRPZ4-36B-F | 112 |
| 38 | DRPZ5-15D-C | 92 |
| 39 | DRPZ5-62A-E | 70 |
| 40 | DRPZ6-37D-C | BLQ |
| 41 | DRPZ7-105B-K | 49 |
| 42 | DRPZ7-28B-I | BLQ |
| 43 | DRPZ7-77B-J | BLQ |
| 44 | DRPZ9-16C-G | BLQ |
| 45 | DRPZ9-86C-C | BLQ |
| 46 | PRPL2-49C6-A | 93 |
| 47 | PRPL2-74C6-A | 32 |
| 48 | PRPL7-21C6-A | BLQ |
| 49 | PRPL9-33C6-A | 116 |

Nebulized Delivery of 4D-710 is Well-Tolerated in NHP

The study design is summarized in Table 18:

TABLE 18

Study Design Summary

| Group | Treatment | Route | # of animals | Dose (vg) | Volume (mL) | Necropsy |
|---|---|---|---|---|---|---|
| 1 | Control/Vehicle | Inhalation | 1 | N/A | 5 | Day 57 |
| 2 | 4D-710 | | 3 | $3 \times 10^{12}$ | 5 | Days 55/56/57 |
| 3 | 4D-710 | | 3 | $3 \times 10^{13}$ | 5 | Days 55/56/57 |

| Tissue Collection | Analysis |
|---|---|
| Lung | qPCR |
| Tracheobronchial lymph node | RT-qPCR (lung & qPCR + tissue) |
| Heart | IHC (lung) |
| Liver | |
| Skeletal Muscle (triceps, quadriceps, diaphragm) | |
| Kidney | |
| Spleen | |
| Pancreas | |
| Brain | |
| Spinal Cord | |

No animal died or was euthanized prematurely during the conduct of this study. None of the animals showed any signs of distress or health issues related to the TA exposure during the study duration. No loss in appetite and change in eating behavior was observed during treatment and sample collections. No treatment related changes in body weight occurred during this study.

Samples for hematology and complete cell count were shipped to an outside reference laboratory (IDEXX) on day of collection and analyzed within less than 48 hours after collection. Samples for clinical chemistry endpoints were analyzed by CRO's Pathology Laboratory on day of collection. Some of the clinical chemistry parameters were altered over time but no difference between vehicle group compared to both dose levels of 4D-710 treated group at any of the time points was observed. Similarly, no major changes in any of the hematology and blood cell counts were seen eight weeks after inhalation treatment compared to baseline levels.

Cell differentials and cell numbers in lavage fluid were determined for right and left lavage side and all data are presented as average from both sides. Total cell numbers and differentials in BALF were not different between treatment groups measured on D28 compared to baseline levels and due to variability and small sample size no further conclusions can be made.

Organ weights and weights relative to the body weight were collected on day of euthanasia for all treatment groups. The organ weights and weights normalized to body weights were not different between any of the treatment groups.

No major findings were reported during gross examination at necropsy. Microscopic examination concluded that there were no treatment related observations in the tissues examined.

4D-710 Mediates Robust Gene Delivery to all Regions of the Lung

Viral genomes were quantified in a tiered approach for samples obtained during necropsy to determine the genomic biodistribution of 4D-710. All lung samples obtained from vehicle, $3\times10^{12}$ vg, and $3\times10^{13}$ vg dosed animals were analyzed. Brain, spinal cord (cervical, thoracic, and lumbar regions), heart, liver, spleen, pancreas, kidney, skeletal muscle (triceps brachii, vastus lateralis, diaphragm), tracheobronchial lymph node, and testes samples collected from $3\times10^{13}$ vg dosed animals were all analyzed. Tissues that had above BLQ levels of viral genomes were then analyzed at the lower $3\times10^{12}$ vg dose (data is pending). Data is reported as viral genomes per µg of DNA.

The results for qPCR analysis indicate a uniform delivery of the virus throughout the different lung regions, which represented samples from the alveolar sacs (distal), tertiary bronchi (medial), and primary/secondary bronchi (proximal), except for samples marked with R6. This sample was hard to collect due to the proximity to the carina and therefore the location for separation and tying off the right and left side of the lung (see FIG. 16). The average number of copies for the remaining sample locations for $3\times10^{12}$ vg and $3\times10^{13}$ vg dose group were $10^4$ and $10^5$, respectively (FIG. 32A). The at least 10-fold difference between low and high dose group is well in line with the 10-fold difference in treatment dose. For all animals within the same treatment group, no significant differences in the quantity of viral genomes within different lung lobes or different lung regions were noted (FIG. 32B).

Non-lung systemic exposure was measured in the animals dosed with $3\times10^{13}$ vg 4D-710 (FIG. 32C). Animals had detectable viral genomes ~$10^4$ vg/µg present in tracheobronchial lymph nodes (FIG. 32C). The pathology reads on these animals for this tissue are normal. One NHP had detectable viral genomes in the spleen (FIG. 32C), with the pathology reads stated as normal. All other samples tested from brain, spinal cord, heart, liver, pancreas, kidney, skeletal muscle, and testes were below the lower limit of quantification (FIG. 32C). No test article related pathologies reported. Therefore, nebulized delivery of 4D-710 results in safe and robust delivery of viral genomes to all regions of the lung, with minimal non-lung systemic exposure.

4D-710 Mediates Transgene Expression to all Regions of the Lung

CFTRΔR transcript was quantified in a tiered approach for samples obtained during necropsy to determine transgene expression of 4D-710. All lung samples obtained from vehicle, $3\times10^{12}$ vg, and $3\times10^{13}$ vg dosed animals were analyzed. Brain, spinal cord, heart, liver, spleen, pancreas, kidney, skeletal muscle, tracheobronchial lymph nodes, and testes samples collected from the $3\times10^{13}$ vg dosed animals were all analyzed (data is pending). Tissues that had above BLQ levels of transcript were then analyzed at the lower $3\times10^{12}$ vg dose (data is pending). Data is reported as copies per reaction of 250 ng RNA and graphed as copies per µg RNA.

The results for RT-qPCR analysis indicate successful transduction and transcript expression in the lung. In the $3\times10^{13}$ vg dosed animals, 44 out of 48 lung samples were above BLQ with –103 copies per µg RNA with no vehicle samples above BLQ (FIG. 33A). Three of the four BLQ samples were from the same R6 sample location where collection was technically challenging, and one NHP had an additional sample BLQ. Transduction throughout the different lung regions (FIG. 33B), which represented samples from the alveolar sacs (distal), tertiary bronchi (medial), and primary/secondary bronchi (proximal), except for samples marked with R6 (see rationale above) was observed. In contrast, in the lung samples from the lower dose $3\times10^{12}$ vg animals, 41 out of 48 samples were BLQ. These data suggest that a dose of $3\times10^{13}$ vg, 4D-710 is able to quantifiably transduce NHP lung tissue and express the therapeutic CFTRΔR transcript.

CFTR protein expression detected by immunohistochemistry shows increased CFTR expression in 4D-710 treated NHP lung when compared to vehicle in tracheal epithelium, bronchial epithelium, and alveoli sections (FIG. 34A). Robust increased CFTR expression is observed in all of the $3\times10^{13}$ vg treated animals (FIG. 34B) compared to vehicle (FIG. 34A). These results demonstrate that nebulized delivery of 4D-710 mediates protein expression to all regions of the lung.

Conclusions

The therapeutic product, 4D-710, was characterized by aerosol delivery to Cynomolgus macaques. Sera was pre-screened to identify animals that were seronegative for pre-existing neutralizing antibodies to the test article capsid 4D-A101. Animals received either vehicle (formulation buffer), a $3\times10^{12}$ vg dose of 4D-710, or a $3\times10^{13}$ vg dose of 4D-710, delivered using the AeroEclipseII device.

A high quantity of viral genomes and resulting CFTRΔR transcript expression and CFTR protein expression was observed in lung samples across the NHPs in the study, which represented samples from the alveolar sacs, tertiary bronchi, and primary/secondary bronchi. A single spleen sample had low but detectable viral genomes present, and all samples from all other tissues showed no detectable viral genomes. These data demonstrate that nebulized delivery of 4D-710 results in safe and robust delivery of viral genomes to all regions of the primate lung (trachea, alveoli and bronchial epithelium), with minimal systemic biodistribution. These data further demonstrate that 4D-710 mediates robust expression of CFTRΔR mRNA and protein product to all regions of the lung, including the alveoli confirming the suitability of rAAV with capsids comprising a capsid protein of SEQ ID NO:12 as a pulmonary delivery vector for the treatment of a variety of pulmonary disorders and specifically support the use of 4D-710 (comprising a capsid protein of SEQ ID NO:12 and a heterologous nucleic acid of SEQ ID NO:45) for the delivery of a biologically active CFTR therapeutic transgene for the treatment of cystic fibrosis in human patients.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A method of delivering a heterologous nucleic acid to a lung cell in a primate comprising administering to the primate a composition comprising a recombinant adeno-associated virus (rAAV) vector, said rAAV vector comprising (i) a capsid comprising a capsid protein comprising the amino acid sequence set forth as SEQ ID NO:12 or an amino acid sequence at least 90% identical to SEQ ID NO:12 and comprising a Thr at amino acid 469 and an Ala at amino acid 598 based on the amino acid numbering set forth in SEQ ID NO: 12 and (ii) a heterologous nucleic acid comprising a nucleotide sequence encoding a gene product, wherein the step of administering comprises pulmonary, endobronchial, intranasal, intratracheal, and/or intrabronchial administration.

2. The method according to claim 1, wherein the lung cell is selected from an airway epithelial cell, a smooth muscle cell, and an endothelial cell.

3. The method according to claim 2, wherein the airway epithelial cell is a basal cell, a goblet cell or a cilia cell.

4. The method according to claim 3, wherein the airway epithelial cell is a lung alveolar epithelial type 1 (AECI) cell, a lung alveolar epithelial type 2 (AECII) cell, a bronchial epithelial cell or a tracheal epithelial cell.

5. The method according to claim 1, wherein the composition is formulated as an aerosol.

6. The method according to claim 1, wherein the method comprises administering the composition by a nebulizer.

7. The method according claim 1, wherein the composition comprises $10^{11}$ to $10^{14}$ vector genomes (vg) of the rAAV per ml.

8. The method according to claim 1, wherein the nucleotide sequence encoding the gene product is operably linked to a promoter.

9. The method according to claim 8, wherein the promoter is a constitutive promoter.

10. The method according to claim 8, wherein the promoter is a tissue-specific promoter.

11. The method according to claim 8, wherein the heterologous nucleic acid comprises a nucleotide sequence encoding a gene product selected from: cystic fibrosis transmembrane conductance regulator (CFTR protein) or a biologically active fragment thereof, SFTPA1 (surfactant A1), Caveolin-1, alpha-1-antitrypsin, alpha-1-antichymotrypsin, alpha-1-macroglobulin, matrix metalloproteinase 1 (MMP1), matrix metalloproteinase 12 (MMP12), microsomal epoxide hydrolyase, CYP1A1, Glutathione S-transferase, heme oxygenase-1, TGF-beta-1, TNF-alpha, IL-1 complex, IL-8, IL-13, human leukocyte antigen, vitamin D binding protein, beta-2-adrenergic receptor.

12. The method according to claim 11, wherein the gene product is a human cystic fibrosis transmembrane conductance regulator (CFTR) protein or a biologically active truncated CFTR protein lacking amino acids 708-759 of the human CFTR protein sequence.

13. The method according to claim 12, wherein the gene product is a biologically truncated CFTR protein lacking amino acids 708-759 of the human CFTR protein sequence.

14. The method according to claim 13, wherein the heterologous nucleic acid comprises the nucleotide sequence set forth in SEQ ID NO:43 or a sequence at least 80% identical thereto.

15. The method according to claim 1, wherein the primate is a human.

16. A nucleic acid sequence comprising a nucleotide sequence set forth in SEQ ID NO:43 or a sequence at least 80% identical thereto.

17. A pharmaceutical composition comprising the nucleic acid sequence of claim 16.

18. A pharmaceutical composition comprising an rAAV vector, said rAAV vector comprising (i) a capsid comprising a capsid protein of SEQ ID NO:12 or an amino acid sequence at least 90% identical to SEQ ID NO:12 and comprising a Thr at amino acid 469 and an Ala at amino acid 598 based on the amino acid numbering set forth in SEQ ID NO: 12 and (ii) a heterologous nucleic acid comprising a nucleotide sequence encoding a CFTR or a biologically active truncated CFTR protein lacking amino acids 708-759 of the human CFTR protein sequence, said nucleotide sequence operably linked to an expression control sequence.

19. The pharmaceutical composition according to claim 18, wherein the nucleotide sequence encoding the CFTR protein is at least 80% identical to the nucleotide sequence set forth as SEQ ID NO:43.

20. The pharmaceutical composition according to claim 19, wherein the nucleotide sequence encoding the CFTR comprises the nucleotide sequence set forth as SEQ ID NO:43.

21. The pharmaceutical composition according to claim 20, wherein the capsid comprises a capsid protein comprising the amino acid sequence set forth as SEQ ID NO:12 and wherein the expression control sequence comprises a CMV173 promoter.

22. The pharmaceutical composition according to any claim 18, wherein the composition is formulated for inhalation.

23. A pharmaceutical composition comprising an rAAV virus, wherein the rAAV virus is formulated in a buffer comprising about 10 mM to about 50 mM citrate, about 70 mM to about 150 mM NaCl and a surfactant and having a pH of about 5.0 to about 7.0.

24. The pharmaceutical composition according to claim 23, comprising about 20 mM to about 50 mM citrate, about 85 mM to about 125 mM NaCl and about 0.005% Pluronic F68 and having a pH of about 6.0.

25. The pharmaceutical composition according to claim 24, comprising about 20 mM citrate, about 125 mM NaCl and about 0.005% Pluronic F68 and having a pH of about 6.0.

26. The pharmaceutical composition according to claim 23, wherein the rAAV vector comprises (i) a capsid protein comprising the amino acid sequence set forth as SEQ ID NO: 12 or an amino acid sequence at least 90% identical to SEQ ID NO: 12 and comprising a Thr at amino acid 469 and an Ala at amino acid 598 based on the amino acid numbering set forth in SEQ ID NO: 12 and (ii) a heterologous nucleic acid comprising the nucleotide sequence set forth as SEQ ID NO: 43 or a nucleotide sequence at least 80% identical to SEQ ID NO: 43.

27. A method of treating cystic fibrosis in a primate comprising administering to the primate a pharmaceutical composition according to claim 18, wherein the step of administering comprises pulmonary, endobronchial, intranasal, intratracheal, and/or intrabronchial administration.

28. The method according to claim 27, wherein the primate is a human.

* * * * *